United States Patent
Abrahamian et al.

(10) Patent No.: US 11,279,677 B2
(45) Date of Patent: Mar. 22, 2022

(54) PHOTOCHROMIC HYDRAZONE SWITCHES

(71) Applicant: THE TRUSTEES OF DARTMOUTH COLLEGE, Hanover, NH (US)

(72) Inventors: Ivan Abrahamian, Hanover, NH (US); Hai Qian, West Lebanon, NH (US); Susnata Pramanik, Hanover, NH (US); Baihao Shao, West Lebanon, NH (US); Quan Li, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 11 days.

(21) Appl. No.: 16/401,942

(22) Filed: May 2, 2019

(65) Prior Publication Data
US 2019/0256472 A1 Aug. 22, 2019

Related U.S. Application Data

(63) Continuation-in-part of application No. PCT/US2017/060070, filed on Nov. 4, 2017.

(60) Provisional application No. 62/417,414, filed on Nov. 4, 2016, provisional application No. 62/489,160, filed on Apr. 24, 2017, provisional application No. 62/517,887, filed on Jun. 10, 2017.

(51) Int. Cl.
| | |
|---|---|
| *C07D 215/00* | (2006.01) |
| *C07D 243/00* | (2006.01) |
| *C07D 251/00* | (2006.01) |
| *C07D 273/00* | (2006.01) |
| *C07D 215/40* | (2006.01) |
| *B01J 19/12* | (2006.01) |
| *C07C 243/22* | (2006.01) |
| *C07D 273/08* | (2006.01) |
| *C07D 333/24* | (2006.01) |
| *C07D 333/36* | (2006.01) |
| *C07D 401/12* | (2006.01) |
| *C09K 9/02* | (2006.01) |
| *G11C 13/04* | (2006.01) |
| *C09K 11/06* | (2006.01) |
| *C07C 251/86* | (2006.01) |
| *C07C 251/82* | (2006.01) |
| *C07C 251/00* | (2006.01) |
| *B82Y 10/00* | (2011.01) |

(52) U.S. Cl.
CPC .......... *C07D 215/40* (2013.01); *B01J 19/127* (2013.01); *C07C 243/22* (2013.01); *C07C 251/00* (2013.01); *C07C 251/82* (2013.01); *C07C 251/86* (2013.01); *C07D 273/08* (2013.01); *C07D 333/24* (2013.01); *C07D 333/36* (2013.01); *C07D 401/12* (2013.01); *C09K 9/02* (2013.01); *C09K 11/06* (2013.01); *G11C 13/041* (2013.01); *B01J 2219/0879* (2013.01); *B01J 2219/1203* (2013.01); *B82Y 10/00* (2013.01); *C07B 2200/09* (2013.01); *C09K 2211/1007* (2013.01); *C09K 2211/1011* (2013.01); *C09K 2211/1014* (2013.01); *C09K 2211/1018* (2013.01)

(58) Field of Classification Search
CPC .. C07D 215/40; C07D 273/08; C07C 243/22; C07C 251/00; C07C 251/82; C07C 251/86
See application file for complete search history.

(56) References Cited

U.S. PATENT DOCUMENTS 4,341,782 A * 7/1982 Konishi ................. A01N 43/54
514/275

FOREIGN PATENT DOCUMENTS

| FR | 2007386 A1 * | 1/1970 | ............ A61K 31/34 |
|---|---|---|---|
| JP | S62103055 A | 5/1987 | |
| WO | WO 2015/031518 A1 | 3/2015 | |

OTHER PUBLICATIONS

Bleger et al. (2012) "o-Fluoroazobenzenes as Readily Synthesized Photoswitches Offering Nearly Quantitative Two-Way Isomerization with Visible Light," J. Am. Chem. Soc., 134, pp. 20597-20600.
Bleger et al. (2015) "Visible-Light-Activated Molecular Switches," Angew. Chem. Int. Ed., vol. 3-5; 54, pp. 11338-11349.
Demchenko et al. (2013) "Excited-state proton coupled charge transfer modulated by molecular structure and media polarization," Chem. Soc. Rev., 42, pp. 1379-1408.
Helmy et al. (2014) "Photoswitching Using Visible Light: A New Class of Organic Photochromic Molecules," J. Am. Chem. Soc., 136, pp. 8169-8172.
Houk et al. (2003) "Binding Affinities of Host-Guest, Protein-Ligand, and Protein-Transition-State Complexes," Angew. Chem. Int. Ed., 42, pp. 4872-4897.
Kawata et al. (2000) "Three-Dimensional Optical Data Storage Using Photochromic Materials," Chem Rev, 100, pp. 1777-1788.
Lerch et al. (2016) "Emerging Targets in Photopharmacology," Angew. Chem. Int. Ed, 55, pp. 10978-10999.
Liu et al. (2013) "Palladium-Catalyzed Carbenoid Based N—H Bond Insertions: Application to the Synthesis of Chiral α-Amino Esters," Org. Biomol. Chem., 11, pp. 5998-6002.
PCT/US2017/060070 International Search Report and Written Opinion dated Jan. 29, 2018, 9 pp.
Piard et al. (2009) "Photoswitching in diarylethene nanoparticles, a trade-off between bulk solid and solution: towards balanced photochromic and fluorescent properties," New J. Chem., 33, pp. 1420-1426.
Pubchem 9604659 deposited on Oct. 24, 2006 (Oct. 24, 2006) pp. 1-11. p. 3.
Qian et al. (2015) "Photochromic Hydrazone Switches with Extremely Long Thermal Half-Lives," Chem. Commun., 51, pp. 11158-11161.

(Continued)

*Primary Examiner* — Sikarl A Witherspoon
(74) *Attorney, Agent, or Firm* — Lathrop GPM LLP

(57) ABSTRACT

Provided herein are compounds for use as photochromic molecular switches having very long thermal isomerization half-lives and switchable fluorescence properties both in solution and the solid state.

13 Claims, 53 Drawing Sheets

(56) References Cited

OTHER PUBLICATIONS

Qian et al. (2017) "An Emissive and pH Switchable Hydrazone-Based Hydrogel," J. Amer. Chem. Soc., 139, pp. 9140-9143.
Ray et al. (2012) "A Switching Cascade of Hydrazone-based Rotary Switches Through Coordination-coupled Proton Relays," Nature Chemistry, vol. 4, pp. 757-762.
Roubinet et al. (2016) "Carboxylated Photoswitchable Diarylethenes for Biolabeling and Super-Resolution RESOLFT Microscopy," Angew. Chem. Int. Ed, 55, pp. 15429-15433.
Weston et al. (2014) "Arylazopyrazoles: Azoheteroarene Photoswitches Offering Quantitative Isomerization and Long Thermal Half-Lives," J. Am. Chem. Soc., 136, pp. 11878-11881.
Yamaguchi et al. (2016) "Fast Negative Photochromism of 1,1'-Binaphthyl-Bridged Phenoxyl-Imidazolyl Radical Complex," J. Am. Chem. Soc., 138, pp. 906-913.
Benincori et al. (1988) "Rearrangements of aromatic carbonyl arylhydrazones of benzene, naphthalene, and azulene", Journal of the Chemical Society, Perkin Transactions, vol. 272, No. 10, pp. 2721-2728.
European Patent Application No. 17867775.3, Extended Search and Opinion dated Mar. 4, 2020, 33 pages.
Fusco et al. (1982) "New rearrangements of arylhydrazones in polyphosphoric acid: extension to the thiophene and indole series". [Retrieved from Chemical Database accession No. 121309].
Su et al. (2011) "Switching Around Two Axles: Controlling the Configuration and Conformation of a Hydrazone-Based Switch", Organic Letters, vol. 13, No. 1, pp. 30-33.

\* cited by examiner

FIG. 11
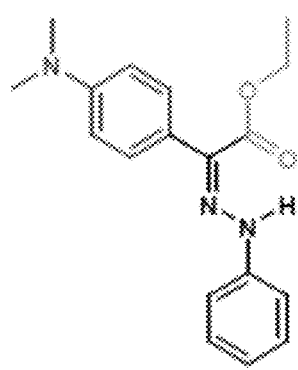
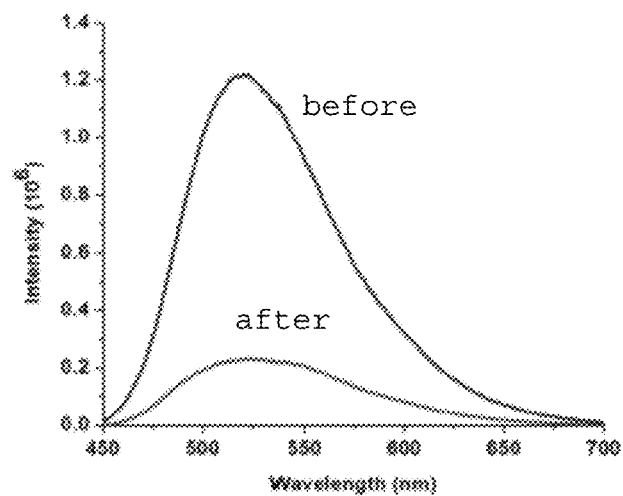

FIG. 12
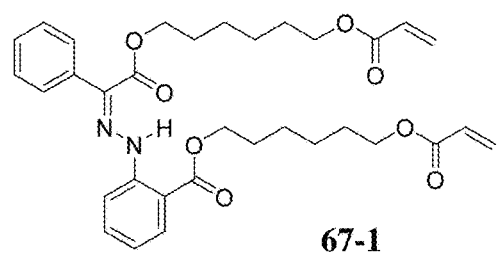
67-1
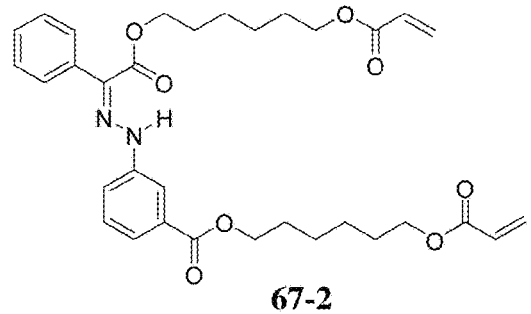
67-2
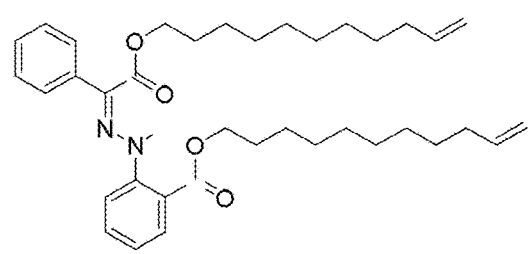
67-3
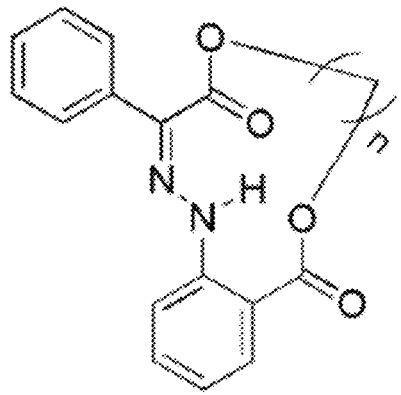
67-4

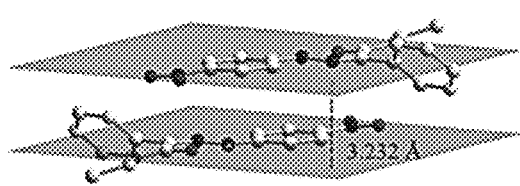
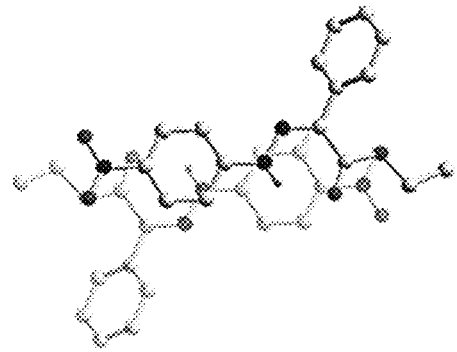
FIG. 43A            FIG. 43B
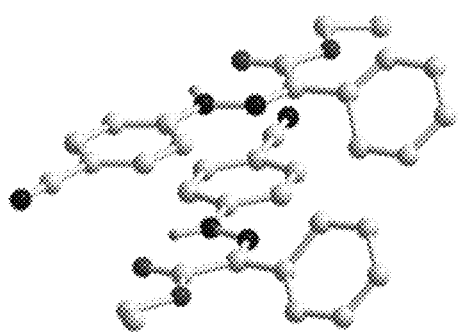
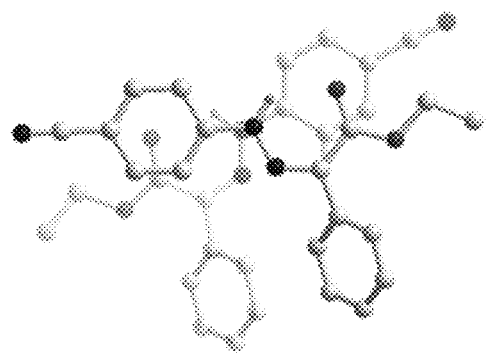
FIG. 44A            FIG. 44B
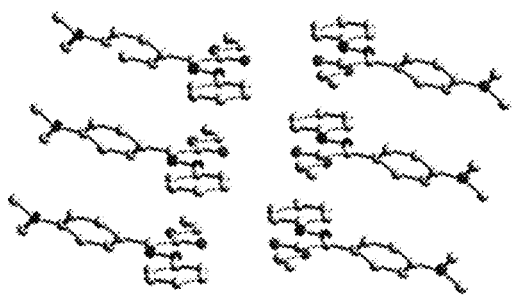
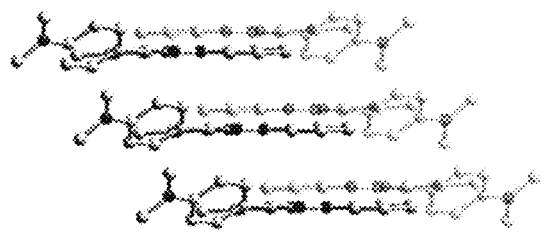
FIG. 45A            FIG. 45B

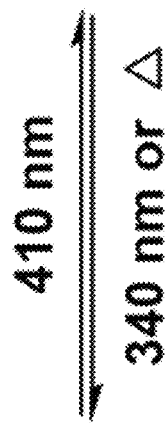
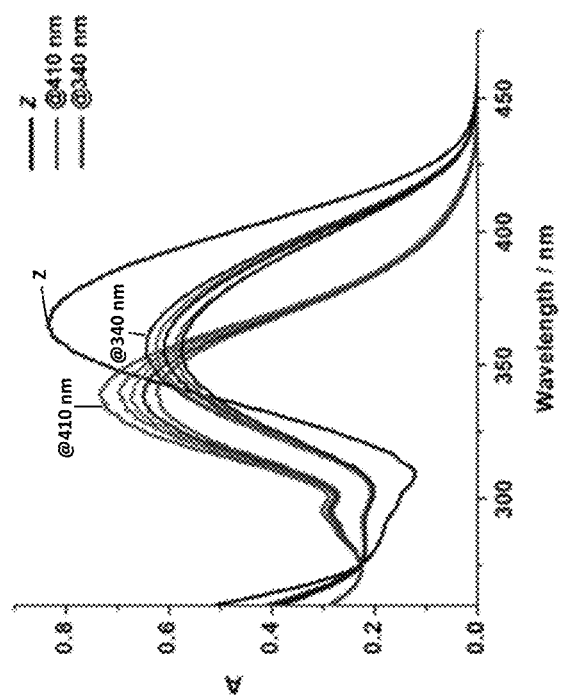
FIG. 48A
FIG. 48B

FIG. 57A  a) Initial: Z/E > 99/1

FIG. 57B  b) PSS480: Z/E = 73/27

PHOTOCHROMIC HYDRAZONE SWITCHES

CROSS-REFERENCE TO RELATED APPLICATIONS

This application is a continuation-in-part of International Patent Application No. PCT/US2017/060070, filed Nov. 4, 2017, which claims the benefit of U.S. Provisional Application No. 62/417,414, filed Nov. 4, 2016; U.S. Provisional Application No. 62/489,160, filed Apr. 24, 2017; and U.S. Provisional Application No. 62/517,887, filed Jun. 10, 2017. Each of these applications is incorporated by reference herein in its entirety.

GOVERNMENT RIGHTS

This invention was made with government support under grant no. CHE-1807428 awarded by the National Science Foundation. The government has certain rights in the invention.

BACKGROUND

Photochromism is the reversible transformation of a chemical species between two forms, e.g., between olefin cis/trans stereoisomers, by the absorption of electromagnetic radiation. Photochromic pairs are characterized as having distinct physical properties, including UV-Vis absorption spectra and/or emission spectra. As such, photochromic molecules are used as molecular switches.

Photochromic molecular switches based on the isomerization of diarylethylene have been used for more than forty years in a variety of applications, and recently, e.g., in ultrahigh density optical storage devices. However, diarylethylene compounds suffer from disadvantages of low quantum yields and photodegradation and require high energy photons for isomerization. To overcome these limitations, efforts have been made to replace diarylethylene-based materials with azobenzene-based materials. However, the most stable azobenzene compounds reported to date have a thermal half-life of only 1000 days.

Thus, there is a need in the art for photochromic molecular switches with the synthetic accessibility and modularity of azobenzenes, but also with commercially practical thermal relaxation rates.

SUMMARY OF THE INVENTION

The invention provides hydrazone compounds which are photochromic switches. Compounds herein also include those that are bistable photochromic switches. Among the compounds herein are those having very long thermal half-lives, which in specific cases are as long as 2700 years at room temperature. Compounds herein also exhibit photostability and quantum yields making them of practical use in various applications. Certain compounds herein also exhibit bistable photochromic switching in solution. Certain compounds herein exhibit solid state switching when, for example, processed into a solid layer or film. Certain compounds herein exhibit fluorescence ON/OFF switching in solution as well as in the solid state.

Accordingly, provided herein is a compound of Formula I, or a salt thereof:

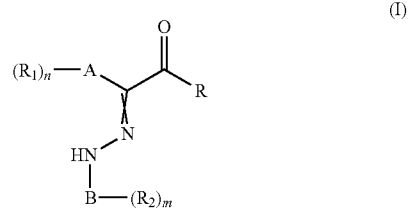
(I)

wherein

⌇ represents a double bond having either E or Z stereochemistry;

A is an aryl or heteroaryl moiety;

B is an aryl or heteroaryl moiety;

R is selected from the group consisting of hydrogen, halogen, alkyl, alkenyl, alkynyl, cycloalkyl, alkoxyalkyl, alkenone, haloalkyl, heteroalkyl, aryl, heterocyclyl, heteroaryl, OH, O—R', O—CO—R', S—H, S—R', $NH_2$, NH(R'), N(R')$_2$, NH(CO—R'), N(R')(CO—R'), NHOH, NR'OH, NR'OR', NC(R")=C(R")$_2$, and C≡C—R", where:

each R' is independently azide, alkyl, alkenyl, alkynyl, cycloalkyl, heterocyclyl, alkoxyalkyl, heteroalkyl, alkoxy, aryl, or heteroaryl, or optionally for N(R')$_2$, N(R')(CO—R'), or NR'OR', the two R' together with the atoms to which they are attached form a 5-10 member carbocyclic ring, which ring is saturated or unsaturated, which ring optionally contains one or two additional heteroatom ring members, which ring is optionally fused to a benzene ring, and which ring is optionally substituted;

each R" is independently hydrogen, alkyl, alkenyl, alkynyl, cycloalkyl, heterocyclyl, alkoxyalkyl, heteroalkyl, alkoxy, aryl, or heteroaryl, and where in the alkenyl and alkynyl groups for R' and R", the double or triple bond is not at the alpha-beta position in the alkenyl or alkynyl group;

$R_1$ and $R_2$ are independently, for each occurrence, selected from the group consisting of azide, alkyl, alkenyl, alkynyl, cycloalkyl, heterocyclyl, alkoxyalkyl, heteroalkyl, alkoxy, aryl, heteroaryl, halo, haloalkyl, alkylamino, dialkylamino, hydroxyl, nitro, cyano, carboxyl, carboxyalkyl, carboxamido, an amino acid group, OH, O—R', O—CO—R', S—H, S—R', $NH_2$, NH(R'), N(R')$_2$, NH(CO—R'), N(R')(CO—R'), NHOH, NR'OH, NR'OR', NC(R")=C(R")$_2$, and C≡C—R", where R' and R" are as defined above; or two adjacent $R_1$ together with the atom(s) to which they are attached optionally form a 5-6-member carbocyclic ring or heterocyclic ring, which ring is saturated or unsaturated, which ring is optionally substituted and which ring optionally contains 1-4 heteroatoms; or R and one of $R_2$ are optionally linked by a 3-8 carbon linker, which is optionally substituted;

n is 0, 1, 2, 3, 4 or 5; and m is 0, 1, 2, 3, 4, 5, 6 or 7.

In specific embodiment of Formula I, when n and m are both 0, at least one of A and B is not phenyl. In specific embodiments, at least one of A or B is a group other than phenyl. In specific embodiments, n+m is 4 or more. In specific embodiments, n is 2 or m is 3.

In specific embodiments, A is not pyridyl. In specific embodiment, A does not contain a ring nitrogen. In a specific embodiment, A is phenyl or naphthyl. In a specific embodiment, A is an amino, alkylamino, dialkyl amino or diphenyl amino-substituted phenyl group.

In specific embodiments, A and B are different aryl or heteroaryl groups. In specific embodiments, A and B are the same aryl or heteroaryl groups.

In specific embodiments, A and B are both substituted phenyl groups. In specific embodiments, A and B are phenyl groups substituted with different substituents. In specific embodiments, A or B is a phenyl groups substituted with a nitro group and the other of A or B is substituted with an amino, alkylamino or dialkyl amino group.

In specific embodiments, A and B group substituents are alkyl, alkoxy, amino, alkyl amino, dialkylamino, diphenylamino, nitro, cyano, or halogen.

In specific embodiments, A and B group substituents are other than hydroxyl.

In specific embodiments, compounds of Formula II are provided

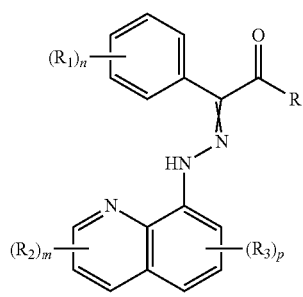

wherein

⌇ represents a double bond having either E or Z stereochemistry;

R is selected from the group consisting of hydrogen, halogen, alkyl, alkenyl, alkynyl, cycloalkyl, alkoxyalkyl, alkenone, haloalkyl, heteroalkyl, aryl, heterocyclyl, heteroaryl, OH, O—R', O—CO—R', S—H, S—R', $NH_2$, NH(R'), N(R')$_2$, NH(CO—R'), N(R')(CO—R'), NHOH, NR'OH, NR'OR', NC(R")=C(R")$_2$, and C≡C—R", where:

each R' is independently azide, alkyl, alkenyl, alkynyl, cycloalkyl, heterocyclyl, alkoxyalkyl, heteroalkyl, alkoxy, aryl, or heteroaryl, or optionally for N(R')$_2$, N(R')(CO—R'), or NR'OR', the two R' together with the atoms to which they are attached form a 5-10 member carbocyclic ring, which ring is saturated or unsaturated, which ring optionally contains one or two additional heteroatom ring members, which ring is optionally fused to a benzene ring, and which ring is optionally substituted;

each R" is independently hydrogen, alkyl, alkenyl, alkynyl, cycloalkyl, heterocyclyl, alkoxyalkyl, heteroalkyl, alkoxy, aryl, or heteroaryl, and where in the alkenyl and alkynyl groups for R' and R", the double or triple bond is not at the alpha-beta position in the alkenyl or alkynyl group;

$R_1$, $R_2$, and $R_3$ are independently, for each occurrence, selected from the group consisting of azide, alkyl, alkenyl, alkynyl, cycloalkyl, heterocyclyl, alkoxyalkyl, heteroalkyl, alkoxy, aryl, heteroaryl, halo, haloalkyl, alkylamino, dialkylamino, hydroxyl, nitro, cyano, carboxyl, carboxyalkyl, carboxamido, an amino acid group, OH, O—R', O—CO—R', S—H, S—R', $NH_2$, NH(R'), N(R')$_2$, NH(CO—R'), N(R')(CO—R'), NHOH, NR'OH, NR'OR', NC(R")=C(R")$_2$, and C≡C—R", where R' and R" are as defined above or two adjacent $R_1$ together form a 5-6-member carbocyclic ring or heterocyclic ring, which ring is saturated or unsaturated, which ring is optionally substituted and which ring optionally contains 1-4 heteroatoms;

n is 0, 1, 2, 3, 4 or 5;

m is 0, 1, 2 or 3; and p is 0, 1, 2 or 3.

In other aspects, provided herein are compositions comprising both the E and Z stereoisomers of a compound of Formula I or Formula II.

In another aspect, provided herein is a molecular switch comprising a compound of Formula I or Formula II herein. In an embodiment, the molecular switch comprises both the E and Z stereoisomers of the compound.

In a specific embodiment, the molecular switch comprises one or more compounds selected from the compounds of Table 1 (below). In an embodiment, the molecular switch comprises one or more compounds selected from the compounds of Table 2 (below) or the corresponding E or Z stereoisomers thereof.

In another aspect is provided a method of optically switching a compound of Formula I, or a salt thereof, or a material or composition comprising the compound of Formula I or a salt thereof. In an embodiment is provided a method of optically switching a compound of Formula II, or a salt thereof, or a material or composition comprising the compound of Formula II or a salt thereof.

The method of optically switching comprising irradiating said compound, material, or composition thereby isomerizing the compound from the E stereoisomer to the Z stereoisomer, or isomerizing the compound from the Z stereoisomer to the E stereoisomer. In an embodiment, the compound or material that is irradiated is in solution or in suspension in a solvent. In an embodiment, the compound or material that is irradiated is in the bulk solid state. In an embodiment, the compound or material that is irradiated is in the form of a powder. In an embodiment, the compound or material that is irradiated is in the form of a film formed on a substrate. In an embodiment, the compound or material that is irradiated is in the form of a film spun onto a substrate. In an embodiment, the compound or material that is irradiated is in the form of a film drop cast onto a substrate. In an embodiment, the compound or material that is irradiated is in a crystalline form. In an embodiment, the compound or material that is irradiated is in an amorphous form. In an embodiment, isomerizing the compound results in a change in absorption wavelength or intensity. In an embodiment, isomerizing the compound results in a change in fluorescence wavelength or intensity. In an embodiment, isomerizing the compound results in a change emission wavelength or intensity.

In an embodiment, switching the compound from a first isomeric configuration to a second isomeric configuration functions to actuate an electrical or mechanical switch. In an embodiment, switching the compound from a first isomeric configuration to a second isomeric configuration functions to start or stop a chemical reaction.

In an embodiment of the method employing a compound of Formula I, R is CO—R'. In an embodiment of the method employing a compound of Formula I, A is phenyl or pyridine-2-yl. In an embodiment of the method employing a compound of Formula I, $R_1$-A is 4-dialkylaminophenyl. In an embodiment of the method employing a compound of Formula I, $R_1$-A is 4-dimethylaminophenyl. In an embodiment of the method employing a compound of Formula I, A is naphth-2-yl. In an embodiment of the method employing a compound of Formula I, A is thien-2-yl or ($R_1$-A) is 5(piperidin-1-yl)thien-2-yl. In an embodiment of the method employing a compound of Formula I, A is naphtha-1-yl. In an embodiment of the method employing a compound of Formula I, A is 4-hydroxyphenyl. In an embodiment of the method employing a compound of Formula I, A is indoyl and more specifically is indo-2-yl. In an embodiment of the method employing a compound of Formula I, A is benzothienyl and more specifically is benzothien-2-yl. In an embodiment of the method employing a compound of Formula I, A is indenyl (also 1H-indenyl) and more specifically is inden-2-yl (also 1H inden-2-yl). In an embodiment of the method employing a compound of Formula I, $R_1$-A is 6-dialkylaminonaphth-2-yl.

Other aspect and embodiments of the invention will be evident to one of ordinary skill in the art in view of the art.

BRIEF DESCRIPTION OF THE FIGURES

FIG. 11 illustrates switchable fluorescence of a hydrazone compound in serum (10% FBS).

FIG. 12 illustrates structures of additional exemplary compounds of the invention.

FIG. 14A is a UV/Vis spectrum, taken at 15 min intervals for 2 hours, of the hydrazone switch in the presence of 1000 equiv. GSH in PBS buffer (50% MeCN, pH=7.4); FIG. 14B illustrates the switching of the hydrazone from Z to E monitored using UV/Vis spectroscopy.

FIG. 43A illustrates the crystal packing of two molecules of 2. The inserted two green planes encompass the hydrazone backbones and distance of 3.232 Å is measured between them; FIG. 43B illustrates the vertical view of the packing mode in 2 (C—H protons are omitted for clarity).

FIG. 44A illustrates the packing between two molecules of 3 in the crystal structure; FIG. 44B illustrates the vertical view of the packing in 3 (C—H protons are omitted for clarity).

FIG. 45A and FIG. 45B illustrate the herringbone packing in 19 (C—H atoms are omitted for clarity).

FIG. 48A illustrates the photo-induced isomerization of hydrazone 10; FIG. 48B illustrates UV-Vis spectra of a drop-casted film of hydrazone 10, and the absorption changes upon alternating irradiation with 410 and 340 nm light.

DETAILED DESCRIPTION OF THE INVENTION

Photochromic Compounds of the Invention

Figure 1A:
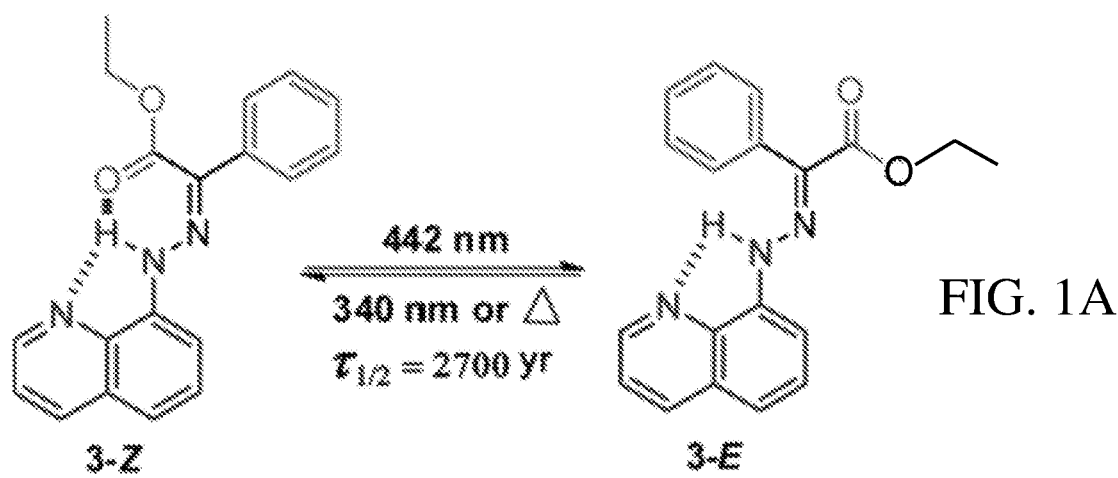
FIGS. 1A-1C illustrate: light induced Z/E isomerization of hydrazone 14 (FIG. 1A); UV-vis spectra (1.0×10-5 M) of 14-E (colorless) and 14-Z (yellow) isomers in toluene (FIG. 1B); and isomerization cycles of 14 in toluene upon alternating irradiation using 442 and 340 nm light sources (FIG. 1C). The absorbance change at λmax=398 nm (3-Z) was monitored.

Provided herein are compounds for use as photochromic molecular switches, i.e., "compounds of the invention." Compounds of the invention are useful, for example, as photochromic optical memory devices which are based on a photochemical (or photon-mode) recording method, which differs from the heat-mode recording employed in current optical media. The photon-mode recording has various advantages over the heat-mode recording in terms of resolution, speed of writing, and multiplex recording, such as wavelength, polarization, and phase. Compounds of the invention comprise hydrazone moieties, which are advantageous in terms of synthetic accessibility, high thermal stability and high isomerization rates.

Accordingly, provided herein is a compound of Formula I, or a salt thereof:

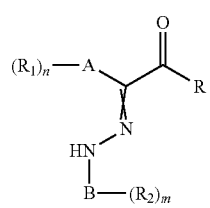

(I)

wherein

⚹ represents a double bond having either E or Z stereochemistry;

A is an aryl or heteroaryl moiety;
B is an aryl or heteroaryl moiety;

R is selected from the group consisting of hydrogen, halogen, alkyl, alkenyl, alkynyl, cycloalkyl, alkoxyalkyl, alkenone, haloalkyl, heteroalkyl, aryl, heterocyclyl, heteroaryl, OH, O—R', O—CO—R', S—H, S—R', $NH_2$, NH(R'), N(R')$_2$, NH(CO—R'), N(R')(CO—R'), NHOH, NR'OH, NR'OR', NC(R")=C(R")$_2$, and C≡C—R", where:

each R' is independently azide, alkyl, alkenyl, alkynyl, cycloalkyl, heterocyclyl, alkoxyalkyl, heteroalkyl, alkoxy, aryl, or heteroaryl, or optionally for N(R')$_2$, N(R')(CO—R'), or NR'OR', the two R' together with the atoms to which they are attached form a 5-10 member carbocyclic ring, which ring is saturated or unsaturated, which ring optionally contains one or two additional heteroatom ring members, which ring is optionally fused to a benzene ring, and which ring is optionally substituted;

each R" is independently hydrogen, alkyl, alkenyl, alkynyl, cycloalkyl, heterocyclyl, alkoxyalkyl, heteroalkyl, alkoxy, aryl, or heteroaryl, and where in the alkenyl and alkynyl groups for R' and R", the double or triple bond is not at the alpha-beta position in the alkenyl or alkynyl group;

$R_1$ and $R_2$ are independently, for each occurrence, selected from the group consisting of azide, alkyl, alkenyl, alkynyl, cycloalkyl, heterocyclyl, alkoxyalkyl, heteroalkyl, alkoxy, aryl, heteroaryl, halo, haloalkyl, alkylamino, dialkylamino, hydroxyl, nitro, cyano, carboxyl, carboxyalkyl, carboxamido, an amino acid group, OH, O—R', O—CO—R', S—H, S—R', $NH_2$, NH(R'), N(R')$_2$, NH(CO—R'), N(R')(CO—R'), NHOH, NR'OH, NR'OR', NC(R")=C(R")$_2$, and C≡C—R", where R' and R" are as defined above; or two adjacent $R_1$ together with the atom(s) to which they are attached optionally form a 5-6-member carbocyclic ring or heterocyclic ring, which ring is saturated or unsaturated, which ring is optionally substituted and which ring optionally contains 1-4 heteroatoms; or R and one of $R_2$ are optionally linked by a 3-8 carbon linker, which is optionally substituted;

n is 0, 1, 2, 3, 4 or 5; and
m is 0, 1, 2, 3, 4, 5, 6 or 7.

In specific embodiment of Formula I, when n and m are both 0, at least one of A and B is not phenyl. In specific embodiments, at least one of A or B is a group other than phenyl. In specific embodiments, n+m is 4 or more. In specific embodiments, n is 2 or m is 3.

In specific embodiments, A is not pyridyl. In specific embodiment, A does not contain a ring nitrogen. In a specific embodiment, A is phenyl or naphthyl. In a specific embodiment, A is an amino, alkylamino, dialkyl amino or diphenyl amino-substituted phenyl group.

In specific embodiments, A and B are different aryl or heteroaryl groups. In specific embodiments, A and B are the same aryl or heteroaryl groups.

In specific embodiments, A and B are both substituted phenyl groups. In specific embodiments, A and B are phenyl groups substituted with different substituents. In specific embodiments, A or B is a phenyl groups substituted with a nitro group and the other of A or B is substituted with an amino, alkylamino or dialkyl amino group.

In specific embodiments, A and B group substituents are alkyl, alkoxy, amino, alkyl amino, dialkylamino, diphenylamino, nitro, cyano, or halogen.

In specific embodiments, A and B group substituents are other than hydroxyl.

In an embodiment of Formula I, R is CO—R'. In an embodiment of Formula I, A is phenyl or pyridine-2-yl. In an embodiment of Formula I, $R_1$-A is 4-dialkylaminophenyl. In an embodiment of Formula I, $R_1$-A is 4-dimethylaminophenyl. In an embodiment of Formula I, A is naphth-2-yl. In an embodiment of Formula I, A is thien-2-yl or ($R_1$-A) is 5(piperidin-1-yl)thien-2-yl. In an embodiment of Formula I, A is naphtha-1-yl. In an embodiment of Formula I, A is 4-hydroxyphenyl. In an embodiment of Formula I, A is indolyl and more specifically is indo-2-yl. In an embodiment of Formula I, A is benzothienyl and more specifically is benzothien-2-yl. In an embodiment of Formula I, A is indenyl (also 1H-indenyl) and more specifically is inden-2-yl (also 1H inden-2-yl). In an embodiment of Formula I, $R_1$-A is 6-dialkylaminonaphth-2-yl.

In an embodiment of Formula I, B is phenyl or pyridine-2-yl. In an embodiment of Formula I, B is bipyridyl, benzoquinolyl, or phenylbenzothiazolyl. In an embodiment of Formula I, B is a 2,2'-bipyridyl, a 4, 4'-bipyridyl or a 2, 4'-bipyridyl. In an embodiment, B is a 7,8-benzoquinol-3-yl or a 5,6-benzoquinol-3-yl. In an embodiment, B is a 7,8-benzoquinolyl or a 5,6-benzoquinol-7-yl. In an embodiment, B is a 2-phenylbenzothiazolyl. In an embodiment of Formula I, B is quinolin-2-yl, quinolin-8-yl, naphth-2-yl, naphtha-1-yl, or naphth-8-yl.

In an embodiment of Formula I, R is OR'. In an embodiment of Formula I, R' is an alkenyl having 2-20 carbon atoms. In an embodiment of Formula I, R' is an alkene having 6-20 carbon atoms. In an embodiment of Formula I, R' is an alkene having 8-20 carbon atoms. In an embodiment of Formula I, R' is an alkene having an omega double bond distal from the bond to the rest of the molecule. In an embodiment of Formula I, R' is an alkoxyalkyl group having from 2 to 20 carbon atoms and 1, 2, 3 or 4 oxygen atoms. In an embodiment of Formula I, R' is an alkenone group having from 3 to 20 carbon atoms or 5 to 20 carbon atoms.

In an embodiment of Formula I, R' is an alkenyl group having 2-20 carbon atoms and one of $R_2$ is a —CO—O—$R_5$ group where $R_5$ is an alkenyl group having 2-20 carbon atoms. In an embodiment of Formula I, R' and $R_5$ are the same alkenyl group.

In an embodiment of Formula I, R' is an alkenone group having 3-20 carbon atoms and one of $R_2$ is a —CO—O—$R_5$ group where $R_5$ is an alkenone group having 3-20 carbon atoms. In an embodiment of Formula I, R' and $R_5$ are the same alkenone group.

In an embodiment of Formula I, R' is an alkoxyalkyl group having 2-20 carbon atoms and 1-4 oxygen atoms and one of $R_2$ is a —CO—O—$R_5$ group where $R_5$ is an alkoxyalkyl group having 2-20 carbon atoms. In an embodiment of Formula I, R' and $R_5$ are the same alkoxyalkyl group.

In an embodiment of Formula I, R is selected from the group consisting of hydrogen, halogen, alkyl, alkenyl, alkynyl, cycloalkyl, alkoxyalkyl, alkenone, heteroalkyl, aryl, heteroaryl, OH, O—R', O—CO—R', S—H, S—R', $NH_2$, NH(R'), N(R')$_2$, NH(CO—R'), N(R')(CO—R'), NHOH, NR'OH, NR'OR', NC(R'')=C(R'')$_2$, and C≡C—R'', where each R' is independently azide, alkyl, alkenyl, alkynyl, cycloalkyl, heterocyclyl, alkoxyalkyl, heteroalkyl, alkoxy, aryl, or heteroaryl and where each R'' is independently hydrogen, alkyl, alkenyl, alkynyl, cycloalkyl, heterocyclyl, alkoxyalkyl, heteroalkyl, alkoxy, aryl, or heteroaryl.

In an embodiment of Formula I, for the R group, each R' is hydrogen, alkyl, aryl, heteroaryl or heterocyclyl. In an embodiment of Formula I for the R group, each R' is hydrogen, alkyl, alkenyl, alkynyl or phenyl. In an embodiment of Formula I for the R group, each R' is hydrogen, alkyl or phenyl.

In an embodiment of Formula I, R is alkyl, alkenyl, alkynyl, cycloalkyl, alkoxy, amino, alkylamino, or dialkylamino. In an embodiment of Formula I, R is alkoxy. In an embodiment of Formula I, R is $C_{1-6}$ alkoxy. In an embodiment of Formula I, R is $C_{1-3}$ alkoxy.

In an embodiment of Formula I, R is a 5-6 member heterocyclyl ring which is saturated or unsaturated having one to four ring heteroatoms, preferably selected from N, O or S. In an embodiment, R is 4-morpholinyl, 1-piperdinyl, 1-piperazinyl, 1-pyrrolyl, 1-pyrrolidyl, 1-imidazoyl, 1-pyrazolyl, 1-indolyl, 1-benzimidazolyl, oxazolyl, 2-oxazoyl, thiazolyl, or 2-thiazolyl.

In an embodiment of Formula I, $R_1$ is selected from the group consisting of hydrogen, halogen, alkyl, alkenyl, alkynyl, cycloalkyl, alkoxyalkyl, alkenone, heteroalkyl, aryl, heteroaryl OH, O—R', O—CO—R', S—H, S—R', $NH_2$, NH(R'), N(R')$_2$, NH(CO—R'), N(R')(CO—R'), NHOH, NR'OH, NR'OR', NC(R'')=C(R'')$_2$, and C≡C—R'', where each R' is independently azide, alkyl, alkenyl, alkynyl, cycloalkyl, heterocyclyl, alkoxyalkyl, heteroalkyl, alkoxy, aryl, or heteroaryl and where each R'' is independently hydrogen, alkyl, alkenyl, alkynyl, cycloalkyl, heterocyclyl, alkoxyalkyl, heteroalkyl, alkoxy, aryl, or heteroaryl.

In an embodiment of Formula I for $R_1$, each R' is hydrogen, alkyl, aryl, heteroaryl or heterocyclyl. In an embodiment of Formula I for $R_1$, each R' is hydrogen, alkyl, alkenyl, alkynyl or phenyl. In an embodiment of Formula I for $R_1$, each R' is hydrogen, alkyl or phenyl.

In an embodiment of Formula I, $R_1$ is alkyl, alkenyl, alkynyl, cycloalkyl, alkoxy, amino, alkylamino, or dialkylamino.

In an embodiment of Formula I, $R_1$ is a 5-12 member heterocyclyl ring which is saturated or unsaturated having one to four ring heteroatoms, preferably selected from N, O or S. In an embodiment, R is 4-morpholinyl, 1-piperdinyl, 1-piperazinyl, 1-pyrrolyl, 1-pyrrolidyl, 1-imidazoyl, 1-pyrazolyl, 1-indolyl, 1-benzimidazolyl, oxazolyl, 2-oxazoyl, thiazolyl, or 2-thiazolyl.

In embodiments of Formula I, $R_1$ is morpholinyl, piperidinyl, piperazinyl, pyrrolyl, pyrrolidinyl, pyrazolyl, benzimidazolyl, oxazolyl, indolyl, thiazolyl, or hexamethylenetetraminyl. In embodiments of Formula I, $R_1$ is one of 4-morpholinyl, 1-piperidinyl, 1-piperazinyl, 1-pyrrolyl, 1-pyrrolidinyl, 1-pyrazolyl, 1-benzimidazolyl, 1-indolyl, 1-imidazolyl, 2-imidazolyl, 3-imidazolyl, hexamethylenetetraminyl, 2-benzimidazolyl, 2-indolyl, 2-oxazolyl, 2-thiazolyl, 3-pyrazolyl, 4-piperidinyl, 2-pyrrolidinyl, 3-pyrrolidinyl, 2-pyrrolyl, 3-pyrrolyl, 2-pyrazolyl, or 3-pyrazolyl.

In embodiments of Formula I, $R_1$ is dimethylamino, diethylamino, or diphenylamino. In embodiments of Formula I, $R_1$ is 4-dimethyl amino, 4-diethylamino or 4-diphenylamino.

In embodiments of Formula I, $R_1$ is an amino acid of formula: —$NH_2$—$CR_{AC}$—COOH or a salt thereof, where $R_{AC}$ is hydrogen, a unsubstituted or substituted straight-chain or branched alkyl group, a 5 or 6-member cycloalkyl group, a 5-6 member heterocyclyl group, an unsubstituted or substituted phenyl group, an unsubstituted or substituted benzyl group, an unsubstituted or substituted heteroaryl group or an unsubstituted or substituted heterocycyl. In specific embodiments, $R_{AC}$ groups are substituted with one hydroxyl, amino, alkyl amino or dialkylamino (or protonated versions thereof), —SH, —S-alkyl, —CO—$NH_2$, —NH—C($NH_2$)=$NH_2$, -4-imidazoyl, —SeH, 2-pyrrolidinyl, benzyl, 4-hydroxybenzyl, or indolyl, including 3-indolyl. In specific embodiments, —$NH_2$—$CR_{AC}$—COOH is an L-amino acid group. In specific embodiments, —$NH_2$—

CR$_{AC}$—COOH is a D-amino acid group. In specific embodiments, R$_{AC}$ is a side chain of an amino acid selected from arginine, histidine, lysine, aspartic acid, glutamic acid, serine, threonine, asparagine, glutamine, cysteine, selenocysteine, proline, alanine, valine, isoleucine, leucine, methionine, phenylalanine, tyrosine, or tryptophan. In additional embodiments, the amino acid groups is a carnitine group, a hydroxyproline group, ornithine group or citrulline group.

In embodiments of Formula I, R is different from R$_1$. In embodiments of Formula I, R is the same as R$_1$.

In an embodiment provided herein is a compound of Formula II, or a salt thereof:

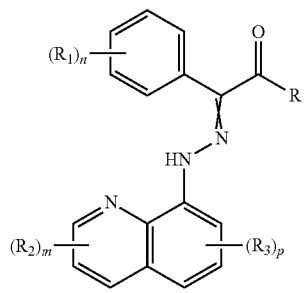

(II)

wherein

⌇ represents a double bond having either E or Z stereochemistry;

R is selected from the group consisting of hydrogen, halogen, alkyl, alkenyl, alkynyl, cycloalkyl, alkoxyalkyl, alkenone, haloalkyl, heteroalkyl, aryl, heterocyclyl, heteroaryl, OH, O—R', O—CO—R', S—H, S—R', NH$_2$, NH(R'), N(R')$_2$, NH(CO—R'), N(R')(CO—R'), NHOH, NR'OH, NR'OR', NC(R")=C(R")$_2$, and C≡C—R",
where:
each R' is independently azide, alkyl, alkenyl, alkynyl, cycloalkyl, heterocyclyl, alkoxyalkyl, heteroalkyl, alkoxy, aryl, or heteroaryl, or optionally for N(R')$_2$, N(R')(CO—R'), or NR'OR', the two R' together with the atoms to which they are attached form a 5-10 member carbocyclic ring, which ring is saturated or unsaturated, which ring optionally contains one or two additional heteroatom ring members, which ring is optionally fused to a benzene ring, and which ring is optionally substituted;
each R" is independently hydrogen, alkyl, alkenyl, alkynyl, cycloalkyl, heterocyclyl, alkoxyalkyl, heteroalkyl, alkoxy, aryl, or heteroaryl, and
where in the alkenyl and alkynyl groups for R' and R", the double or triple bond is not at the alpha-beta position in the alkenyl or alkynyl group;

R$_1$, R$_2$, and R$_3$ are independently, for each occurrence, selected from the group consisting of azide, alkyl, alkenyl, alkynyl, cycloalkyl, heterocyclyl, alkoxyalkyl, heteroalkyl, alkoxy, aryl, heteroaryl, halo, haloalkyl, alkylamino, dialkylamino, hydroxyl, nitro, cyano, carboxyl, carboxyalkyl, carboxamido, an amino acid group, OH, O—R', O—CO—R', S—H, S—R', NH$_2$, NH(R'), N(R')$_2$, NH(CO—R'), N(R')(CO—R'), NHOH, NR'OH, NR'OR', NC(R")=C(R")$_2$, and C≡C—R", where R' and R" are as defined above or
two adjacent R$_1$ together form a 5-6-member carbocyclic ring or heterocyclic ring, which ring is saturated or unsaturated, which ring is optionally substituted and which ring optionally contains 1-4 heteroatoms;
n is 0, 1, 2, 3, 4 or 5;
m is 0, 1, 2 or 3; and
p is 0, 1, 2 or 3.

In an embodiment of Formula II, R is selected from the group consisting of hydrogen, halogen, alkyl, alkenyl, alkynyl, cycloalkyl, alkoxyalkyl, alkenone, heteroalkyl, aryl, heteroaryl, OH, O—R', O—CO—R', S—H, S—R', NH$_2$, NH(R'), N(R')$_2$, NH(CO—R'), N(R')(CO—R'), NHOH, NR'OH, NR'OR', NC(R")=C(R")$_2$, and C≡C—R", where each R' is independently azide, alkyl, alkenyl, alkynyl, cycloalkyl, heterocyclyl, alkoxyalkyl, heteroalkyl, alkoxy, aryl, or heteroaryl and where each R" is independently hydrogen, alkyl, alkenyl, alkynyl, cycloalkyl, heterocyclyl, alkoxyalkyl, heteroalkyl, alkoxy, aryl, or heteroaryl.

In an embodiment of Formula II, for the R group, each R' is hydrogen, alkyl, aryl, heteroaryl or heterocyclyl. In an embodiment of Formula I for the R group, each R' is hydrogen, alkyl, alkenyl, alkynyl or phenyl. In an embodiment of Formula I for the R group, each R' is hydrogen, alkyl or phenyl.

In an embodiment of Formula II, R is alkyl, alkenyl, alkynyl, cycloalkyl, alkoxy, amino, alkylamino, or dialkylamino. In an embodiment of Formula I, R is alkoxy. In an embodiment of Formula I, R is C$_{1-6}$ alkoxy. In an embodiment of Formula I, R is C$_{1-3}$ alkoxy.

In an embodiment of Formula II, R is a 5-6 member heterocyclyl ring which is saturated or unsaturated having one to four ring heteroatoms, preferably selected from N, O or S. In an embodiment, R is 4-morpholinyl, 1-piperdinyl, 1-piperazinyl, 1-pyrrolyl, 1-pyrrolidyl, 1-imidazoyl, 1-pyrazolyl, 1-indolyl, 1-benzimidazolyl, oxazolyl, 2-oxazoyl, thiazolyl, or 2-thiazolyl.

In an embodiment of Formula II, R$_1$ is selected from the group consisting of hydrogen, halogen, alkyl, alkenyl, alkynyl, cycloalkyl, alkoxyalkyl, alkenone, heteroalkyl, aryl, heteroaryl OH, O—R', O—CO—R', S—H, S—R', NH$_2$, NH(R'), N(R')$_2$, NH(CO—R'), N(R')(CO—R'), NHOH, NR'OH, NR'OR', NC(R")=C(R")$_2$, and C≡C—R", where each R' is independently azide, alkyl, alkenyl, alkynyl, cycloalkyl, heterocyclyl, alkoxyalkyl, heteroalkyl, alkoxy, aryl, or heteroaryl and where each R" is independently hydrogen, alkyl, alkenyl, alkynyl, cycloalkyl, heterocyclyl, alkoxyalkyl, heteroalkyl, alkoxy, aryl, or heteroaryl.

In an embodiment of Formula II for R$_1$, each R' is hydrogen, alkyl, aryl, heteroaryl or heterocyclyl. In an embodiment of Formula I for R$_1$, each R' is hydrogen, alkyl, alkenyl, alkynyl or phenyl. In an embodiment of Formula II for R$_1$, each R' is hydrogen, alkyl or phenyl.

In an embodiment of Formula II, R$_1$ is alkyl, alkenyl, alkynyl, cycloalkyl, alkoxy, amino, alkylamino, or dialkylamino.

In an embodiment of Formula II, R$_1$ is a 5-12 member heterocyclyl ring which is saturated or unsaturated having one to four ring heteroatoms, preferably selected from N, O or S. In an embodiment, R is 4-morpholinyl, 1-piperdinyl, 1-piperazinyl, 1-pyrrolyl, 1-pyrrolidyl, 1-imidazoyl, 1-pyrazolyl, 1-indolyl, 1-benzimidazolyl, oxazolyl, 2-oxazoyl, thiazolyl, or 2-thiazolyl.

In embodiments of Formula II, R$_1$ is morpholinyl, piperidinyl, piperazinyl, pyrrolyl, pyrrolidinyl, pyrazolyl, benzimidazolyl, oxazolyl, indolyl, thiazolyl, or hexamethylenetetraminyl. In embodiments of Formula II, R$_1$ is one of 4-morpholinyl, 1-piperidinyl, 1-piperazinyl, 1-pyrrolyl, 1-pyrrolidinyl, 1-pyrazolyl, 1-benzimidazolyl, 1-indolyl, 1-imidazolyl, 2-imidazolyl, 3-imidazolyl, hexamethylenetetraminyl, 2-benzimidazolyl, 2-indolyl, 2-oxazolyl, 2-thiazolyl, 3-pyrazolyl, 4-piperidinyl, 2-pyrrolidinyl, 3-pyrrolidinyl, 2-pyrrolyl, 3-pyrrolyl, 2-pyrazolyl, or 3-pyrazolyl.

In embodiments of Formula II, $R_1$ is dimethylamino, diethylamino, or diphenylamino. In embodiments of Formula II, $R_1$ is 4-dimethyl amino, 4-diethylamino or 4-diphenylamino.

In embodiments of Formula II, $R_1$ is an amino acid of formula: —$NH_2$—$CR_{AC}$—COOH or a salt thereof, where $R_{AC}$ is hydrogen, a unsubstituted or substituted straight-chain or branched alkyl group, a 5 or 6-member cycloalkyl group, a 5-6 member heterocyclyl group, an unsubstituted or substituted phenyl group, an unsubstituted or substituted benzyl group, an unsubstituted or substituted heteroaryl group or an unsubstituted or substituted heterocycyl. In specific embodiments, $R_{AC}$ groups are substituted with one hydroxyl, amino, alkyl amino or dialkylamino (or protonated versions thereof), —SH, —S-alkyl, —CO—$NH_2$, —NH—$C(NH_2)$=$NH_2$, -4-imidazoyl, —SeH, 2-pyrrolidinyl, benzyl, 4-hydroxybenzyl, or indolyl, including 3-indolyl. In specific embodiments, —$NH_2$—$CR_{AC}$—COOH is an L-amino acid group. In specific embodiments, —$NH_2$—$CR_{AC}$—COOH is a D-amino acid group. In specific embodiments, $R_{AC}$ is a side chain of an amino acid selected from arginine, histidine, lysine, aspartic acid, glutamic acid, serine, threonine, asparagine, glutamine, cysteine, selenocysteine, proline, alanine, valine, isoleucine, leucine, methionine, phenylalanine, tyrosine, or tryptophan. In additional embodiments, the amino acid groups is a carnitine group, a hydroxyproline group, ornithine group or citrulline group.

In embodiments of Formula II, R is different from $R_1$. In embodiments of Formula I, R is the same as $R_1$.

In embodiments of Formula II:
n, m and p are each 0;
n, m or p are 1;
n and m are both 1;
n and p are both 1;
R is OR' and R' is $C_{1-6}$ alkyl;
R is OR' and R' is ethyl;
n, m and p are each 0, R is OR' and R' is R is $C_{1-6}$ alkyl;
R is $C_{1-12}$ alkyl;
R is $C_{1-6}$ alkyl;
R is $C_{1-3}$ alkyl;
n is 1 and $R_1$ is dialkylamino;
n is 1 and $R_1$ is dimethylamino;
n is 1 and $R_1$ is diphenylamino;
n is 1 and $R_1$ is 1-morpholinyl;
n is 1 and $R_1$ is 1-piperidinyl;
n is 1 and $R_1$ is 1-pyrrolidinyl;
n is 1 and $R_1$ is 1-indoyl;
n is 1 and $R_1$ is —$NH_2$—$CR_{AC}$—COOH or a salt thereof;
n is 1 and $R_1$ is an L-amino acid of formula —$NH_2$—$CR_{AC}$—COOH or a salt thereof;
n is 1 and $R_1$ is an D-amino acid of formula —$NH_2$—$CR_{AC}$—COOH or a salt thereof;
n is 1 and $R_1$ is 1-imidazoyl;
n is 1 and $R_1$ is 1-pyrrolyl;
n is 1 and $R_1$ is 1-piperazinyl;
n is 1 and $R_1$ is 1-benzimidazolyl;
n is 1 and $R_1$ is 1-pyrazoyl;
n is 1 and $R_1$ is oxazoyl;
n is 1 and $R_1$ is 2-oxazoyl;
n is 1 and $R_1$ is thiazoyl;
n is 1 and $R_1$ is $_2$.thiazoyl;
at least one $R_1$ is a 4-dialkylamino group;
at least one $R_1$, $R_2$ or $R_3$ is azide;
$R_1$ is azide;
$R_2$ is azide;
$R_3$ is azide;
n is 1 and $R_1$ is a 4-dialkylamino group; and/or
n is 1 and $R_1$ is a 4-dimethylamino group.

In other aspects, provided herein are compositions comprising both the E and Z stereoisomers of a compound of Formula I or Formula II.

In another aspect, provided herein is a molecular switch comprising a compound of Formula I or Formula II herein. In an embodiment, the molecular switch comprises both the E and Z stereoisomers of the compound.

In a specific embodiment, the molecular switch comprises one or more compounds selected from the compounds of Table 1 (below). In an embodiment, the molecular switch comprises one or more compounds selected from the compounds of Table 2 (below) or the corresponding E or Z stereoisomers thereof.

TABLE 1

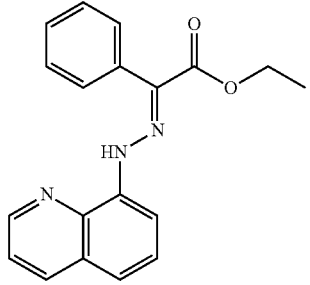 [SMILES: CCOC(=O)/C(=N/Nc1cccc2cccnc12)c1ccccc1]

PhQ-E (QPhH-E)

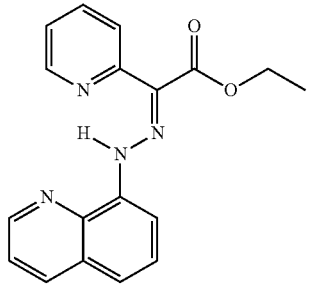 [SMILES: CCOC(=O)/C(=N/Nc1cccc2cccnc12)c1ccccn1]

QPH-E

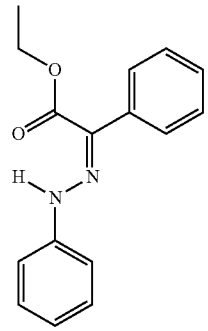 [SMILES: CCOC(=O)/C(=N\Nc1ccccc1)c1ccccc1]

1PhHzH-Z

TABLE 1-continued
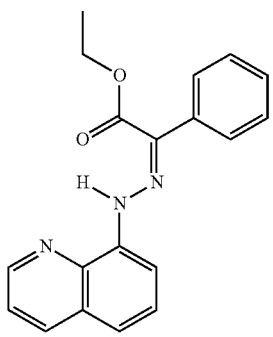 [SMILES: CCOC(=O)/C(=N\Nc1cccc2cccnc12)c1ccccc1]
PhQ-Z (QPhH-Z)
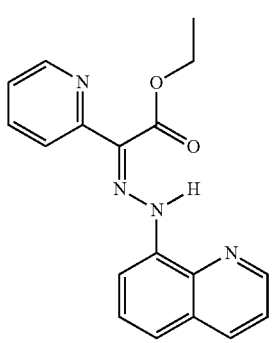 [SMILES: CCOC(=O)/C(=N\Nc1cccc2cccnc12)c1ccccn1]
QPH-Z
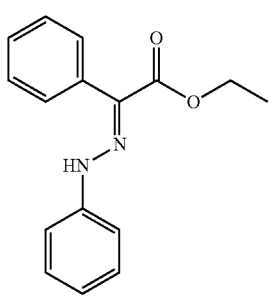 [SMILES: CCOC(=O)/C(=N/Nc1ccccc1)c1ccccc1]
1PhHzH-E
TABLE 2
Exemplary Compounds of the Invention
| Structure Number | Structure |
|---|---|
| 1<br>Z-isomer | 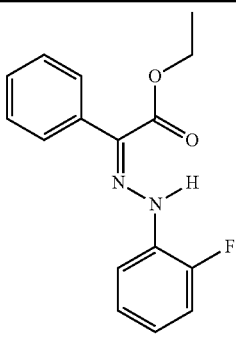 |
TABLE 2-continued
Exemplary Compounds of the Invention
| Structure Number | Structure |
|---|---|
| 2<br>Z-isomer | 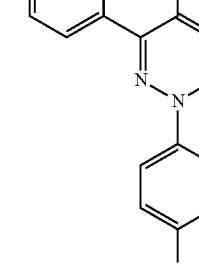 |
| 3<br>Z-isomer | 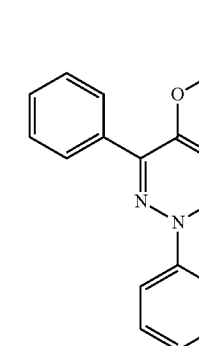 |
| 4<br>Z-isomer | 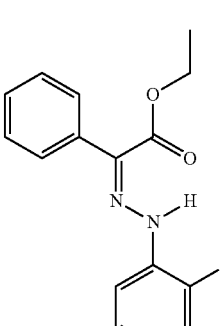 |
| 5<br>Z-isomer | 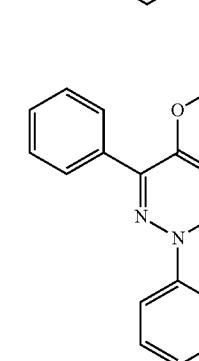 |

TABLE 2-continued

Exemplary Compounds of the Invention

| Structure Number | Structure |
|---|---|
| 6<br>Z-isomer | ethyl 2-phenyl-2-(2-(2,4-dimethoxyphenyl)hydrazinyl)acetate |
| 7<br>Z-isomer | ethyl 2-phenyl-2-(2-(4-carboxyphenyl)hydrazinyl)acetate |
| 8<br>Z-isomer | ethyl 2-phenyl-2-(2-(3-carboxyphenyl)hydrazinyl)acetate |
| 9<br>Z-isomer | ethyl 2-phenyl-2-(2-(2-carboxyphenyl)hydrazinyl)acetate |
| 10<br>Z-isomer | ethyl 2-phenyl-2-(2-phenylhydrazinyl)acetate |
| 11<br>E-isomer | ethyl 2-(thiophen-2-yl)-2-(2-(4-nitrophenyl)hydrazinyl)acetate |
| 12<br>Z-isomer | ethyl 2-(6-(dimethylamino)naphthalen-2-yl)-2-(2-(4-nitrophenyl)hydrazinyl)acetate |
| 13<br>Z-isomer | ethyl 2-phenyl-2-(2-(naphthalen-1-yl)hydrazinyl)acetate |

TABLE 2-continued
Exemplary Compounds of the Invention
| Structure Number | Structure |
|---|---|
| 14 Z-isomer | 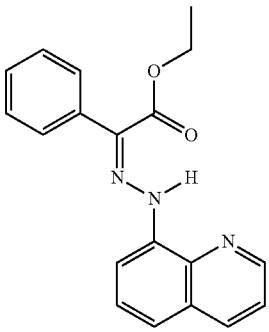 [SMILES: CCOC(=O)/C(=N\Nc1cccc2cccnc12)c1ccccc1] |
| 15 Z-isomer | 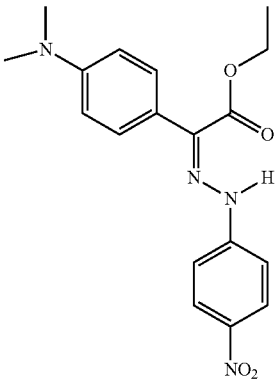 [SMILES: CCOC(=O)/C(=N\Nc1ccc([N+](=O)[O-])cc1)c1ccc(N(C)C)cc1] |
| 16 Z-isomer | 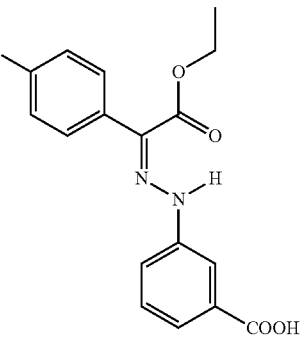 |
| 17 Z-isomer | 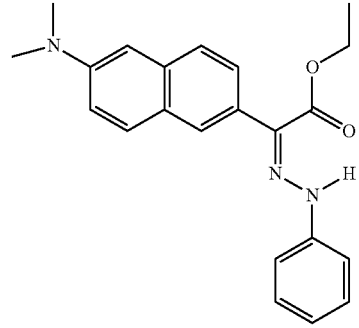 [SMILES: CCOC(=O)/C(=N\Nc1ccccc1)c1ccc2cc(N(C)C)ccc2c1] |
| 18 E-isomer | 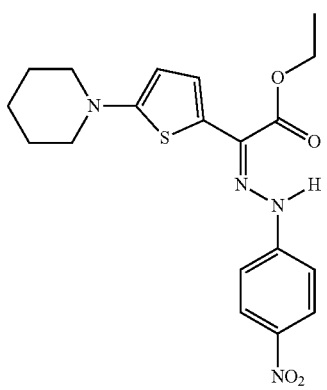 [SMILES: CCOC(=O)/C(=N\Nc1ccc([N+](=O)[O-])cc1)c1ccc(N2CCCCC2)s1] |
| 19 Z-isomer | 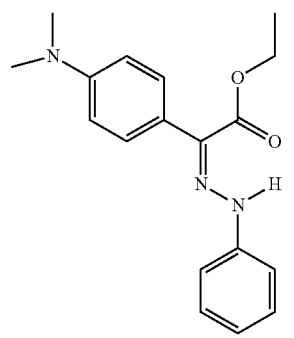 [SMILES: CCOC(=O)/C(=N\Nc1ccccc1)c1ccc(N(C)C)cc1] |
| 120 Z-isomer | 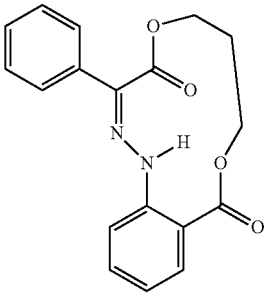 [SMILES: O=C1OCCCOC(=O)c2ccccc2N/N=C\1c1ccccc1] |
| 121 Z-isomer | 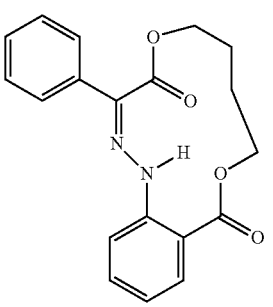 [SMILES: O=C1OCCCCOC(=O)c2ccccc2N/N=C\1c1ccccc1] |

TABLE 2-continued

Exemplary Compounds of the Invention

| Structure Number | Structure |
|---|---|
| 122 Z-isomer | 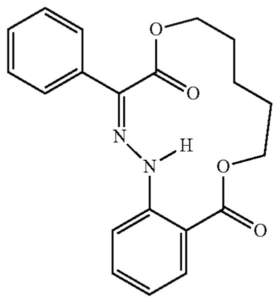 [SMILES: O=C1OCCCCCOC(=O)c2ccccc2N/N=C\1c1ccccc1] |
| 123 Z-isomer | 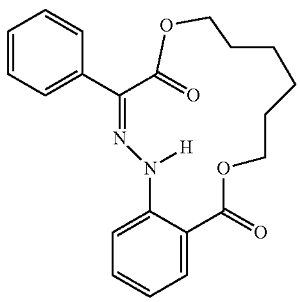 [SMILES: O=C1OCCCCCCOC(=O)c2ccccc2N/N=C\1c1ccccc1] |
| 124 Z-isomer | 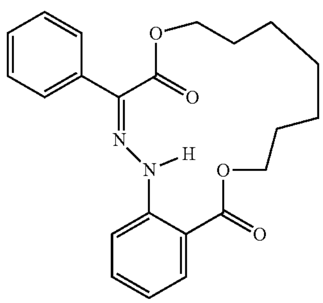 [SMILES: O=C1OCCCCCCCOC(=O)c2ccccc2N/N=C\1c1ccccc1] |
| 125 Z-isomer | 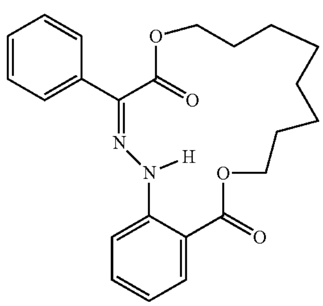 [SMILES: O=C1OCCCCCCCCOC(=O)c2ccccc2N/N=C\1c1ccccc1] |
| 126 Z-isomer | 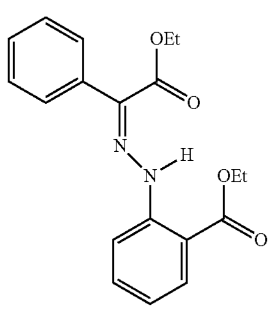 [SMILES: CCOC(=O)/C(=N\Nc1ccccc1C(=O)OCC)c1ccccc1] |
| 127 Z-isomer | 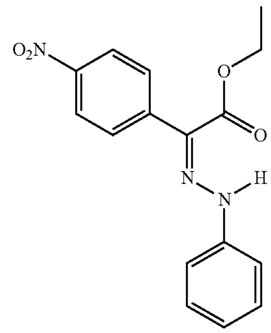 [SMILES: CCOC(=O)/C(=N\Nc1ccccc1)c1ccc([N+](=O)[O-])cc1] |
| 128 Z-isomer | 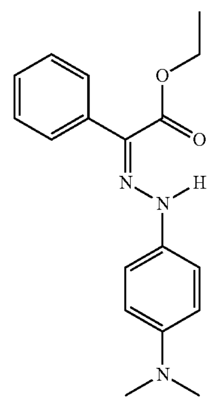 [SMILES: CCOC(=O)/C(=N\Nc1ccc(N(C)C)cc1)c1ccccc1] |
| 129 Z-isomer | 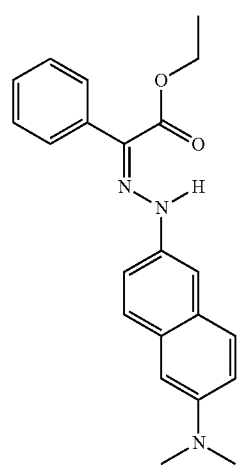 [SMILES: CCOC(=O)/C(=N\Nc1ccc2cc(N(C)C)ccc2c1)c1ccccc1] |

TABLE 2-continued

Exemplary Compounds of the Invention

| Structure Number | Structure |
|---|---|
| 130 Z-isomer | |
| 131 Z-isomer | |

In another aspect herein is provided a compound of formula III:

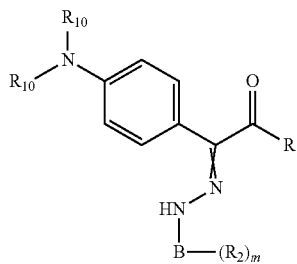

(III)

or a salt thereof,
wherein

⁄ represents a double bond having either E or Z stereochemistry;

B is an aryl or heteroaryl moiety;

R is selected from the group consisting of hydrogen, halogen, alkyl, alkenyl, alkynyl, cycloalkyl, alkoxyalkyl, alkenone, heteroalkyl, aryl, heteroaryl, OH, O—R', O—CO—R', S—H, S—R', NH$_2$, NH(R'), N(R')$_2$, NH(CO—R'), N(R')(CO—R'), NHOH, NR'OH, C(R")=C(R")$_2$, and C≡C—R", where:

each R' is independently alkyl, alkenyl, alkynyl, cycloalkyl, alkoxyalkyl, azide, azide substituted alkyl, halogen substituted alkyl, heteroalkyl, alkoxy, aryl, heterocyclyl or heteroaryl, and each R" is independently hydrogen, alkyl, alkenyl, alkynyl, cycloalkyl, heterocyclyl, alkoxyalkyl, heteroalkyl, alkoxy, aryl, or heteroaryl, and where in the alkenyl and alkynyl groups for R' and R", the double or triple bond is not at the alpha-beta position in the alkenyl or alkynyl group;

each R$_2$ is independently, for each occurrence, selected from the group consisting of hydrogen, alkyl, heteroalkyl, cycloalkyl, heterocyclyl, alkoxy, aryl, heteroaryl, halo, haloalkyl, alkylamino, dialkylamino, hydroxyl, nitro, cyano, carboxyl, carboxyalkyl, and carboxamido;

m is 0, 1, 2, 3, 4, 5, 6 or 7;

each R$_{10}$ independently is hydrogen, alkyl, a cycloalkyl group, an —NH—CHR$_{AC}$—COOH amino acid group (or salt thereof), an aryl group, a heterocyclic group, a heteroaryl group, or the two R$_{10}$ together with the N to which they are both attached forms a 5-6 member carbocyclic ring, which ring is optionally substituted, which ring optionally contains 1-4 heteroatoms and which ring is saturated or unsaturated.

In an embodiment of Formula III, R is OR'. In an embodiment of Formula III, R is OR' and R' is alkyl, cycloalkyl, alkenyl, alkynyl, aryl or heteroaryl.

In embodiments of Formula III, one R$_{10}$ is hydrogen and the other of R$_{10}$ is an alkyl, a cycloalkyl group, an —NH—CHR$_{AC}$—COOH amino acid group (or salt thereof), an aryl group, a heterocyclic group, or a heteroaryl group, where R$_{AC}$ is as defined above. In specific embodiments, R$_{AC}$ is hydrogen, an unsubstituted or substituted alkyl group, an unsubstituted or substituted benzyl group, or an alkyl substituted with a heterocyclic or heteroaryl group. In specific embodiments, R$_{AC}$ is a side chain of a proteinogenic amino acid (as this term is understood in the art). In specific embodiments, the amino acid group is an L-amino acid group. In an embodiment, the amino acid group is a D-amino acid group.

In embodiments of Formula III, one R$_{10}$ is hydrogen and the other of R$_{10}$ an —NH—CHR$_{AC}$.COOH amino acid group (or salt thereof), an aryl group, a heterocyclic group, or a heteroaryl group. In embodiments of Formula III, one R$_{10}$ is hydrogen and the other of R$_{10}$ is an —NH—CHR$_{AC}$.COOH amino acid group (or salt thereof), a heterocyclic group, or a heteroaryl group. In embodiments of Formula III both R$_{10}$ are alkyl.

In an embodiment of Formula III, B is phenyl, R$_1$-substituted phenyl, or 4-R$_1$-substituted phenyl. In an embodiment of Formula III, B is naphtha-1-yl. In an embodiment of Formula III, B is naphtha-2-yl. In an embodiment of Formula III, B is 6-dialkylaminonaphth-2-yl. In an embodiment of Formula III, B is quinolin-2-yl. In an embodiment of Formula III, B is bipyridyl, benzoquinolyl, or phenylbenzothiazolyl. In an embodiment of Formula III, B is a 2,2'-bipyridyl, a 4, 4'-bipyridyl or a 2, 4'-bipyridyl. In an embodiment of Formula III, B is a 7,8-benzoquinol-3-yl or a 5,6-benzoquinol-3-yl. In an embodiment of Formula III, B is a 7,8-benzoquinolyl or a 5,6-benzoquinol-7-yl. In an embodiment of Formula III, B is a 2-phenylbenzothiazolyl.

In an embodiment of Formula III, R is OR' and B is phenyl, R$_1$-substituted phenyl, or 4-R$_1$-substituted phenyl. In an embodiment of Formula III, R is OR' and B is naphtha-1-yl. In an embodiment of Formula III, B is naphtha-2-yl. In an embodiment of Formula III, R is OR' and B is 6-dialkylaminonaphth-2-yl. In an embodiment of Formula III, R is OR' and B is quinolin-2-yl.

In an embodiment of Formula III, when B is a phenyl group, each $R_2$ is hydrogen. In an embodiment of formula III, when B is a phenyl group, there is at least one $R_2$ group which is other than hydrogen. In an embodiment of formula III, each $R_2$ is selected from halogen, nitro, cyano, alkyl or alkoxy. In an embodiment of formula III, each $R_2$ is selected from nitro or cyano. In an embodiment of formula III, each $R_{10}$ is a methyl group.

In an embodiment of Formula III, when R is OR' and B is a phenyl group, each $R_2$ is hydrogen. In an embodiment of formula III, when R is OR' and B is a phenyl group, there is at least one $R_2$ group which is other than hydrogen. In an embodiment of formula III, R is OR' and each $R_2$ is selected from halogen, nitro, cyano, alkyl or alkoxy. In an embodiment of formula III, R is OR' and each $R_2$ is selected from nitro or cyano. In an embodiment of formula III, each $R_{10}$ is a methyl group.

In an embodiment, is provided a compound of formula (IV)

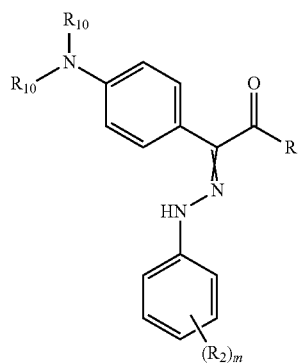

(IV)

or a salt thereof
wherein R, each $R_2$, m and each $R_{10}$ are as defined for formula III and, represents ⁄ a double bond having either E or Z stereochemistry. In an embodiment, R is OR'.

In an embodiment of formula IV, R' is an alkyl group having 1-3 carbon atoms. In an embodiment of formula IV, R' is an ethyl group. In an embodiment of Formula IV, R' is an alkenyl or alkenone. In an embodiment of formula IV, each $R_{10}$ is an alkyl group having 1-3 carbon atoms. In an embodiment of formula IV, each $R_{10}$ is a methyl group. In an embodiment of formula IV, each $R_2$ is hydrogen. In an embodiment of formula IV, each $R_2$ is halogen, nitro, cyano, alkyl or alkoxy. In an embodiment of formula IV, each $R_2$ is halogen, nitro, or cyano. In an embodiment of formula IV, m is 1 and $R_2$ is halogen, nitro, alkoxy, or cyano. In an embodiment of formula IV, m is 1 and $R_2$ is halogen, nitro, alkoxy, cyano substituted at the 4-ring position.

In an embodiment of formula IV, R is OR' and R' is an alkyl group having 1-3 carbon atoms. In an embodiment of formula IV, R is OR' and R' is an ethyl group. In an embodiment of Formula IV, R is OR' and R' is an alkenyl or alkenone. In an embodiment of formula IV, R is OR' and each $R_{10}$ is an alkyl group having 1-3 carbon atoms. In an embodiment of formula IV, R is OR' and each $R_{10}$ is a methyl group. In an embodiment of formula IV, R is OR' and each $R_2$ is hydrogen. In an embodiment of formula IV, R is OR' and each $R_2$ is halogen, nitro, cyano, alkyl or alkoxy. In an embodiment of formula IV, R is OR' and each $R_2$ is halogen, nitro, or cyano. In an embodiment of formula IV, R is OR' and m is 1 and $R_2$ is halogen, nitro, or cyano. In an embodiment of formula IV, R is OR' and m is 1 and $R_2$ is halogen, nitro, or cyano substituted at the 4-ring position.

In an embodiment is provided a compound of Formula V:

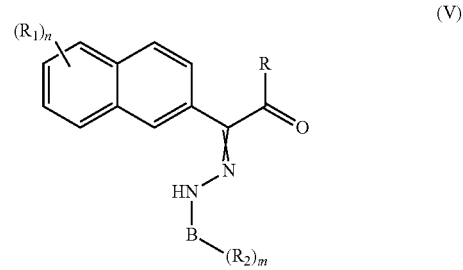

(V)

or a salt thereof
wherein R, each $R_1$, n, each $R_2$, m and B are as defined for formula III and ⁄ represents a double bond having either E or Z stereochemistry. In an embodiment R is OR'.

In embodiments of Formula V, B is phenyl or $R_2$-substituted phenyl. In embodiments of Formula V, B is naphtha-2-yl or $R_2$-substituted naphth-2yl. In embodiments of Formula V, B is naphtha-1-yl or $R_2$-substituted napht-1-yl. In embodiments of Formula V, B is quinolin-2-yl. In embodiments of Formula V, B is bipyridyl, benzoquinolyl, or phenylbenzothiazolyl. In embodiments of Formula V, B is a 2,2'-bipyridyl, a 4, 4'-bipyridyl or a 2, 4'-bipyridyl. In embodiments of Formula V, B is a 7,8-benzoquinol-3-yl or a 5,6-benzoquinol-3-yl. In embodiments of Formula V, B is a 7,8-benzoquinolyl or a 5,6-benzoquinol-7-yl. In embodiments of Formula V, B is a 2-phenylbenzothiazolyl.

In embodiments of Formula V, $R_2$ is halogen, alkoxy, nitro or cyano. In embodiments of formula V, m is 0. In embodiments of Formula V, n is 0 (unsubstituted naphthyl). In embodiments of Formula V, n is 1 and $R_1$ is dialkylamino. In embodiments of Formula V, n is 1 and $R_1$ is dimethylamino. In embodiments of Formula V, n is 1 and $R_1$ is 6-dialkylamino. In embodiments of Formula V, n is 1 and $R_1$ is 6-dimethylamino. In embodiments of Formula V, each R' is $C_1$-$C_6$ alkyl. In embodiments of Formula V, each R' is $C_1$-$C_3$ alkyl. In embodiments of Formula V, each R' is ethyl. In embodiments of Formula V, one or more R' is an alkenyl or alkenone. In embodiments of Formula V, each R" is $C_1$-$C_6$ alkyl. In embodiments of Formula V, each R" is $C_1$-$C_3$ alkyl. In embodiments of Formula V, each R" is ethyl. In embodiments of Formula V, one or more of R" is an alkenyl or alkenone.

In embodiments of Formula V, R is OR' and B is phenyl or $R_2$-substituted phenyl. In embodiments of Formula V, R is OR' and B is naphtha-2-yl or $R_2$-substituted naphth-2-yl. In embodiments of Formula V, R is OR' and B is naphtha-1-yl or $R_2$-substituted napht-1-yl. In embodiments of Formula V, R is OR' and B is quiolin-2-yl. In embodiments of Formula V, R is OR' and $R_2$ is halogen, nitro or cyano. In embodiments of formula V, m is 0. In embodiments of Formula V, R is OR' and n is 0 (unsubstituted naphthyl). In embodiments of Formula V, R is OR' and n is 1 and $R_1$ is dialkylamino. In embodiments of Formula V, R is OR' and n is 1 and $R_1$ is dimethylamino. In embodiments of Formula V, R is OR' and n is 1 and $R_1$ is 6-dialkylamino. In embodiments of Formula V, R is OR' and n is 1 and $R_1$ is 6-dimethylamino. In embodiments of Formula V, R is OR' and each R' is $C_1$-$C_6$ alkyl. In embodiments of Formula V, R is OR' and each R' is $C_1$-$C_3$ alkyl. In embodiments of Formula V, R is OR' and each R' is ethyl. In embodiments of Formula V, one or more R' is an alkenyl or alkenone.

In an embodiment is provided a compound of Formula VI:

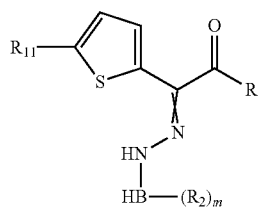

VI or a salt thereof,
wherein R, each $R_2$, m and B are as defined for formula III, $R_{11}$ is selected from hydrogen, alkyl, heteroalkyl, cycloalkyl, heterocyclyl, alkoxy, aryl, heteroaryl, halo, haloalkyl, alkylamino, dialkylamino, hydroxyl, nitro, cyano, carboxyl, carboxyalkyl, and carboxamido; and ⌇ represents a double bond having either E or Z stereochemistry. More specifically, $R_{11}$ is alkyl, cycloalkyl, heterocyclyl, aryl or heteroaryl. In a specific embodiment, R is OR'.

In embodiments of Formula VI, B is phenyl or $R_2$-substituted phenyl. In embodiments of Formula VI, B is naphtha-2-yl or $R_2$-substituted naphth-2yl. In embodiments of Formula VI, B is naphth-1-yl or $R_2$-substituted naphth-1-yl. In embodiment of Formula VI, B is bipyridyl, benzoquinolyl, or phenylbenzothiazolyl. In embodiments of Formula VI, B is a 2,2'-bipyridyl, a 4, 4'-bipyridyl or a 2, 4'-bipyridyl. In embodiments of Formula VI, B is a 7,8-benzoquinol-3-yl or a 5,6-benzoquinol-3-yl. In embodiments of Formula VI, B is a 7,8-benzoquinolyl or a 5,6-benzoquinol-7-yl. In embodiments of Formula VI, B is a 2-phenylbenzothiazolyl. In embodiments of Formula VI, $R_2$ is halogen, nitro or cyano. In embodiments of Formula VI, B is quinolin-2-yl. In embodiments of formula VI, m is 0. In embodiments of Formula VI, $R_{11}$ is hydrogen (unsubstituted thienyl). In embodiments of Formula VI, $R_{11}$ is heterocyclyl. In embodiments of Formula VI, $R_{11}$ is a 6-member heterocyclic ring having one or two nitrogen atoms. In embodiments of Formula VI, $R_{11}$ is piperidin-1-yl. In embodiments of Formula VI, R' is $C_1$-$C_6$ alkyl. In embodiments of Formula VI, R' is $C_1$-$C_3$ alkyl. In embodiments of Formula VI, R' is ethyl. In embodiments of Formula VI, one or more of R' is alkenyl or alkenone. In embodiments of Formula VI, R" is $C_1$-$C_6$ alkyl. In embodiments of Formula VI, R" is $C_1$-$C_3$ alkyl. In embodiments of Formula VI, R" is ethyl. In embodiments of Formula VI, R" is alkenyl or alkenone.

In embodiments of Formula VI, R is OR' and B is phenyl or $R_2$-substituted phenyl. In embodiments of Formula VI, R is OR' and B is naphtha-2-yl or $R_2$-substituted naphth-2yl. In embodiments of Formula VI, R is OR' and B is naphth-1-yl or $R_2$-substituted naphth-1-yl. In embodiments of Formula VI, R is OR' and $R_2$ is halogen, nitro or cyano. In embodiments of Formula VI, R is OR' and B is quinolin-2-yl. In embodiments of formula VI, R is OR' and m is 0. In embodiments of Formula VI, R is OR' and $R_{11}$ is hydrogen (unsubstituted thienyl). In embodiments of Formula VI, R is OR' and $R_{11}$ is heterocyclyl. In embodiments of Formula VI, R is OR' and $R_{11}$ is a 6-member heterocyclic ring having one or two nitrogen atoms. In embodiments of Formula VI, R is OR' and $R_{11}$ is piperidin-1-yl. In embodiments of Formula VI, R is OR' and R' is $C_1$-$C_6$ alkyl. In embodiments of Formula VI, R is OR' and R' is $C_1$-$C_3$ alkyl. In embodiments of Formula VI, R is OR' and R' is ethyl. In embodiments of Formula VI, R is OR' and one or more of R' is alkenyl or alkenone.

In another aspect, provided herein is a method of optically switching a compound of any one of Formulas III-VI, or a salt thereof, or a material comprising the compound of Formulas III-VI or a salt thereof from a first isomeric configuration to a second isomeric configuration with respect to the C=N bond.

In embodiments, each R' in compounds I-IV is an alkyl group having 1-3 carbon atoms. In embodiments of formulas I-IV herein each R' is an ethyl group. In embodiments, one R' in compounds I-IV is an alkenyl or an alkenone. In embodiments, each R' in compounds I-IV is an alkyl group having 1-3 carbon atoms. In embodiments of formulas I-IV herein each R' is an ethyl group. In embodiments, one R' in compounds I-IV is an alkenyl or an alkenone.

In embodiments, each R" in compounds I-IV is an alkyl group having 1-3 carbon atoms. In embodiments of formulas I-IV herein each R" is an ethyl group. In embodiments, one R" in compounds I-IV is an alkenyl or an alkenone.

In embodiments, R is OR' and each R' in compounds I-IV is an alkyl group having 1-3 carbon atoms. In embodiments of formulas I-IV herein, R is OR' and each R' is an ethyl group. In embodiments, R is OR' and one R' in compounds I-IV is an alkenyl or an alkenone.

In a specific embodiment of the Formulas herein, R' is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms. In a specific embodiment of the Formulas herein, R" is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms. In a specific embodiment of the Formulas herein one or $R_2$ is a carboxyalkenyl group where the alkenyl group is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms. In a specific embodiment of the Formulas herein, R' is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms and one or $R_2$ is a carboxyalkenyl group where the alkenyl group is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms. In a specific embodiment of the Formulas herein, R" is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms and one or $R_2$ is a carboxyalkenyl group where the alkenyl group is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms.

In further embodiment of the foregoing embodiments, A is selected from phenyl, pyridine-2-yl, naphtha-2-yl, naphth-1-yl, thien-2-yl, quinolin-8-yl, or quinolin-2-yl or $R_1$-A is selected from 4-dialkylaminophenyl, dimethylaminophenyl, 6-dialkylaminonaphth-2-yl, 5(piperidin-1-yl)thien-2-yl, or 4-hydroxyphenyl. In further embodiment of the foregoing embodiments, B is selected from phenyl, pyridine-2-yl, naphtha-2-yl, naphth-1-yl, thien-2-yl, quinolin-8-yl, quinolin-2-yl or $R_1$-A is selected from 4-dialkylaminophenyl, dimethylaminophenyl, 6-dialkylaminonaphth-2-yl, 5(piperidin-1-yl)thien-2-yl, or 4-hydroxyphenyl. In further embodiment of the foregoing embodiments, $R_1$ except as designated in forgoing embodiments is hydrogen. In further embodiment of the foregoing embodiments, $R_2$ except as designated in forgoing embodiments is hydrogen.

In a specific embodiment of the Formulas herein, R is OR' and R' is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms. In a specific embodiment of the Formulas herein, one R" is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms. In a specific embodiment of the Formulas herein one or more of $R_2$ is a carboxyalkenyl group where the alkenyl group is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms. In a specific embodiment of the Formulas herein, R is OR' and R' is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms and one or $R_2$ is a carboxyalkenyl group where the alkenyl group is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms. In a specific embodiment of the Formulas herein, one or more R" is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms and one or $R_2$ is a carboxyalkenyl group where the alkenyl group is an omega alkenyl group having 2-20 carbon atoms or more specifically, 2-6, 2-8, 2-12, 2-16, 3-6, 3-8, 3-12, 3-16, 6-12, 6-16, 6-20, 8-16, 9-13 or 10-12 carbon atoms. In further embodiment of the foregoing embodiments, A is selected from phenyl, pyridiene-2-yl, naphtha-2-yl, naphth-1-yl, thien-2-yl, quinolin-8-yl, or quinolin-2-yl or $R_1$-A is selected from 4-dialkylaminophenyl, dimethylaminophenyl, 6-dialkylaminonaphth-2-yl, 5(piperidin-1-yl)thien-2-yl, or 4-hydroxyphenyl. In further embodiment of the foregoing embodiments, B is selected from phenyl, pyridiene-2-yl, naphtha-2-yl, naphth-1-yl, thien-2-yl, quinolin-8-yl, or quinolin-2-yl or $R_2$—B is selected from 4-dialkylaminophenyl, dimethylaminophenyl, 6-dialkylaminonaphth-2-yl, 5(piperidin-1-yl)thien-2-yl, or 4-hydroxyphenyl. In further embodiment of the foregoing embodiments, $R_1$ except as designated in forgoing embodiments is hydrogen. In further embodiment of the foregoing embodiments, $R_2$ except as designated in forgoing embodiments is hydrogen.

In another aspect the invention provides compounds of Formula VII or VIIA:

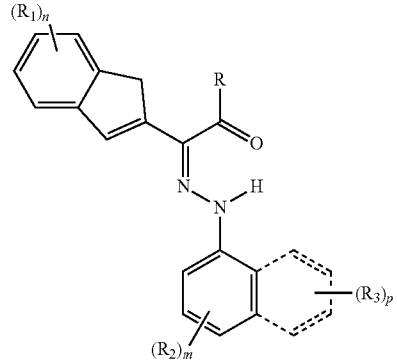
(VIIA)

or salts thereof
where:
dashed lines represent optional bonds;
X is $CH_2$, O, S, or $NR_{12}$, where $R_{12}$ is hydrogen or a C1-C3 alkyl;
Y is CH, or N,
R, R', R", $R_1$, and $R_2$ are as defined in Formula II;
n is 0-5, and preferably 0, 1, 2 or 3;
m is 0-3, and preferably 0, 1 or 2;
each $R_3$ independently takes any value defined for $R_1$ or $R_2$; and
p is 0-3 and preferably 0, 1 or 2.

In specific embodiments, R is OR'.

In specific embodiments, X is S or NH. In specific embodiments, X is $CH_2$. In specific embodiments, Y is N. In specific embodiments, n, m and p are all 0. In specific embodiments, n+m+p=1 or 2. In specific embodiments, each $R_1$, $R_2$ and $R_3$ is independently selected from halo, nitro, cyano, carboxylate, alkyl or alkoxy. In specific embodiments, R is a $C_1$-$C_6$ alkyl. In specific embodiments, R is OR' and X is S or NH. In specific embodiments, R is OR' and Y is N. In specific embodiments, R is OR' and n, m and p are all 0. In specific embodiments, R is OR' and n+m+p=1 or 2. In specific embodiments, R is OR' and each $R_1$, $R_2$ and $R_3$ are independently selected from halo, nitro, cyano, carboxylate, alkyl or alkoxy. In specific embodiments, R is OR' and R' is a $C_1$-$C_6$ alkyl.

In specific embodiments of Formula VII, the compound is of Formula VIIB, VIIC, VIID or VIIE, where R is R':

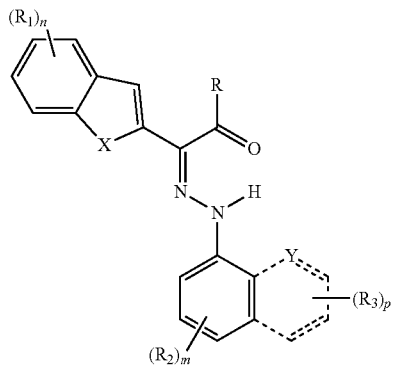
(VII)

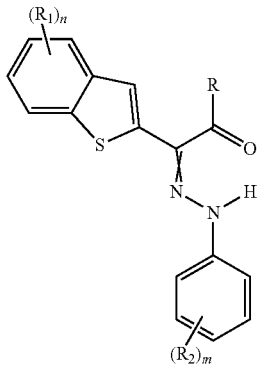
VIIB

-continued

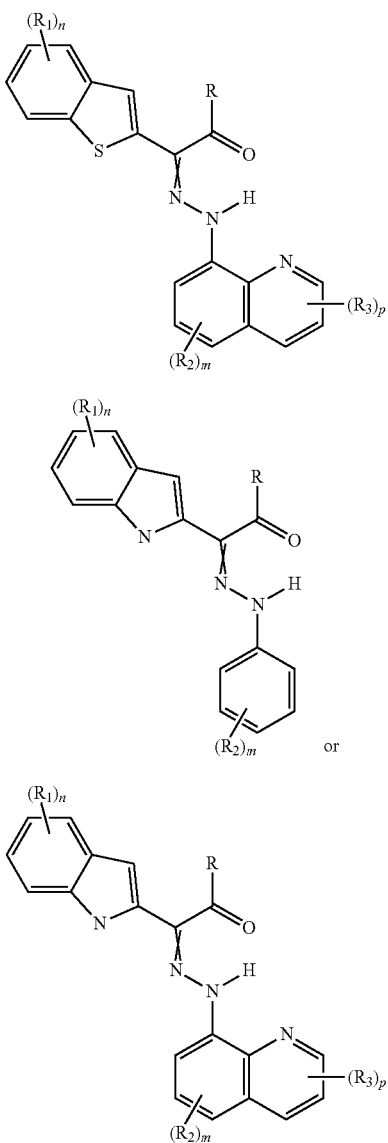

VIIC

VIID or

VIIE or salts thereof.

Variables for VIIB-E are as defined above. In specific embodiments, R is OR'. In specific embodiments, R' is C1-C6 alkyl or C1-C3 alkyl.

In an embodiment, the invention provides compounds of Formula VIII:

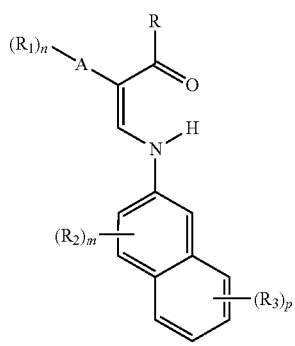

(VIII)

or salts thereof where:

A, R, R', R", $R_1$, and $R_2$ are as defined in Formula II;
n is 0-5, and preferably 0, 1, 2 or 3;
m is 0-3, and preferably 0, 1 or 2;
each $R_3$ independently takes any value defined for $R_1$ or $R_2$; and
p is 0-3 and preferably 0, 1 or 2.

In specific embodiments, R is OR'.
In specific embodiments, A is unsubstituted phenyl or a substituted phenyl.
In specific embodiments, A is a nitro-substituted phenyl.
In specific embodiments, A is 4-nitrophenyl.
In specific embodiments, p is 1. In specific embodiments, n, m are 0 and p is 1. In specific embodiments, p is 1 and m is 0. In specific embodiments, n+m+p=1 or 2. In specific embodiments, each $R_1$, $R_2$ and $R_3$ is independently selected from halo, nitro, cyano, carboxylate, alkyl or alkoxy. In specific embodiments, R is a C1-C6 alkyl. In specific embodiments, R is OR'. In specific embodiments, R is OR'. In specific embodiments, R is OR' and n, m and p are all 0. In specific embodiments, R is OR' and n+m+p=1 or 2. In specific embodiments, R is OR' and each $R_1$, $R_2$ and $R_3$ are independently selected from halo, nitro, cyano, carboxylate, alkyl or alkoxy. In specific embodiments, R is OR' and R' is a C1-C6 alkyl. In specific embodiments, $R_3$ is a single —$NH_2$ group. In specific embodiments, $R_3$ is a 6-$NH_2$, on a naphth-2-yl group.

In an embodiment, the invention provides compounds of Formula IX:

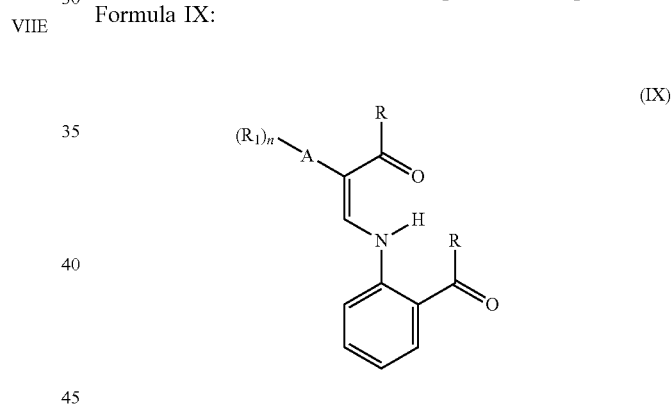

(IX)

or salts thereof where A, R, R', R", and $R_1$, are as defined in Formula II; and
n is 0-5, and preferably 0, 1, 2 or 3.

In specific embodiments, R is OR'.
In specific embodiments, A is unsubstituted phenyl or a substituted phenyl.
In specific embodiments, A is a nitro-substituted phenyl.
In specific embodiments, A is 4-nitrophenyl.
In specific embodiments, A is unsubstituted phenyl.
In specific embodiments, A is 4-aminophenyl.
In specific embodiments, n is 0. In specific embodiments, n is 1. In specific embodiments, each $R_1$, is independently selected from halo, nitro, cyano, carboxylate, alkyl or alkoxy. In specific embodiments, both R groups are C1-C6 alkyl. In specific embodiments, both R groups are OR'. In specific embodiments, R' is a C1-C6 alkyl. In specific embodiments, R' is a C1-C3 alkyl. In specific embodiments, both R groups are the same. In specific embodiments, both R' groups are the same.

In one aspect, cyclic hydrazones are prepared from compounds of Formula II, wherein R is OH and one of the substituents on the B ring is a carboxylate by reaction with diols. Exemplary cyclic hydrazones have formula X:

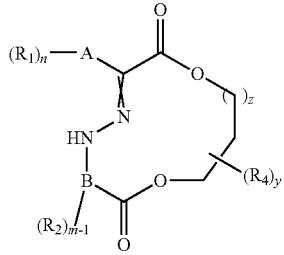

or salts thereof,
where:

⌇ represents a double bond having either E or Z stereochemistry;

A, B, $R_1$, $R_2$, n, and m are as defined in Formula II; and z is 1-5;

y is the number of $R_4$ substituents on the linking alkyl chain and preferably y is 0, 1, 2, 3, 4, . . . or 2z+4;

each $R_4$ is selected from selected from the group consisting of alkyl, heteroalkyl, cycloalkyl, heterocyclyl, alkoxy, aryl, heteroaryl, halo, haloalkyl, alkylamino, dialkylamino, hydroxyl, nitro, cyano, carboxyl, carboxyalkyl, and carboxamido.

Preferably y is 0, 1, 2, 3, 4, 5, or 6.

Preferably $R_4$ is alkyl, alkoxy, halo, hydroxyl, nitro, or cyano. More specifically A and B are an aryl or heteroaryl moieties. In an embodiment, A is unsubstituted phenyl or $R_1$-substituted phenyl. In an embodiment, A is naphthyl or quinolinyl. In an embodiment, B is unsubstituted phenyl or $R_2$-substituted phenyl. In an embodiment, B is naphthyl or quinolinyl. In an embodiment of Formula X, B is bipyridyl, benzoquinolyl, or phenylbenzothiazolyl. In an embodiment of Formula X, B is a 2,2'-bipyridyl, a 4, 4'-bipyridyl or a 2, 4'-bipyridyl. In an embodiment of Formula X, B is a 7,8-benzoquinol-3-yl or a 5,6-benzoquinol-3-yl. In an embodiment of Formula X, B is a 7,8-benzoquinolyl or a 5,6-benzoquinol-7-yl. In an embodiment of Formula X, B is a 2-phenylbenzothiazolyl.

$R_1$ and $R_2$ are independently, for each occurrence, selected from the group consisting of halogen, hydroxyl, alkyl, heteroalkyl, cycloalkyl, heterocyclyl, alkoxy, aryl, heteroaryl, halo, haloalkyl, alkylamino, dialkylamino, hydroxyl, nitro, cyano, carboxyl, carboxyalkyl, and carboxamido. More specifically, $R_1$ and $R_2$ are independently selected from alkyl, alkoxy, halo, hydroxyl, nitro, or cyano. In specific embodiments of Formula X, $R_1$ and $R_2$ are not carboxylate groups. In specific embodiments, n is 0, 1, 2 or 3 and m is 0, 1, 2 or 3. In specific embodiments, n is 0. In specific embodiments, n is 1. In specific embodiments, m is 0. In specific embodiments, m is 1.

In specific embodiments y is 1-3. In specific embodiments, y is 0. In specific embodiments, y is 1. In specific embodiments, z is 1. In specific embodiments, z is 2. In specific embodiments, z is 3. In specific embodiments, z is 4.

In specific embodiments, the compound of Formula X is the isomer having structure:

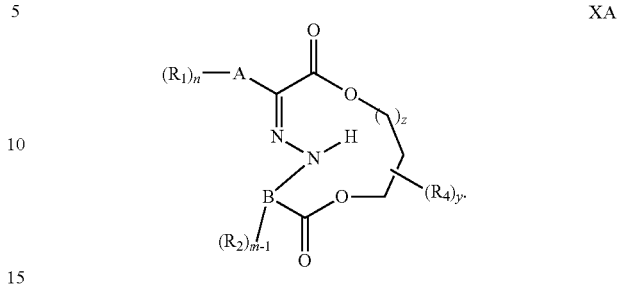

In specific embodiments of Formulas X and XA, A is phenyl. In specific embodiments of Formulas X and XA, B is phenyl. In specific embodiments of Formulas X and XA, A and B are both phenyl. In specific embodiments, y is 0. In specific embodiments, n, m and y are all 0. In specific embodiments, $R_1$ is a dialkylamino group and n is 1. In a specific embodiment, A is phenyl, n is 1 and $R_1$ is a 4-dialkyamino group. In a specific embodiment, A is phenyl, n is 1 and $R_1$ is a 4-dimethylamino group.

The invention also provides compositions and materials containing one or more compounds of Formulas I, II or III-VIIX and XA herein. Compositions may be in solution in an appropriate organic or aqueous solvent. In specific embodiments, compositions are aqueous solutions. In specific embodiments, compositions are biologically compatible fluids. In specific embodiments, compositions are serum. In specific embodiments, compositions are powders or other solid forms. In specific embodiments, compositions are films or coatings. Materials include substrates coated or impregnated with one or more compounds herein. Substrates include glass, quartz, plastic, ceramic and like materials. Materials include substrates formed from one or more compounds herein.

Compounds of the invention are useful in a method of optically switching. In this method, for example, a compound of Formula I, or a salt thereof, or a material or composition comprising the compound of Formula I or a salt thereof is irradiated at one or more selected wavelengths to generate switching. This method of switch can be reversible, for example, a compound of Formula I, or a salt thereof, or a material or composition comprising the compound of Formula I or a salt thereof is selectively irradiated at a first selected wavelength to generate switching by causing isomerization (from E to Z or Z to E) and thereafter is selectively irradiated at a second selected wavelength to cause reverse isomerization to the starting isomer (from Z to E or E to Z). In specific embodiments, switching occurs between two stable isomer states. In specific embodiments, the isomer states exhibit relatively stable (with respect to the needs of a given switching application) with appropriately long thermal lifetimes.

The method of optically switching comprising irradiating said compound, material, or composition at a first selected wavelength thereby isomerizing the compound from the E stereoisomer to the Z stereoisomer, or isomerizing the compound from the Z stereoisomer to the E stereoisomer. The method further comprises irradiating said compound, material, or composition at a second selected wavelength thereby isomerizing the compound back to the starting stereoisomer prior to irradiation at said first selected wavelength.

Formulas IA and IB illustrate two isomers of Formula I:

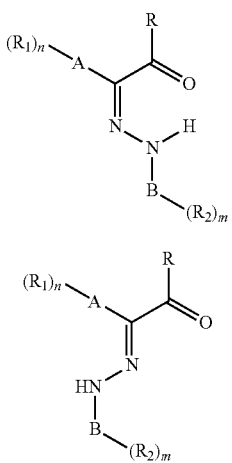

In isomer IA, the —COR group and the —NH—B(R$_2$)$_m$ groups are on the same side of the C=N double bond in a cis relationship. In isomer IB, the —COR group and the —NH—B(R$_2$)$_m$ groups are on opposite sides of the C=N double bond in a trans relationship. As is well known in the art, the E/Z naming convention is based on assigning a priority to the groups on either side of the double bond. Thus, it will be appreciated by one of ordinary skill in the art, that the E or Z designation of isomers of formula IA and IB will depend upon the selection of the A group. For example, when A is a phenyl group, isomer IA is designated a Z isomer and isomer IB is designated an E isomer. For example, when A is a thien-2-yl, the isomer of formula IA is designated an E-isomer and the isomer of formula IB is designated a Z isomer. Thus dependent upon the selection of A, the switch from the IA isomer to the IB isomer can be a switch from the Z to E isomer or a switch from the E to Z isomer.

In an embodiment, the compound or material that is irradiated is in solution or in suspension in a solvent. In an embodiment, the compound or material that is irradiated is in the bulk solid state. In an embodiment, the compound or material that is irradiated is in the form of a powder. In an embodiment, the compound or material that is irradiated is in the form of a film formed on a substrate. In an embodiment, the compound or material that is irradiated is in the form of a film spun onto a substrate. In an embodiment, the compound or material that is irradiated is in the form of a film drop cast onto a substrate. In an embodiment, the compound or material that is irradiated is in a crystalline form. In an embodiment, the compound or material that is irradiated is in an amorphous form. In an embodiment, isomerizing the compound results in a change in absorption wavelength or intensity. In an embodiment, isomerizing the compound results in a change in fluorescence wavelength or intensity. In an embodiment, isomerizing the compound results in a change emission wavelength or intensity.

In an embodiment of the method employing a compound of Formula I, R is CO—R'. In an embodiment of the method employing a compound of Formula I, A is phenyl or pyridine-2-yl. In an embodiment of the method employing a compound of Formula I, R$_1$-A is 4-dialkylaminophenyl. In an embodiment of the method employing a compound of Formula I, R$_1$-A is 4-dimethylaminophenyl. In an embodiment of the method employing a compound of Formula I, A is naphth-2-yl. In an embodiment of the method employing a compound of Formula I, A is thien-2-yl or (R$_1$-A) is 5(piperidin-1-yl)thien-2-yl. In an embodiment of the method employing a compound of Formula I, A is naphtha-1-yl. In an embodiment of the method employing a compound of Formula I, A is 4-hydroxyphenyl. In an embodiment of the method employing a compound of Formula I, A is indoyl and more specifically is indo-2-yl. In an embodiment of the method employing a compound of Formula I, A is benzothienyl and more specifically is benzothien-2-yl. In an embodiment of the method employing a compound of Formula I, A is indenyl (also 1H-indenyl) and more specifically is inden-2-yl (also 1H inden-2-yl). In an embodiment of the method employing a compound of Formula I, R$_1$-A is 6-dialkylaminonaphth-2-yl.

In an embodiment, the compound of Formula II has a structure selected from:

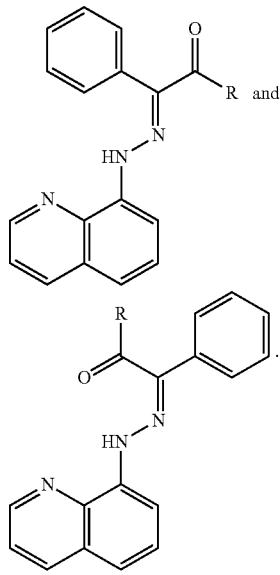

In certain embodiments, the E stereoisomer of Formula II has a thermal relaxation half-life of at least 10, 20, 50, 100, 1000 or 2000 years.

In certain embodiments, the stereoisomer s of compounds of Formulas herein have a thermal relaxation half-life of at least 10, 20, 50, 100, 1000 or 2000 years. In certain embodiments, the E stereoisomer of compounds of formulas herein has a thermal relaxation half-life of at least 10, 20, 50, 100, 1000 or 2000 years. In certain embodiments, the Z stereoisomer of compounds of formulas herein has a thermal relaxation half-life of at least 10, 20, 50, 100, 1000 or 2000 years.

In another aspect, provided herein is a composition comprising both the E and Z stereoisomers of a compound of Formula II.

In another aspect, provided herein is a molecular switch comprising a compound of any formula herein. In an embodiment, the molecular switch comprises both the E and Z stereoisomers of the compound. In an embodiment, the molecular switch comprises one or more compounds selected from the compounds of Table 1. In an embodiment, the molecular switch comprises one or more compounds selected from the compounds of Table 2 or the corresponding E or Z stereoisomers thereof.

Photoisomerizable Group

A photoisomerizable group is one that changes from a first isomeric form to a second isomeric form upon exposure to electromagnetic radiation of different wavelengths, or upon a change in exposure from dark to light, or from light to dark. For example, in some embodiments, the photoisomerizable group is in a first isomeric form of a compound of Formula I-VI when exposed to electromagnetic radiation of a first wavelength, and is in a second isomeric form of that compound of Formula I-XA when exposed to electromagnetic radiation of a second wavelength.

The first wavelength and the second wavelength can differ from one another by from about 1 nm to about 600 nm or more, for example, from about 1 nm to about 10 nm, from about 10 nm to about 20 nm, from about 20 nm to about 50 nm, from about 50 nm to about 75 nm, from about 75 nm to about 100 nm, from about 100 nm to about 125 nm, from about 125 nm to about 150 nm, or from about 150 nm to about 200 nm, from about 200 nm to about 500 nm, from about 500 nm to about 600 nm, or more than 600 nm.

In an embodiment, the compound of Formulas I-XA is in a first isomeric form (e.g., the E stereoisomer of the C=N bond of a hydrazone) when exposed to light of a first wavelength $\lambda_1$, and then in a second isomeric form (e.g., the Z stereoisomer of the C=N bond of a hydrazone) when exposed to light of a second wavelength $\lambda_2$.

In some embodiments provided herein, the compound of Formulas herein is in a Z configuration in the absence of light, or when exposed to light of a first wavelength; and the photoisomerizable group is in an E configuration when exposed to light of a second wavelength that is different from the first wavelength.

In some embodiments, the wavelength of light that effects a change in the compound of Formulas I-VI from a first isomeric form to a second isomeric form ranges from 400 nanometers to 1000 nanometers.

In other embodiments, the wavelength of light that effects a change in the compound of Formulas I-VI from a first isomeric form to a second isomeric form ranges from 450 nanometers to 850 nanometers.

The difference between the first wavelength and the second wavelength can range from about 1 nm to about 600 nm or more, as described above. Of course, where the synthetic light regulator is switched from light to darkness, the difference in wavelength is from the wavelength $\lambda_2$ to essentially zero.

Methods of Using Molecular Switches

The select application of electromagnetic radiation to a compound of Formulas herein, or a material or composition comprising a compound of Formulas herein, can be used to transform the irradiated compound from an E isomeric form to a Z isomeric form, or a Z isomeric form to an E isomeric form. In this way, the compounds of Formulas herein can be used as a molecular switch, with the electromagnetic radiation serving as a switching means.

In some embodiments, the compounds of Formulas herein or salts thereof respond to electromagnetic radiation that is generated by an infrared light source and/or a visible light source. Therefore, in some of these embodiments, the compounds of Formulas herein respond to a first wavelength $\lambda_1$ ranging from 400 nanometers to 1 millimeter to convert the Z isomer to the E isomer; and a second wavelength $\lambda_2$ ranging from 400 nanometers to 1 millimeter causes the E isomer to convert back to the Z isomer.

The skilled artisan will appreciate that the photochromic materials described herein need not be limited to those responsive to the exemplary wavelength ranges described herein.

In other embodiments, the compounds of the invention can be employed or adapted for labeling of biological molecules, for example, for imaging. Compounds of the invention can for example be chemically ligated to a peptide, protein, nucleic acid or carbohydrate. Various means for ligation of small molecule labels to biological molecules are known in the art and can be employed with only routine adaptation to the compounds herein. For example, one $R_1$, $R_2$ or $R_3$ group of a compound herein can be provided with a functional group that can react with an amine, carboxylate, or other functional group of the peptide, protein, nucleic acid or carbohydrate and thereby to label the peptide, protein, nucleic acid or carbohydrate.

Definitions

In this disclosure, "comprises," "comprising," "containing," and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless otherwise specified, "a" or "an" means "one or more".

The term "electromagnetic radiation" as used herein, refers to a form of energy exhibiting wave like behavior and having both electric and magnetic field components, which oscillate in phase perpendicular to each other as well as perpendicular to the direction of energy propagation. Electromagnetic radiation is classified according to the frequency of its wave. In order of increasing frequency (f) and decreasing wavelength ($\lambda$), electromagnetic radiation includes: radio waves (3 Hz≤f≤300 MHz; 1 m≤$\lambda$≤100,000 Km), microwaves (300 MHz≤f≤300 GHz; 1 mm≤$\lambda$≤1 m), infrared radiation (300 GHz≤f≤400 THz; 750 nm≤$\lambda$≤1 m), visible light (400 THz≤f≤770 THz; 400 nm≤$\lambda$≤1 m), ultraviolet radiation (750 THz≤f≤30 PHz; 10 nm≤$\lambda$≤400 nm), X-rays (300 PHz≤f≤30 EHz; 0.01 nm≤$\lambda$≤10 nm), and gamma rays (f≥15 EHz; $\lambda$≤0.02 nm). Hence, the term "electromagnetic radiation", as used herein, denotes photons, particularly in the visible range and/or in the infrared region.

The term "photochromism", as used herein, indicates a photoinduced change in color. Herein, the interconversion usually occurs between two colored states. A photochromic transformation is always accompanied by profound absorbance changes in the visible region. In fact, visible absorption spectroscopy is the most convenient analytical method to study these processes.

The term "photostationary state", as used herein, indicates a state where no further changes in the UV/Vis spectra are observed. For example, application of additional electromagnetic energy to a sample or molecule in a photostationary state does not produce a change in absorption or emission spectra.

As used herein, the term "molecular switch" refers to a molecule that generates a change in state in response to a signal. In one aspect, a molecular switch is capable of switching from at least one state to at least one other state in response to the signal.

As used herein, the expression "a group corresponding to" an indicated species expressly includes a radical (including a monovalent, divalent and trivalent radical), for example an aromatic radical or heterocyclic aromatic radical, of the species or group of species provided in a covalently bonded configuration.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc.

As used herein, the term "substituted" refers to a compound or a group wherein a hydrogen in the compound or group is replaced by another functional group.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, 1 to 6 carbons, 1 to 4 carbons, or 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

As used herein, the term "alkenyl" refers to a branched or unbranched hydrocarbon group having at least one double bond. Preferably the alkenyl comprises 2 to 20 carbon atoms, more preferably 2 to 16 carbon atoms, 2 to 10 carbon atoms, 2 to 7 carbon atoms, 2 to 6 carbons, 2 to 4 carbons, or 2 to 3 carbon atoms. Representative examples of alkenyl include, but are not limited to, ethenyl, n-propenyl, prop-1-en-2-yl, n-butenyl, but-1-en-2-yl, but-3-en-2-yl, n-pentenyl, n-hexenyl, n-heptenyl, n-octenyl, n-nonenyl, n-decenyl and the like. The one or more double bonds can be positioned at any positions within the carbon chain of the group. Typically, two double bonds do not share a carbon atoms. Two or more double bonds may be conjugated. The formula —C═C—C═C— illustrates conjugation of two double bonds. For alkenyl groups having 4 or more carbons, the position of a double bond can be designated in the group name. For example, $CH_3$—CH═CH—$CH_2$— is designated but-2-enyl. Furthermore, the expression "$C_x$-$C_y$-alkenyl", wherein x and y are integers indicates a particular alkenyl group (straight- or branched-chain) having a particular range of carbons atoms. Alkenyl groups can contain a single double bond which may be positioned anywhere in the carbon chain except where the alkenyl group is bonded into a given compound. Alkenyl groups can contain a single double bond at the omega (last) position on the carbon chain. The formula —$(CH_2)_r$—CH═$CH_2$, where r is 1-18, represents a linear alkenyl group, having an omega double bond. Omega double bond alkenyl groups can be branched or unbranched. As is known and appreciated in the art, alkenyl groups can have different isomeric forms dependent upon the orientation of bonding of moieties to the double bond in the group. Such isomers can be designated cis or trans isomers or now more commonly as E and Z isomers. One of ordinary skill in the art understands how to designate such isomers. As is known in the art, a double bond can function for the formation of polymers.

As used herein, the term "alkenone" refers to an alkyl group substituted with an enone group or carrying an enone moiety (an enone group or moiety is also designated an α,β-unsaturated carbonyl group or moiety). For example, an alkyl group may be substituted with an enone group, such as —CO—CH═$CH_2$, or an enone moiety, such as —CO—CH═CH—, can be introduced between two carbon atoms of an alkyl group. An alkenone group having a single enone group or moiety can have 3-20 carbon atoms. In embodiments, alkenone groups can have 3-6, 3-9, 3-12, 3-15, 3-10, 6-12, 6-20, 8-12, 8-16 or 8-20 carbon atoms. In specific embodiments, the enone group is bonded to the last carbon in an alkyl group distal from the point at which the alkyl group is bonded into a molecule. As is known in the art an enone group can react under selective conditions. For example, an enone group can function for the formation of polymers.

As used herein, the term "cycloalkyl" refers to saturated or unsaturated monocyclic, bicyclic or tricyclic hydrocarbon groups of 3-12 carbon atoms, preferably 3-9, or 3-7 carbon atoms. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

The term "heteroalkyl," by itself or in combination with another term, means, unless otherwise stated, a stable straight or branched chain, or combinations thereof, consisting of the stated number of carbon atoms and from one to five heteroatoms, more preferably from one to three heteroatoms, selected from the group consisting of O, N, Si and S, and wherein the nitrogen and sulfur atoms may optionally be oxidized and the nitrogen heteroatom may optionally be quaternized. The heteroalkyl group is attached to the remainder of the molecule through a carbon atom or a heteroatom.

The term "haloalkyl" refers to an alkyl group, as defined herein, wherein one or more hydrogen substituents are substituted with a halogen.

The term "alkylamino" refers to a monovalent moiety according to the formula —NH(R), wherein R is an alkyl group as defined herein. Similarly, the term "dialkylamino" refers to a monovalent moiety according to the formula —$NR_2$, wherein R is an alkyl group as defined herein.

As used herein, the term "alkoxyalkyl" refers to a monovalent moiety having alkyl and alkoxy moieties. The term includes alkyl groups substituted with alkoxy groups. Formally, the group can be described as an ether from which a hydrogen has been removed. An alternative description of the group is an alkyl group in which one or more non-adjacent —$CH_2$— moieties are replaced with —O—. For example, the group —$CH_2$—O—$CH_2$—$CH_3$ is a methyl group substituted with an ethoxy group.

The term "carboxyl" refers to a divalent moiety according to the formula —$CO_2$—. The term encompasses carboxylic acids (i.e., —$CO_2H$) and salts thereof (e.g., —$CO_2Na$).

The term "carboxyalkyl" refers to monovalent moieties according to the formula —CO$_2$R, wherein R is an alkyl group as defined herein.

The term "carboxyalkenyl" refers to monovalent moieties according to the formula —CO$_2$R, wherein R is an alkenyl group as defined herein. In a specific embodiment, the carboxyalkenyl group has an omega double bond distal from the carboxy moiety.

The term "carboxamido" refers to monovalent moieties according to the formula —CONR$_2$, wherein each R is independently a hydrogen, alkyl, heteroalkyl, aryl, heteroaryl or the like.

"Alkoxy" refers to those alkyl groups, having from 1 to 20 carbon atoms, 1 to 16 carbon atoms, 1 to 10 carbon atoms, 1 to 7 carbon atoms, 1 to 6 carbons, 1 to 4 carbons, 1 to 3 carbon atoms, or one carbon atom, attached to the remainder of the molecule via an oxygen atom. The alkyl portion of an alkoxy may be linear, cyclic, or branched, or a combination thereof. Examples of alkoxy groups include methoxy, ethoxy, isopropoxy, butoxy, cyclopentyloxy, and the like. Alkoxy groups also include those that are substituted with one or more alkoxy groups. For example, —O—CH$_2$—CH$_2$—OCH$_3$ is an ethoxy group substituted with a methoxy group. Alkoxy substituted alkoxy groups include those having 2 to 20 carbon atoms, 2 to 12 carbon atoms or 2-6 carbon atoms and those having 2-4 oxygen atoms, 2 or 3 oxygen atoms or 2 oxygen atoms.

The term "aryl" includes aromatic monocyclic or multicyclic (e.g., tricyclic, bicyclic), hydrocarbon ring systems consisting only of hydrogen and carbon and containing from six to nineteen carbon atoms, or six to ten carbon atoms, where the ring systems may be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include, but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocyclyl" refers to a five-member to ten-member, partially or fully saturated nonaromatic heterocyclic group containing at least one heteroatom such as O, S or N. In one embodiment, "heterocyclyl" refers to a cyclic group having 4-5 carbon atoms and 1-2 heteroatoms selected from O and N in the ring structure. Common examples of heterocyclyl radicals include piperidinyl, morpholinyl, piperazinyl, and pyrrolidinyl. Attachment of a heterocyclyl substituent can occur via a carbon atom or via a heteroatom.

Moreover, the alkyl, alkenyl, cycloalkyl, alkoxy, aryl, heteroaryl, heterocyclyl and heterocycle groups described above can be "unsubstituted" or "substituted."

The term "substituted" is intended to describe moieties having substituents replacing a hydrogen on one or more atoms, e.g. C, O or N, of a molecule. Such substituents can independently include, for example, one or more of the following: straight or branched alkyl (preferably C$_1$-C$_5$), cycloalkyl (preferably C$_3$-C$_8$), alkoxy (preferably C$_1$-C$_6$), thioalkyl (preferably C$_1$-C$_6$), alkenyl (preferably C$_2$-C$_6$), alkynyl (preferably C$_2$-C$_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, (CR'R")$_{0-3}$NR'R" (e.g., —NH$_2$), (CR'R")$_{0-3}$CN (e.g., —CN), —NO$_2$, halogen (e.g., —F, —Cl, —Br, or —I), (CR'R")$_{0-3}$C(halogen)$_3$ (e.g., —CF$_3$), (CR'R")$_{0-3}$CH(halogen)$_2$, (CR'R")$_{0-3}$CH$_2$(halogen), (CR'R")$_{0-3}$CONR'R", (CR'R")$_{0-3}$(CNH)NR'R", (CR'R")$_{0-3}$S(O)$_{1-2}$NR'R", (CR'R")$_{0-3}$CHO, (CR'R")$_{0-3}$O(CR'R")$_{0-3}$H, (CR'R")$_{0-3}$S(O)$_{0-3}$R' (e.g., —SO$_3$H, —OSO$_3$H), (CR'R")$_{0-3}$O(CR'R")$_{0-3}$H (e.g., —CH$_2$OCH$_3$ and —OCH$_3$), (CR'R")$_{0-3}$S(CR'R")$_{0-3}$H (e.g., —SH and —SCH$_3$), (CR'R")$_{0-3}$OH (e.g., —OH), (CR'R")$_{0-3}$COR', (CR'R")$_{0-3}$(substituted or unsubstituted phenyl), (CR'R")$_{0-3}$(C$_3$-C$_8$ cycloalkyl), (CR'R")$_{0-3}$CO$_2$R' (e.g., —CO$_2$H), or (CR'R")$_{0-3}$OR' group, or the side chain of any naturally occurring amino acid; wherein R' and R" are each independently hydrogen, a C$_1$-C$_5$ alkyl, C$_2$-C$_5$ alkenyl, C$_2$-C$_5$ alkynyl, or aryl group.

As is customary and well known in the art, hydrogen atoms are not always explicitly shown on chemical structures, for example, hydrogen atoms bonded to the carbon atoms of aromatic, heteroaromatic, and alicyclic rings are not always explicitly shown.

The description of the disclosure herein should be construed in congruity with the laws and principals of chemical bonding. For example, it may be necessary to remove a hydrogen atom in order accommodate a substituent at any given location. Furthermore, it is to be understood that definitions of the variables (i.e., "R groups"), as well as the bond locations of the generic formula of the invention (i.e., Formula I or Formula II), will be consistent with the laws of chemical bonding known in the art. It is also to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

The compounds of this invention may include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof.

Schemes 1-7, Methods A, B, C and D and Examples 1-5 illustrate exemplary synthetic methods for preparation of hydrazone compounds of the formulas herein. In view of the information provided herein and what is well known in the art, one of ordinary skill in the art can prepare the full range of compounds of the invention with no more than routine adaptation of such methods employing known starting materials and reagents and without resort to undue experimentation.

It will also be noted that the substituents of some of the compounds of this invention include isomeric cyclic structures. It is to be understood accordingly that constitutional isomers of particular substituents are included within the scope of this invention, unless indicated otherwise. Constitutional isomers are compounds that have the same molecular formula and different connectivity. For example, the term "tetrazole" includes tetrazole, 2H-tetrazole, 3H-tetrazole, 4H-tetrazole and 5H-tetrazole.

U.S. provisional application 62/417,414, filed Nov. 4, 2016 is incorporated by reference herein in its entirety. U.S. provisional application 62/489,160, filed Apr. 24, 2017 is incorporated by reference herein in its entirety. Kawato et al. (2000) Chem Rev 100:1777-1788 is incorporated by reference herein in its entirety for descriptions of certain applications of photochromic materials in data storage. Piard et al, (2009) New J. Chem. 33:1420-1426 is incorporated by reference herein in its entirety herein as an example of photoswitching in the solid state. Each of the following is incorporated by reference herein with respect to fluorescence switching in solution and its applications: Hofmann et al. (2005) PNAS 102:17565-17569; Betzig et al. (2006) Science 313:1642-1645; Bates et al. (2007) Science 317: 1749-1753; and Roubinet et al. (2016) Angew. Chem. Int'l Ed. 55:15429-15433. Qian, H.; Aprahamian, I. *Chem. Commun.* 2015, 51, 11158-11161 is incorporated by reference herein in its entirety at least for methods of synthesis that can be applied and or readily adapted by choice of starting materials to synthesis of compounds herein. Qian H.; Pramanik, S.; Aprahamian, I. (June 2017) J. Amer. Chem. Soc. 139:9140-9143 is incorporated by reference herein in its entirety at least for descriptions of synthesis, properties and applications of photochromic hydrazone switches with extremely long thermal half-lives.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately.

When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Isotopic variants of the compounds disclosed herein are part of the invention. Isotopic variants include those in which one or more hydrogens are substituted with deuterium or tritium. Isotopic variants include those in which one or more carbons, nitrogens, oxygens or fluorines are substituted at least in part with one or more stable isotopes such that the isotopic content of a given chemical species is different from the isotopic natural abundance. Isotopic variants of compounds of the invention are useful for example in biological assays and as isotopic labels.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein. Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1. Synthesis of Compounds 14-Z and 14-E

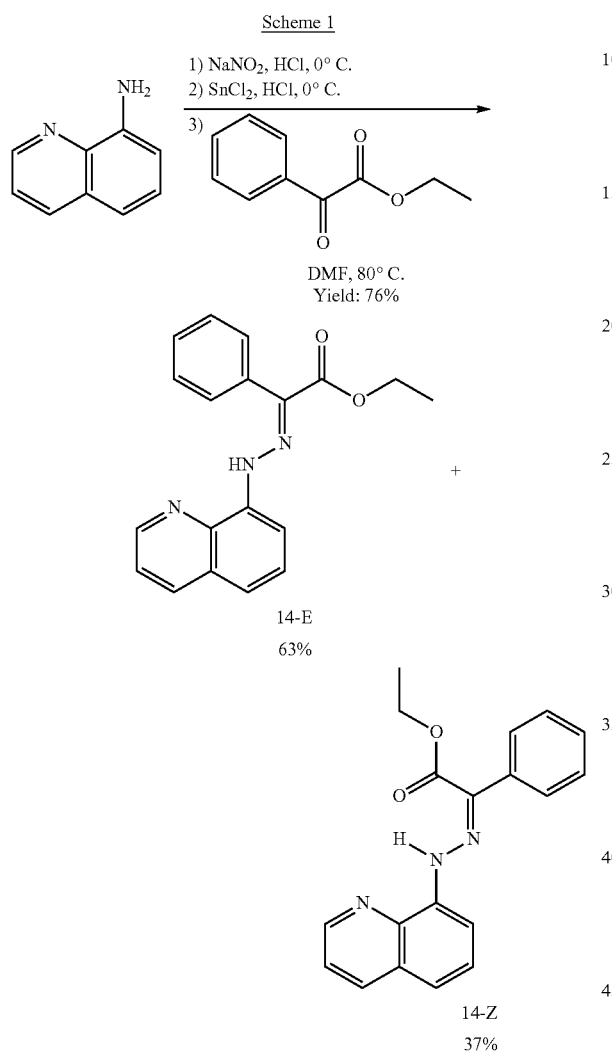

As shown in Scheme 1, a pre-cooled solution of sodium nitrite (NaNO$_2$, 1.0 equiv, 0.172 g, 2.5 mmol) in 0.8 mL water was added dropwise to a solution of 8-aminoquinoline (0.36 g, 2.5 mmol) in 20% HCl (4.5 mL) over a period of 30 min, followed by 1 h stirring at 0° C. Then a solution of tin chloride (SnCl$_2$, 2 equiv, 0.95 g, 5 mmol) in 37% HCl (3 mL) was added dropwise to the above solution at 0° C. The reaction mixture was warmed and left to stir at r.t. for 1 h. Ethyl phenylglyoxylate (1 equiv, 0.40 mL) in dimethylformamide (DMF, 6 mL) was then added to the obtained crude hydrazone crude. After 1 h of heating at 80° C., the reaction mixture was cooled to r.t., followed by neutralization using a saturated bicarbonate solution. The suspension mixture was diluted with water, and extracted with CH$_2$Cl$_2$. The obtained organic phase was further washed with bicarbonate and brine, and dried over MgSO$_4$. The solvent was removed under reduced pressure and the residue was subject to silica gel column chromatography using 20:1 hexanes/ethyl to afford 14-E as a pale solid and 14-Z as a yellow solid, respectively (overall yield: 274 mg, 74%, 14-E/14-Z=1.7/1). NMR characterization of these compounds and comparison to related compounds is provided in Qian H.; Pramanik, S.; Aprahamian, I. (June 2017) J. Amer. Chem. Soc. 139:9140-914 which is incorporated by reference herein at least for this characterization and comparison.

Example 2: General Synthetic Routes for Replacing the Hydrogen Bond Acceptor in Photochromic Hydrazones General strategy for obtaining various carbonyl containing functional groups.

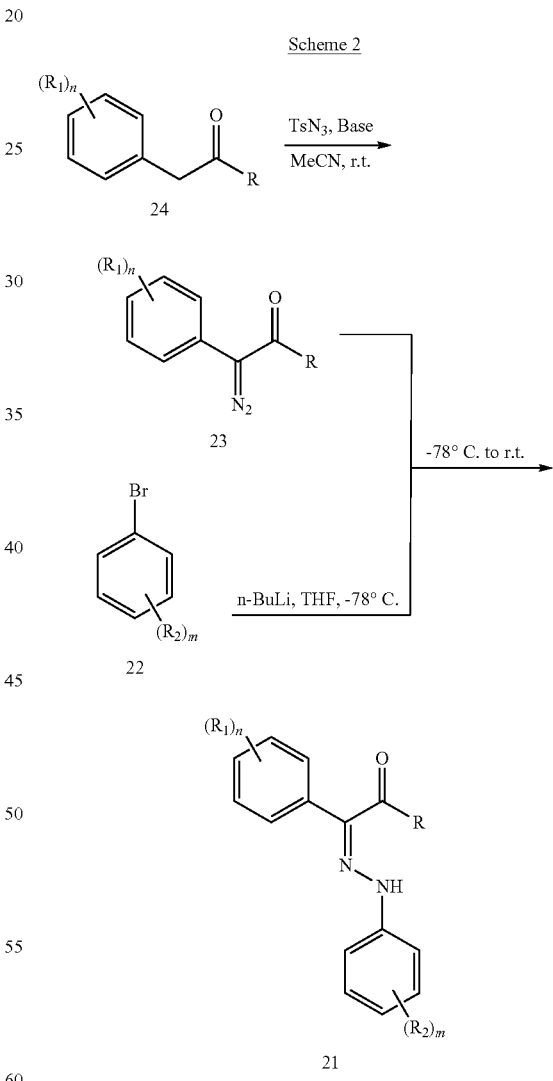

R = R', OR', -NHR', -N(R')$_2$, -SR', for example

Compound 24 is either commercial available, or can be synthesized through one step condensation between carboxylic acid and corresponding amine, alcohol, and thiol. Base (3 equiv) is added dropwise to a solution of compound 24 (1 mmol) and p-toluenesulfonyl azide (TsN$_3$) (1.5 equiv) in MeCN at 0° C. (Scheme 2). The reaction mixture is then stirred at r.t. for 12 hours to afford crude compound 23, which can be purified using silica gel column chromatography. [Liu, G.; Li, J.; Qiu, L.; Liu, L.; Xu, G.; Ma, B.; Sun, J. Org. Biomol. Chem. 2013, 11, 5998-6002] The aryllithium is prepared from the corresponding aryl bromide 22 (1 mmol) and butyllithium (1.1 equiv) in dry tetrahydrofuran (THF) at −78° C. The lithiated compound (1.1 equiv) is then added dropwise to the pre-cooled diazo compound 23 (1 mmol) at −78° C. in dry THF. The reaction mixture is stirred at −78° C. for hours then at r.t. for overnight. The reaction mixture is concentrated under vacuum, and dissolved in methylene chloride. The organic mixture can then be washed with sodium bicarbonate, water, and brine, and after evaporating the organic solvent, the crude produce is subjected to silica gel column chromatography to afford the appropriate hydrazone (21).

General Strategy for Obtaining Switches with Aldehyde as H-Bond Acceptor

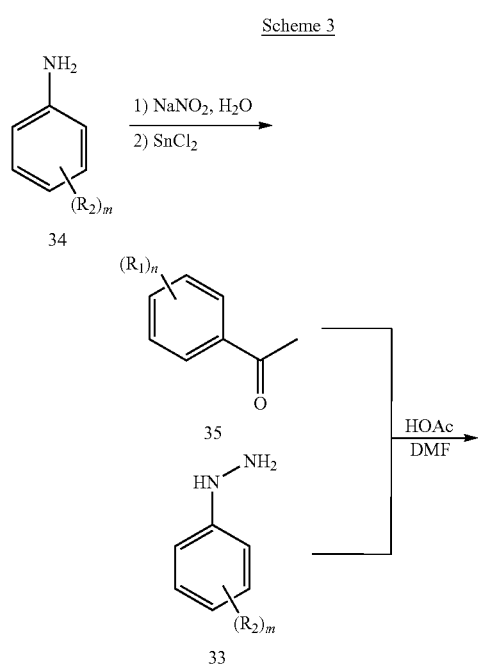

Scheme 3

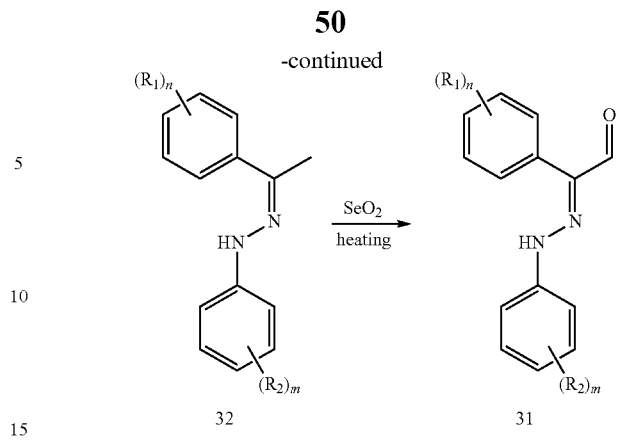

A pre-cooled solution of sodium nitrite (NaNO$_2$, 1.0 equiv) in 0.8 mL water is added dropwise to a solution of compound 34 (2.5 mmol) in 20% HCl (4.5 mL) over a period of 30 min, followed by 1 h stirring at 0° C. (Scheme 2). Then a solution of tin chloride (SnCl$_2$, 2 equiv) in 37% HCl (3 mL) is added dropwise to the solution. The reaction mixture is then warmed up and left to stir at r.t. for 1 h. A solution of compound 35 (1 equiv) in dimethylformamide (DMF, 6 mL) is then added to the obtained crude hydrazone 33. After stirring for 1 h at r.t., the reaction mixture is neutralized using saturated bicarbonate. The suspension mixture is then diluted with water, and extracted with CH$_2$Cl$_2$. The obtained organic phase is further washed with bicarbonate and brine, and dried over MgSO$_4$. The solvent is finally removed under reduced pressure and the residue subjected to silica gel column chromatography to afford compound 32. Compound 22 (1 mmol) and SeO$_2$ (2 equiv) are dissolved in dioxane solution, followed by heating at 90° C. for overnight. The resulting mixture is filtered over Celite, and subject to silica gel column chromatography to afford compound 31.

General Strategy for Obtaining Switches with Acid, Acyl Halides and Acid Anhydrides as H-Bond Acceptor

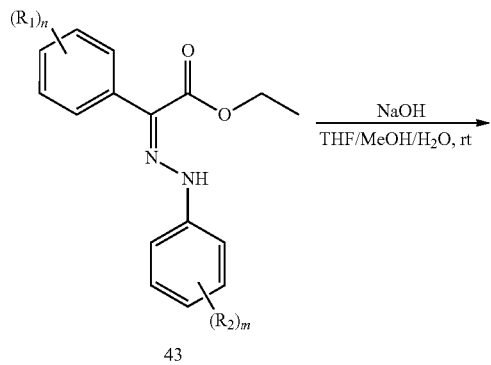

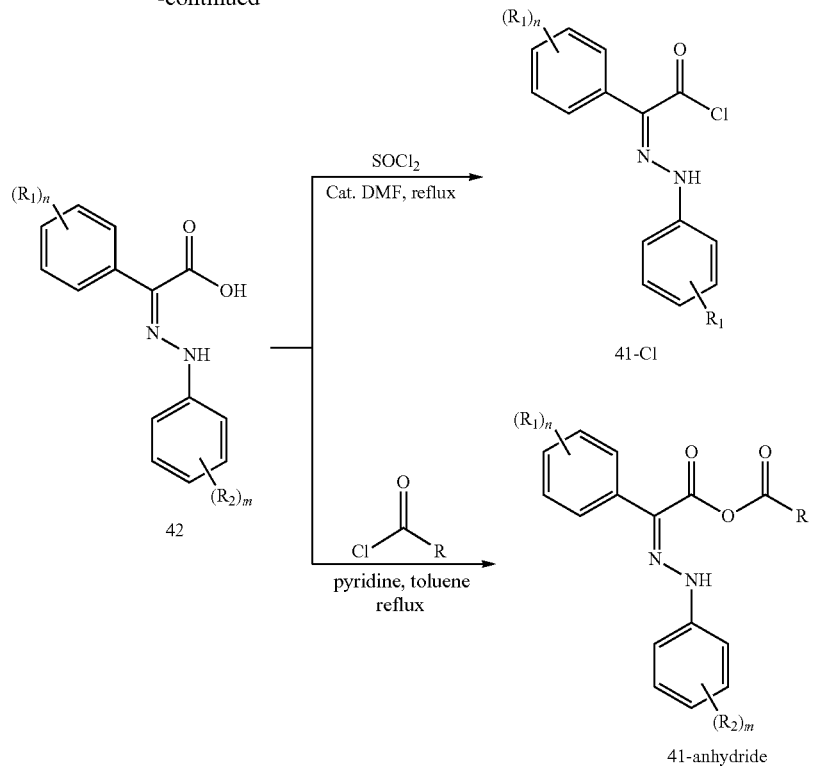

Preparation of 42: A solution of NaOH (1.2 eq. to ester group) in water (3 ml) is added to a solution of 43 in THF/MeOH (3 ml/3 ml). The mixture is stirred at room temperature overnight and then water is added. The pH of the solution is adjusted to 6 with 1M HCl. This leads to the precipitation of 42, which is then filtered and collected as a yellow solid.

Preparation of 41-Cl: The obtained acid 42 (1 mmol) is added to a flame-dried flask, followed by addition of $SOCl_2$ (10 ml) and catalytic amount of DMF. The solution is then heated to reflux for 1-2 hours and cooled down to room temperature afterwards. The solvent is removed under vacuum to afford the targeted hydrazone bearing an acyl chloride group.

Preparation of 41-Anhydride: Hydrazone 42, pyridine (1.3 equiv.) and appropriate acid chloride (1 equiv.) are dissolved in toluene (10 ml). The resulting mixture is refluxed for 12 h. After cooling down to room temperature, the mixture is washed with 1M HCl. The aqueous layer is extracted with $CHCl_3$. The combined organic layers are then dried over $Na_2SO_4$ and evaporated under vacuum. The crude product is subjected to silica gel column chromatography (EtOAc/hexane) to afford the targeted anhydride.

Example 3: Exemplary Synthesis of Macrocycles

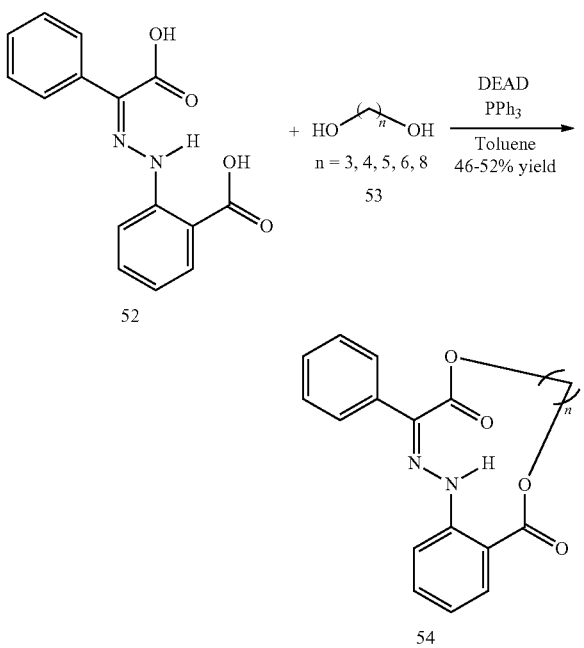

In Scheme 5, n can be any integer >2, but preferably n is 2-12 or 2-8, or 2-6. More specifically n is 3, 4, 5, 6 or 8. A solution of bis-acid 52 (0.18 mmol), diol 53 (0.18 mmol) in toluene/THF (28 mL/2 mL) is added dropwise via a syringe pump to a solution of PPh₃ (184 mg), DEAD (0.11 mL) in toluene (15 mL) over 3 h at 0° C. The mixture is stirred at 0° C., and allowed to reach room temperature overnight. After removal of the solvent in vacuum, the product macrocycle 54 is purified by flash column chromatography.

When the hydrazone switches are incorporated into a macrocycle, their half-lives are modulated from years to days depending on the size of the macrocycle; the smaller the macrocyclic ring the faster the process indicating that strain is accelerating isomerization. Also, their solid emission properties vary with the size of the ring (see FIGS. 68A-68F) below; Samples were irradiated with 365 nm using the TLC lamp).

Example 5: Hydrazone Synthesis from Diazo Precursors

Scheme 6 illustrates hydrazone syntheses starting from diazo precursors. a) Synthesis of diazo fragment using ethyl α-keto ester or its derivatives as starting materials; b) Synthesis of diazo fragment using ethyl phenylacetate or its derivatives as starting material; c) Synthesis of hydrazones via coupling of diazo moiety with lithium reagents or Grignard reagents.

Scheme 6

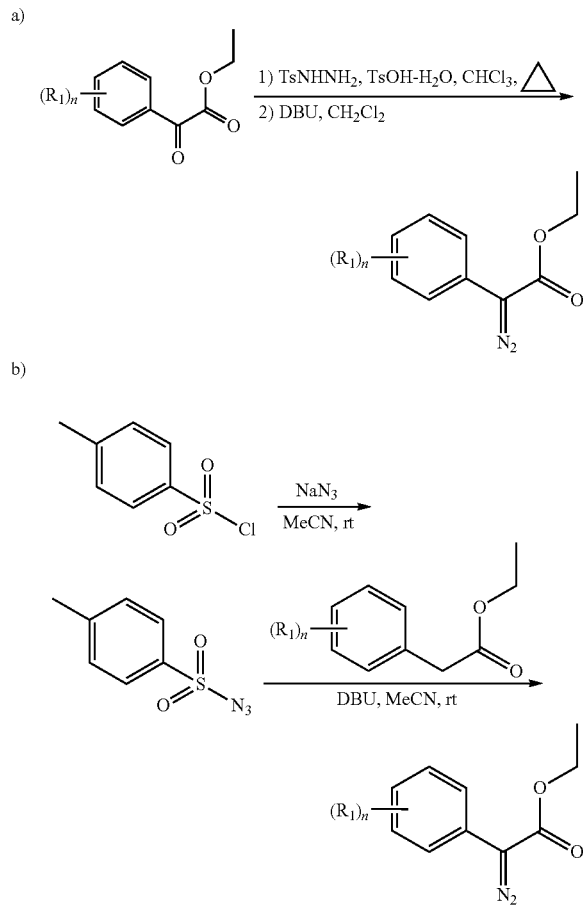

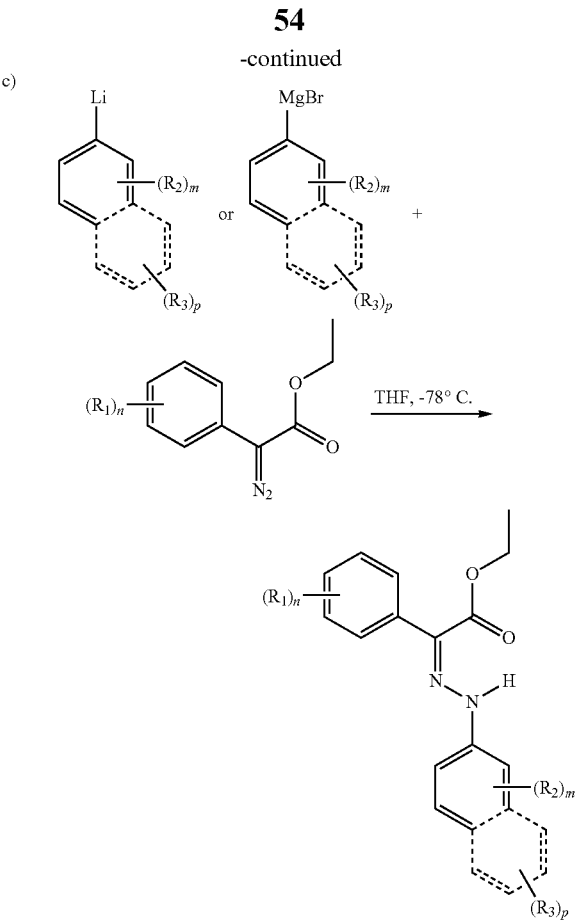

Method D: Steps a and b of Scheme 6 exemplary methods for making diazo precursors. a) TsNHNH₂ (1.5 equiv.) and TsOH.H₂O (0.1 equiv) are added to a solution of α-keto ester or its derivatives (1 equiv.) in CHCl₃. The reaction mixture is refluxed for 5 h. After cooling to room temperature, the solvent is evaporated under reduced pressure and the resulting crude product is dissolved in DCM. DBU (1.5 equiv.) is then added and the reaction mixture is stirred at room temperature for another 2 h. The reaction mixture is washed with saturated ammonium chloride aqueous solution, saturated aqueous sodium bicarbonate, and brine in sequence. The organic layer is dried with anhydrous Na₂SO₄. After removal of the solvent under reduced pressure, the crude product is subjected to column chromatography.

b) NaN₃ (1.7 equiv.) is added to a solution of p-toluensulfonyl chloride (1.5 equiv.) in MeCN, followed by 1-2 hours stirring at room temperature. The reaction mixture is then cooled to 0° C., and DBU (1.5 equiv.) and ethyl 2-phenylacetate or its derivatives (1 equiv.) are added, and the reaction is left to warm up back to room temperature. The reaction mixture is washed with saturated ammonium chloride aqueous solution, saturated aqueous sodium bicarbonate, and brine in sequence. The organic layer is dried over anhydrous Na₂SO₄. After removal of the solvent under reduced pressure, the crude product is subjected to column chromatography.

Step c generates the hydrazone of the invention by reaction of the diazo precursor. c) Lithium reagents: n-BuLi (1.7 equiv.) is added dropwise to a flame-dried flask of bromobenzene or its derivatives (1.5 equiv.) in THF at −78° C., and the solution is left to stir for 30 min. The diazo compound (1.0 equiv.) dissolved in THF is then added dropwise to the lithium reagent, and the solution is stirred for 1 hour. Then reaction is then left to reach room temperature and stirred for another 2 hours. The reaction is quenched with ammonium chloride aqueous solution. The mixture is diluted with water, and extracted with $CH_2Cl_2$. The organic layer is separated and washed with brine. After removal of the solvent under reduced pressure, the crude product is subjected to column chromatography.

Grignard reagents: The Grignard reagent of benzene or its derivatives (1.1 equiv.) is added dropwise to a flame-dried flask containing the diazo compound (1.0 equiv.) dissolved in THF and cooled to −78° C. The solution is left to stir for 30 min and then left to warm up to room temperature, at which point it is stirred for another 2 hours. The reaction mixture is subsequently quenched with ammonium chloride aqueous solution and the mixture diluted with water, and extracted with $CH_2Cl_2$. The organic layer is separated and washed with brine. After removal of the solvent under reduced pressure, the crude compound is subjected to column chromatography.

General synthetic approach for photochromic hydrazone switches.

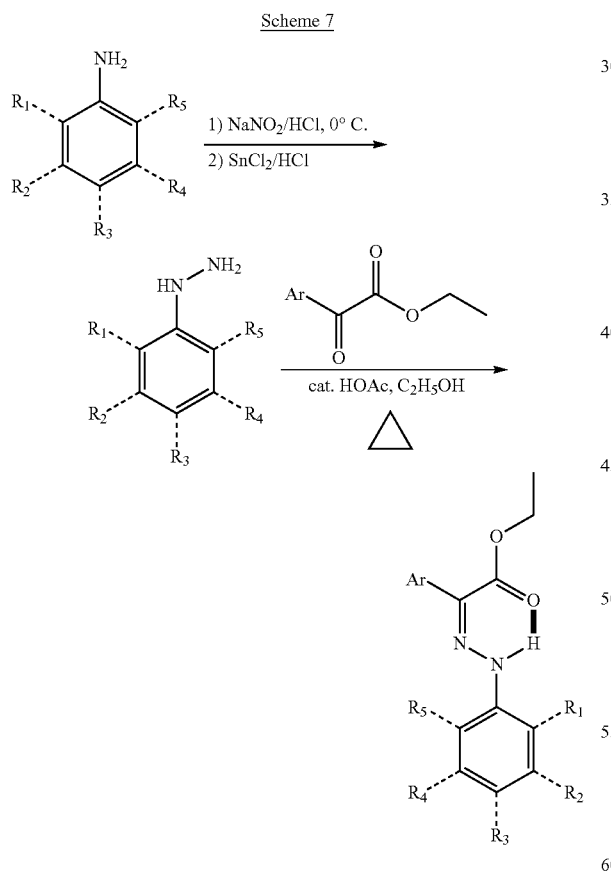

Scheme 7

Method A: Photochromic hydrazone switches are directly synthesized from the corresponding α-keto ester and phenylhydrazine derivatives using a modified reported procedures. [Qian, H.; Aprahamian, I. *Chem. Commun.* 2015, 51, 11158-11161.] Phenylhydrazine derivatives (1 mmol) and catalytic amount of acetic acid (HOAc) are added to an ethanol solution of α-keto ester (1 equiv.) derivatives under $N_2$ atmosphere. The resulting mixture is stirred and refluxed for 3 hrs, and then cooled to room temperature. Ethanol is removed under vacuum. The crude residue is redissolved in methylene chloride, washed with water, saturated sodium bicarbonate, and brine, dried over magnesium sulfate, and subject to column chromatography.

Method B: In this method, the hydrazone switches are synthesized from the corresponding α-keto ester and aniline derivatives. A pre-cooled solution of sodium nitrite ($NaNO_2$, 1.0 equiv) in water is added dropwise to a solution of aniline derivatives (1 mmol) in 20% HCl over a period of 30 min, followed by 1 h stirring at 0° C. Then a solution of tin chloride ($SnCl_2$, 2 equiv) in 37% HCl is added dropwise to the solution. The reaction mixture is warmed up and left to stir at r.t. for 1 h. Phenylhydrazine crude solutions are immediately used in following condensation reaction with α-keto ester derivatives, according to Method A.

Example 5: Syntheses of Certain Exemplary Compounds

With respect to synthetic methods herein, all reagents and starting materials are purchased from commercial vendors and used as supplied unless otherwise indicated. Fetal bovine serum is stored at −20° C. before usage. All experiments are conducted in air unless otherwise noted. Compounds are purified by column chromatography using silica gel (SiliCycle®, 60 Å, 230-400 mesh) as stationary phase and solvent mixtures used during chromatography are reported as volume ratios unless otherwise noted. Deuterated solvents are purchased from Cambridge Isotope Laboratories, Inc. and used as received. $^1$H NMR, $^{13}$C NMR and 2D NMR spectra are recorded on a 500 or 600 MHz NMR spectrometer, with working frequencies of 500.13 or 600.13 MHz for $^1$H nuclei, and 125.8 or 150.9 MHz for $^{13}$C nuclei, respectively. Chemical shifts are quoted in ppm relative to tetramethylsilane (TMS), using the residual solvent peak as the reference standard. ESI mass spectra are obtained on a Shimadzu LCMS-8030 mass spectrometer. Melting points are measured on an Electrothermal Thermo Scientific IA9100X1 digital melting point instrument. UV-Vis spectra are recorded on a Shimadzu UV-1800 UV-Vis spectrophotometer.

1

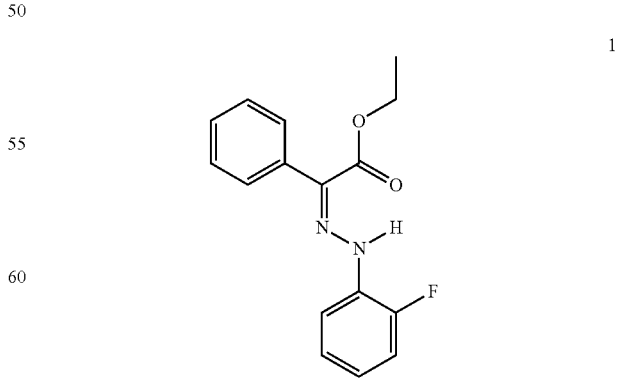

This compound was synthesized following procedure A, while using ethyl phenylglyoxylate and 2-fluorophenylhydrazine hydrochloride as the starting materials. 1 was obtained as a light yellow powder; yield 77%. m.p. 78.0-78.9° C.; $^1$H NMR (600 MHz, CD$_3$CN) δ 12.33 (s, 1H), 7.73-7.68 (m, 2H), 7.66 (t, J=8.4 Hz, 1H), 7.46-7.36 (m, 3H), 7.21-7.17 (m, 2H), 7.03-6.96 (m, 1H), 4.37 (qd, J=7.1, 1.3 Hz, 2H), 1.34 (t, J=7.1 Hz, 3H) ppm; $^{13}$C NMR (151 MHz, CD$_3$CN) δ 164.41, 152.37, 150.78, 137.27, 128.93, 128.86, 126.19, 126.12, 123.10, 123.05, 116.25, 116.14, 115.64, 115.63, 62.45, 14.33 ppm; ESI-MS: m/z found [M-H$^+$] for C$_{16}$H$_{16}$N$_2$O$_2$F$^+$ 287.15 (calcd. 287.12).

2

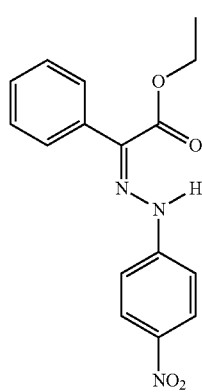

This compound was synthesized following procedure A, while using ethyl phenylglyoxylate and 4-nitrophenylhydrazine hydrochloride as the starting materials. 2 was obtained as a yellow crystalline powder; yield 83%. m.p. 185.0-185.7° C.; $^1$H NMR (600 MHz, CD$_3$CN) δ 12.13 (s, 1H), 8.23 (d, J=9.3 Hz, 2H), 7.76-7.71 (m, 2H), 7.48-7.43 (m, 5H), 4.41 (q, J=7.1 Hz, 2H), 1.35 (t, J=7.1 Hz, 3H) ppm; $^{13}$C NMR (151 MHz, CD$_3$CN) δ 163.53, 149.50, 136.29, 134.19, 129.88, 129.70, 129.20, 129.13, 128.62, 126.27, 114.16, 62.45, 13.85 ppm; ESI-HRMS: m/z found [M-H+] for C$_{16}$H$_{16}$N$_3$O$_4$$^+$ 314.1144 (calcd. 314.1141).

3

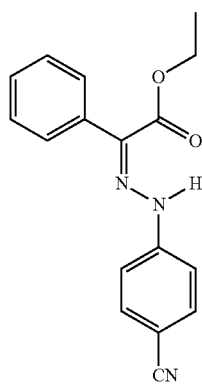

This compound was synthesized following procedure A, while using ethyl phenylglyoxylate and 4-cyanophenylhydrazine hydrochloride as the starting materials. 3 was obtained as a beige crystalline powder; yield 78%. m.p. 162.4-162.6° C.; $^1$H NMR (600 MHz, CD$_3$CN) δ 12.08 (s, 1H), 7.71 (d, J=6.8 Hz, 2H), 7.67 (d, J=8.5 Hz, 2H), 7.49-7.37 (m, 5H), 4.39 (q, J=7.1 Hz, 2H), 1.34 (t, J=7.1 Hz, 3H) ppm; $^{13}$C NMR (151 MHz, CD$_3$CN) δ 163.61, 147.64, 136.47, 134.30, 132.98, 129.18, 128.90, 128.56, 119.84, 114.82, 104.56, 62.29, 13.86 ppm; ESI-MS: m/z found [M-Na$^+$] for C$_{17}$H$_{15}$N$_3$O$_2$Na$^+$ 316.15 (calcd. 316.11).

4

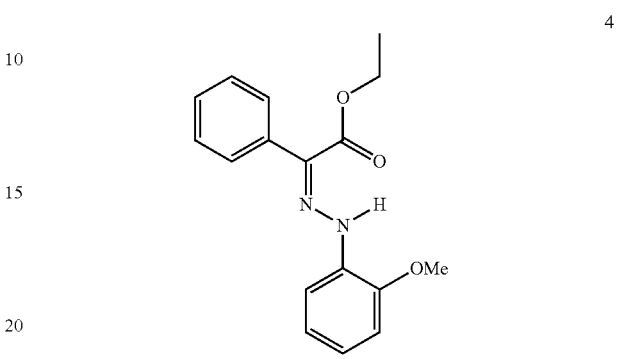

This compound was synthesized following method A, while using ethyl phenylglyoxylate and (2-methoxy-phenyl)-hydrazine hydrochloride as the starting materials. 4 was obtained as a bright yellow crystalline powder; yield 68%. m.p. 57.6-58.0° C.; $^1$H NMR (600 MHz, CD$_3$CN) δ 12.41 (s, 1H), 7.70 (dt, J=8.4, 1.8 Hz, 2H), 7.62-7.54 (m, 1H), 7.45-7.39 (m, 2H), 7.38-7.34 (m, 1H), 7.07-6.98 (m, 3H), 4.38 (q, J=7.1 Hz, 2H), 3.96 (s, 3H), 1.35 (t, J=7.1 Hz, 3H) ppm; $^{13}$C NMR (151 MHz, CD$_3$CN) δ 138.70, 138.56, 137.41, 133.16, 129.22, 128.45, 128.39, 128.15, 122.72, 121.99, 113.33, 111.60, 61.71, 56.21, 13.97 ppm; ESI-MS: m/z found [M-H$^+$] for C$_{17}$H$_{19}$N$_2$O$_3$$^+$ 299.15 (calcd. 299.14).

5

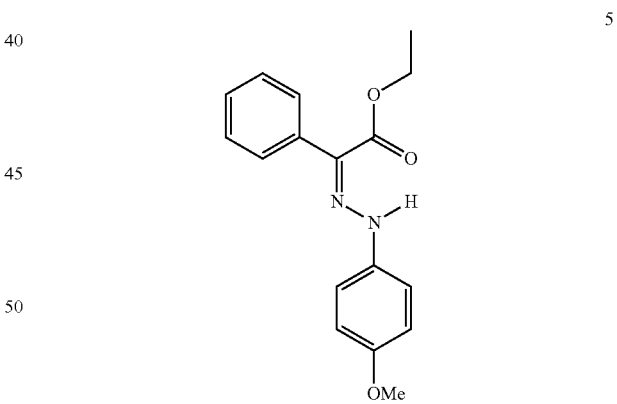

5: This compound was synthesized following method A, while using ethyl phenylglyoxylate and 4-dimethoxyaniline hydrochloride as the starting materials. 5 was obtained as a yellow powder; yield 52%. m.p. 60.9-61.7° C.; $^1$H NMR (600 MHz, CD$_3$CN) δ 12.38-12.16 (m, 1H), 7.74-7.63 (m, 2H), 7.44-7.39 (m, 2H), 7.37-7.33 (m, 1H), 7.31-7.25 (m, 2H), 7.00-6.89 (m, 2H), 4.35 (q, J=7.1 Hz, 2H), 3.79 (s, 3H), 1.33 (t, J=7.1 Hz, 3H) ppm; $^{13}$C NMR (151 MHz, CD$_3$CN) δ 164.11, 156.15, 137.81, 137.49, 129.11, 128.38, 127.92, 115.90, 115.25, 61.53, 55.74, 13.98 ppm; ESI-MS: m/z found [M-H$^+$] for C$_{17}$H$_{19}$N$_2$O$_3$$^+$ 299.15 (calcd. 299.14).

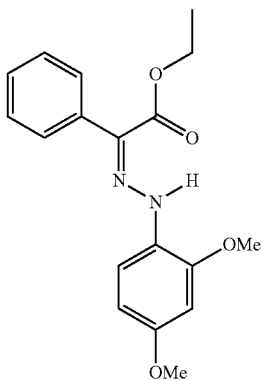

6

6: This compound was synthesized following method B, while using ethyl phenylglyoxylate and 2,4-dimethoxyaniline as the starting materials. 6 was obtained as a bright yellow crystalline powder; yield 7%. m.p. 129.9-130.9° C.; $^1$H NMR (600 MHz, CD$_3$CN) δ 12.40 (s, 1H), 7.72-7.66 (m, 2H), 7.49 (d, J=8.8 Hz, 1H), 7.43-7.38 (m, 2H), 7.37-7.32 (m, 1H), 6.65 (d, J=2.6 Hz, 1H), 6.57 (dt, J=6.0, 3.0 Hz, 1H), 4.36 (q, J=7.1 Hz, 2H), 3.95 (s, 3H), 3.80 (s, 3H), 1.34 (t, J=7.1 Hz, 3H) ppm; $^{13}$C NMR (151 MHz, CD$_3$CN) δ 164.12, 156.56, 148.30, 137.64, 129.17, 128.35, 127.87, 127.10, 114.05, 105.83, 99.58, 61.50, 56.35, 55.83, 14.01 ppm; ESI-MS: m/z found [M-Na$^+$] for C$_{18}$H$_{20}$N$_2$O$_4$Na$^+$ 351.15 (calcd. 351.13).

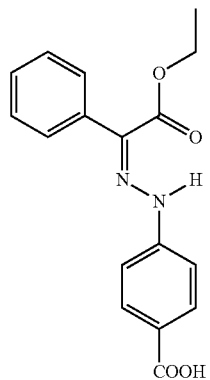

7

7: This compound was synthesized following method A, while using ethyl phenylglyoxylate and 4-hydrazinobenzoic acid as the starting materials. 7 was obtained as a beige powder; yield 71%. m.p. 258.3-258.9° C.; $^1$H NMR (600 MHz, DMSO) δ 12.55 (s, 1H), 11.59 (s, 1H), 7.90 (d, J=8.7 Hz, 2H), 7.69-7.64 (m, 2H), 7.43 (t, J=7.4 Hz, 2H), 7.41-7.35 (m, 3H), 4.40 (q, J=7.1 Hz, 2H), 1.32 (t, J=7.1 Hz, 3H) ppm; $^{13}$C NMR (151 MHz, DMSO) δ 167.55, 163.24, 147.80, 135.62, 132.96, 131.52, 128.76, 128.71, 127.88, 123.72, 113.72, 61.99, 14.36 ppm; ESI-MS: m/z found [M-H$^+$] for C$_{17}$H$_{17}$N$_2$O$_4^+$ 313.15 (calcd. 313.12).

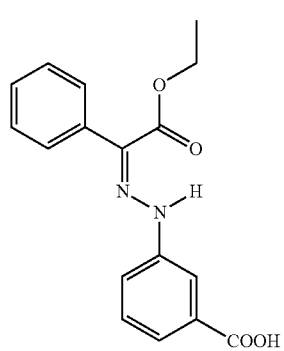

8

This compound was synthesized following method A, while using ethyl phenylglyoxylate and 3-hydrazinobenzoic acid as the starting materials. 8 was obtained as a yellow powder; yield 72%. m.p. 180.1-180.6° C.; $^1$H NMR (600 MHz, CD$_3$CN) δ 12.15 (s, 1H), 9.48 (s, 1H), 7.96-7.84 (m, 1H), 7.72-7.67 (m, 2H), 7.64 (d, J=7.6 Hz, 1H), 7.56 (dd, J=8.1, 1.4 Hz, 1H), 7.49-7.42 (m, 3H), 7.42-7.37 (m, 1H), 4.38 (q, J=7.1 Hz, 2H), 1.34 (t, J=7.1 Hz, 3H) ppm; $^{13}$C NMR (151 MHz, CD$_3$CN) δ 167.13, 163.83, 144.47, 142.99, 137.03, 131.83, 130.65, 130.18, 129.17, 128.50, 128.46, 123.73, 119.18, 115.32, 61.93, 13.92 ppm; ESI-MS: m/z found [M-H$^+$] for C$_{17}$H$_{17}$N$_2$O$_4^+$ 313.15 (calcd. 313.12).

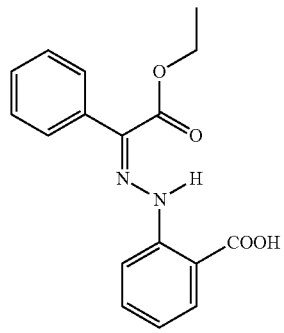

9

This compound was synthesized following method A, while using ethyl phenylglyoxylate and 2-hydrazinobenzoic acid hydrochloride as the starting materials. 9 was obtained as a yellow crystalline powder; yield 98%. m.p. 172.4-173.1° C.; $^1$H NMR (600 MHz, DMSO) δ 13.47 (s, 1H), 7.93 (dd, J=7.9, 1.4 Hz, 1H), 7.86-7.80 (m, 1H), 7.72-7.67 (m, 2H), 7.58 (t, J=7.8 Hz, 1H), 7.43 (t, J=7.5 Hz, 2H), 7.38 (t, J=8.3, 6.2 Hz, 1H), 7.01 (t, J=7.5 Hz, 1H), 4.40 (q, J=7.1 Hz, 2H), 1.34 (t, J=7.1 Hz, 3H) ppm; $^{13}$C NMR (151 MHz, DMSO) δ 169.21, 162.39, 145.95, 136.17, 134.84, 131.80, 129.60, 129.19, 129.16, 128.60, 128.56, 128.38, 120.88, 114.34, 61.86, 14.44 ppm; ESI-MS: m/z found [M-H$^+$] for C$_{17}$H$_{17}$N$_2$O$_4^+$ 313.15 (calcd. 313.12).

11

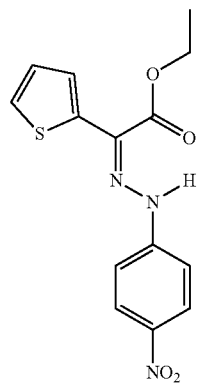

This compound was synthesized following method A, while using ethyl thiophene-2-glyoxylate and 4-nitrophenylhydrazine as the starting materials. 11 was obtained as an orange powder; yield 94%. m.p. 126.2-126.4° C.; $^1$H NMR (600 MHz, toluene-d$_8$) δ 12.24 (s, 1H), 7.90 (d, J=9.2 Hz, 2H), 7.54 (dd, J=3.7, 1.0 Hz, 1H), 6.94 (dd, J=5.1, 1.0 Hz, 1H), 6.84 (dd, J=5.1, 3.8 Hz, 1H), 6.73 (d, J=8.8 Hz, 2H), 3.92 (q, J=7.1 Hz, 2H), 0.99 (t, J=7.1 Hz, 3H) ppm; $^{13}$C NMR (151 MHz, toluene-d) δ 162.11, 147.34, 142.55, 139.94, 137.11, 129.15, 129.07, 127.14, 126.89, 126.26, 125.32, 125.10, 113.23, 61.42, 13.36 ppm; Hi-Res MS (ESI): m/z found [M-H$^+$] for $C_{14}H_{14}N_3O_4S^+$ 320.0705 (calcd. 320.0705).

12

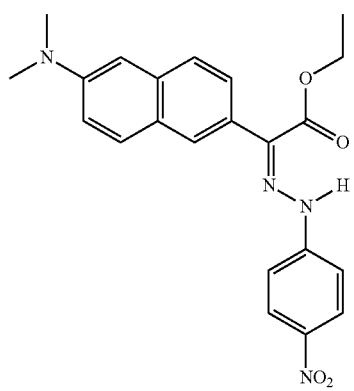

This compound was synthesized following method A, while using ethyl 2-(6-(dimethylamino)naphthalen-2-yl)-2-oxoacetate and 4-nitrophenylhydrazine as the starting materials. 12 was obtained as a dark red crystalline powder; yield 56%. m.p. 205.7-208.1° C.; 1H NMR (500 MHz, CD2Cl2) δ 12.23 (s, 1H), 8.13 (d, J=9.3 Hz, 2H), 7.91 (d, J=1.4 Hz, 1H), 7.69-7.61 (m, 2H), 7.57 (d, J=8.7 Hz, 1H), 7.28 (t, J=6.0 Hz, 2H), 7.11 (dd, J=9.1, 2.6 Hz, 1H), 6.84 (d, J=2.5 Hz, 1H), 4.36 (q, J=7.1 Hz, 2H), 3.00 (s, 6H), 1.31 (t, J=7.1 Hz, 3H) ppm; 13C NMR (126 MHz, CD2Cl2) δ 163.57, 149.29, 148.86, 148.78, 141.79, 134.97, 133.65, 129.28, 128.68, 127.98, 126.23, 125.82, 125.66, 116.34, 114.86, 113.27, 105.50, 100.00, 61.94, 40.40, 29.68, 13.91 ppm; ESI-MS: m/z found [M-H+] for C22H23N4O4+ 407.20 (calcd. 406.16).

13

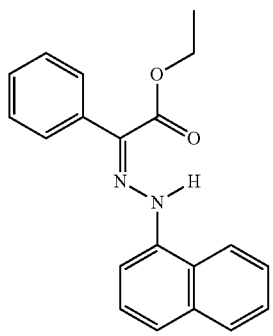

This compound was synthesized following method B, while using ethyl phenylglyoxylate and 1-naphthylamine as the starting materials. 13 was obtained as a dark yellow powder; yield 63%. m.p. 90.7-91.1° C.; 1H NMR (600 MHz, CD3CN) δ 13.09 (s, 1H), 7.86 (dd, J=15.8, 8.3 Hz, 2H), 7.65 (d, J=7.3 Hz, 2H), 7.63 (d, J=7.6 Hz, 1H), 7.55 (t, J=7.6 Hz, 1H), 7.49 (t, J=7.7 Hz, 2H), 7.42 (t, J=7.9 Hz, 1H), 7.34 (t, J=7.4 Hz, 2H), 7.30 (t, J=7.3 Hz, 1H), 4.33 (q, J=7.1 Hz, 2H), 1.26 (q, J=7.3 Hz, 3H) ppm; 13C NMR (151 MHz, CD3CN) δ 164.63, 138.79, 137.27, 134.95, 131.25, 129.49, 129.38, 128.60, 128.54, 127.21, 126.92, 126.82, 122.91, 122.72, 120.09, 109.40, 62.19, 14.10 ppm; Hi-Res MS (ESI): m/z found [M-H+] for C20H19N2O2+ 319.1435 (calcd. 319.1447).

15

This compound was synthesized following method A, while using ethyl 2-(4-(dimethylamino)phenyl)-2-oxoacetate and 4-nitrophenylhydrazine hydrochloride as the starting materials. 15 was obtained as a shiny red crystalline powder; yield 68%. m.p. 171.9-172.1° C.; 1H NMR (500 MHz, CD3CN) δ 11.52 (s, 1H), 8.20 (d, J=9.3 Hz, 2H), 7.71-7.54 (m, 2H), 7.39 (d, J=9.2 Hz, 2H), 6.85-6.72 (m, 2H), 4.42 (q, J=7.1 Hz, 2H), 3.01 (s, 6H), 1.37 (t, J=7.1 Hz, 3H) ppm; 13C NMR (151 MHz, CD3CN) δ 163.92, 151.65, 150.00, 135.92, 129.77, 126.33, 123.32, 113.53, 112.10, 62.40, 40.09, 13.90 ppm; ESI-MS: m/z found [M-H+] for C18H21N4O4+ 357.20 (calcd. 357.16).

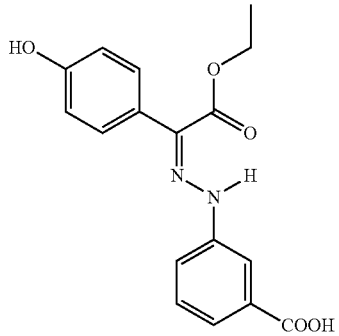

16

This compound was synthesized following method A, while using ethyl ethyl 2-(4-hydroxyphenyl)-2-oxoacetate and 3-hydrazinobenzoic acid as the starting materials. 16 was obtained as a yellow powder; yield 53%. m.p. 71.8-72.2° C.; 1H NMR (600 MHz, CD3CN) δ 11.95 (s, 1H), 7.89 (s, 1H), 7.61 (d, J=6.9 Hz, 1H), 7.54 (d, J=8.4 Hz, 2H), 7.51 (d, J=7.8 Hz, 1H), 7.44 (t, J=7.6 Hz, 1H), 6.86 (d, J=8.4 Hz, 2H), 4.37 (q, J=7.1 Hz, 2H), 1.34 (t, J=7.1 Hz, 3H) ppm; 13C NMR (151 MHz, CD3CN) δ 167.27, 163.96, 158.38, 157.57, 144.67, 131.40, 130.54, 130.13, 123.36, 118.95, 116.55, 115.25, 115.09, 61.88, 13.93 ppm; ESI-MS: m/z found [M-H+] for C18H21N4O4+ 329.15 (calcd. 329.11).

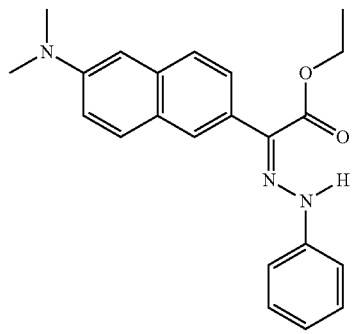

17

This compound was synthesized following method A, while using ethyl 2-(6-(dimethylamino)naphthalen-2-yl)-2-oxoacetate and phenylhydrazine as the starting materials. 17 was obtained as a dark yellow crystalline powder; yield 75%. m.p. 98.3-98.6° C.; 1H NMR (500 MHz, CD3CN) δ 11.97 (s, 1H), 8.01 (d, J=1.5 Hz, 1H), 7.78 (d, J=9.1 Hz, 1H), 7.75 (dd, J=8.7, 1.9 Hz, 1H), 7.68 (d, J=8.7 Hz, 1H), 7.39-7.34 (m, 4H), 7.26 (dd, J=9.1, 2.6 Hz, 1H), 7.04-6.99 (m, 2H), 4.42 (q, J=7.1 Hz, 2H), 3.08 (s, 6H), 1.37 (t, J=7.1 Hz, 3H) ppm; 13C NMR (151 MHz, CD3CN) δ 164.20, 149.76, 144.32, 135.14, 130.45, 130.18, 129.95, 129.60, 127.78, 127.03, 126.60, 126.03, 122.55, 117.06, 114.48, 106.20, 61.81, 40.47, 13.98 ppm; ESI-HRMS: m/z found [M-H+] for C22H24N3O2+ 362.1866 (calcd. 362.1869).

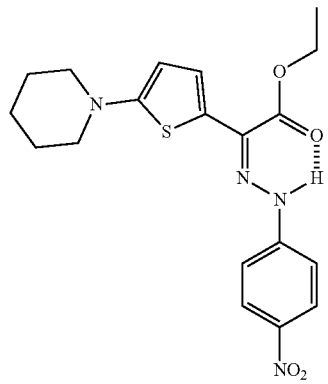

18

This compound was synthesized following procedure A, while using ethyl 2-oxo-2-(5-(piperidin-1-yl)thiophen-2-yl)acetate and 4-nitrophenylhydrazine as the starting materials. 18 was obtained as a dark red solid; yield 25%. m.p. 144.8-145.3 oC.; 1H NMR (600 MHz, toluene-d8) δ 12.01 (s, 1H), 7.93 (d, J=9.2 Hz, 2H), 7.47 (d, J=4.2 Hz, 1H), 6.78 (d, J=8.1 Hz, 2H), 5.90 (d, J=4.2 Hz, 1H), 3.94 (q, J=7.1 Hz, 2H), 3.01-2.97 (m, 4H), 1.41-1.36 (m, 7H), 1.01 (t, J=7.1 Hz, 3H) ppm; 13C NMR (151 MHz, toluene-d8) δ 162.38, 160.86, 147.96, 141.78, 136.89, 125.41, 125.27, 112.63, 103.68, 61.21, 51.13, 29.93, 24.94, 23.54, 13.42 ppm; Hi-Res MS (ESI): m/z found [M-H]– for C19H21N4O4S– 401.1283 (calcd. 401.1284).

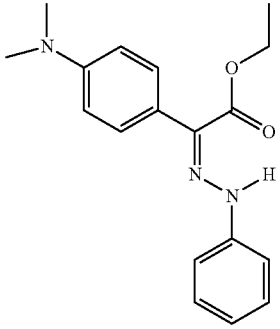

19

Phenylhydrazine (0.1 mL, 1 mmol) and several drops of acetic acid were added to a 50 mL flask containing 3 (0.2 g, 0.9 mmol) dissolved in 30 mL of ethanol. The reaction mixture was then refluxed for 3 hours under nitrogen. After cooling to room temperature, 20 mL of water was added to afford a yellow precipitate, which was collected by filtration and washed with water. The crude residue was subjected to column chromatography using 15:1 hexanes/ethyl acetate as eluent to give hydrazone 19 as a yellow solid (0.23 g, 82%). m.p. 93.1-94.0° C., 1H NMR (500 MHz, CD3CN) δ 11.77 (s, 1H), 7.52 (d, J=9.0 Hz, 2H), 7.34-7.29 (m, 2H), 7.26 (d, J=7.5 Hz, 2H), 6.95 (t, J=7.2 Hz, 1H), 6.74 (d, J=9.0 Hz, 2H), 4.34 (q, J=7.1 Hz, 2H), 2.96 (s, 6H), 1.32 (t, J=7.1 Hz, 3H) ppm; 13C-NMR (151 MHz, CD3CN) δ 164.28, 151.02, 144.51, 130.65, 129.90, 129.78, 122.14, 114.22, 112.88, 112.18, 61.64, 40.23, 14.00 ppm. ESI-HRMS (m/z): [M-H+] calculated for C18H22N3O2: 312.1712, found 312.1707.

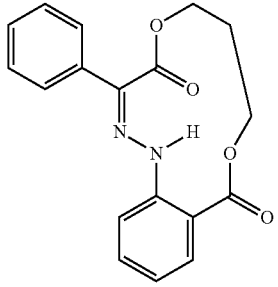

120

This compound was synthesized using method C. After removal of the solvent under reduced pressure, the product was purified by flash column chromatography (silica gel, EtOAc-hexane=1:100→1:50→1:25→15:10→1:6) affording a yellow solid. Yield 44%. m.p. 160.4-161.5° C.; $^1$H NMR (600 MHz, CD$_2$Cl$_2$) δ 13.25 (s, 1H), 7.98 (dd, J=7.8, 1.2 Hz, 1H), 7.82 (d, J=7.2 Hz, 2H), 7.80 (d, J=8.4 Hz, 1H), 7.54 (t, J=7.8 Hz, 1H), 7.41-7.38 (m, 2H), 7.36-7.34 (m, 1H), 6.98 (t, J=7.2 Hz, 1H), 4.65 (t, J=5.1 Hz, 2H), 4.60 (t, J=5.4 Hz, 2H), 2.33 (m, 2H). $^{13}$C NMR (151 MHz, CD$_2$Cl$_2$) δ 165.62, 160.67, 144.35, 135.96, 135.00, 132.87, 132.68, 128.65, 128.50, 127.97, 120.80, 113.79, 113.46, 65.44, 64.98, 27.97. Hi-Res MS (ESI): m/z found [M-H$^+$] for C$_{18}$H$_{17}$N$_2$O$_4$ 325.1184 (calcd. 325.1188).

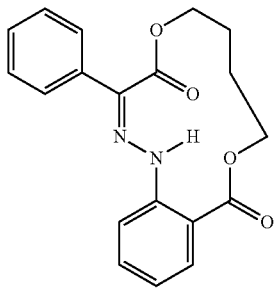

121

This compound was synthesized using method C. After removal of the solvent under reduced pressure, the product was purified by flash column chromatography (silica gel, EtOAc-hexane=1:50→1:30→1:20) affording a yellow solid. Yield 46%. m.p. 147.0-147.7° C.; $^1$H NMR (500 MHz, CD$_2$Cl$_2$) δ 12.37, 8.10 (dd, J=8.0, 2.0 Hz), 7.92 (d, J=9.0 Hz, 1H), 7.79-7.77 (m, 2H), 7.54 (t, J=8.0 Hz, 1H), 7.42-7.39 (m, 2H), 7.37-7.34 (m, 1H), 7.03 (t, J=7.5 Hz, 1H), 4.44-4.39 (m, 4H), 2.12-2.11 (m, 4H). $^{13}$C NMR (151 MHz, CD$_2$Cl$_2$) δ 166.98, 161.70, 144.73, 137.20, 134.90, 133.14, 131.35, 128.93, 128.47, 128.30, 121.39, 115.27, 113.84, 68.14, 68.02, 25.73, 25.57. Hi-Res MS (ESI): m/z found [M-H$^+$] for C$_{19}$H$_{19}$N$_2$O$_4$ 339.1343 (calcd. 339.1345).

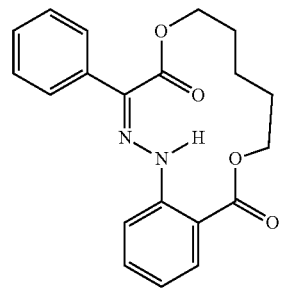

122

This compound was synthesized using method C. After removal of the solvent under reduced pressure, the product was purified by flash column chromatography (silica gel, EtOAc-hexane=1:50→1:30→1:25) affording a yellow solid. Yield 47%. m.p. 115.1-115.5° C.; $^1$H NMR (600 MHz, CD$_2$Cl$_2$) δ 10.82 (s, 1H), 8.03 (dd, J=7.8, 1.2 Hz, 1H), 7.91 (d, J=8.4 Hz, 1H), 7.73 (d, J=7.2 Hz, 1H), 7.53 (t, J=7.8 Hz, 1H), 7.41 (t, J=7.2 Hz, 2H), 7.38-7.35 (m, 1H), 6.98 (t, J=7.2 Hz, 1H), 4.66 (t, J=6.0 Hz, 2H), 4.44 (t, J=5.4 Hz, 2H), 2.00-1.95 (m, 2H), 1.92-1.88 (m, 2H), 1.69-1.64 (m, 2H). $^{13}$C NMR (151 MHz, CD$_2$Cl$_2$) δ 166.89, 163.62, 144.85, 135.34, 135.22, 134.68, 133.00, 129.05, 128.75, 127.21, 120.79, 115.41, 113.96, 65.97, 63.50, 26.79, 25.52, 20.59. Hi-Res MS (ESI): m/z found [M-H$^+$] for C$_{20}$H$_{21}$N$_2$O$_4$ 353.1494 (calcd. 353.1501).

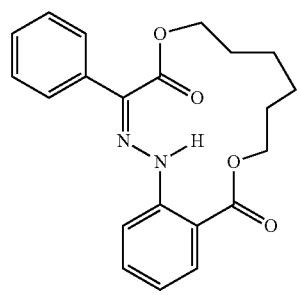

123

This compound was synthesized using method C. After removal of the solvent under reduced pressure, the product was purified by flash column chromatography (silica gel, EtOAc-hexane=1:200→1:100→1:60) affording a yellow solid. Yield 46%. m.p. 86.2-86.9° C.; $^1$H NMR (500 MHz, CD$_2$Cl$_2$) δ 11.32 (s, 1H), 7.95 (dd, J=7.5, 2.0 Hz, 1H), 7.85 (d, J=8.5 Hz, 1H), 7.73-7.70 (m, 2H), 7.51 (t, J=8.5 Hz, 1H), 7.42-7.39 (m, 2H), 7.38-7.35 (m, 1H), 6.97 (t, J=8.0 Hz, 1H), 4.61 (t, J=5.0 Hz, 2H), 4.59 (t, J=5.0 Hz, 2H), 1.79-1.73 (m, 4H), 1.67-1.62 (m, 2H), 1.61-1.55 (m, 2H). $^{13}$C NMR (151 MHz, CD$_2$Cl$_2$) δ 167.37, 164.02, 144.75, 135.67, 135.31, 134.49, 132.37, 128.96, 128.70, 127.33, 120.64, 115.05, 114.49, 66.52, 65.62, 29.46, 29.43, 27.24, 26.22. Hi-Res MS (ESI): m/z found [M-H$^+$] for C$_{21}$H$_{23}$N$_2$O$_4$ 367.1655 (calcd. 367.1658).

124

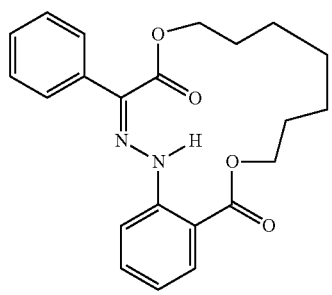

This compound was synthesized using method C. After removal of the solvent under reduced pressure, the product was purified by flash column chromatography (silica gel, EtOAc-hexane=1:100→1:50) affording a yellow oil, that gradually solidified upon standing at room temperature. Yield 37%. m.p. 94.2-95.0° C.; $^1$H NMR (500 MHz, CD$_2$Cl$_2$) δ 12.65 (s, 1H), 7.96 (dd, J=7.5, 1.5 Hz, 1H), 7.89 (d, J=8.5 Hz, 1H), 7.75-7.72 (m, 2H), 7.52 (dt, J=7.5, 1.0 Hz, 1H), 7.42-7.38 (m, 2H), 7.37-7.33 (m, 1H), 6.95 (dt, J=8.0, 1.0 Hz, 1H), 4.67 (t, J=5.0 Hz, 2H), 4.66 (t, J=5.5 Hz, 2H), 1.78-1.73 (m, 4H), 1.64-1.57 (m, 2H), 1.33-1.23 (m, 4H). $^{13}$C NMR (151 MHz, CD$_2$Cl$_2$) δ 167.69, 163.31, 145.87, 135.88, 134.69, 134.15, 131.71, 128.71, 128.55, 127.90, 120.35, 114.39, 113.38, 63.38, 62.54, 28.55, 28.01, 24.96, 24.78, 23.73. Hi-Res MS (ESI): m/z found [M-H$^+$] for C$_{22}$H$_{25}$N$_2$O$_4$ 381.1818 (calcd. 381.1814).

125

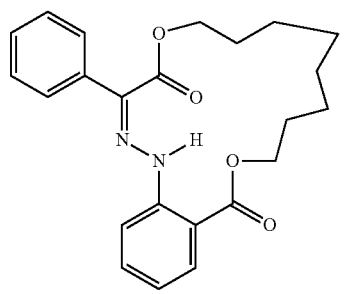

This compound was synthesized using method C. After removal of the solvent under reduced pressure, the product was purified by flash column chromatography (silica gel, EtOAc-hexane=1:250) affording a yellow solid. Yield 52%. m.p. 114.1-115.0° C.; $^1$H NMR (500 MHz, CD$_2$Cl$_2$) δ 12.66 (s, 1H), 7.98 (dd, J=8.0, 1.5 Hz, 1H), 7.92 (d, J=8.5 Hz, 1H), 7.73-7.71 (m, 2H), 7.52 (t, J=8.5 Hz, 1H), 7.41-7.38 (m, 2H), 7.36-7.34 (m, 1H), 6.97 (t, J=8.0 Hz, 1H), 4.53 (t, J=4.0 Hz, 2H), 4.52 (t, J=4.0 Hz, 4.5 Hz, 2H), 1.92-1.87 (m, 2H), 1.87-1.82 (m, 2H), 1.52-1.46 (m, 4H), 1.44-1.40 (m, 2H), 1.38-1.33 (m, 2H). $^{13}$C NMR (151 MHz, CD$_2$Cl$_2$) δ 168.18, 163.19, 146.08, 136.75, 134.60, 133.12, 131.76, 128.52, 128.42, 128.41, 120.62, 115.06, 113.71, 66.32, 64.74, 29.61, 28.92, 27.78, 26.88, 24.33, 24.00. Hi-Res MS (ESI): m/z found [M-H$^+$] for C$_{23}$H$_{27}$N$_2$O$_4$ 395.1965 (calcd. 395.1971).

126

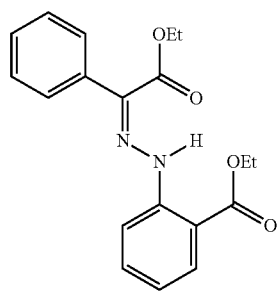

DIAD (76 μL, 2.2 eq.) was added to a solution of bis-acid 2 (50 mg, 0.18 mmol), EtOH (23 μL, 2.2 eq.) and PPh$_3$ (102 mg, 2.2 eq.) in toluene (5 mL) at 0° C. The mixture was then left to stir overnight while it reached room temperature. After removal of the solvent under reduced pressure, the product was purified by flash column chromatography (silica gel, EtOAc-hexane=1:100→1:50) affording a yellow solid (50 mg, 84% yield). m.p. 68.3-69.3° C.; $^1$H NMR (600 MHz, CD$_2$Cl$_2$) δ 13.78 (s, 1H), 8.01 (dd, J=8.4, 1.2 Hz, 1H), 7.92 (d, J=8.4 Hz, 1H), 7.69 (d, J=7.2 Hz, 1H), 7.52 (dt, J=8.4, 1.2 Hz, 1H), 7.41-7.38 (m, 2H), 7.36-7.34 (m, 1H), 6.97 (t, J=7.2 Hz, 1H), 4.44 (q, J=7.2 Hz, 2H), 4.41 (q, J=7.2 Hz, 2H), 1.42 (t, J=7.2 Hz, 3H), 1.38 (t, J=7.2 Hz, 3H); $^{13}$C NMR (151 MHz, CD$_2$Cl$_2$) δ 167.64, 162.93, 146.45, 137.00, 134.65, 132.01, 131.37, 128.97, 128.31, 128.29, 120.77, 114.88, 113.36, 61.84, 61.51, 14.52, 14.38. Hi-Res MS (ESI): m/z found [M-H$^+$] for C$_{19}$H$_{21}$N$_2$O$_4$ 341.1506 (calcd. 341.1501).

127

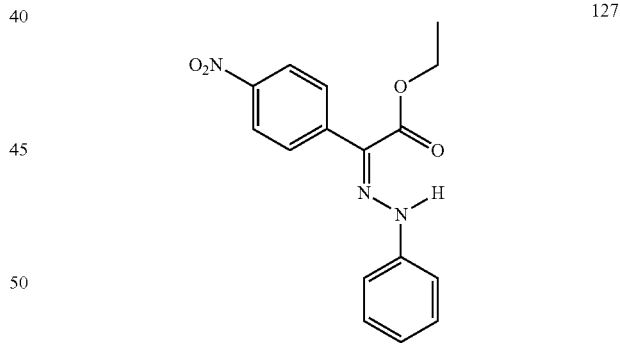

This compound was synthesized using method D, while using ethyl 2-diazo-2-(4-nitrophenyl) acetate and phenylmagnesium bromide as the starting materials. Compound 27 was obtained as a yellow solid. Yield 49%. m.p. 91.3-92.4° C.; $^1$H NMR (600 MHz, CD$_3$CN) δ 12.46 (s, 1H), 8.28-8.21 (m, 2H), 8.02-7.95 (m, 2H), 7.44-7.37 (m, 4H), 7.15-7.06 (m, 1H), 4.41 (q, J=7.1 Hz, 2H), 1.37 (t, J=7.1 Hz, 3H). $^{13}$C NMR (151 MHz, CD$_3$CN) δ 163.49, 143.63, 143.52, 131.66, 130.06, 129.86, 129.67, 123.82, 123.63, 115.19, 62.10, 13.91. ESI-MS: m/z found [M-Na$^+$] for C$_{16}$H$_{15}$N$_3$O$_4$Na$^{30}$ 336.05 (calcd. 336.10)

128

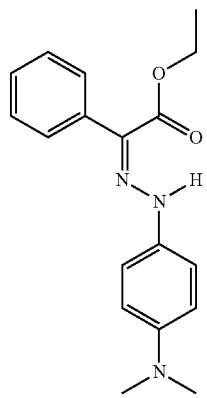

This compound was synthesized using method D, while using ethyl 2-diazo-2-phenylacetate and 4-bromo-N,N-dimethylaniline as the starting materials. Compound 128 was obtained as an orange solid. Yield 85%. m.p. 90.1-91.1° C.; $^1$H NMR (500 MHz, CDCl$_3$) δ 12.45 (s, 1H), 7.59 (m, 2H), 7.32-7.27 (m, 2H), 7.25-7.20 (m, 1H), 7.16-7.12 (m, 2H), 6.72-6.66 (m, 2H), 4.27 (q, J=7.1 Hz, 2H), 2.85 (s, 6H), 1.29 (t, J=7.1 Hz, 3H). $^{13}$C NMR (151 MHz, CD$_3$CN) δ 164.24, 148.05, 137.75, 134.78, 129.63, 129.07, 128.33, 127.65, 115.92, 114.39, 61.32, 40.90, 14.01. ESI-MS: m/z found [M-H$^+$] for C$_{18}$H$_{22}$N$_3$O$_2{}^+$ 312.15 (calcd. 312.17)

129

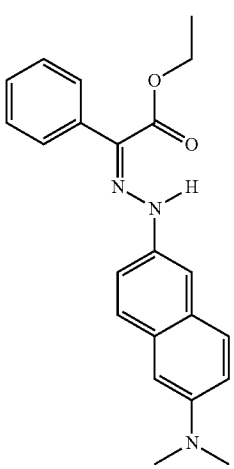

This compound was synthesized using method D, while using ethyl 2-diazo-2-phenylacetate and 6-bromo-N,N-dimethylnaphthalen-2-amine as the starting materials. Compound 29 was obtained as an orange solid. Yield 85%. m.p. 100.6-101.4° C.; $^1$H NMR (600 MHz, CD$_3$CN) δ 12.42 (s, 1H), 7.76-7.71 (m, 2H), 7.71-7.66 (m, 2H), 7.57 (d, J=2.0 Hz, 1H), 7.49 (dd, J=8.9, 2.2 Hz, 1H), 7.43 (t, J=7.5 Hz, 2H), 7.37 (t, J=7.3 Hz, 1H), 7.24 (dd, J=9.1, 2.6 Hz, 1H), 7.00 (d, J=2.4 Hz, 1H), 4.38 (q, J=7.1 Hz, 2H), 3.02 (s, 6H), 1.35 (t, J=7.1 Hz, 3H). $^{13}$C NMR (151 MHz, CD$_3$CN) δ 164.16, 148.54, 138.76, 137.50, 132.35, 129.95, 129.86, 129.83, 129.19, 128.41, 128.25, 128.10, 128.00, 127.90, 118.12, 116.51, 110.02, 107.23, 61.60, 40.73, 13.99. ESI-MS: m/z found [M-H$^+$] for C$_{22}$H$_{24}$N$_3$O$_2{}^+$ 362.15 (calcd. 362.19)

130

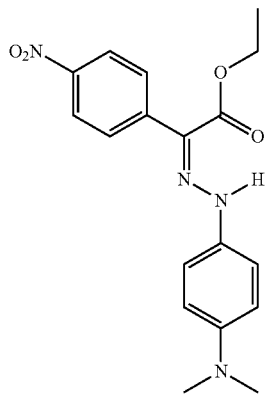 [SMILES: CCOC(=O)/C(=N\Nc1ccc(N(C)C)cc1)c1ccc([N+](=O)[O-])cc1]

This compound was synthesized using method D, while using ethyl 2-diazo-2-(4-nitrophenyl) acetate and 4-bromo-N,N-dimethylaniline as the starting materials. Compound 130 was obtained as a dark red solid. Yield 18%. m.p. 113.9-114.8° C.; $^1$H NMR (600 MHz, CD$_3$CN) δ 12.65 (s, 1H), 8.21 (d, J=9.0 Hz, 2H), 7.97 (d, J=9.0 Hz, 2H), 7.30 (d, J=9.0 Hz, 2H), 6.83-6.81 (d, J=9.0 Hz, 2H), 4.39 (q, J=7.1 Hz, 2H), 2.94 (s, 6H), 1.37 (dd, J=9.1, 5.2 Hz, 3H). $^{13}$C NMR (151 MHz, CD$_3$CN) δ 163.89, 148.65, 144.22, 133.92, 129.19, 124.11, 123.60, 116.59, 114.11, 61.68, 40.72, 13.98. ESI-MS: m/z found [M-H$^+$] for C$_{18}$H$_{21}$N$_4$O$_4{}^+$ 357.15 (calcd. 357.16)

131

This compound was synthesized using method D, while using ethyl 2-diazo-2-(4-nitrophenyl) acetate and 6-bromo-N,N-dimethylnaphthalen-2-amine as the starting materials. Compound 131 was obtained as a dark red solid. Yield 25%. m.p. 153.1-153.6° C.; $^1$H NMR (600 MHz, CD$_3$CN) δ 12.71 (s, 1H), 8.27-8.22 (m, 2H), 8.04-7.99 (m, 2H), 7.71 (t, J=9.0 Hz, 2H), 7.63 (d, J=2.0 Hz, 1H), 7.55 (dd, J=8.8, 2.2 Hz, 1H), 7.26 (dd, J=9.0, 2.5 Hz, 1H), 7.00 (d, J=2.4 Hz, 1H), 4.42 (q, J=7.1 Hz, 2H), 3.03 (s, 6H), 1.38 (t, J=7.1 Hz, 3H). ¹³C NMR (151 MHz, CD₃CN) δ163.74, 148.81, 147.17, 143.90, 138.08, 132.86, 129.51, 128.44, 128.22, 127.63, 123.62, 118.13, 116.51, 111.15, 107.06, 61.95, 40.64, 13.95. ESI-MS: m/z found.

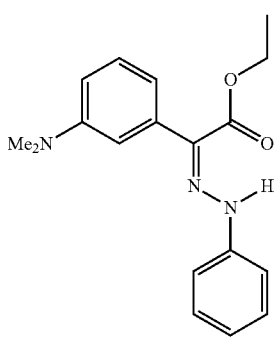

201

This compound was synthesized using method A, while using ethyl 2-(3-(dimethylamino)phenyl)-2-oxoacetate and phenylhydrazine as the starting materials. Compound 201 was obtained as a light yellow powder. Yield 41%. m.p. 58.1-58.7° C. ¹H NMR (600 MHz, CD₂Cl₂) δ 12.28 (s, 1H), 7.32 (td, J=8.6, 7.1 Hz, 2H), 7.26 (d, 2H), 7.22 (t, J=7.9 Hz, 1H), 7.01 (t, J=1.9 Hz, 1H), 7.01-6.94 (m, 2H), 6.73 (dd, J=8.5 Hz, 2.5 Hz, 1H), 4.34 (q, J=7.1 Hz, 2H), 2.97 (s, 6H), 1.35 (t, J=7.1 Hz, 3H) ppm; ¹³C NMR (151 MHz, CD₂Cl₂) δ 164.17, 150.87, 143.88, 137.57, 129.71, 129.51, 128.74, 122.57, 117.59, 114.42, 113.54, 112.52, 61.45, 40.91, 14.41 ppm; ESI-HRMS: m/z found [M-H⁺] for C₁₈H₂₂N₃O₂⁺ 312.1708 (calcd. 312.1707).

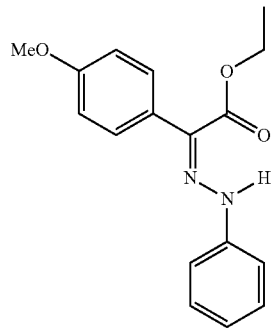

202

This compound was synthesized using method A, while using ethyl 2-(4-methoxyphenyl)-2-oxoacetate and phenylhydrazine as the starting materials. Compound 202 was obtained as an orange oil; yield 80%. ¹H NMR (600 MHz, CDCl₃) δ ¹H NMR (600 MHz, Chloroform-d) δ 12.36 (s, 1H), 7.65 (d, J=8.8 Hz, 2H), 7.35 (t, J=8.1 Hz, 2H), 7.30 (d, J=8.2 Hz, 2H), 7.01 (t, J=7.1, 1H), 6.95 (d, J=8.8 Hz, 2H), 4.38 (d, J=7.3 Hz, 2H), 3.86 (s, 3H), 1.40 (t, J=7.2 Hz, 3H) ppm; ¹³C NMR (151 MHz, CDCl₃) δ 163.86, 159.31, 143.47, 129.95, 129.40, 129.28, 127.88, 122.29, 114.18, 113.42, 61.09, 55.38, 14.30. ppm; ESI-HRMS: m/z found [M-Na⁺] for C₁₇H₁₈N₂O₃Na³⁰ 321.1211 (calcd. 321.1210).

Compounds 152-E and Z were prepared for use as a control compound without the OH group for comparisons with compound 19.

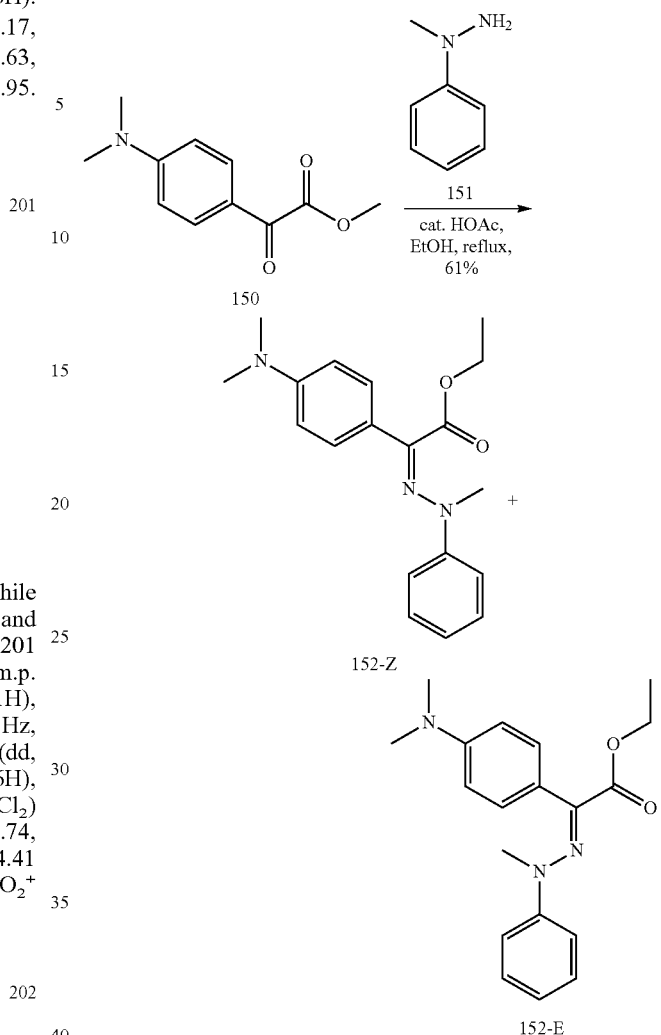

1-methyl-phenylhydrazine 151 (0.16 mL, 1.27 mmol) and several drops of acetic acid were added to a 50 mL flask containing compound 150 (200 mg, 0.90 mmol) dissolved in 10 mL of ethanol. The mixture was refluxed for 6 hours under nitrogen. After cooling to room temperature, 10 mL of water was added, and then solution was extracted with methylene chloride (2×20 ml). The organic phase was washed with brine (30 ml) and dried over anhydrous Na₂SO₄. Solvent was removed under reduced pressure, and the residue was subjected to column chromatography using 20:1 hexanes/ethyl acetate to afford 2-Z as a yellow solid (140 mg, 47%), and a 6:1 mixture of 152-E and 152-Z (40 mg, overall yield 14%). 152-Z: m.p. 85.1-86.0° C.; ¹H-NMR (600 MHz, CD₃CN) δ 7.39-7.32 (m, 4H), 7.25-7.20 (m, 2H), 7.03-6.99 (m, 1H), 6.77-6.74 (m, 2H), 4.27 (q, J=7.1 Hz, 2H), 3.02 (s, 3H), 3.00 (s, 6H), 1.33 (t, J=7.1 Hz, 3H) ppm; ¹³C NMR (151 MHz, CD₃CN) δ 166.78, 158.87, 153.06, 151.36, 129.23, 128.84, 121.13, 119.84, 116.34, 112.28, 61.87, 41.77, 39.93, 14.00 ppm; ESI-HRMS (m/z): [M-H⁺] calculated for C₁₉H₂₄N₃O₂: 326.1869, found 326.1866. 152-E: ¹H-NMR (600 MHz, CD₃CN) δ 7.39-7.32 (m, 4H), 7.25-7.20 (m, 2H), 7.03-6.99 (m, 1H), 6.77-6.74 (m, 2H), 4.27 (q, J=7.1 Hz, 2H), 3.02 (s, 3H), 3.00 (s, 6H), 1.33 (t, J=7.1 Hz, 3H) ppm; ¹³C NMR (151 MHz, CD₃CN) δ 166.85, 151.20, 149.79, 137.75, 131.08, 129.44, 122.51, 122.00, 116.14, 111.60, 61.37, 40.91, 40.04, 14.27 ppm. [M-H$^+$] for C$_{22}$H$_{23}$N$_4$O$_4^+$ 407.15 (calcd. 407.17).

Example 6: Photochromic Hydrazone Switches with Extremely Long Thermal Half-Lives, Exemplified by Compound 10

Compound 14 was synthesized through the condensation reaction between quinolinyl hydrazine and the corresponding ketone. After column chromatography, both the E and Z isomers were separated (48 and 28% yield, respectively) and then fully characterized using NMR spectroscopy, mass spectrometry, and X-ray crystallography (See Qian et al. 2017). The hydrazone N—H proton signal of 14-E resonates at 10.49 ppm in toluene-d8 indicating the presence of a weak intramolecular H-bond with the quinolinyl ring. This conclusion was corroborated with the analysis of the single crystal structure of 14-E. Switch 14-Z, however, has a characteristic N—H proton resonance at 13.96 ppm indicating that the N—H is H-bonded with both the quinolinyl nitrogen and carbonyl oxygen. The $^1$H NMR spectrum of each individual isomer of 14 reveals only a set of proton signals, and no interconversion between the two isomers is observed even after a week of equilibration at r.t. This fact is an indication that the barrier for E/Z isomerization in 14 is very high.

Compounds examined in this example:

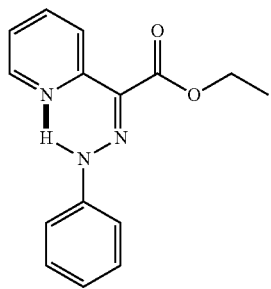

115

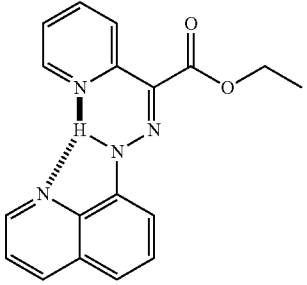

114

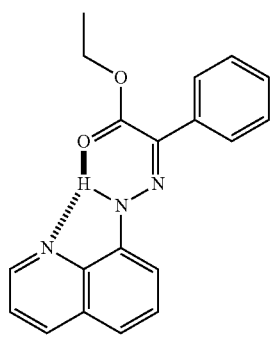

14

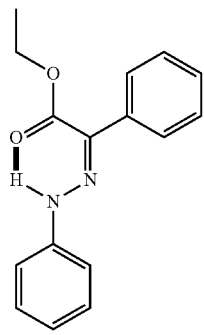

10

Figure 1B:
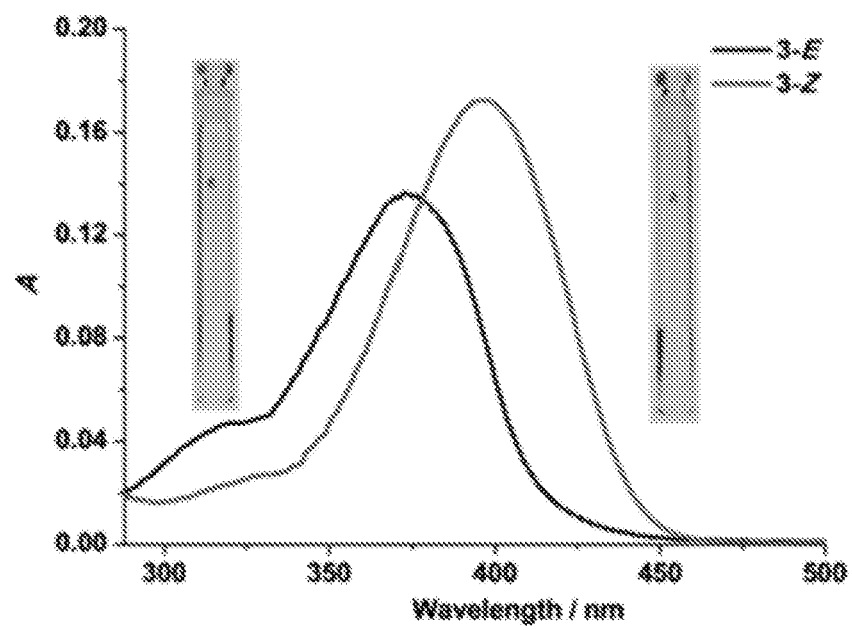

The UV spectra of 14-E and 14-Z were measured separately (FIG. 1B). The λmax (373 nm; absorption coefficient constant (ε) of 13637 M-1·cm-1) of 10-E is shifted hypsochromically by 25 nm as compared to 114-E, while in 14-Z the absorption band is shifted bathochromically by 8 nm to λmax=398 nm (ε=17267 M-1·cm-1). The separation in the absorption bands caused by these shifts allows both the forward and backward E/Z isomerization processes of 14 to be accessed. The photoisomerization efficiency of 14 was studied using $^1$H NMR spectroscopy. Upon 340 nm light irradiation a sample of 100% 10-E yields a PSS consisting of 76% 3-Z isomer. The quantum yield of the process was determined to be 2.4±0.3%. Irradiation of the obtained sample with 442 nm light yields a PSS consisting of 91% 3-E isomer with ΦZ→E of 0.3±0.1%. During the isomerization from 14-Z to 14-E isomer (FIG. 1A) a significant color change from yellow to colorless was observed. This behavior, which is known as negative photochromism, is quite rare and can be used in many interesting applications. [Helmy, S.; Leibfarth, F. A.; Oh, S.; Poelma, J. E.; Hawker, C. J.; Read de Alaniz, J. J. Am. Chem. Soc. 2014, 136, 8169-8172; Yamaguchi, T.; Kobayashi, Y.; Abe, J. J. Am. Chem. Soc. 2016, 138, 906-913.]

Photophysical data for compounds of this example is presented:

| hydrazone | $\lambda_{max}$ (nm) | $\Phi_{E\to Z}^a$ (%) | $\Phi_{Z\to E}^a$ (%) |
|---|---|---|---|
| 114-E | 398 | 3.7 ± 0.6 | b |
| 114-Z | 390 | | |
| 14-E | 373 | 2.4 ± 0.3 | 0.3 ± 0.1 |
| 14-Z | 398 | | |
| 10-E | 334 | 10.2 ± 0.1 | 1.7 ± 0.1 |
| 10-Z | 367 | | |

$^a$Photoisomerization quantum yield.
b Because of the poor band separation an optimal irradiation wavelength was not found to initiate the Z → E isomerization process.

Figure 1C:
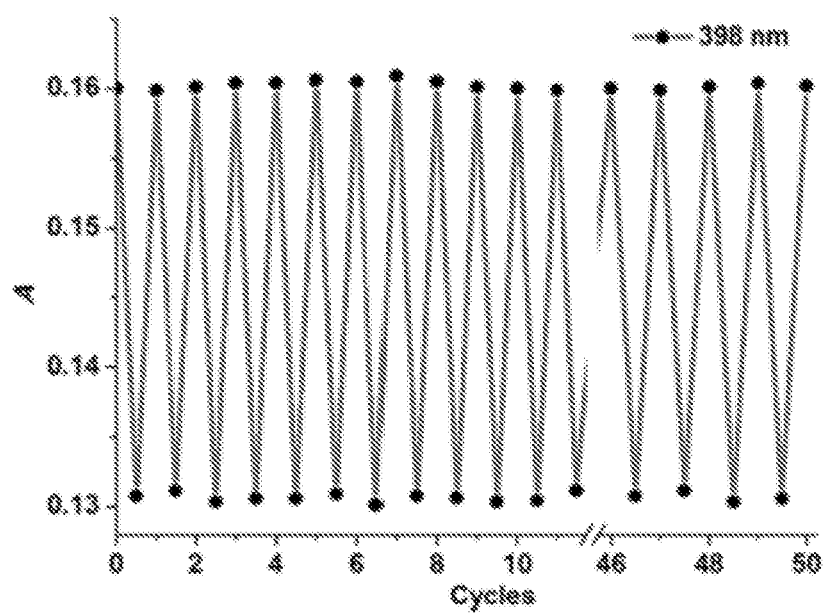

UV/vis spectroscopy (FIG. 1C) was used to study the fatigue resistance of the switch and no photodegradation was observed up to 50 isomerization cycles. This result attests to the robustness of the photochromic hydrazone switch. Thermal isomerization process of switch 14 was studied. It was surprising to find that at elevated temperatures, pure 14-E isomerizes to 14-Z with an extremely slow first-order rate. This finding shows that the Z isomer is the thermodynamically more stable isomer, and not a kinetically trapped configuration obtained during synthesis. The intramolecular H-bond in the Z isomer and the steric effect between the rotor phenyl ring (red) and N—H proton in the E configuration is believed to explain this unusual stability.

The temperature dependency of the thermal isomerization of 14-E was studied in both toluene and DMSO, and the activation energy barriers were determined to be 32.8±0.6 and 28.7±0.1 kcal·mol−1, respectively. These barriers are much higher than the barriers found for hydrazone 114 (14.8±0.1 and 16.0±0.1 kcal·mol−1 in toluene and DMSO, respectively), where thermal isomerization occurs from Z to E. Extrapolation of the obtained Arrhenius plot yields an extraordinarily slow isomerization rate ($8.2 \times 10^{-12}$ s−1) for 14 in toluene, which translates into an isomerization half-life ($\tau \frac{1}{2}$) of 2700±100 years at 298 K. Even in DMSO, the estimated halflife ($\tau \frac{1}{2}$=265+6 years) of 14 is ca. 138 and 97 times longer than the systems developed by Hecht (o-fluoroazobenzene) and Fuchter (arylazopyrazole). [Ble'ger, D.; Schwarz, J.; Brouwer, A. M.; Hecht, S. J. Am. Chem. Soc. 2012, 134, 20597-20600; Weston, C. E.; Richardson, R. D.; Haycock, P. R.; White, A. J. P.; Fuchter, M. J. J. Am. Chem. Soc. 2014, 136, 11878-11881.] The difference in isomerization kinetics of 14 in toluene and DMSO is currently believed to originate from the latter's competition with and hence weakening of the intramolecular H-bond. The lower $\Delta H^{\ddagger}$ value and larger negative $\Delta S^{\ddagger}$ value in DMSO, which can indicate disruption of intramolecular H-bond and more solvent reorganization in transition state, support this conclusion. A direct comparison with 114 is not possible because its thermal isomerization process (i.e., Z→E and not the other way round) and mechanism are different.

In order to have a better understanding of the effect of the intramolecular H-bond with the quinolinyl ring on isomerization half-life, compound 10. The replacement of the quinolinyl with a phenyl ring induces a hypochromic shift of 39 and 31 nm in 10-E and 10-Z, respectively. The Z isomer was found to be the thermally stable configuration in 10 as well. The photoisomerization of 10 is achieved using 340 and 412 nm light sources. Irradiation with a 412 nm light, leads to 10-E with a $\Phi Z \rightarrow E$=1.7±0.1%, and PSS412 of 95%. Irradiation with 340 nm light leads to 76% of 10-Z (PSS340), with $\Phi E \rightarrow Z$=10.2±0.1%. This photoisomerization process can be repeated multiple times (up to 10 cycles were tried) without any signs of fatigue. The thermal isomerization rate of 10-E was also studied as a function of temperature, and its half-life determined to be 255±19 years in toluene and 23±1 years in DMSO. Compared to 14 in toluene, switch 10 has a smaller $\Delta H^{\ddagger}$ value (29.6±0.6 vs 32.0±0.9 kcal·mol−1, respectively) and a similar $\Delta S^{\ddagger}$ value (−4.7±1.6 vs −1.6±2.3 cal·mol$^{-1}$·K$^{-1}$, respectively). These data indicate that the 10-fold decrease in half-life in 10 compared to 14 is mainly enthalpy driven. It is believed that this effect is due to the absence of the intramolecular H bond with the quinolinyl ring in 10. In DMSO, which can compete with the quinolinyl ring over the H-bond, a similar $\Delta H^{\ddagger}$ value (27.5±0.5 vs 27.7±0.8 kcal·mol−1 for 10 and 14, respectively) but a less negative $\Delta S^{\ddagger}$ value (−7.4±1.2 vs −11.1±2.0 cal·mol$^{-1}$·K$^{-1}$ for 10 and 14, respectively) are obtained indicating that less solvent reorganization happens in the transition state of 10 (i.e., the non-intramolecularly H-bonded molecule). This effect again explains the 10-fold decrease in the half-life for 10 compared to 14 in DMSO. The lack of intramolecular H-bond in addition to a hypothesized polar transition state that is affected by the solvent polarity, can explain the 10-fold changes in half-lives of 14 and 10 when going from toluene to DMSO.

Compound 14 is an example of a family of photochromic hydrazone-based compounds which exhibit extraordinary thermal stability, with half-lives as long as 2700 years. This property, in addition to their ease of synthesis and derivatization, very good band separation, very high photostationary states, and good quantum yields make these switches highly valuable tools in the development of responsive and adaptive materials.

Example 7: Solution and Solid-State Emission Toggling in a Photochromic Hydrazone Certain compounds of formula III and IV, for example compound 19, are bistable photochromic compounds whose functions, switching in organic solution, aqueous solvents and serum, and fluorescence ON/OFF. The switch design of compounds of formula III, particularly compound 19, is based on the bistable compound 10 (having lifetimes up to 2,600 years) hydrazone photochromic compounds. By introducing a dimethyl-amino group ($NMe_2$) to the para-position of the rotor phenyl group, the activation wavelength of the switch will be red-shifted relative to the parent compound. In addition to this desired effect, the system also became emissive in the thermodynamically stable Z state. Irradiation of a Z rich solution with visible light leads to the E configuration, which is accompanied with emission quenching.

This example employs exemplary compounds of formula III, compounds 19-Z and E. Hydrazone 19 in $CD_3CN$ exhibits a characteristic N—H proton signal at δ=11.8 ppm, indicating that this proton is H-bonded with the carbonyl group, i.e., the compound adopts the Z configuration. The compound appears to exclusively adopt the Z configuration (>99%) in solution because no other signals can be detected in the $^1$H NMR spectrum with the naked eye. The single crystal structure of 19 also shows the presence of an intramolecular H-bond between C=N—N—H proton and the carbonyl oxygen (N—H . . . O=C, 2.626(3) Å, 132.54°). The switch 19 adopts the Z configuration in the solid-state as well.

An equilibrated solution (Toluene; under dark) of compound 19 shows an absorption maximum ($\lambda_{max}$) at 395 nm, with an absorption coefficient constant (ε) of 14377 $M^{-1} \cdot cm^{-1}$. The absorption maximum of 19-Z is shifted bathochromically by 28 nm compared to the hydrazone compound 10 ($\lambda_{max}$=367 nm), as a result of the introduction of the electron donating dialkyl amino group. Irradiation of the solution of 19 with a 442 nm light source induces a Z→E photoisomerization, accompanied by the appearance of a new absorption band at $\lambda_{max}$=343 nm (ε=14670 $M^{-1} \cdot cm^{-1}$) and a color change from light yellow to colorless. The reverse process (E→Z isomerization) is triggered by using a 340 nm light source. Repeating the process cycles the system between the two isomers. The efficiency of this process was evaluated using $^1$H-NMR spectroscopy. A sample of 19 (>99% Z isomer; toluene-$d_8$) was first irradiated with 442 nm light to reach a photostationary state ($PSS_{442}$) consisting of >99% of 19-E isomer. The photoisomerization quantum yield ($\Phi_{Z \rightarrow E}$) of this process was calculated to be 9.1±0.7%. Upon 340 nm light irradiation, the E-dominant sample yielded a $PSS_{340}$ consisting of 82% of 19-Z, with a quantum yield ($\Phi_{E \rightarrow Z}$) of 13.1±1.3%. The thermal back-isomerization of 19-E, and found it to be very slow ($k_{E \rightarrow Z}$=(1.1±0.1)×10$^{-6}$ h$^{-1}$). The isomerization half-life ($\tau_{1/2}$) at 298 K was determined to be 75±3 years, which is about 3 times smaller than that of the compound 10 ($\tau_{1/2}$=255±19 years). It was found that the half-life of compound 19 hydrazone can be accelerated by addition of acid.

Unlike compound 10, the 19-Z isomer is emissive. Upon excitation ($\lambda_{ex}$) at 420 nm, a toluene solution of 19-Z exhibits an intense emission band ($\lambda_{em}$) at 525 nm (Stokes shift of 130 nm). The fluorescence decay lifetime was determined to be 193±2 ps.). It is currently considered that the emission in 19-Z stems from excited-state intramolecular proton transfer (ESIPT) coupled with charge transfer from the $NMe_2$ group. Switching 19-Z to 19-E using 442 nm light, leads to quenching of fluorescence. Complete quenching is not observed because a tiny fraction of the Z isomer is still present at the PSS. Irradiation of the E dominant solution with 340 nm light leads to a Z-dominant solution, which turns the emission ON again. Such an On-Off fluorescence response in photochromic compounds, especially those that function upon configurational changes, is highly unusual. The fluorescence modulation can be cycled at least 10 times with no signs of photobleaching.

In general, fluorescence emission from configurational switches, such as azobenzene, is very rare. The switching process of compounds herein is very robust and occurs even in serum, without loss of fluorescence emission ON/OFF toggling. This property opens the way for using this system in super-resolution fluorescence microscopy and photopharmacology. [Lerch, M. M., Hansen, M. J., V Dam, G. M., Szymanski, W., Feringa, B. L., Angew. Chem. Int. Ed. 2016, 55, 10978-10999]. Switching also occurs in the solid-state (powder, crystal, drop casted films, etc.). Again, photoswitching in the solid-state, while common in diarylethene, is very rare in other photochromic compounds. Moreover, the emission of the Z isomer is sustained in the solid-state, as is the toggling between the ON/OFF states, which is also highly unusual in such systems. In addition, two photon absorption can be used to switch the system from the Z to the E states in both solution and solid-state. These latter properties enable the use of such systems in super-high density memory devices, among other applications.

Irradiation experiments were conducted with a stand-alone xenon arc lamp system (Model: LB-LS/30, Sutter Instrument Co.), outfitted with a SMART SHUTTER controller (Model: LB10-B/IQ, Sutter Instrument Co.) and a liquid light guide LLG/250. 340 (part number: 340HC10-25), and 442 (part number: 442F5X10-25) nm light filters, purchased from Andover Corporation, were used in the irradiation experiments.

Stock solutions were prepared by dissolving appropriate amounts of 19 in toluene, followed by stirring to ensure sample homogeneity. The desired concentration was reached by consecutive dilutions. The fluorescence spectra were collected immediately after the sample was prepared. A Photon Technology International QuantaMaster 4 spectrofluorometer outfitted with a LPS-100 lamp power supply and Xenon arc lamp housing, ASOC-10 electronics interface, MD-4 motor driver control, and a model 914D photomultiplier detector system was used to collect fluorescence spectra. Data were acquired with a step size of 0.5 nm, an integration time of 0.1 s, and slit widths of 5 nm.

For fluorescence lifetime measurements, toluene solutions of 19 ($5\times10^{-6}$ M) were used. Fluorescence lifetime was determined by time-correlated single photon-counting (TCSPC) using a Photon Technology International QuantaMaster 4 spectrofluorometer integrated with Deltadiode-375L diode laser ($\lambda_{ex}$=373 nm, <70 ps pulse width) as the excitation source. The fluorescence decays were detected using a fast PPD-850 detector. In all cases, decays were recorded until peak counts reached 10,000. The decay traces were analyzed by the one-exponential fitting method using Felix data analysis from Horiba Scientific Ltd.

For photoisomerization studies in the solid state, absorption spectra were recorded at room temperature (ca. 25° C.) with a Perkin Elmer Lambda 750 spectrophotometer. Luminescence spectra were recorded at 25° C. on an Edinburgh FLS 980 spectrofluorimeter. Polarizing optical micrographs were taken using a Nikon Eclipse 80i polarizing optical microscope. Photochemical experiments were performed at room temperature on films deposited on a quartz plate by drop casting from a dichloromethane solution (1 mg in 1 ml). The light source used for irradiation was a CoolLED pE-300. The selection of the desired irradiation wavelength (360 or 450 nm) was accomplished by the use of an appropriate interference filter.

Photoisomerization Studies in Solution

UV-Vis and $^1$H NMR spectroscopies were employed to study the photoisomerization of hydrazone switches, exemplified by compound 19. Spectrophotometric grade solvents were used for the UV/Vis absorption studies. Hydrazone switch solutions (3.0 mL, $1.0\times10^{-5}$ M) in toluene were prepared and transferred into a 1.0 cm quartz cuvette for immediate UV/Vis absorption measurements. The solutions were irradiated with appropriate light sources, and the corresponding UV spectra were recorded. Isomerization cycles were measured by alternating irradiation wavelengths and monitoring the absorbance change at a chosen wavelength. The photostationary states (PSS) were determined upon continuous irradiation of the sample until no further isomerization was observed using $^1$H NMR spectroscopy.

An initial state for compound 19 (E/Z), the E/Z ratio was 1<99. After photo-irradiation at 442 nm, a PSS (in toluene-d8 at 294 K) had an E/Z ratio of >99/1 (PSS442). From initial state of compound 19 (E/Z) with E/Z >99/1, photo-irradiation at 340 nm resulted in a PSS (in toluene-d8 at 294 K) with E/Z ratio of 18/82. No back isomerization was observed at 340 nm.

Switching cycles of compound 19 (E/Z) were monitored in toluene at 294 K by following absorbance at 400 nm while alternating irradiation wavelength between 442 nm and 340 nm. Switching was found to be relatively stable over 10 cycles with absorbance decrease less than about 30% over 10 cycles. Similar monitoring of switching cycle of compound 19 isomers was performed (monitoring at 400 nm) in aqueous medium (MeOH:$H_2O$: 1:1 by vol) at 294K. Absorbance intensity was relatively constant over 9 switching cycles.

Switching of Compound 19 in Serum Buffer

Figure 16:
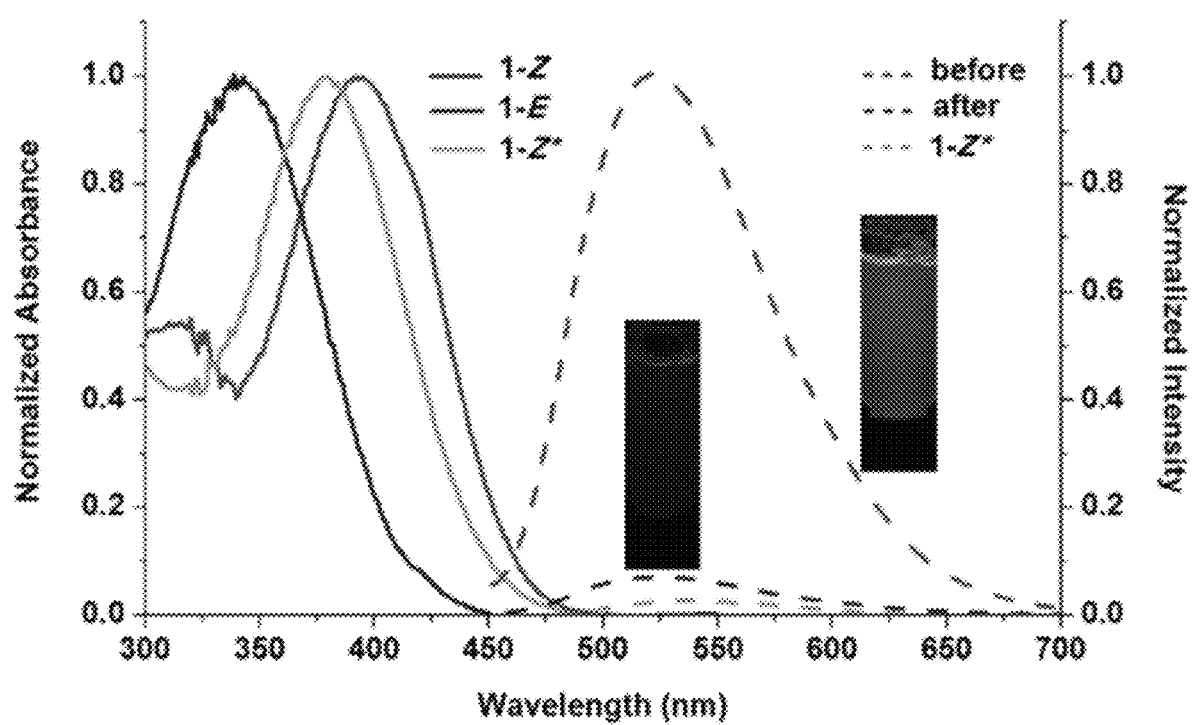
FIG. 16 illustrates various spectra of compounds 19 Z and E. Solid lines: UV-Vis spectra (5.0×10$^{-6}$ M) of 19-Z and 19-E in 10% FBS buffer; Dashed lines: Fluorescence emission spectra (5.0×10$^{-6}$ M, $\lambda_{ex}$=420 nm) of 19 in 10% FBS buffer, before irradiation (red) and after irradiation (blue); 19-Z* refers to 19-Z (5.0×10$^{-6}$ M) in water (with 10% DMSO).

A 10 mM phosphate-buffer saline (PBS) solution was prepared by dissolving 8.00 g sodium chloride (NaCl), 0.20 g potassium chloride (KCl), 1.44 g sodium phosphate dibasic dihydrate ($Na_2HPO_4.2H_2O$) and 0.24 g potassium phosphate monobasic ($K_2HPO_4$) in 800 ml distilled water. 2 M HCl was used to adjust the pH to 7.4, followed by adjusting the volume to 1 liter with additional distilled water. To prepare a 10% fetal bovine serum (FBS) buffer for switching studies, FBS, DMSO, and 10 mM PBS buffer were mixed at a ratio of 1:1:8. DMSO was used to solubilize the switch in the FBS buffer solution. The emission of 19-Z is quenched in a water/DMSO solution (10% DMSO). However, emission is regained in the FBS buffer (see FIG. 16). Interaction with proteins in the buffer might explain this phenomenon. Switching cycles of compound 19 (E/Z) were monitored in FBS buffer at 294 K by following absorbance at 400 nm while alternating irradiation wavelength between 442 nm and 340 nm. Switching was found to be relatively stable over 10 cycles with absorbance decrease less than about 10% (after the first cycle) over 10 cycles.

Photoisomerization Quantum Yield

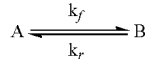

In a photochemical reaction, species A absorbs light to generate the product B. The general kinetics of a basic photochemical reaction can be expressed using Eq. 1.

$$r_{A \to B} = \frac{I_0 \Phi_{A \to B}}{V}(1 - 10^{-\varepsilon_A C_A l}). \qquad \text{Eq. 1}$$

where $r_{A \to B}$ indicates photoisomerization rate from A to B; $I_0$ indicates molar photon flux; $\Phi_{A \to B}$ indicates photoisomerization yield from A to B; V indicates sample volume; $\varepsilon_A$ indicates molar absorption coefficient of sample A; $C_A$ indicates the concentration of sample; and l indicates the light path length. When $\varepsilon_A \cdot C_A \cdot l \cdot \ln 10 \ll 1$ (or $\text{Abs}_A \ll 0.43$), the Taylor expansion can be truncated at the first-order term, simplifying Eq. 1 to Eq. 2.

$$k_{A \to B} = \frac{I_0 \Phi_{A \to B}}{V} \varepsilon_A \cdot l \cdot \ln 10. \qquad \text{Eq. 2}$$

Rearranging Eq. 2 gives Eq. 3, $$\Phi_{A \to B} = \frac{k_{A \to B} V}{I_0 \varepsilon_A l \ln 10}. \qquad \text{Eq. 3}$$

where $\Phi_{A \to B}$ indicates the photoisomerization yield from A to B; $k_{A \to B}$ represents the rate constant (obtained from the exponential fit of a graph of Abs vs. time); V indicates sample volume; $I_0$ indicates molar photon flux; $\varepsilon_A$ indicates molar absorption coefficient of sample A; and l indicates the light path length.

The molar photon flux $I_0$ at 340 and 442 nm were determined using chemical actinometry. A 0.002 L ($=V_0$) solution of potassium ferrioxalate in 0.05 M $H_2SO_4$ was placed in a 1.0 cm cuvette and irradiated for 30 s ($=t_0$). The irradiated solution was combined with 3.5 equiv. of ferrozine, and stirred under the dark for an hour. The resulting solution, containing reddish-purple $[\text{Fe}(\text{ferrozine})_3]^{2+}$ complex, was diluted by a factor of 30 ($=n$), and its absorbance was measured at 563 nm ($A_{563}$), where its molar absorption coefficient ($\varepsilon_{563}$) is 27,900 cm$^{-1}$ M$^{-1}$. The molar photon flux $I_0$ of light source at different wavelengths was determined using the following Eq. 4.

$$I_0 (\text{mol} \cdot \text{s}^{-1}) = \frac{A_{563} \cdot n \cdot V_0}{\varepsilon_{563} \cdot l \cdot t_0 \cdot \phi_\lambda}. \qquad \text{Eq. 4}$$

where l indicates the length of the cuvette; and $\phi_\lambda$ stands for the quantum yield of the photo-reduction of Fe(III) oxalate induced by the light source ($\phi_{340}=1.25$ and $\phi_{442}=1.11$). The rate law for the formation of species B is described in Eq. 5.

$$C_B = \frac{k_f}{k_f + k_r} C_{total} \left(1 - e^{-(k_f + k_r)t}\right). \qquad \text{Eq. 5}$$

where $C_{total}$ is the total concentration of the photoswitch ($C_A + C_B$), and $k_f$ and $k_r$ are the first order approximate rate constants for the forward and reverse photochemical reactions under the low absorption approximation discussed above.

Rearranging Eq. 5 gives the rate law for the formation of species A (Eq. 6), $$C_A = \frac{C_{total} \cdot k_r}{k_f + k_r} + \frac{C_{total} \cdot k_f}{k_f + k_r} e^{-(k_f + k_r)t}. \qquad \text{Eq. 6}$$

$C_A$ is proportional to the absorbance of species A. An exponential fit of absorbance as a function of time gives the observed rate constant $k_{obs} = k_f + k_r$. For this family of photochromic hydrazone switches, the thermal relaxation is extremely slow at room temperature and so $k_{A \to B} \approx k_{obs}$.

Fluorescence Property Studies with Compounds 19-Z and E

Figure 17:
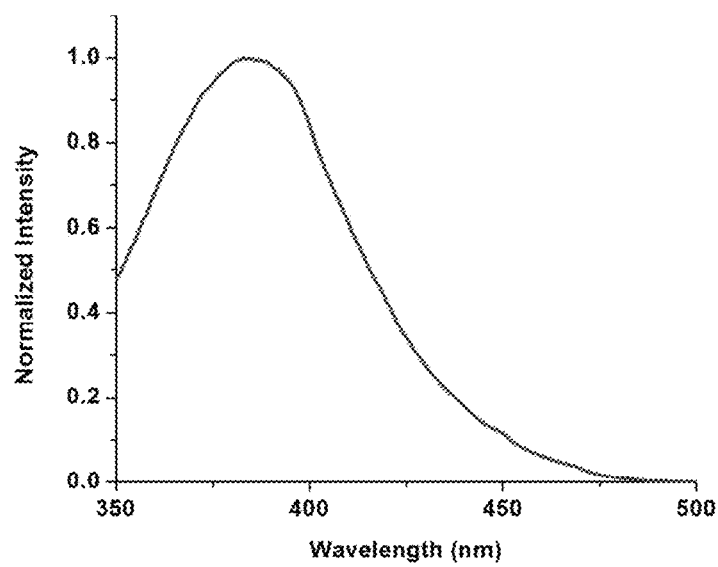
FIG. 17 illustrates an excitation spectrum of 19-Z (5×10$^{-6}$ M) in toluene with $\lambda_{em}$=525 nm.
Figure 18:
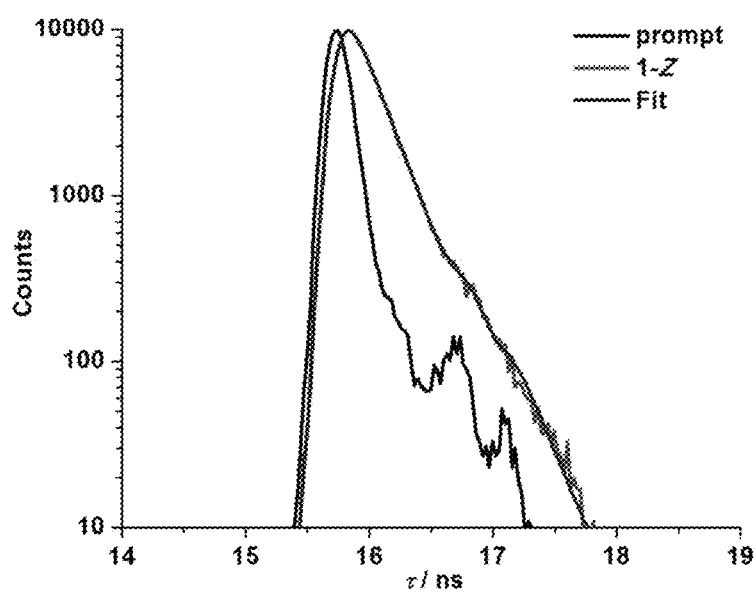
FIG. 18 is a graph showing fluorescence lifetime decay of 19-Z (5×10$^{-6}$ M) in toluene.
Figure 19:
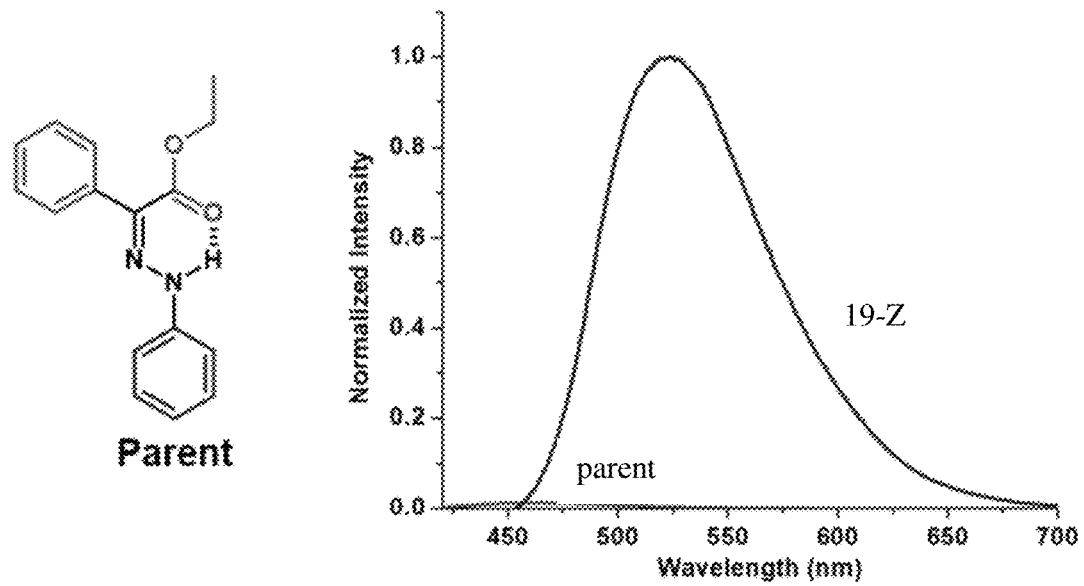
FIG. 19 illustrates a comparison of the fluorescence spectrum of hydrazone compound 10 (1; 5×10$^{-6}$ M) and 19-Z (2; 5×10$^{-6}$ M) in toluene at $\lambda_{ex}$=367 nm, and $\lambda_{ex}$=420 nm, respectively.
Figure 20:
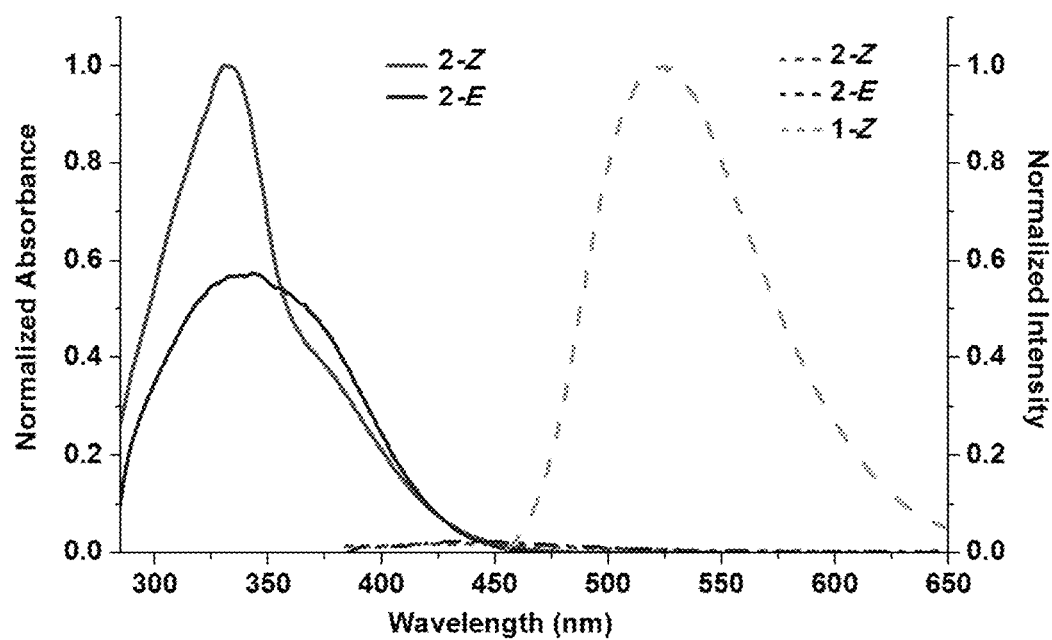
FIG. 20 illustrates the normalized UV-Vis absorption spectra (solid lines; 1×10$^{-5}$ M) and fluorescence spectra (dashed lines; 5×10$^{-6}$ M) of 152-Z, 152-E and 19-Z in toluene.

The excitation spectrum of 19-Z ($5 \times 10^{-6}$ M) in toluene with $\lambda_{em}=525$ nm is show in FIG. 17. The ON/OFF fluorescence switching cycles of switch 19 were monitored in toluene at 294 K. The fluorescence intensity change at $\lambda=525$ nm was monitored using a fluorimeter while alternating the irradiation wavelength between 442 and 340 nm. Fluorescence intensity was maintained within about 10% over the 10 cycles monitored. FIG. 18 is a graph of fluorescence lifetime decay of 19-Z ($5 \times 10^{-6}$ M) in toluene. FIG. 19 illustrates a comparison of the fluorescence spectrum of analogous unsubstituted parent hydrazine (compound 10 E and Z isomers) (1; $5 \times 10^{-6}$ M) and 19-Z (2; $5 \times 10^{-6}$ M) in toluene at $\lambda_{ex}=367$ nm, and $\lambda_{ex}=420$ nm, respectively. FIG. 20 illustrates normalized UV-Vis absorption spectra (solid lines; $1 \times 10^{-5}$ M) and fluorescence spectra (dashed lines; $5 \times 10^{-6}$ M) of control compounds 152-Z, 152-E and 19-Z in toluene.

Switching of Control Compound 152

To gain insight into the emission mechanism, the methylated compounds 152 Z and E were synthesized. The Z and E isomers of 152 were separated and characterized using NMR spectroscopy and mass spectrometry. The photoisomerization of 152 is inefficient because of the overlap of the UV bands of the isomers. Moreover, no emission is observed upon excitation at the absorption maximum of either 152-Z or 152-E. These results indicate that the intramolecular H-bond in 19-Z is crucial for its fluorescence emission, giving support to the ESIPT mechanism.

Figure 3:
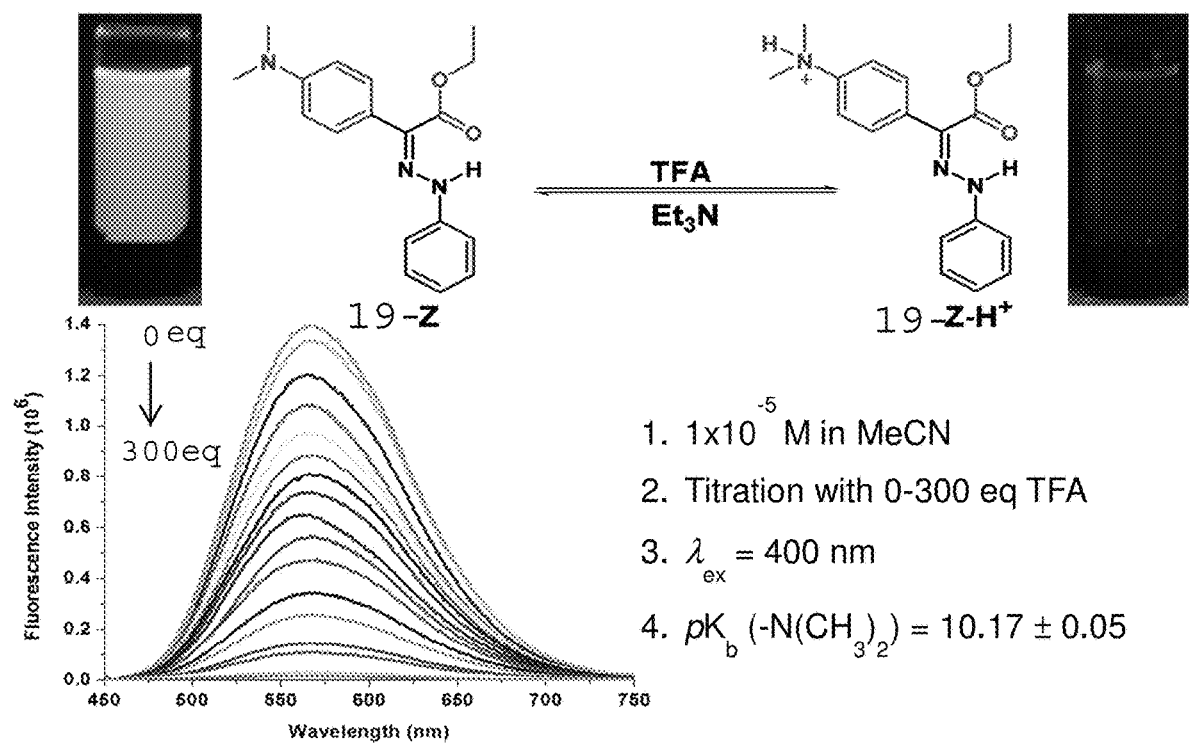
FIG. 3 illustrates the acid-base fluorescence response of compound 19-Z on protonation of the dimethylamino group employing Trifluoroacetic acid (TFA). The change in fluorescence intensity of 19-Z is shown as a function of titration (from 0 to 300 equivalents) with acid. Protonated 19-Z (19-Z-H+) does not exhibit fluorescence.

The absorption spectrum of 19-Z exhibits variation with solvent polarity. In particular, the wavelength of maximum absorption ($\lambda_{max}$) varies from about 400 nm in toluene to about 380 nm in ethanol. Spectra can be measure, for example, in toluene, dioxane, DCM, acetonitrile, DMSO, methanol and ethanol, see Table 4. As expected polar solvents lower the emission intensity and lead to bathachromic shifts vs non-polar solvents. Polar protic solvents on the other hand normally lead to substantial emission quenching. However, as part of our solvent screening studies, photoisomerization was observed in the presence of fetal bovine serum (FBS) buffer. An equilibrated solution of 19 in 10% FBS buffer (PBS with 10% DMSO, pH=7.4) shows an absorption maximum at 395 nm, which shifts to $\lambda_{max}=343$ nm upon isomerization with 442 nm light. The back E→Z isomerization process is triggered by irradiating with 340 nm light, everting the system to its original state. Interestingly, the emission of 19-Z in the serum buffer is regained, with a maximum emission band at 525 nm ($\lambda_{ex}$=420 nm) (FIG. 3). This behavior is in apparent contradiction to the diminished fluorescence intensity observed for 19-Z in polar protic solvents and aqueous solutions. It is currently believed that 19-Z is interacting with the proteins in the buffer, which are providing a hydrophobic environment that enables/reinstates emission. [Houk, K. N., Leach, A. G., Kim, S. P., Zhang, X. *Angew. Chem. Int, Ed.* 2003, 42, 4872-4897.] Similar to what happens in organic solvents, switching of 19-Z to 19-E leads to emission turn OFF, which can be restored by 340 nm light driven E→Z photoisomerization.

Figure 21:
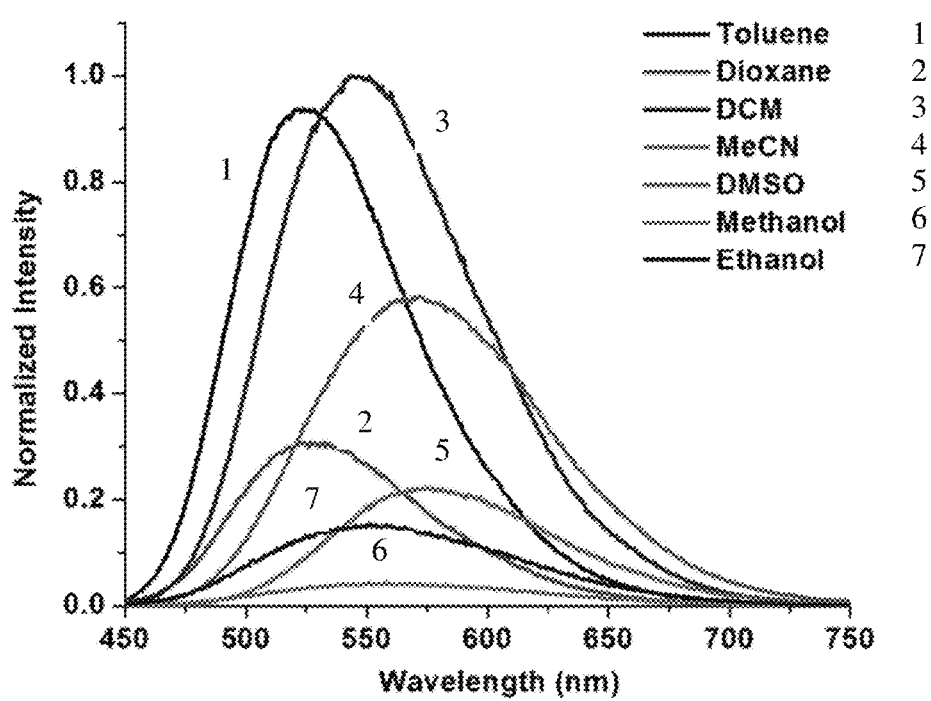
FIG. 21 illustrates solvent-dependent fluorescence emission of 19-Z (1.0×10$^{-5}$ M). Absorption maxima ($\lambda_{max}$) of 1-Z in corresponding solvents (FIG. S33) were used as the excitation wavelengths.

Fluorescence emission of 19-Z ($1.0 \times 10^{-5}$ M) is also solvent dependent as illustrated in FIG. 21. The $\lambda_{max}$ of 19-Z in the corresponding solvents were used as the excitation wavelengths in obtaining the emission spectra. In the absorption spectra, a bathochromic shift of 17 nm is observed in MeCN as compared to toluene, which is the largest shift in the series. However, the emission profile of 19-Z is highly dependent on solvent polarity and presence of acidic protons. Compared to MeCN, solutions of 19-Z exhibit hypsochromic shifts and intensified emission bands in apolar solvents (e.g. toluene, DCM). The biggest bathochromic shift (51 nm) in emission wavelength is found between toluene and DMSO, which indicates that there may be a polarized charge-transfer state formed in the excited state. A diminished emission band was observed in H-bond acceptor solvents, e.g. dioxane and DMSO. More importantly, it was found that the fluorescence emission of 19-Z was quenched to a large extent in polar protic solvents (e.g. methanol and ethanol). These results are consistent with ESIPT coupled with charge transfer from $NMe_2$ being responsible for the observed emission in 19-Z. [A. P. Demchenko, K-C. Tang, P-T Chou, *Chem. Soc. Rev.* 2013, 42, 1379-1408.]

As expected polar solvents lower the emission intensity and lead to bathachromic shifts vs non-polar solvents. Polar protic solvents on the other hand normally lead to substantial emission quenching. However, as part of our solvent screening studies, photoisomerization was observed in the presence of fetal bovine serum (FBS) buffer. An equilibrated solution of 19 in 10% FBS buffer (PBS with 10% DMSO, pH=7.4) shows an absorption maximum at 395 nm, which shifts to $\lambda_{max}$=343 nm upon isomerization with 442 nm light. The back E→Z isomerization process is triggered by irradiating with 340 nm light, everting the system to its original state. Interestingly, the emission of 19-Z in the serum buffer is regained, with a maximum emission band at 525 nm ($\lambda_{ex}$=420 nm) (FIG. 3). This behavior is in apparent contradiction to the diminished fluorescence intensity observed for 19-Z in polar protic solvents and aqueous solutions. It is currently believed that 19-Z is interacting with the proteins in the buffer, which are providing a hydrophobic environment that enables/reinstates emission. Similar to what happens in organic solvents, switching of 19-Z to 19-E leads to emission turn OFF, which can be restored by 340 nm light driven E→Z photoisomerization.

TABLE 4

Emission maxima of 19-Z ($1 \times 10^{-5}$M) and their corresponding intensities in various solvents. The absorption maxima of 19-Z in the different solvents were used as the excitation wavelengths for fluorescence emission spectra.

|  | Toluene | Dioxane | DCM | MeCN | DMSO | MeOH | EtOH |
|---|---|---|---|---|---|---|---|
| $\lambda_{ex}$/nm | 395 | 388 | 392 | 378 | 387 | 385 | 388 |
| $\lambda_{em}$/nm | 524 | 527 | 544 | 571 | 575 | 551 | 558 |
| Relative Intensity[a] | 0.95 | 0.31 | 1 | 0.62 | 0.22 | 0.04 | 0.16 |

[a]The fluorescence intensity of 1-Z in DCM was set to 1.

Kinetic Studies

The thermal isomerization rates of 19 were studied using $^1$H NMR spectroscopy at different temperatures. Solutions of hydrazone switches 19 ($1 \times 10^{-3}$ M) in toluene-$d_8$ were irradiated at 442 nm wavelength, and then left in a Haake F3 circulating oil bath at a preset temperature. $^1$H NMR spectra were then acquired at different intervals at room temperature to monitor the change in ester $CH_2$ proton signal intensity as a function of time. The time that each measurement takes (~5 min) is much shorter than the half-life of the hydrazone switch at room temperature, and so was ignored when processing the data. Changes in the intensity of the ester $CH_2$ protons were used to calculate the ratio and concentration of the Z and E isomers. The thermal isomerization rates (k) were determined by least-square curve fittings using an integrated and combined rate equation of a single-species reversible reaction (Eq. 9)

$$E \underset{k_{-1}}{\overset{k_1}{\rightleftharpoons}} Z$$

$$K_{eq} = \frac{k_1}{k_{-1}} = \frac{C_A^0 - C_A^{eq}}{C_A^{eq}} \qquad \text{Eq. 7}$$

$$\ln\left(\frac{C_A - C_A^{eq}}{C_A^0 - C_A^{eq}}\right) = -(k_1 + k_{-1})t \qquad \text{Eq. 8}$$

Combining Eq. 7 and 8 gives Eq. 9.

$$C_A = (C_A^0 - C_A^{eq}) \times e^{\left(\frac{-k_1 \cdot C_A^0 \cdot t}{C_A^0 - C_A^{eq}}\right)} + C_A^{eq} \qquad \text{Eq. 9}$$

where $C_A$, $C_A^0$, and $C_A^{eq}$ are the experimental, initial, and equilibrium concentrations of the metastable configuration of the hydrazone switch, respectively; t stands for the thermal relaxation time. Thermal isomerization of 19-E→19-Z in toluene-$d_8$ as a function of concentration of 19-Z as a function of time was measured at temperatures ranging from 368 K to 380 K. An Arrhenius plot of the thermal isomerization of 19 E to 19 Z gave an intercept value of 33.593 (standard error of 1.246) and a slope of −14124 (standard error 466). An Erying plot of the thermal isomerization of 19 E to 19Z gave an intercept of 26.669 (standard error 1.244) and a slope of −13750 (standard error 465).

Example 8: Stability of the Switches Towards Glutathione

Figure 14A:
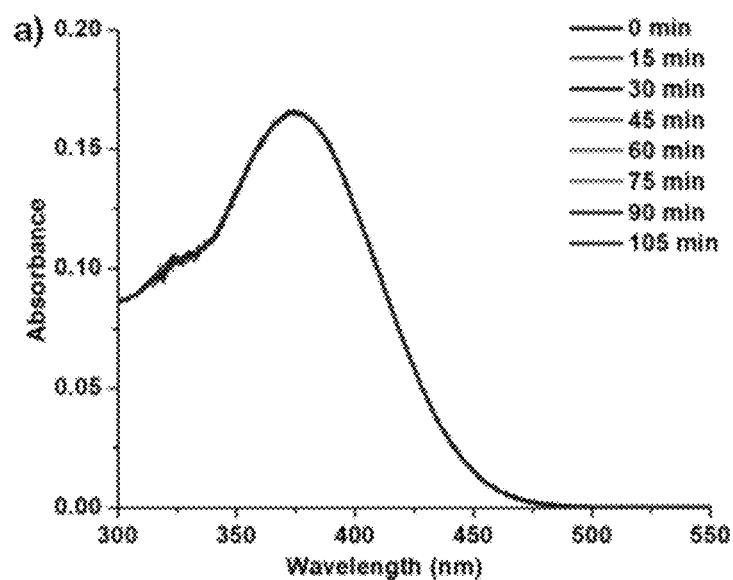
FIGS. 14A and 14B.
Figure 14B:
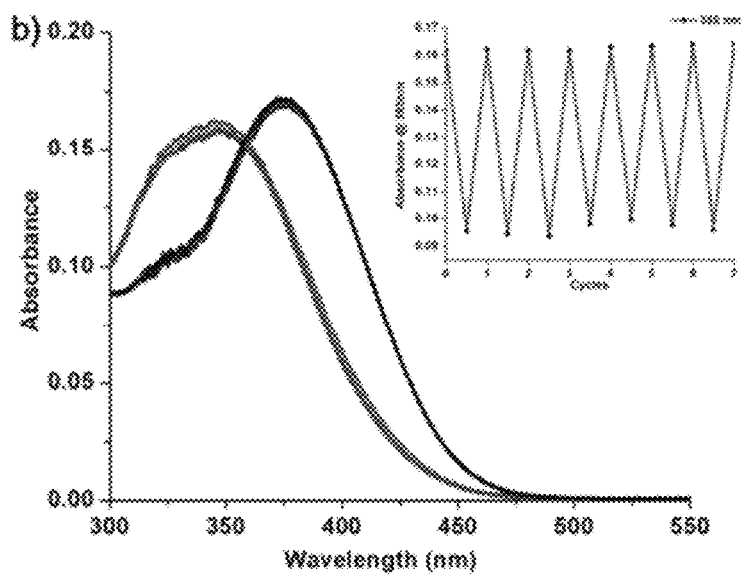
Figure 15A:
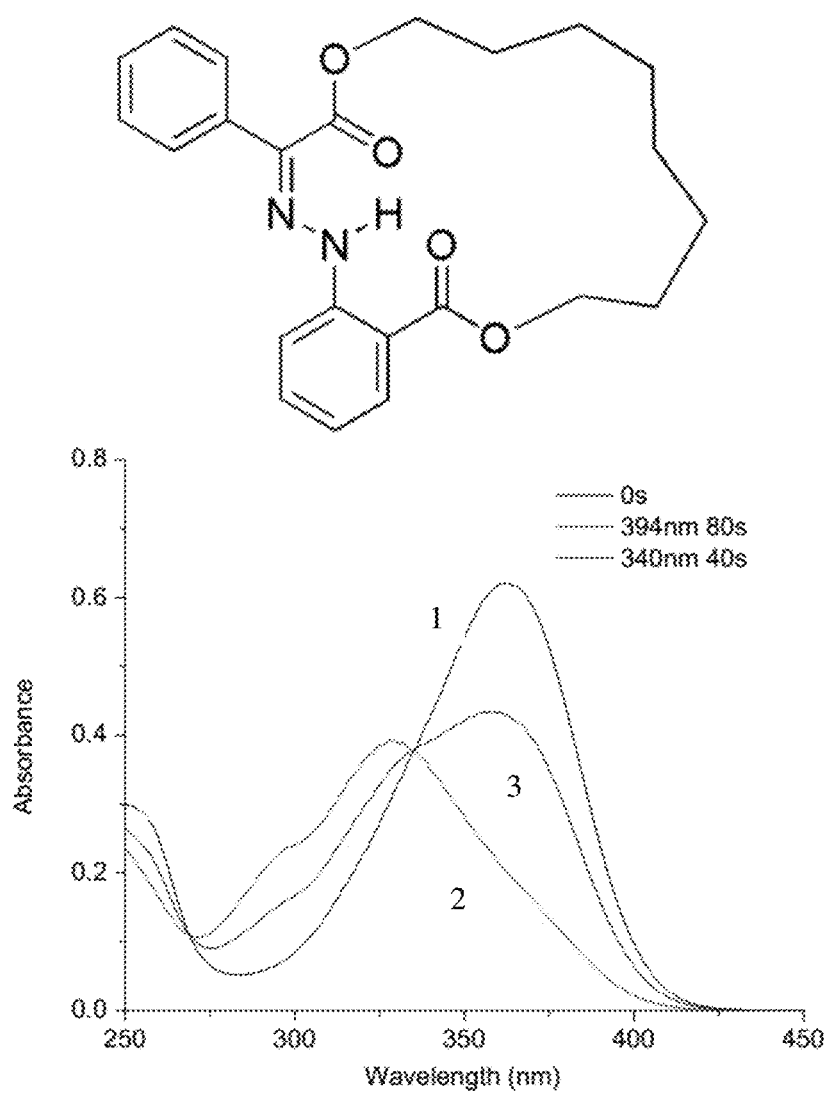
FIGS. 15A and 15B illustrate the UV/VIS spectra of the macrocycle switch where n is 8 and the macrocycle switch where n is 3, when; kept under the dark (i.e., mainly Z isomer—black trace 1); After irradiation at 394 nm (i.e., mainly E isomer—red trace 2); and after irradiation at 340 nm (photostationary state—blue trace 3).
Figure 15B:
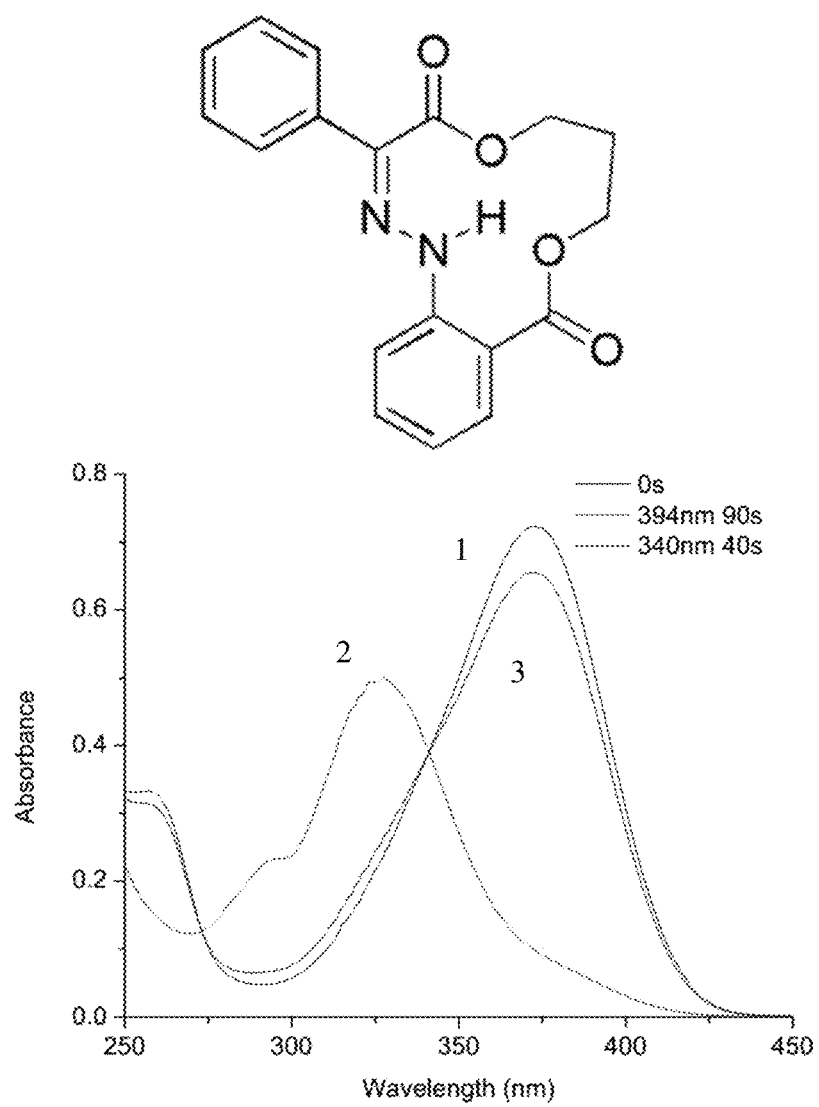

Azobenzene-based photoswitches usually undergo reduction in the presence of glutathione (GSH), which limits their use in bio-related applications. In order to test the stability of the hydrazone switch towards reduction by GSH, 10 mM GSH was added to a solution of 19-Z ($1\times10^{-5}$M) in PBS buffer (10 mM, 50% MeCN, pH=7.4). The UV/Vis spectra of this solution was monitored at intervals of 15 min for two hours, and no change in absorption was observed, i.e., the switch is not reduced by GSH. Similar stability was observed for the 19-E isomer, which was obtained by irradiating the solution at 442 nm (FIG. 14A). The presence of GSH in the buffer did not affect the switching process either (FIG. 14B; insert).

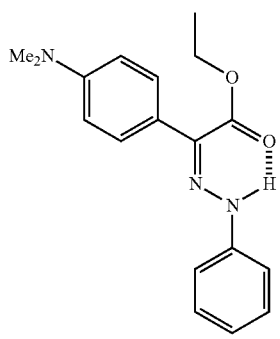

Example 7: Two Photon Absorption of the Hydrazone Photochromes

Two-photon absorption (TPA), and subsequent emission and/or isomerization of a photochromic compound, allows for the writing of data in the three dimensional (3D) volume of a material. By utilizing the z or longitudinal axis, in addition to the typical surface dimension (x-y space) used in regular data storage systems, the amount and density of data that can be written in a material can be greatly enhanced. Another benefit of TPA-based 3D optical data storage is that there is less crosstalk between multiple memory layers. This property leads to highly confined excitation and intrinsic 3D resolution, which further enhances the amount of information that can be stored in the material (up to 1012 bits $cm^{-3}$).

Compound 19 was used as a representative example of the hydrazone photoswitch compound of this invention. The two photon absorption properties of 19 in both solution and the solid state were examined. The two photon abortion properties are very similar, if not identical, to what is observed with one photon. More importantly the two photon (800 and 750 nm) process can be used to drive the reversible Z to E isomerization and accompanied fluorescence ON/OFF toggling. The two photon absorption cross-section was measured to be 12.6 GM for the Z→E process. This value, while relatively low, is quite surprising considering the size of the chromophore. Nonetheless, it is sufficiently high to drive the photo isomerization process, and enable in the future 3D writing applications using photochromic hydrazones.

Compound 19 was dissolved in spectroscopic grade toluene ($1.0\times10^{-5}$ M) and the solution was transferred to a quartz cuvette. A 800 nm light source (laser) was used to irradiate the sample, which led to visible emission (with naked eye) in the path the laser light passed through the solution. This experiment shows that the molecule can emit bright light through two-photon absorption. The experiment was repeated with a more dilute sample ($1.0\times10^{-6}$ M) and a similar behavior was observed. The only difference being that the intensity of the emission was weaker, as expected.

Thus certain materials of the invention which exhibit two photon absorption are additionally useful in devices for the writing of data in the three dimensional (3D) volume of a material, e.g., in TPA-based 3D optical data storage. Certain compounds of the disclosure are useful in methods of data storage that rely upon two photon absorption and which methods are known in the art. The invention provides certain compounds exhibiting two photon absorption for use in methods of data storage which rely upon two photon absorption.

The ability of the compounds to switch (including emission) in biologically relevant environments, with 1 and 2 photons sources makes them useful for super-resolution fluorescence microscopy imaging applications as well. [Roubinet, B.; Bossi, M. L.; Alt, P.; Leutenegger, M.; Shojaei, H.; Schnorrenbery, S.; Nizamov, S.; Irie, M.; Belov, V. N.; Hell, S. W. *Angew. Chem. Int. Ed.* 2016, 55, 15429-15433.]

Certain Photopysical Properties of Hydrazones

Figure 2:
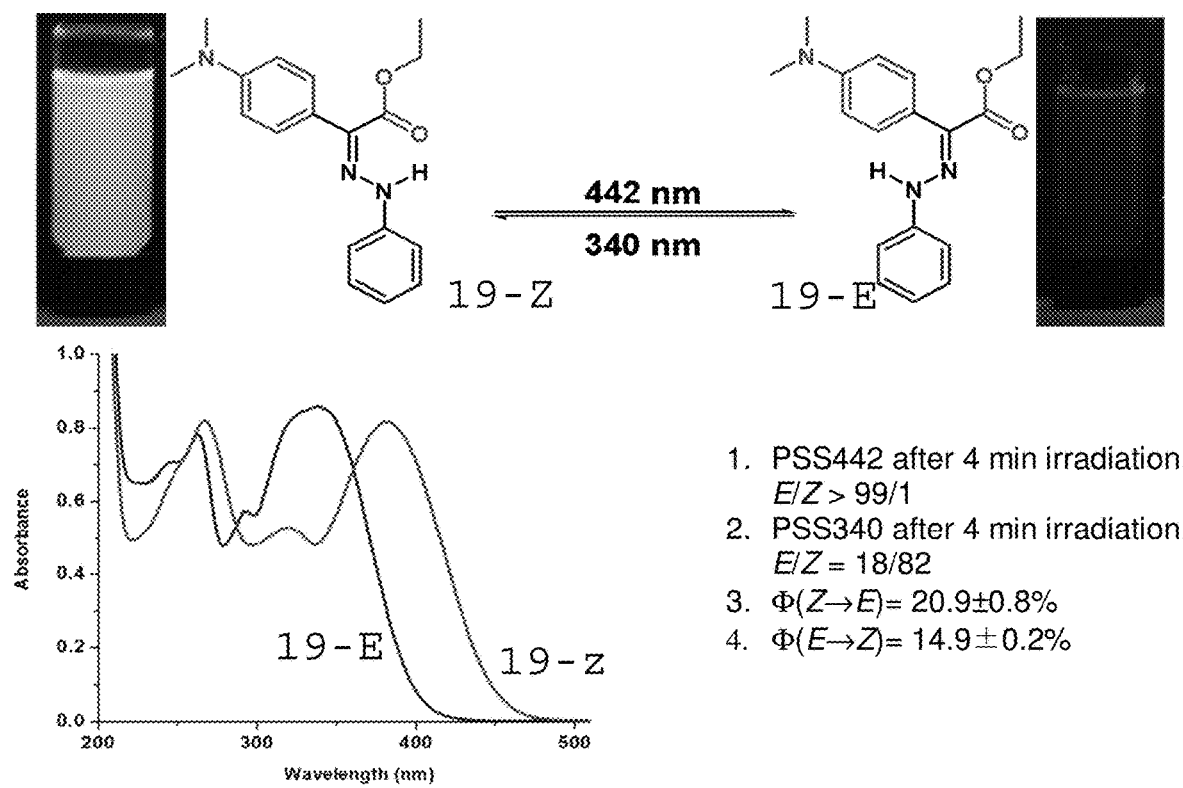
FIG. 2 illustrates certain photophysical properties of compound 19 E and 19Z. The absorption spectra for the E and Z isomers are given and fluorescence of the Z isomer is shown. Certain parameters are noted in the figure (1-4).

FIG. 2 illustrates certain photophysical properties of compound 19 E and 19Z. The absorption spectra for the E and Z isomers are given and fluorescence of the Z isomer is shown. Certain parameters are noted in the figure (1-4).

FIG. 3 illustrates the acid-base fluorescence response of compound 19-Z on protonation of the dimethylamino group employing Trifluoroacetic acid (TFA). The change in fluorescence intensity of 19-Z is shown as a function of titration (from 0 to 300 equivalents) with acid. Protonated 19-Z (19-Z-H+) does not exhibit fluorescence.

Figure 4:
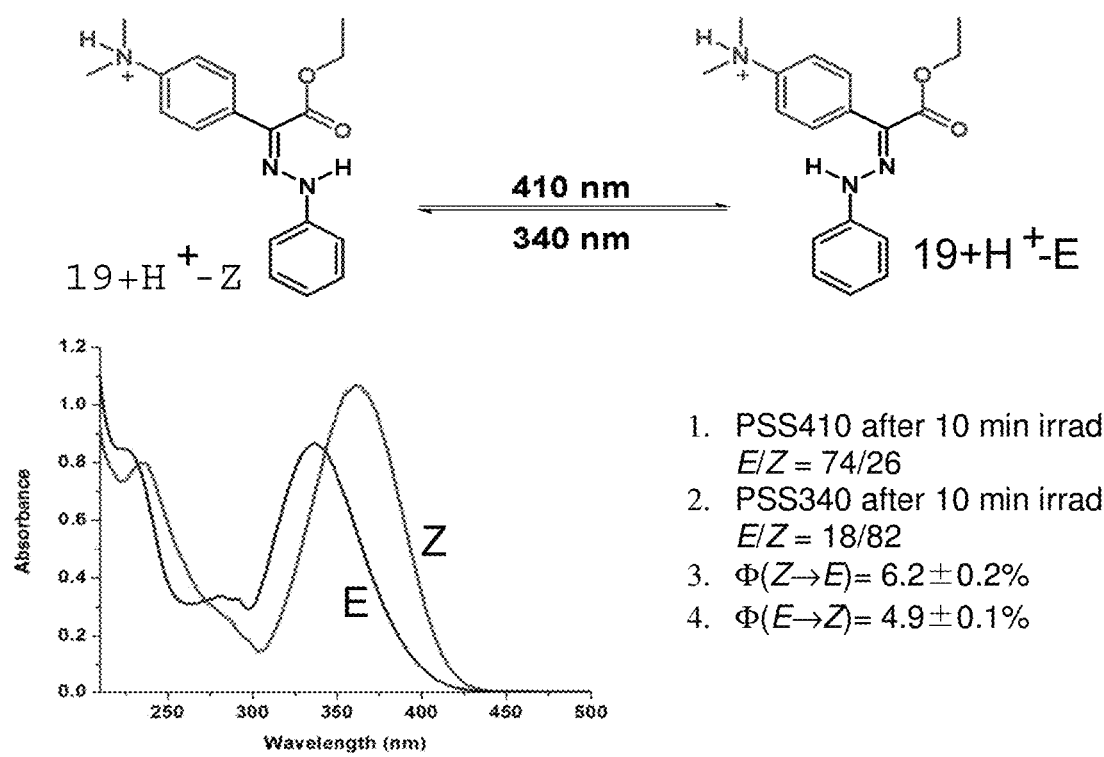
FIG. 4 illustrates photoswitchable performance of compounds protonated 19 Z and protonated 19E after acidification. The absorption spectra for 19-Z-H+ and 19SH+ are shown.

FIG. 4 illustrates photoswitchable performance of compounds protonated 19 Z and protonated 19E after acidification. The absorption spectra for 19Z-H+ and 19SH+ are shown.

Figure 5:
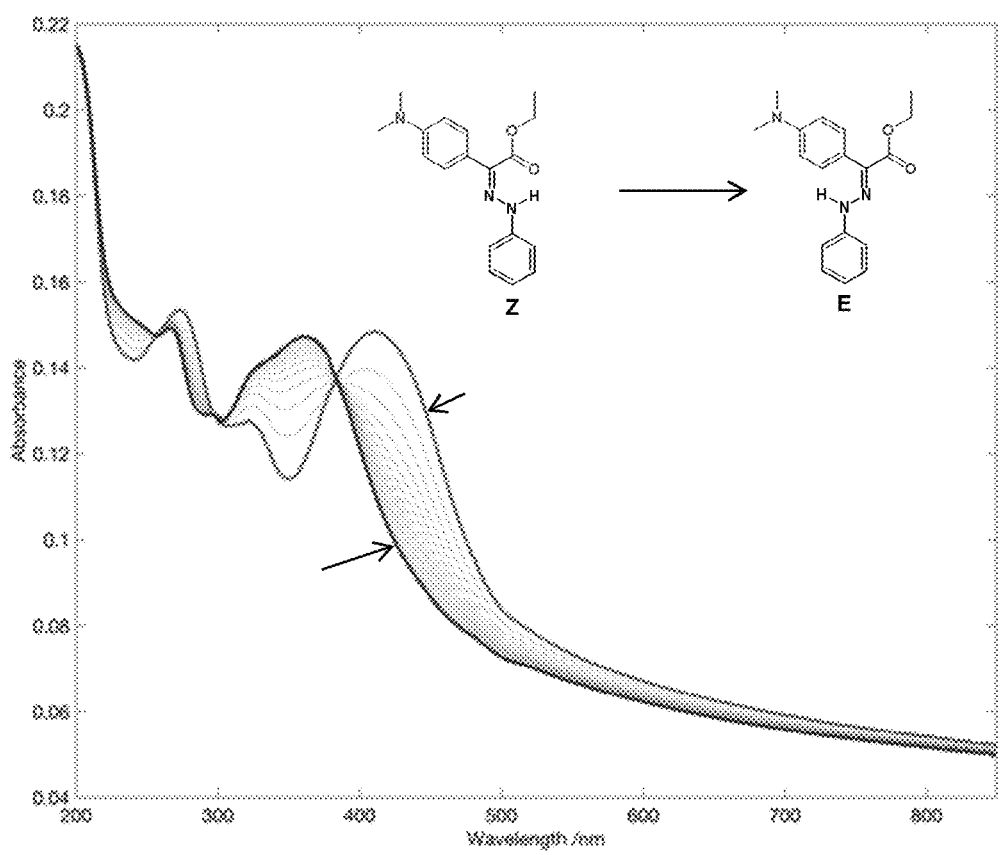
FIG. 5 illustrates photophysical properties of compounds 19Z and 19E in the solid state as a spin coated film on a substrate (quartz). Absorption spectra of 19Z (red line, furthest right) and those of 19E (blue line, furthest left). The blue line represents the PSS obtained after irradiation for 10 min with LED light at 450 nm. Intermediate time spectra are shown in gray.

FIG. 5 illustrates photophysical properties of compounds 19Z and 19E in the solid state as a spin coated film on a substrate (quartz). Absorption spectra of 19Z (red line, furthest right) and those of 19E (blue line, furthest left). The blue line represents the PSS obtained after irradiation for 10 min with LED light at 450 nm. Intermediate time spectra are shown in gray.

Figure 6:
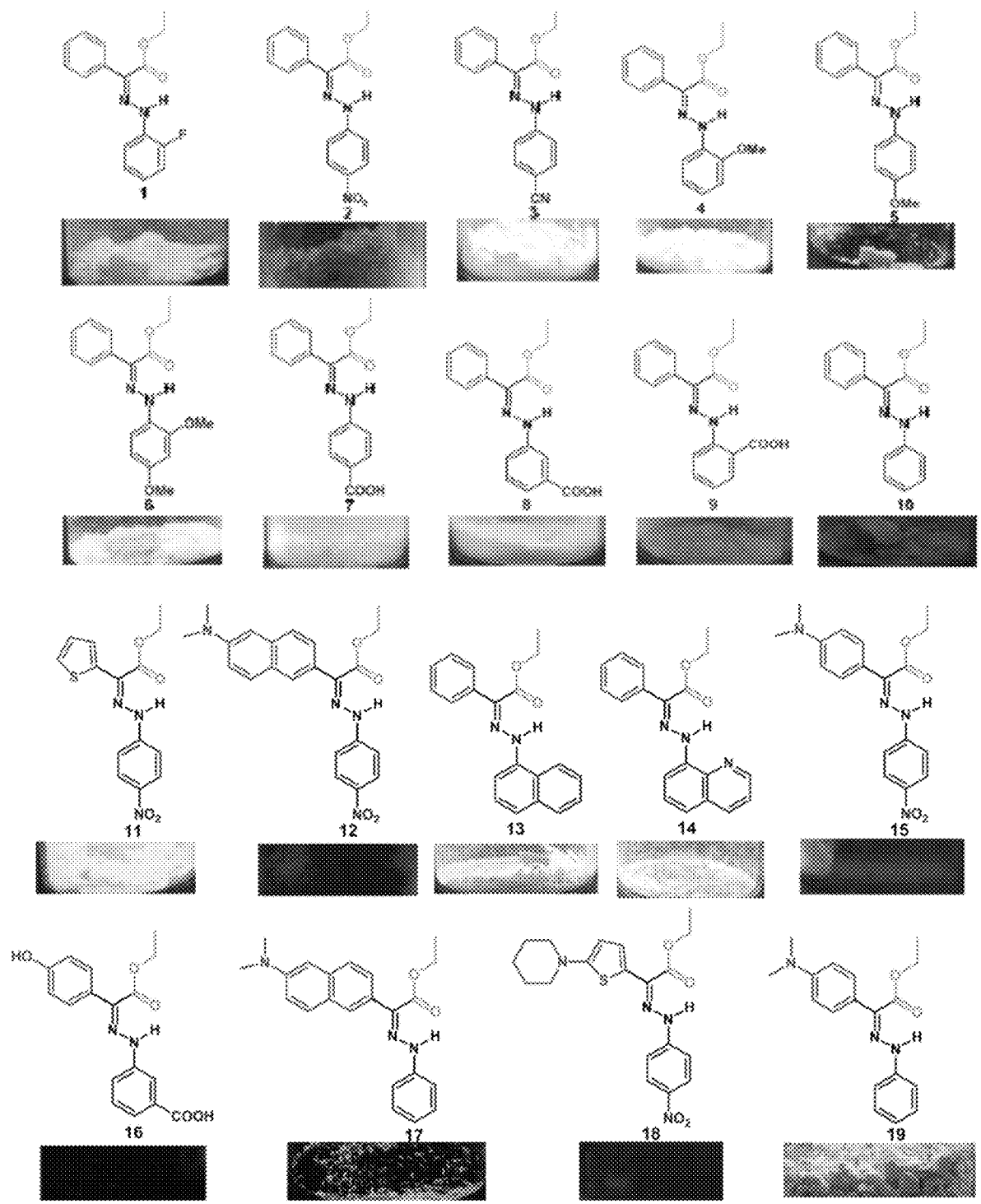
FIG. 6 illustrates solid state emission under UV light of certain photochromic hydrazones.

FIG. 6 illustrates solid state emission under UV light of certain photochromic hydrazones.

Figure 7:
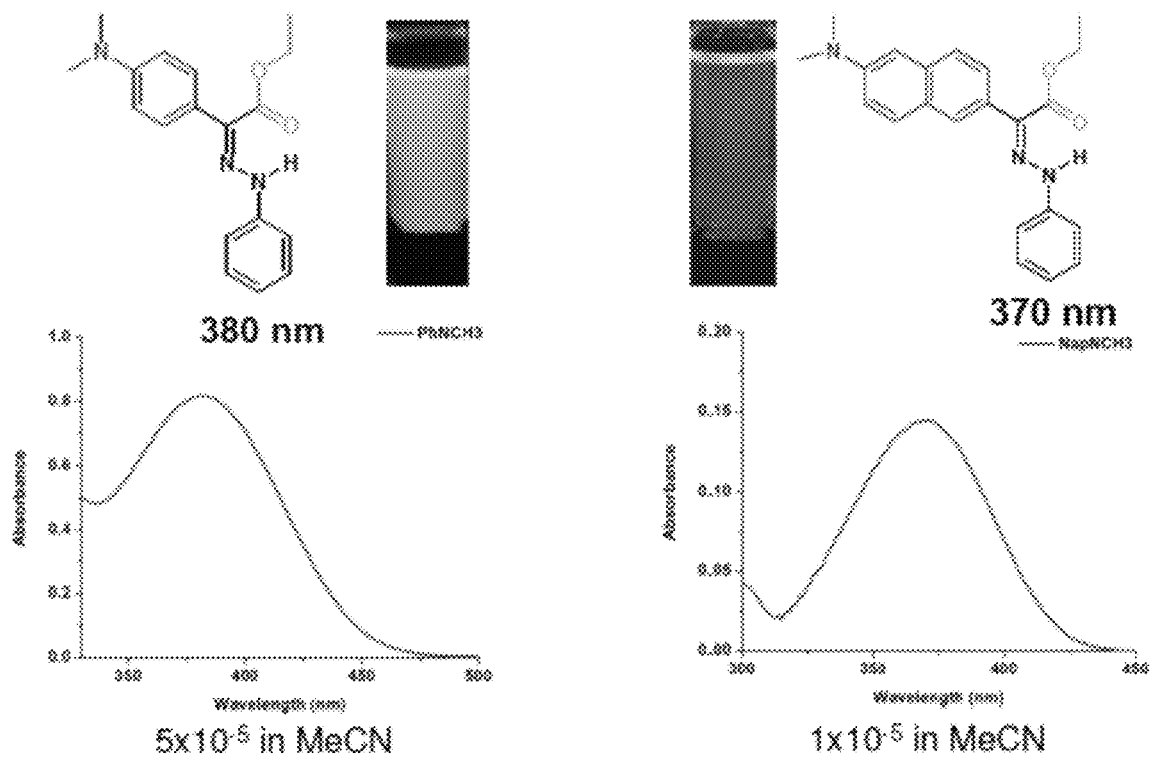
FIG. 7 illustrates photochromic studies on certain hydrazones having dimethylamino substituents on the A ring.

FIG. 7 illustrates photochromic studies on certain hydrazones having dimethylamino substituents on the A ring.

Figure 8:
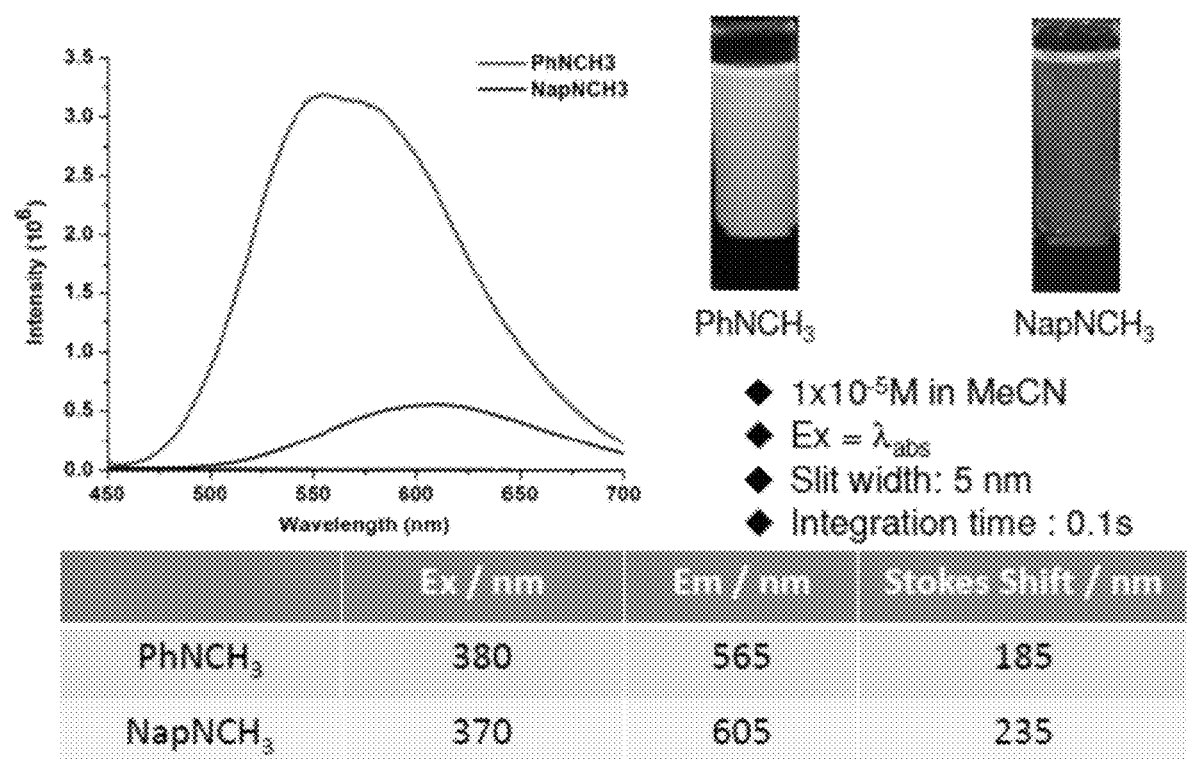
FIG. 8 summarizes fluorescent studies for hydrazone compounds of FIG. 7.

FIG. 8 summarizes fluorescent studies for hydrazone compounds of FIG. 7.

Figure 9:
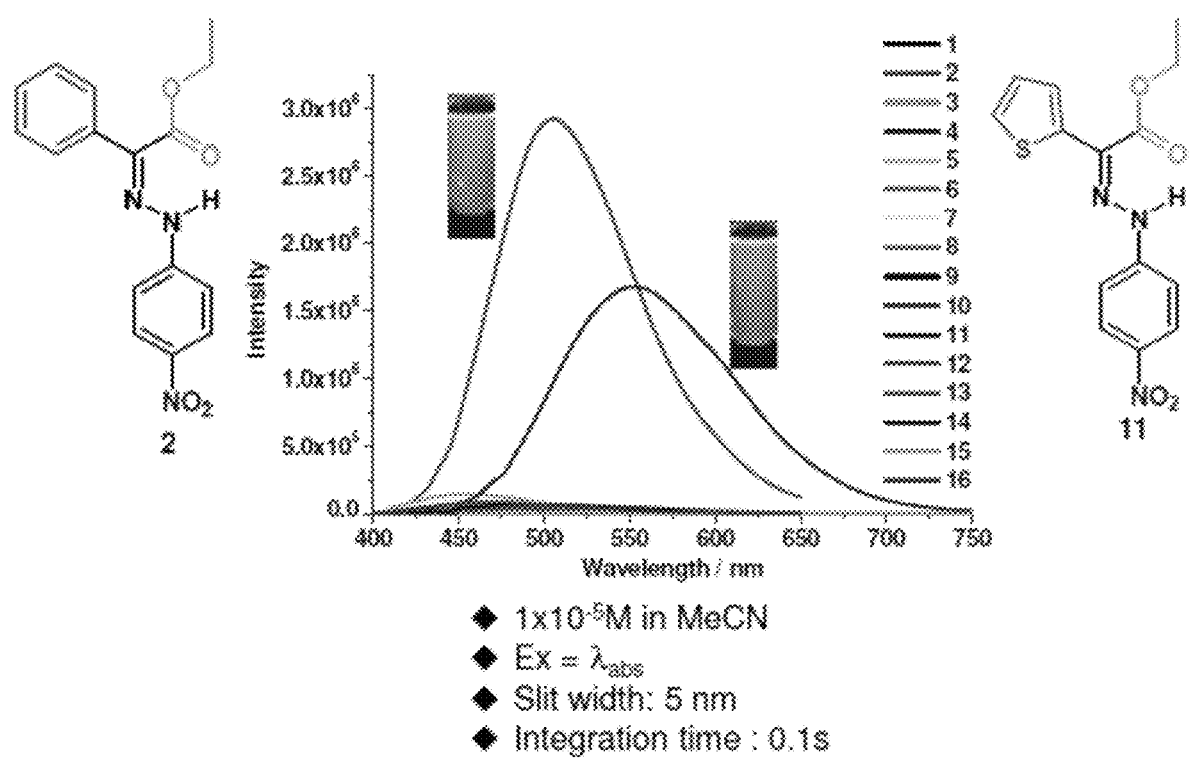
FIG. 9 illustrates fluorescent spectra of compounds 2 and 11 which have different A group rings.

FIG. 9 illustrates fluorescent spectra of compounds 2 and 11 which have different A group rings.

Figure 10:
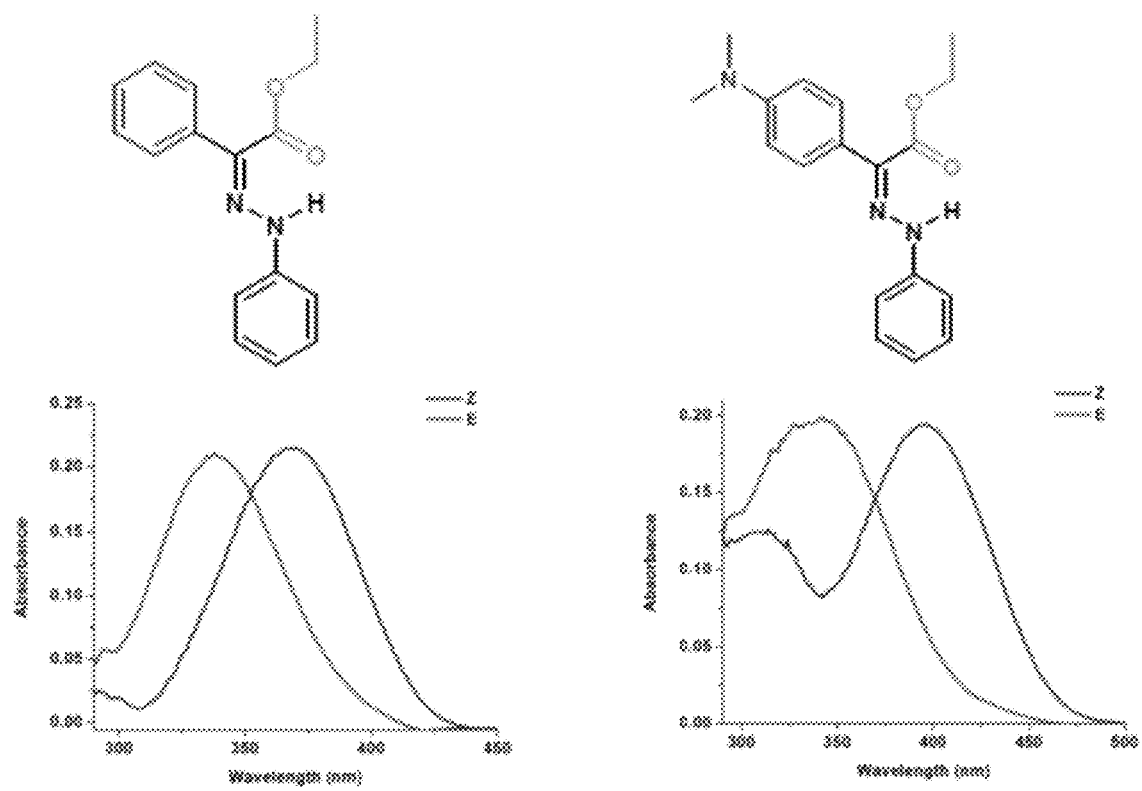
FIG. 10 illustrates photochromism of certain hydrazones in serum (10% FBS). 10% (v/v) FBS buffer (pH≈7.45) is made by adding FBS to 10 mM PBSbuffer. PBS buffer is formed by dissolving NaCl (8 g), KCl (0.2 g), $Na_2HPO_4$. (1.44 g), and $K_2H_2PO_4$ (0.24 g) in 1 liter of deionized water.
Figure 13A:
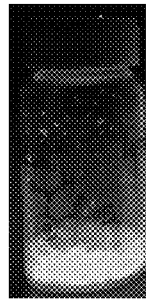
FIGS. 13A-13F illustrate solid emission properties of macrocycles which vary with the size of the ring. Macrocyle is shown in figures. Samples were irradiated with 365 nm using a TLC lamp.
Figure 13B:
Figure 13C:
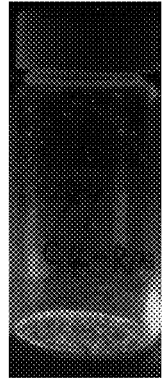
Figure 13D:
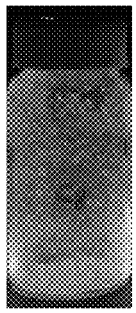
Figure 13E:
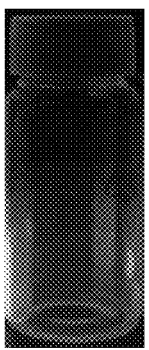
Figure 13F:
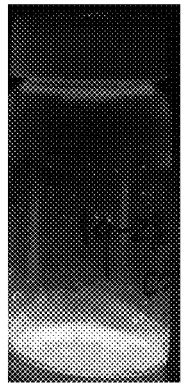

FIG. 10 illustrates photochromism of certain hydrazones in serum (10% FBS). 10% (v/v) FBS buffer (pH≈7.45) is made by adding FBS to 10 mM PBSbuffer. PBS buffer is formed by dissolving NaCl (8 g), KCl (0.2 g), $Na_2HPO_4$. (1.44 g), and $K_2HPO_4$ (0.24 g) in 1 liter of deionized water.

FIG. 11 illustrates switchable fluorescence of a hydrazone compound in serum (10% FBS).

FIG. 12 illustrates structures of additional exemplary compounds of the invention.

FIGS. 13A-13F illustrate solid emission properties of macrocycles which vary with the size of the ring. Macrocyle is shown in figures. Samples were irradiated with 365 nm using a TLC lamp. FIGS. 14A and 14B: FIG. 14A is a UV/Vis spectrum, taken at 15 min intervals for 2 hours, of the hydrazone switch in the presence of 1000 equiv. GSH in PBS buffer (50% MeCN, pH=7.4); FIG. 14B illustrates the switching of the hydrazone from Z to E monitored using UV/Vis spectroscopy.

Example 9: Summary of Photophysical Properties of Exemplary Compounds of the Invention

TABLE 3

Photophysical parameters for hydrazones 1-19 and 120-131

|   | $\lambda_Z$/nm[a] | $\lambda_E$/nm[b] | $\lambda_{em}$/nm[c] | PSS(Z→E)[d] | PSS(E→Z)[e] | $\Phi_{(Z\to E)}$%[f] | $\Phi_{(E\to Z)}$%[g] | $\tau_{1/2}$/yrs[h] |
|---|---|---|---|---|---|---|---|---|
| 1 | 364 | 329 | 465 | >99% | 68% | — | — | — |
| 2 | 391 | 366 | 452 | 98% | 82% | 0.64 ± 0.04 | 10.6 ± 0.1 | 631 ± 161 |
| 3 | 368 | 333 | 450 | >99% | 86% | 0.74 ± 0.01 | 4.8 ± 0.4 | 665 ± 58 |
| 4 | 382 | 347 | — | — | — | — | — | — |
| 5 | 383 | 351 | — | 93% | 88% | 0.54 ± 0.01 | 7.3 ± 0.5 | 0.039 ± 0.002 |
| 6 | 394 | 361 | — | — | — | — | — | — |
| 7 | 362[aa] | — | — | — | — | — | — | — |
| 8 | 358[aa] | — | — | — | — | — | — | — |
| 9 | 366[aa] | — | — | — | — | — | — | — |
| 10 | 367 | 334 | — | 95% | 76% | 1.7 ± 0.1 | 10.2 ± 0.1 | 255 ± 19 |
| 11 | 375 | 419 | 487 | 97% | 97% | — | — | — |
| 12 | 427 | 372 | 565 | >99% | 93% | 19.0 ± 1.4 | 6.3 ± 0.1 | 0.92 ± 0.07 |
| 13 | 383[aa] | — | — | — | — | — | — | — |
| 14 | 398 | 373 | 480 | 91% | 76% | 2.4 ± 0.1 | 0.3 ± 0.1 | 2700 ± 100 |
| 15 | 435 | 384 | 560 | >99% | 96% | 16.6 ± 1.5 | 6.8 ± 1.0 | 1.5 ± 0.1 |
| 16 | 362[aa] | — | — | — | — | — | — | — |
| 17 | 370[aa] | — | 605[ca] | 94% | 63% | — | — | — |
| 18 | 487 | —[ba] | — | — | — | — | — | — |
| 19 | 395 | 343 | 525 | >99% | 82% | 9.1 ± 0.2 | 13.6 ± 1.0 | 75 ± 3 |
| 120 | 381 | 327 | — | >99% | 91% | 3.4 ± 0.3 | 9.2 ± 0.5 | 103 ± 2 |
| 121 | 371 | 324 | — | >99% | 84% | 4.1 ± 0.1 | 8.1 ± 0.4 | 2978 ± 52 |
| 122 | 362 | 326 | — | 98% | 67% | 4.0 ± 0.1 | 8.4 ± 1.0 | 12379 ± 568 |
| 123 | 366 | 327 | — | 98% | 75% | 2.4 ± 0.1 | 5.6 ± 0.2 | 0.48 ± 0.01 |
| 124 | 372 | 326 | — | >99% | 70% | 4.1 ± 0.2 | 6.6 ± 0.4 | 0.18 ± 0.02 |
| 125 | 370 | 328 | — | 88% | 79% | 2.4 ± 0.1 | 5.6 ± 0.3 | 0.05 ± 0.003 |
| 126 | 372 | 353 | — | 88% | 77% | 2.2 ± 0.1 | 4.1 ± 0.2 | 31813 ± 2884 |
| 127 | 392 | 314 | — | 92% | 52%[ea] | 1.6 ± 0.1 | 4.5 ± 0.6 | 23 ± 1 |
| 128 | 410 | —[bb] | — | 27% | —[eb] | 12.3 ± 1.2 | —[eb] | 0.0015 ± 0.0001 |
| 129 | 412 | — | 423/550[cb] | 15% | — | — | — | — |
| 130 | 458 | — | — | — | — | — | — | — |
| 131 | 454 | — | 423/610[cb] | 10% | — | — | — | — |

[a]Absorption maximum of the Z isomer in toluene;
[aa]Absorption maximum of the Z isomer in acetonitrile;
[b]Absorption maximum of the E isomer in toluene;
[ba]no significant isomerization was observed;
[bb]The $\lambda_{max}$ of the E isomer cannot be determined as a result of low Z→E photoconversion;
[c]Emission maximum of the fluorescent hydrazones in toluene. The corresponding absorption maximum was applied as the excitation wavelength;
[ca]Emission maximum of the Z isomer in acetonitrile;
[cb]Dual emission maxima observed in toluene;
[d]Photostationary state in toluene-d$_8$ reached by irradiating the Z isomer with different irradiation wavelengths;
[e]Photostationary state in toluene-d$_8$ reached by irradiating the E isomer or E-rich mixtures with different irradiation wavelengths;
[ea]Irradiation wavelength close to the isosbestic point results in a low photoisomerization ratio;
[eb]Because of the poor band separation, an optimal irradiation wavelength was not found to initiate the E→Z isomerization process;
[f]The photoisomerization quantum yield for the Z→E isomerization process based on three consecutive measurements;
[g]The photoisomerization quantum yield for the E→Z isomerization process based on three consecutive measurements;
[h]Thermal relaxation half-life for the E→Z process based on three parallel measurements.

Example 10: Certain Applications of Compounds of the Invention

This example demonstrates the combined benefit of bistability and ON/OFF fluorescence switching of the compounds herein, particularly compound 19.

Writing in Solution

Employing compound 19, an efficient and reversible solution-based writing-and-recording system was demonstrated. A laser pointer (λ=450 nm) is utilized as a "pen", a 365 nm UV lamp is used as a reading/erasing platform, and solvent is used as canvas! A toluene solution of 19 is irradiated under the UV light leading to fluorescence emission. The laser pointer is then used to draw different patterns in the solution by quenching the emission using the "pen" strokes. When the UV light is turned off at this stage the drawing persists in solution for up to an hour, after which diffusion erases it. It is noteworthy that the 19-E molecules formed through this process persist in solution because of their long-thermal lifetime, and the apparent quenching mainly results from diffusion assisted dilution. Another way to erase the drawings is to keep the UV light on, which will lead to E→Z isomerization and turn ON of emission at the quenched areas. This technique is used to allow use the solvent canvas in multiple write-erase cycles.

Figure 22:
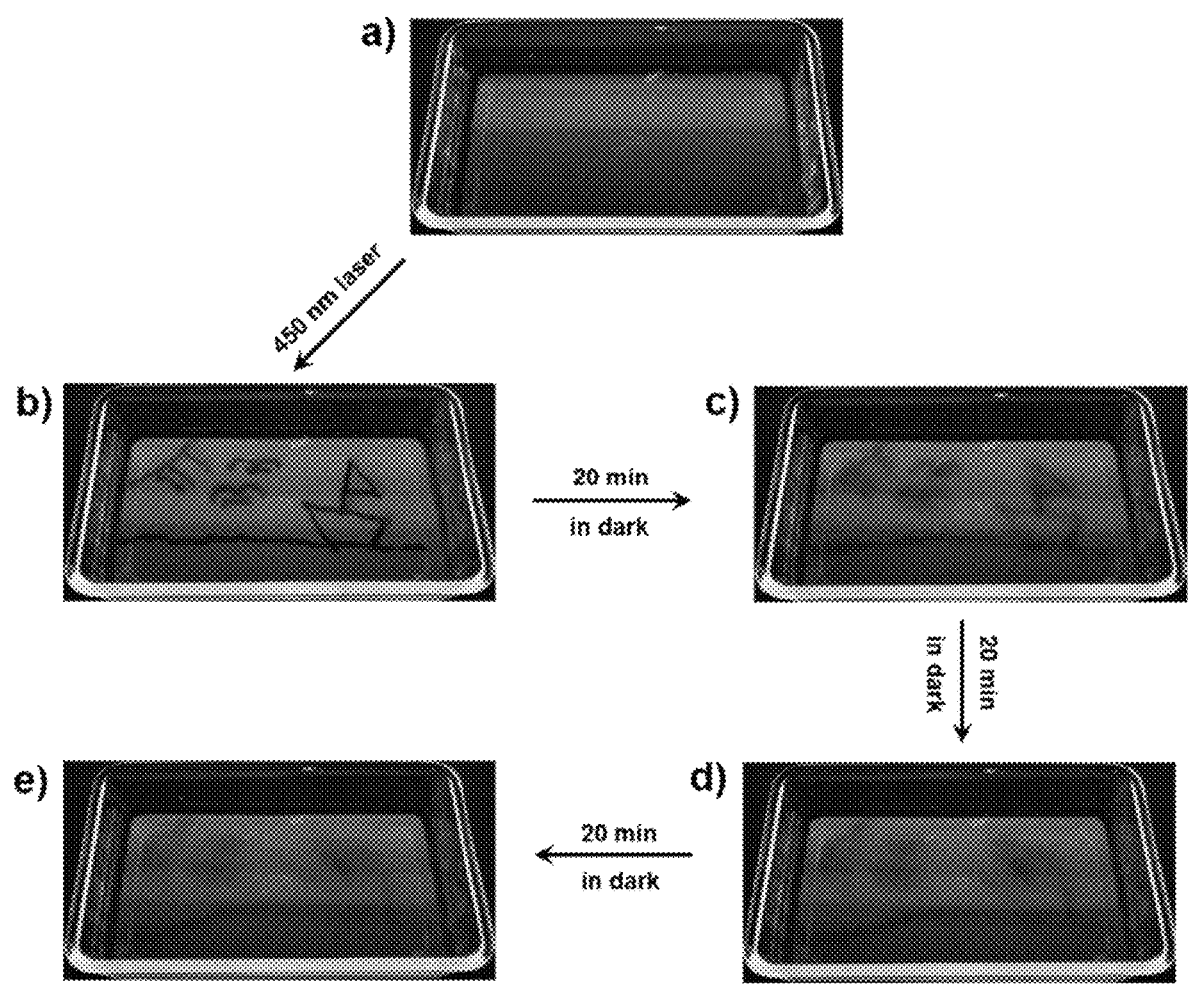
FIG. 22, a-e illustrates a writing in solution experiment. a) Before writing; b) after writing; at c) 20-min d) 40-min and e) 60-min interval after writing. The UV light was turned OFF during intervals and only turned ON every 20 minutes to capture the changes in image.

Spectrophotometric grade toluene was used for solution writing experiments. A solution of 19 (40 ml, 1.0×10$^{-4}$ M) in toluene was prepared and transferred into a rectangular glass container and used as a writing substrate (canvas). The solution thickness was set at around 0.5 cm. The glass container was then placed under a 365 nm UV lamp, and a 450 nm laser pointer was applied to do the writing (FIG. 22).

On irradiation with the laser pointer Compound 19 emits fluorescence. When the UV lamp is turned off after writing and the whole setup left under dark, then the writing disappears in ca. 1 hour as a result of diffusion. When left under the UV light, the writing will disappear after ca. 15 mins, because of the E→Z isomerization.

Solid State Imaging

Similar writing or imaging is demonstrated in the solid state by irradiating drop-casted films (1 mg in 1 ml dichloromethane) of 19-Z with appropriate light sources. The absorption and emission spectra ($\lambda_{ex}$=380 nm, isosbestic point) of 19-Z in the solid film are very similar to that recorded in solution. Irradiation of the film at 450 nm brings about absorption spectral changes that are almost identical to those observed in solution, indicating efficient Z→E isomerization in the solid state. From an analysis of the absorption spectra, it can be estimated that at the photostationary state ($PSS_{450}$), more than 90% of 19-Z is converted to the E configuration. The characteristic emission of the Z form at $\lambda_{max}$=560 nm is quenched at the photostationary state, confirming that the 19-E form is also non-emissive in the solid state. The complete suppression of emission, which is not observed in solution, suggests that the tiny fraction of 19-Z molecules present at $PSS_{450}$ could be quenched by nearby 19-E species. FRET from 19-Z to 19-E is expected to be inefficient because of minimal spectral overlap. Hence, quenching may be ascribed to photoinduced electron transfer, presumably involving the dimethylaniline residue as the electron donor and the hydrazone system as the acceptor.

Figure 23:
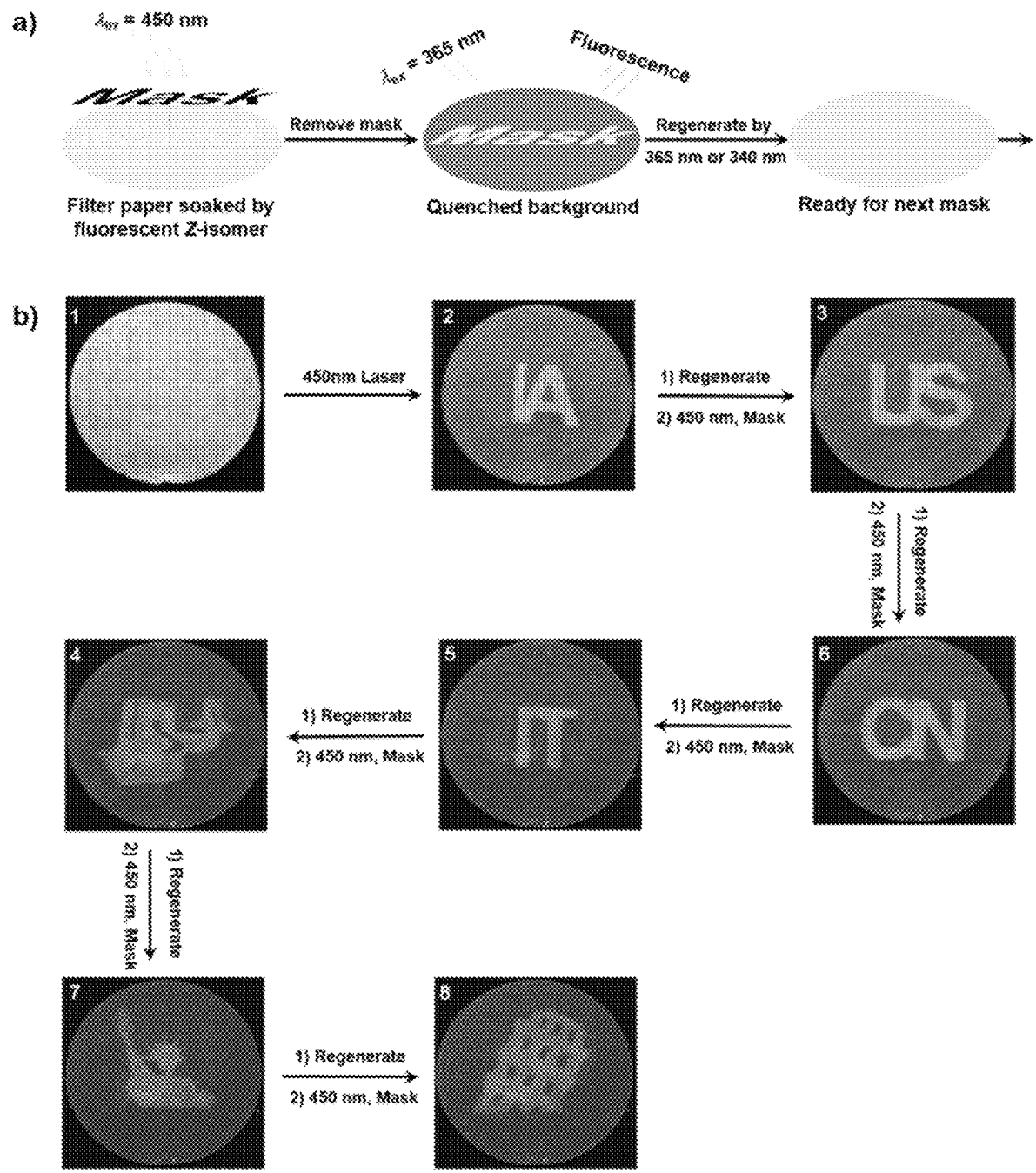
FIG. 23, a-b illustrates photomasks on a single filter paper. a) The mask was put on the filter paper and surrounding area was irradiated with 450 nm. Removing the mask and monitoring under 365 nm showed the image left behind, which disappeared with time. b) Original filter paper (1) and seven photomasks (2-8) were used for the write/erase cycles using the same filter paper.

Exposing the 19-E enriched film to 360 nm light causes spectral changes consistent with E→Z photoisomerization, and results in a photostationary state ($PSS_{360}$) enriched with 19-Z. The initial absorption and fluorescence spectra cannot be fully recovered by irradiation at 360 nm because of the extensive overlap, at this wavelength, between the absorption spectra of the E and Z forms. The thus obtained photostationary state ($PSS_{360}$) is composed of a 60:30 mixture of the Z and E forms. Nevertheless, the system displays high fatigue resistance in the solid state, as its absorption and emission characteristics can be reversibly switched multiple times by alternate irradiation at 450 and 360 nm (FIG. 23). Nonetheless, a decrease in the emission intensity is observed after the first switching cycle, which stabilizes in subsequent cycles. This effect might be attributed to an annealing effect (e.g., reorganization of the solid state structure) that the film undergoes after the first switching cycle (vide infra).

It is noted that despite the fact that $PSS_{360}$ contains 60% of emissive 19-Z, the fluorescence intensity is only 15% of that of the pure 19-Z film. This observation is consistent with the quenching of excited 19-Z by nearby 19-E species.

Photoswitching in Solid Films

Drop casted films were imaged with an epifluorescence polarizing optical microscope during photoswitching. The films exhibit strong fluorescence emission when excited with 360 nm light and significant optical birefringence under cross-polarized light illumination. This confirms an ordered arrangement of the molecules in the solid that gives rise to anisotropic crystals. Upon irradiation with high intensity blue light in a central spot, the morphology of the film changes and both the optical birefringence and fluorescence emission disappear in the irradiated area. This observation indicated that isomerization induces a phase transition leading to a loss of crystalline order, that is, amorphization of the material. The emission intensity and birefringence of the material are partially restored upon irradiation with high intensity near-UV light. This result confirms the reversible nature of the light induced switching process, and rules out local thermal effects as the cause of the observed phenomenon.

Writing in Solid

Taking advantage of the solid-state switching of 19 and accompanied ON/OFF emission toggling, compound 19 was used as a solid dye on different surfaces. In one example, a filter paper was soaked with a MeCN solution of 19 and let it dry under air. Once completely dry, the paper was covered with a mask and irradiated with 442 nm light to quench the fluorescence of the unmasked area. Removing the mask, and observing the filter paper under 365 nm UV lamp, showed an emissive pattern that matches the mask. Continued exposure under a 365 nm UV lamp erases the writing allowing for the cycling of this process with other masks. In another example, a transparency paper was coated and a laser pointer was used to draw pictures by quenching the emission at the "pen" strokes. Again UV light was used to visualize, and depending on exposure time eventually erase the drawing.

A solution of 19-Z ($3.0\times10^{-3}$ M) in dichloromethane was prepared, and 5-10 ml of it were dispersed on a transparency slide. After the DCM evaporated, a thin layer of 19-Z was deposited onto the transparency slide.

The transparency slide was then anchored on a 365 nm UV lamp. A laser pointer was used to write on the slide. The 365 nm UV lamp, which was used to both excite the molecules to enable reading, and to erase the writing. The images were made visible by the excitation of UV light. Long exposure to the light erases the writing, allowing for another write/erase cycle. Glass microfiber filters (circle, diameter=42.5 mm) from Whatman® were used for the preparation of the hydrazone-deposited filters. A solution of 19-Z ($5.0\times10^{-4}$ M) in dichloromethane (spectroscopic grade) was prepared, and the filters were fully immersed into the solution for approx. 10 s, and then left to air-dry. The resulting hydrazone-deposited filters were used for the solid-state photomask imaging experiments.

Figure 24:
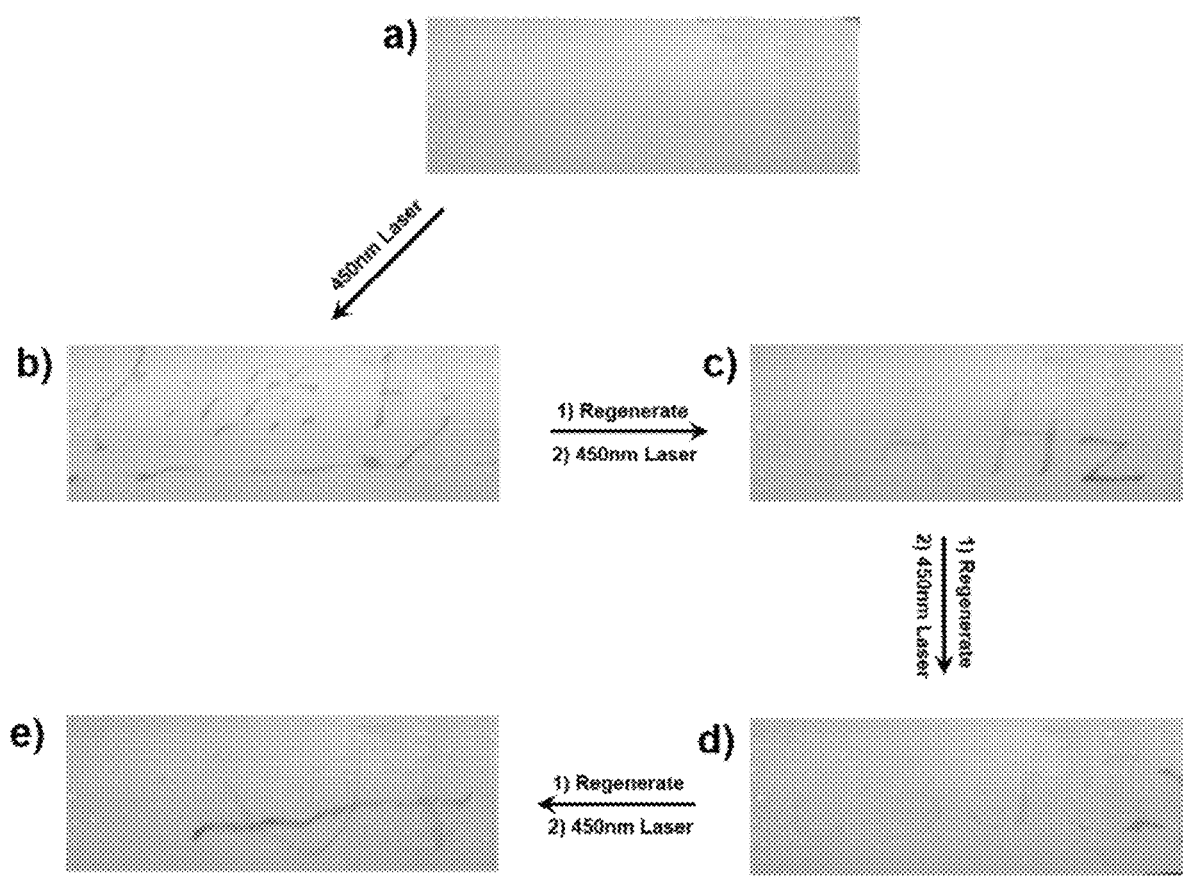
FIG. 24, a-e illustrates a writing in solid experiment. a) Slide before writing; b-e) four different patterns were drawn successively, using the same transparency slide. The UV lamp was on throughout the write/erase cycles.
Figure 25A:
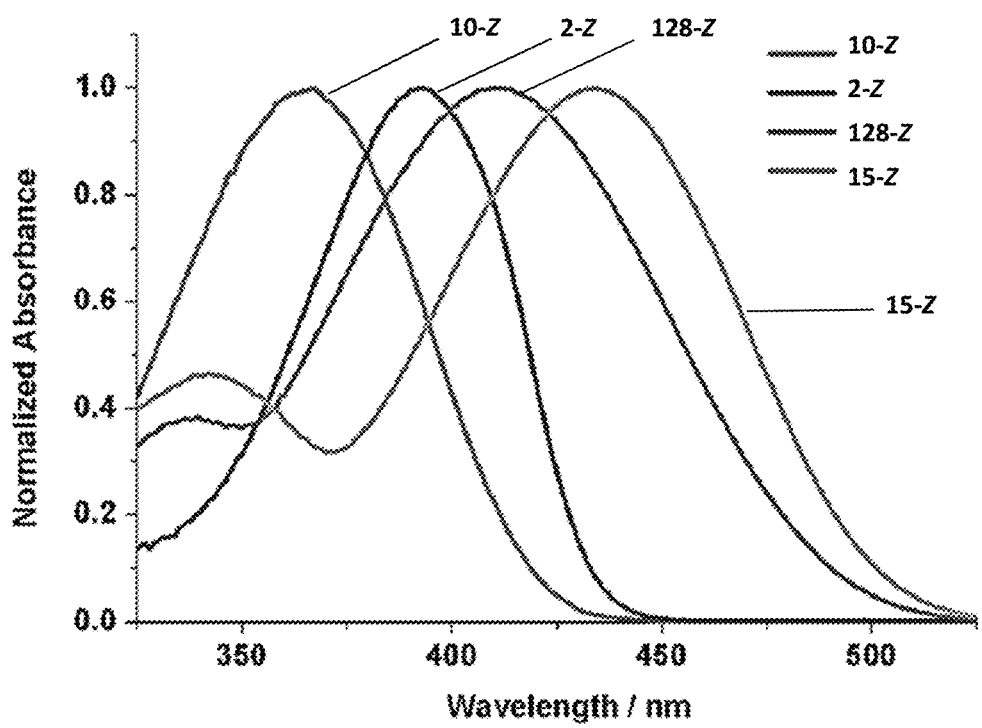
FIG. 25A illustrates normalized UV-Vis spectra for the Z isomers of hydrazones 10, 2, 128 and 15 in toluene.
Figure 25B:
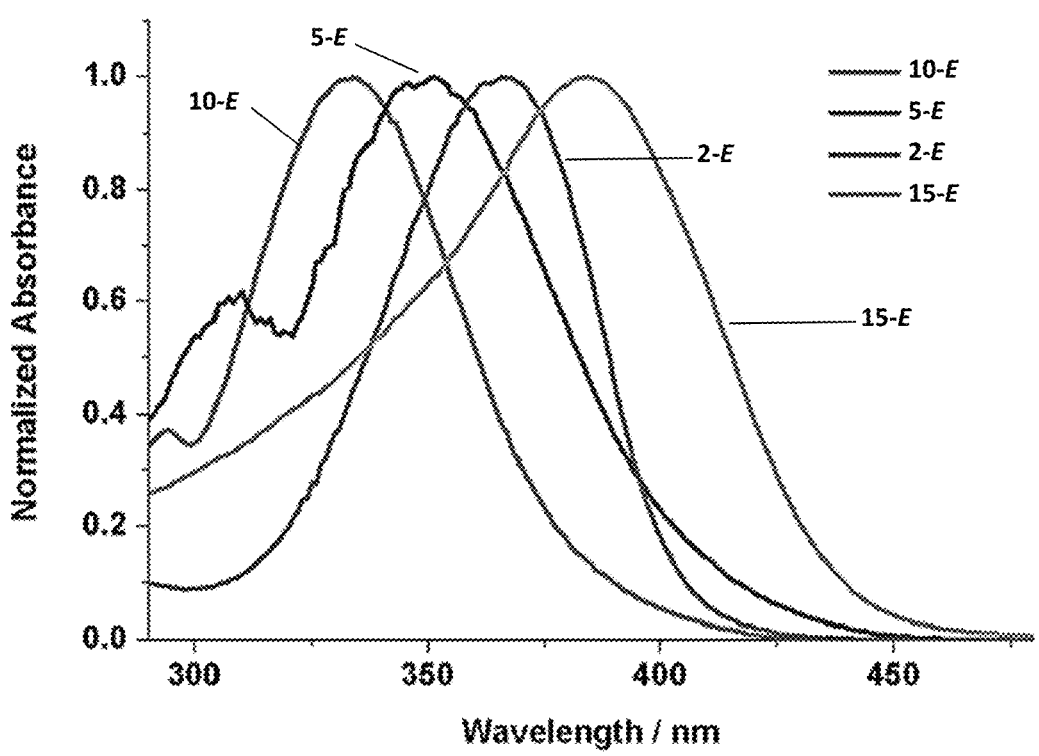
FIG. 25B illustrates normalized UV-Vis spectra for the E isomers of hydrazones 10, 2, 5 and 15 in toluene.

A mask was placed on the filter paper and then the laser pointer was applied to thoroughly erase the unmasked area. The mask was then removed and the filter paper was placed under the 365 nm UV lamp to visualize the fluorescent image. Several minutes exposure under 365 nm UV lamp leads to the recovery of background fluorescence. A second mask having a different pattern was then placed onto the same filter paper for another write/erase cycle. This process was repeated at least 7 times using the same filter paper (see FIG. 24).

Example 11 Structure Property Analysis of the Solution and Solid-State Properties of Bistable Photochromic Hydrazones

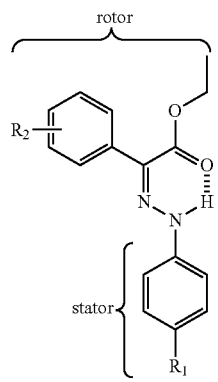

10 $R_1$ = H, $R_2$ = 4-H
19 $R_1$ = H, $R_2$ = 4-NMe$_2$
201 $R_1$ = H, $R_2$ = 3-NMe$_2$
202 $R_1$ = H, $R_2$ = 4-OMe
127 $R_1$ = H, $R_2$ = 4-NO$_2$
3 $R_1$ = CN, $R_2$ = H
2 $R_1$ = NO$_2$, $R_2$ = H
5 $R_1$ = OMe, $R_2$ = H
128 $R_1$ = NMe$_2$, $R_2$ = H
15 $R_1$ = NO$_2$, $R_2$ = 4-NMe$_2$

Figure 26A:
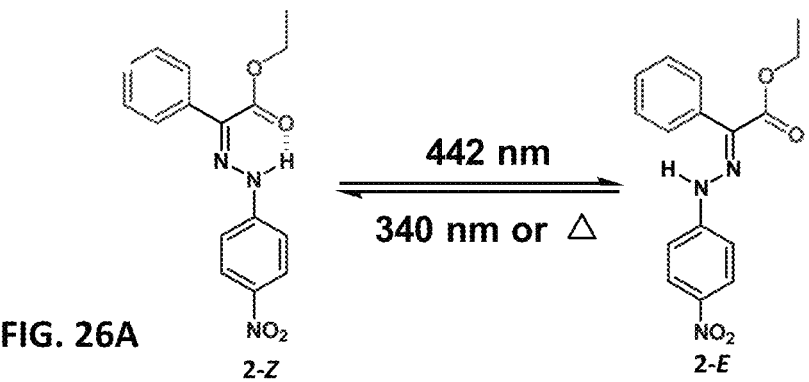
FIG. 26A illustrates light-activated photoisomerization of hydrazone 2.
Figure 26B:
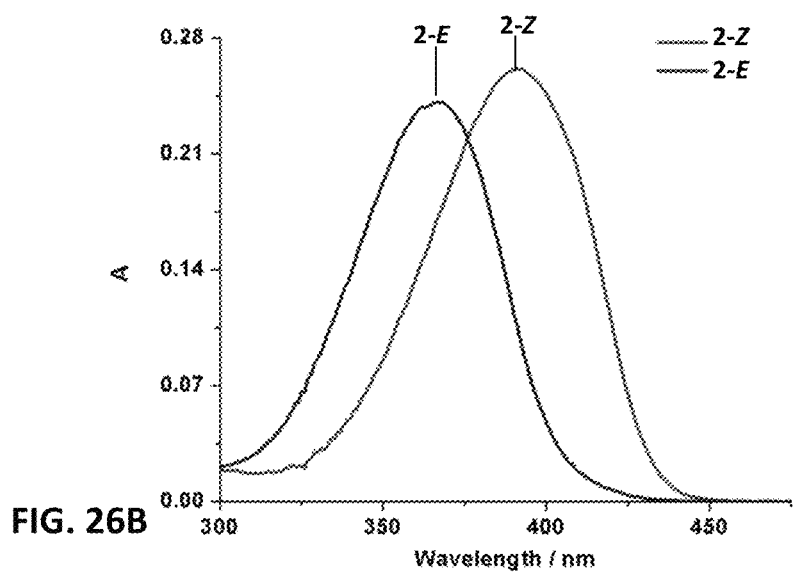
FIG. 26B illustrates UV-Vis spectra (1×10$^{-5}$ M) of 2-Z and 2-E isomers in toluene.
Figure 26C:
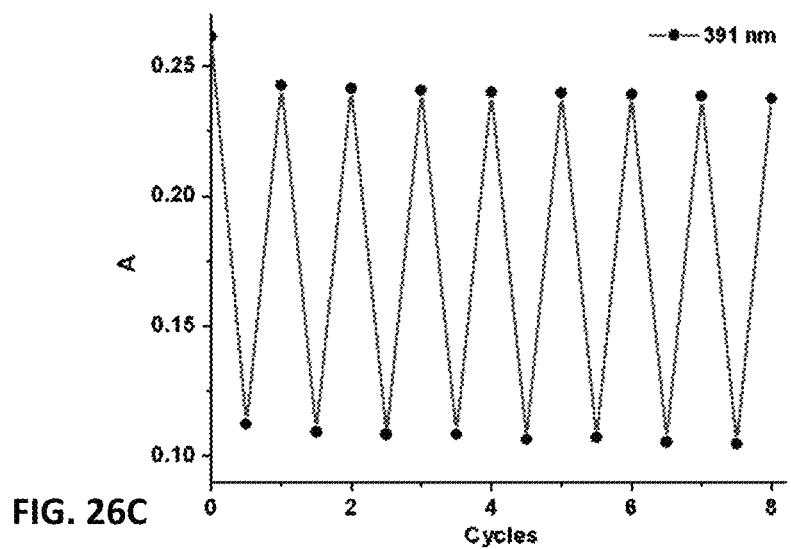
FIG. 26C illustrates photoswitching cycles of 2 in toluene upon alternating the irradiation wavelength between 442 and 340 nm light.
Figure 29:
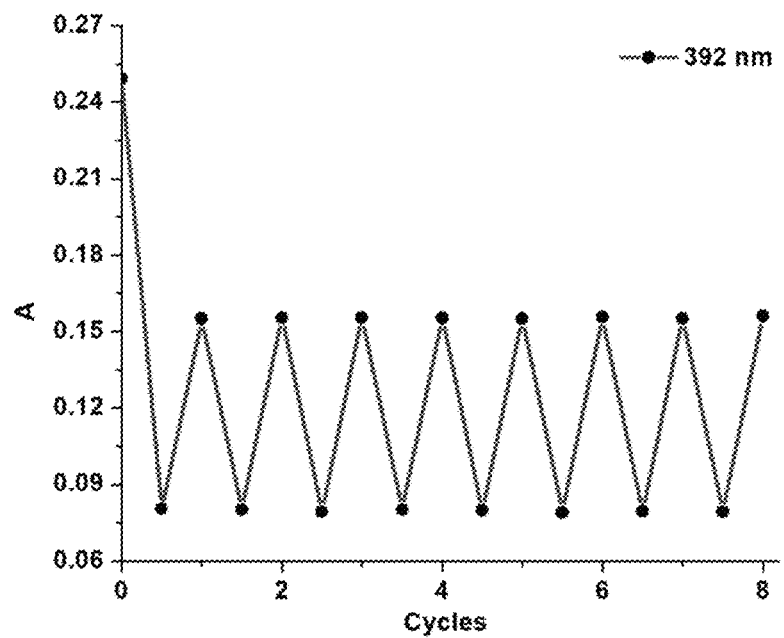
FIG. 29 illustrates photoisomerization cycles of hydrazone 127 ($1\times10^{-5}$ M) in toluene at 294 K. The absorbance change at 392 was monitored while alternating the irradiation wavelength between 442 and 340 nm.
Figure 30:
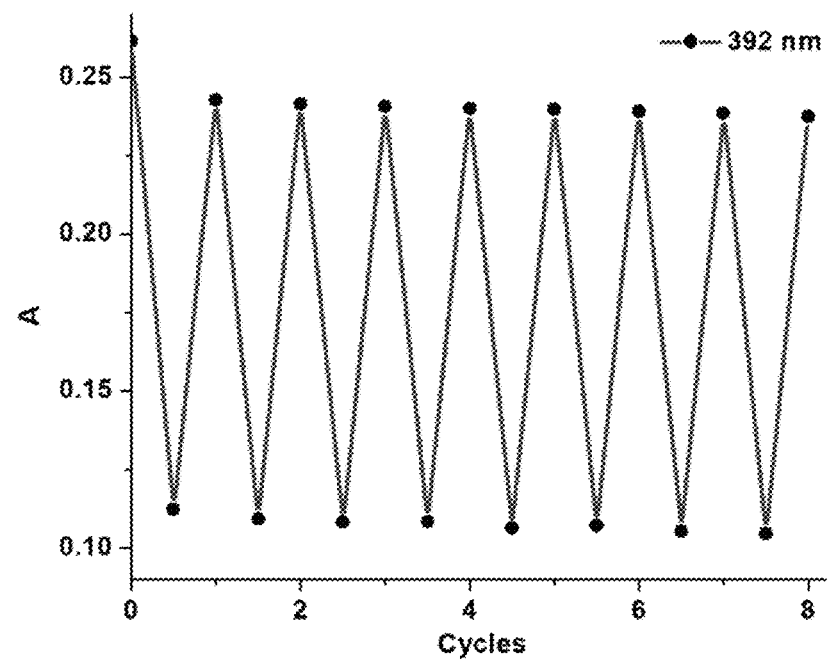
FIG. 30 illustrates photoisomerization cycles of hydrazone 2 ($1\times10^{-5}$ M) in toluene at 294 K. The absorbance change at 392 nm was monitored while alternating the irradiation wavelength between 442 and 365 nm.
Figure 54:
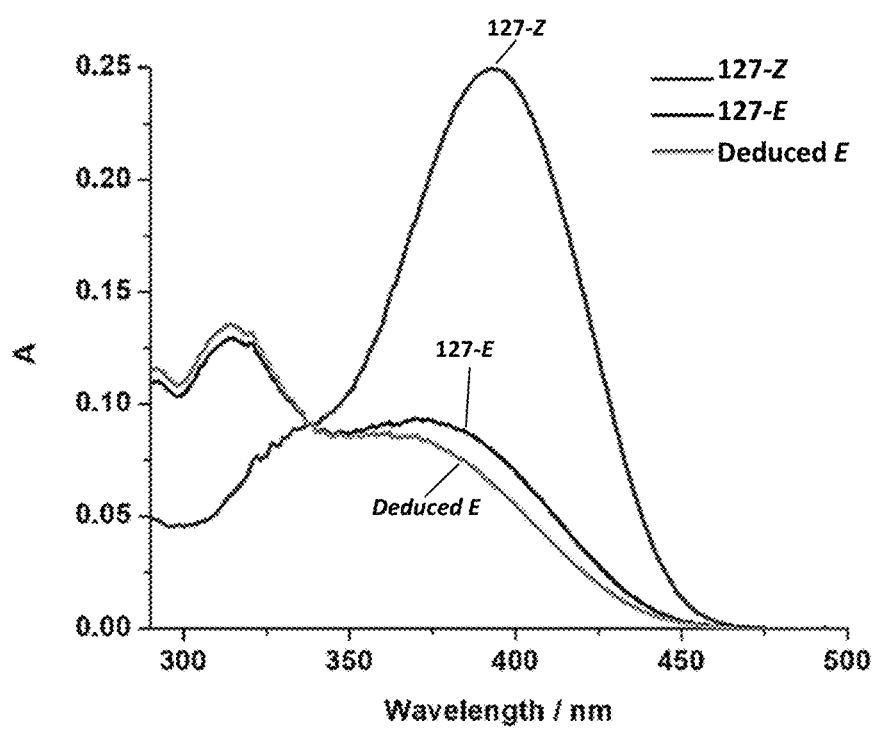
FIG. 54 illustrates UV-Vis absorption spectra of 127-Z and 127-E ($1\times10^{-5}$ M) in toluene: the UV spectrum of 127-E was obtained upon 442 nm light irradiation; 127-E can be photochemically switched back to 127-Z upon 340 nm light irradiation (The spectrum of E isomer is deduced following the aforementioned equations).
Figure 55:
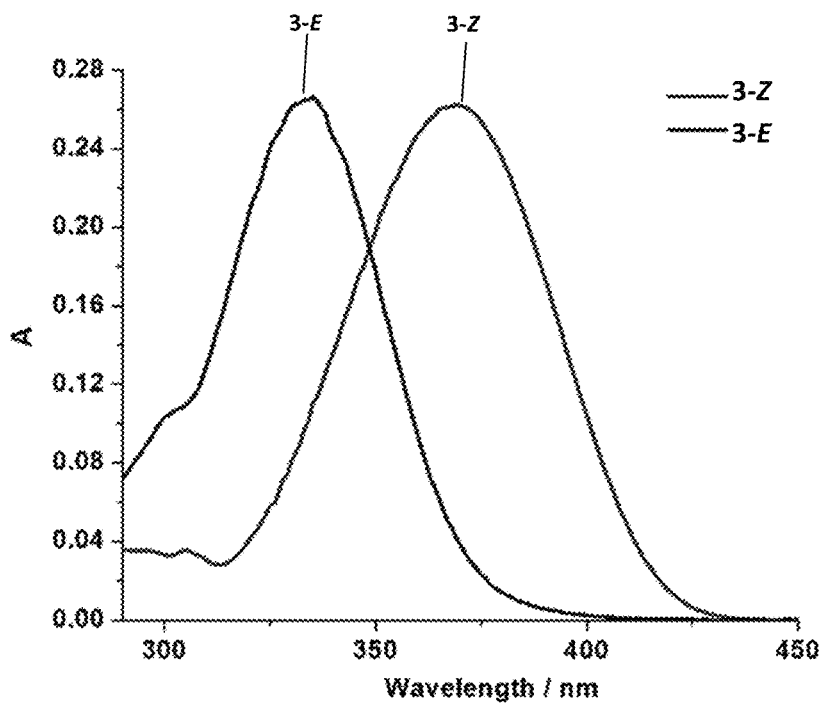
FIG. 55 illustrates UV-Vis absorption spectra of 3-Z and 3-E ($1\times10^{-5}$ M) in toluene: the UV spectrum of 3-E was obtained upon 410 nm light irradiation; 3-E can be photochemically switched back to 3-Z upon 340 nm light irradiation.

Photophysical Properties: The UV spectra of the Z and E isomers (obtained after irradiation at appropriate wavelength or by data extrapolation) of compounds were measured (or derived) in toluene. The absorption maxima ($\lambda_{max}$) of the Z and E forms of the para-CN substituted hydrazone 3 are almost identical to those of 10 (Table 5). Conversely, para-NO$_2$ substitution on either the rotor (127) or stator (2) phenyl ring induces a ca. 20 nm red-shift in the $\lambda_{max}$ of the Z isomers. This unusual effect could be attributed to the formation of a "quinoid" form in 2 which leads to the extension of the it-system through resonance between the hydrazone NH nitrogen and the NO$_2$ group, and a more stabilized LUMO (i.e., narrower HOMO-LUMO gap) in 127. The red-shift (33 nm) is retained in the E isomer of 2 relative to 10 as the effect stems from the stator part, which is not effected by isomerization, while a 20 nm blue-shift is observed in 127-E, which is the expected outcome upon NO$_2$-substitution, and loss of H-bonding induced planarity of hydrazone skeleton. All three hydrazones have excellent PSSs (>90%; 410/442 nm irradiation) going from Z to E (Table 5), thanks to the well-separated absorption bands of the two isomers (FIGS. 26b,54 and 55). The PSSs for the reverse process are also very high (>80%; 340/365 nm irradiation) for compounds 3 and 2, while for 127 a PSS$_{340}$ of 52% was measured because irradiation was done very close to the isosbestic point. Good quantum yields (>10%) were measured for both isomerization directions in 127 and 2, and particularly high (35.3%) for the Z→E isomerization process in 2. Compound 3 on the other hand exhibits lower $\Phi$ values ($\Phi_{Z\to E}$=4.1±0.1% and $\Phi_{E\to Z}$=5.1±0.3%). All three compounds exhibit good fatigue resistance as well (FIG. 26c and FIGS. 29 and 30).

TABLE 5

Photophysical data for some compounds in toluene.

| Hydrazone | $\lambda_{max}$ (nm)/$\varepsilon^a$ | | $\Phi$ | | | |
| --- | --- | --- | --- | --- | --- | --- |
| | Z | E | Z→E | E→Z | PSS @ $\lambda_{irr}$ (nm) | |
| 10[b] | 367/18300 | 334/18000 | 7.5 ± 0.1% | 10.6 ± 0.2% | 95% of E @ 410 | 76% of Z @ 340 |
| 19[c] | 395/14500 | 343/13800 | 32.0 ± 0.9% | 14.7 ± 1.0% | >99% of E @ 442 | 82% of Z @ 340 |
| 201 | 366/19200 | 331/19300 | 16.2 ± 0.5% | 10.7 ± 0.5% | >99% of E @ 410 | 54% of Z @ 340[d] |
| 202 | 376/21100 | 330/19500 | 4.7 ± 0.1% | 9.1 ± 0.6% | 98% of E @ 410 | 84% of Z @ 340 |
| 127 | 392/24900 | 314/13500 | 11.7 ± 0.3% | 12.6 ± 1.3% | 92% of E @ 442 | 52% of Z @ 340[d] |
| 3 | 368/26300 | 333/26600 | 4.1 ± 0.1% | 5.1 ± 0.3% | >99% of E @ 410 | 86% of Z @ 340 |
| 2 | 391/26800 | 366/24300 | 35.3 ± 2.1% | 11.4 ± 0.1% | 98% of E @ 442 | 82% of Z @ 365 |
| 5 | 383/17200 | 351/13900 | 5.3 ± 0.1% | 9.5 ± 0.5% | 93% of E @ 442 | 88% of Z @ 340 |
| 128 | 410/17800 | 398/11900 | 65.4 ± 6.1% | —[e] | 27% of E @ 480 | —[e] |
| 15 | 435/18300 | 384/17600 | 46.2 ± 4.2% | 7.4 ± 1.1%[f] | >99% of E @ 480 | 96% of Z @ 375[f] |

[a]The extinction coefficient ($\varepsilon$) is calculated in L mol$^{-1}$ cm$^{-1}$;
[b]Ref Error! Bookmark not defined.a;
[c]Ref Error! Bookmark not defined.;
[d]Band overlap and hence no access to optimal switching wavelength;
[e]Because of the poor band separation, an optimal irradiation wavelength was not found to initiate the E→Z isomerization process;
[f]$\Phi$ = 19.4 ± 0.6% and PSS = 90% of Z when 410 nm light is used for the E → Z process.

Figure 56:
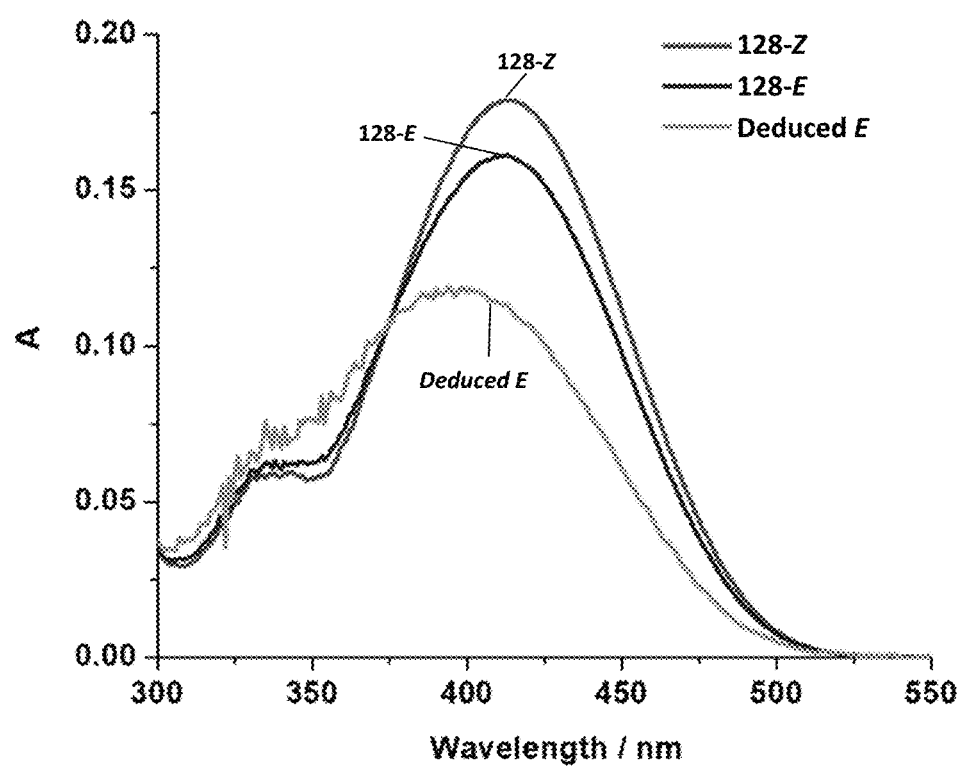
FIG. 56 UV-Vis absorption spectra of 128-Z and 128-E ($1\times10^{-5}$ M) in toluene: the UV spectrum of 128-E was obtained upon 480 nm light irradiation; unfortunately, no optimal irradiation wavelength was found to photochemically switch 128-E back to 128-Z (The spectrum of E isomer is deduced following the aforementioned equations).
Figure 57:
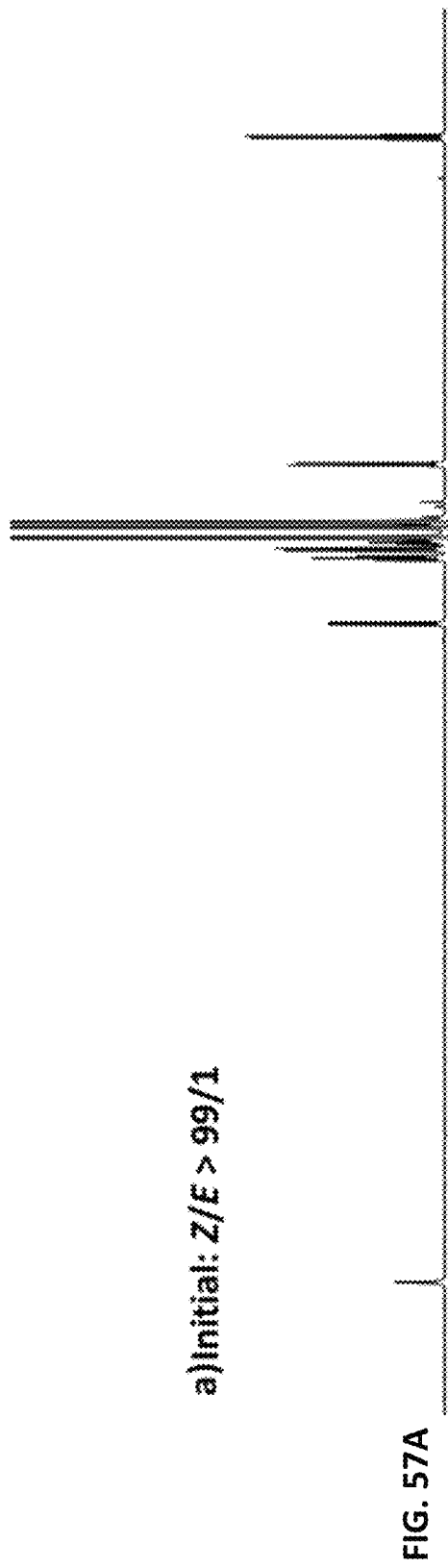
FIG. 57A and FIG. 57B illustrates $^1$H NMR spectra of hydrazone 128-Z 57A) before and 57B) after 480 nm photo-irradiation to reach PSSs in toluene-$d_8$ at 294 K (The ethyl $CH_2$ signal was used for isomer ratio determination).

Hydrazones 202, 5 and 128, having EDGs at the para-position of the stator or rotor phenyl groups all show a red-shift in the $\lambda_{max}$ of their Z isomer relative to 10, which also holds for the E isomer of 5 and 128 (Table 5). Compounds 202 and 5 also show excellent PSSs (84%-98%) and moderate t values (4.7%-9.5%). Switch 128 exhibits the largest bathochromic shifts in both the Z (42 nm) and E (64 nm) forms, compared with 10, and the highest $\Phi_{Z \to E}$ (65.4±6.1%) among all switches. Unfortunately the overlap between the E and Z absorption bands (FIG. 56) resulted in a low PSS for the Z→E process (FIG. 57). The red-shifts observed in 128 results from the strong ED nature of para-NMe$_2$ and the conjugation of the stator phenyl ring with the hydrazone core.

Figure 31A:
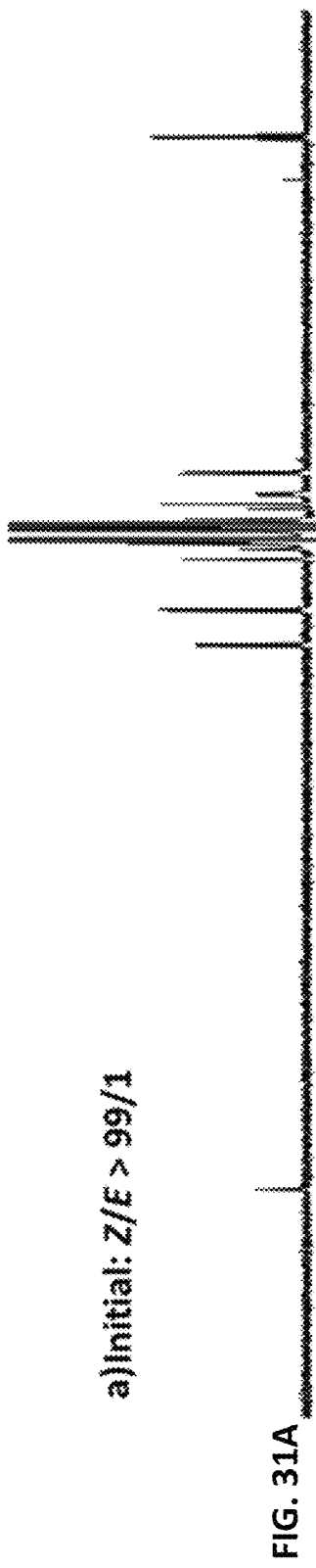
FIG. 31A-31C illustrates $^1$H NMR spectra of hydrazone 15-Z 31A) before and 31B) after 480 or 31C) 375 nm photo-irradiation to reach PSSs in toluene-$d_8$ at 294 K (The ethyl $CH_2$ signal was used for isomer ratio determination).
Figure 31B:
Figure 31C:
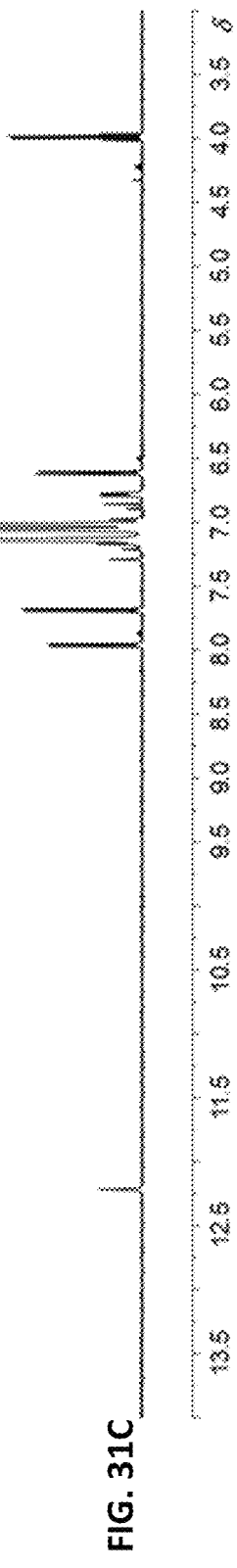
Figure 32:
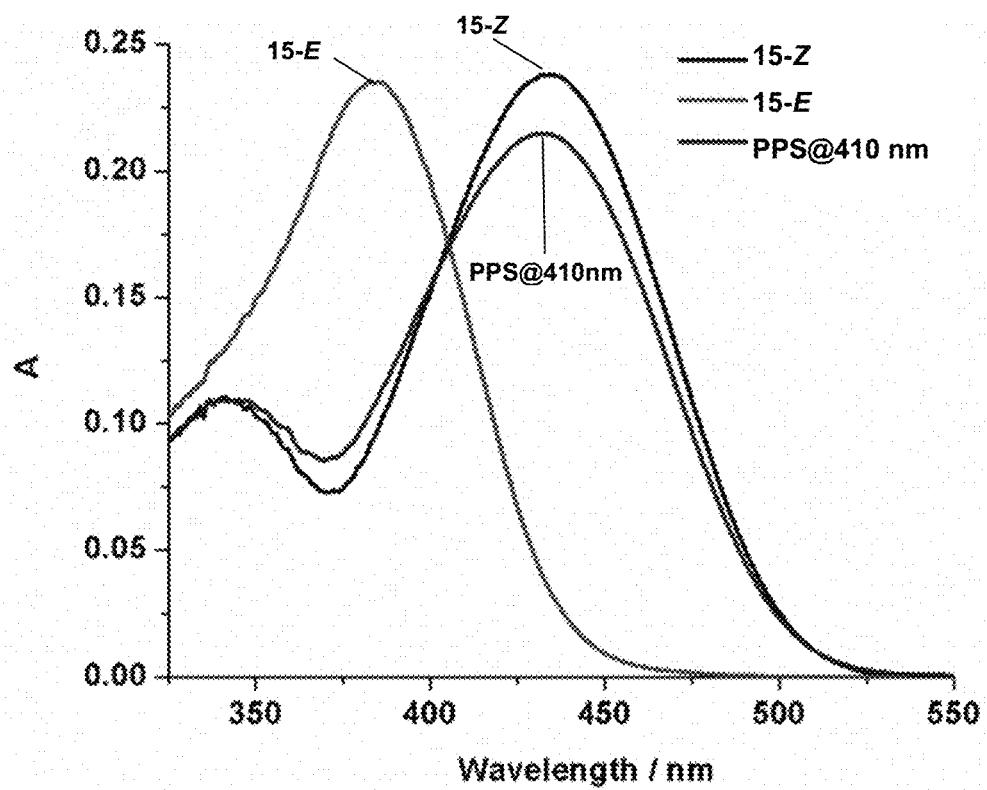
FIG. 32 illustrates UV-Vis absorption spectra ($1\times10^{-5}$ M; toluene) of 15-Z, 15-E and PSS$_{410}$ reached upon irradiation with 410 nm light: the UV spectrum of 10-E was obtained upon 480 nm light irradiation; 15-E can be photochemically switched back to a Z-rich composition (PSS$_{410}$) upon 410 nm light irradiation. The PSS$_{410}$ was calculated to be 90% Z.
Figure 33:
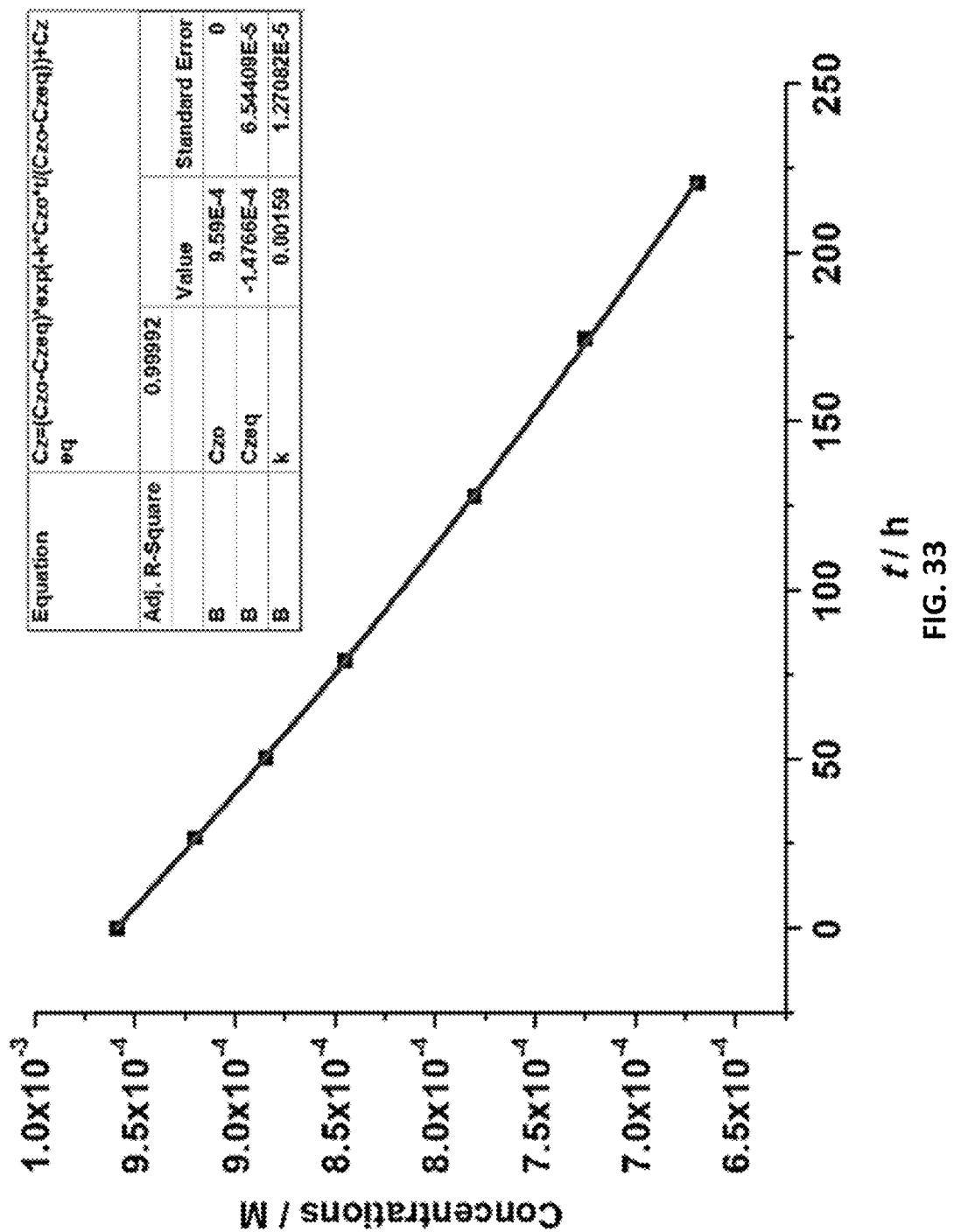
FIG. 33 illustrates thermal isomerization of 201-E→201-Z in toluene-$d_8$ at 368 K. The plot is of the concentration of 201-E as a function of time. The resulting $k_1$ value was calculated to be $(4.44\pm0.14)\times10^{-7}$ s$^{-1}$ based on three consecutive measurements at this temperature.
Figure 34:
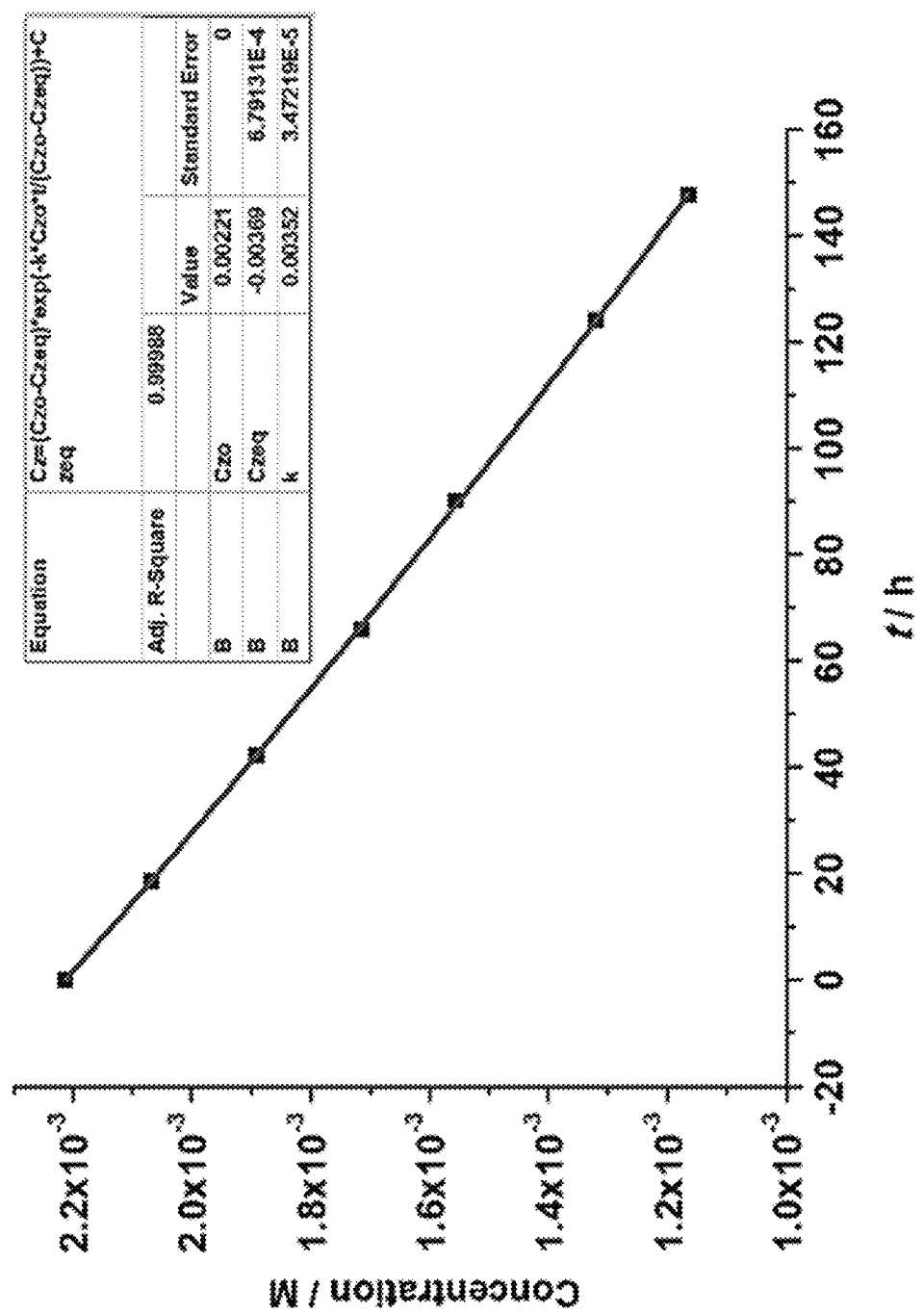
FIG. 34 illustrates thermal isomerization of 202-E→202-Z in toluene-$d_8$ at 368 K. The plot is of the concentration of 202-E as a function of time. The resulting $k_1$ value was calculated to be $(9.19\pm0.49)\times10^{-7}$ s$^{-1}$ based on three consecutive measurements at this temperature.
Figure 35:
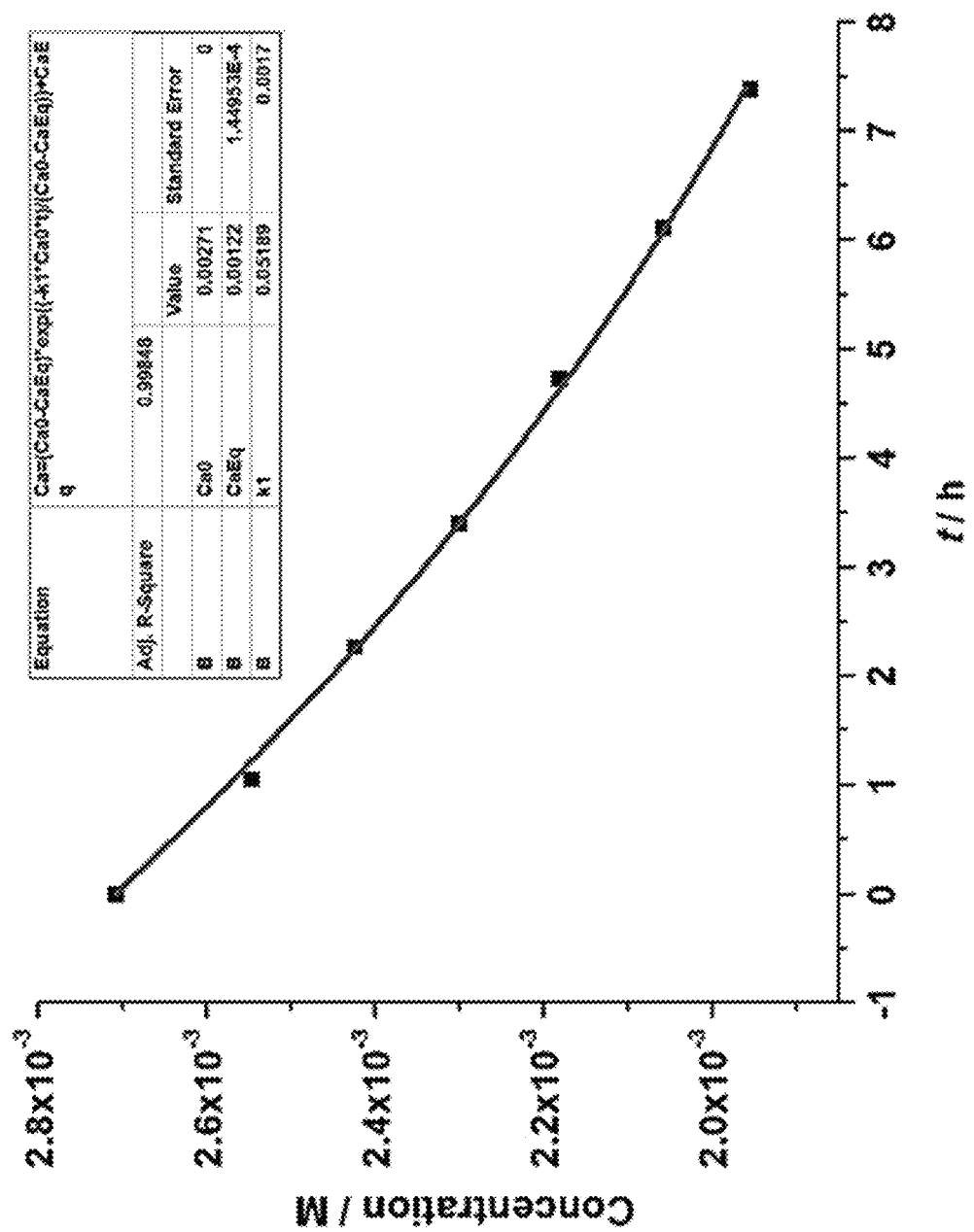
FIG. 35 illustrates thermal isomerization of 127-E→127-Z in toluene-$d_8$ at 368 K. The plot is of the concentration of 127-E as a function of time. The resulting $k_1$ value was calculated to be $(1.60\pm0.20)\times10^{-5}$ s$^1$ based on three consecutive measurements at this temperature.
Figure 36:
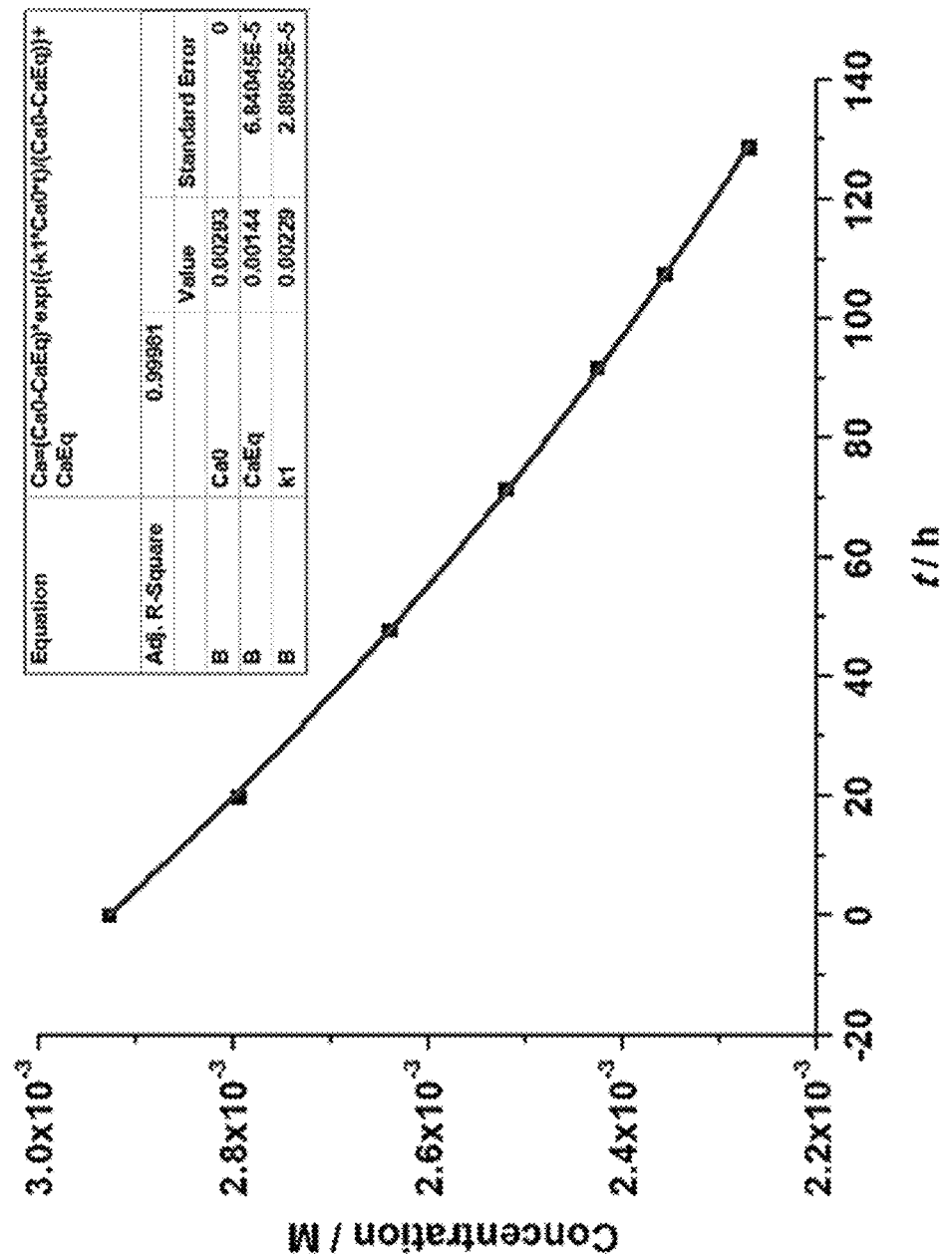
FIG. 36 illustrates thermal isomerization of 3-E→3-Z in toluene-$d_8$ at 368 K. The plot is of the concentration of 3-E as a function of time. The resulting $k_1$ value was calculated to be $(6.43\pm0.26)\times10^{-7}$ s$^{-1}$ based on three consecutive measurements at this temperature.
Figure 37:
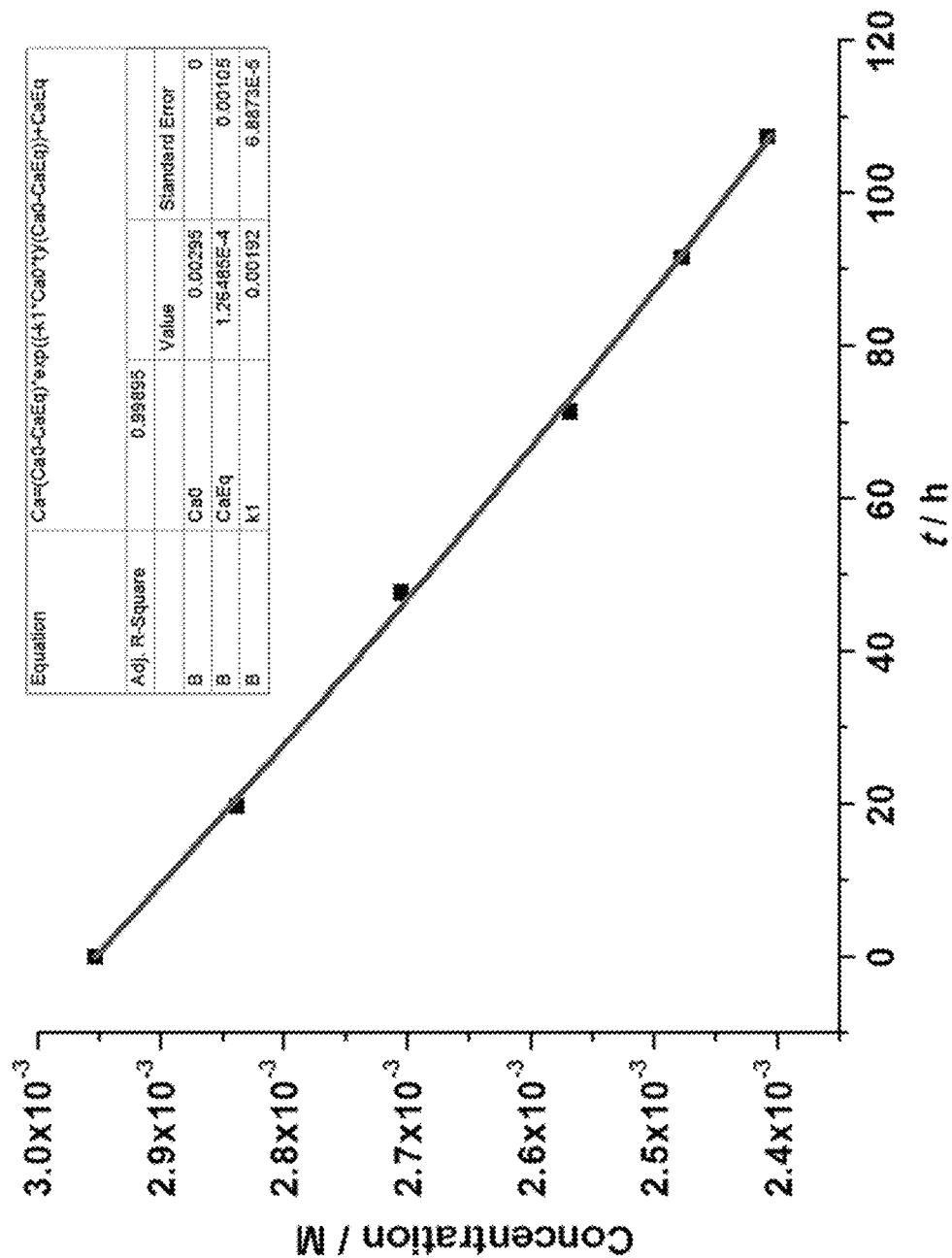
FIG. 37 illustrates thermal isomerization of 2-E→2-Z in toluene-$d_8$ at 368 K. The plot is of the concentration of 2-E as a function of time. The resulting $k_1$ value was calculated to be $(5.37\pm0.09)\times10^{-7}$ s$^{-1}$ based on three consecutive measurements at this temperature.
Figure 38:
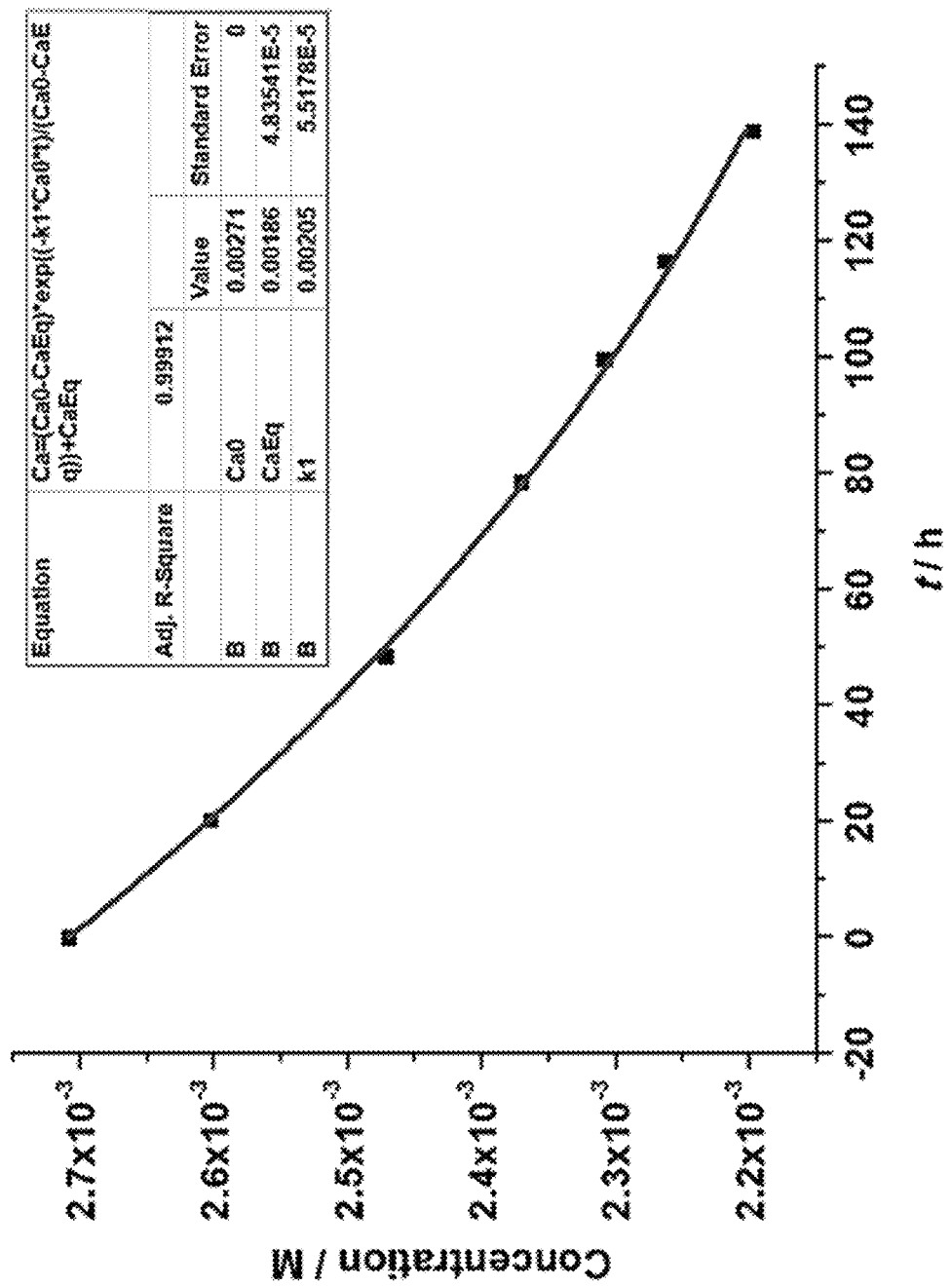
FIG. 38 illustrates thermal isomerization of 5-E→5-Z in toluene-$d_8$ at 298 K. The plot is of the concentration of 5-E as a function of time. The resulting $k_1$ value was calculated to be $(5.56\pm0.22)\times10^{-7}$ s$^{-1}$ based on three consecutive measurements at this temperature.
Figure 39:
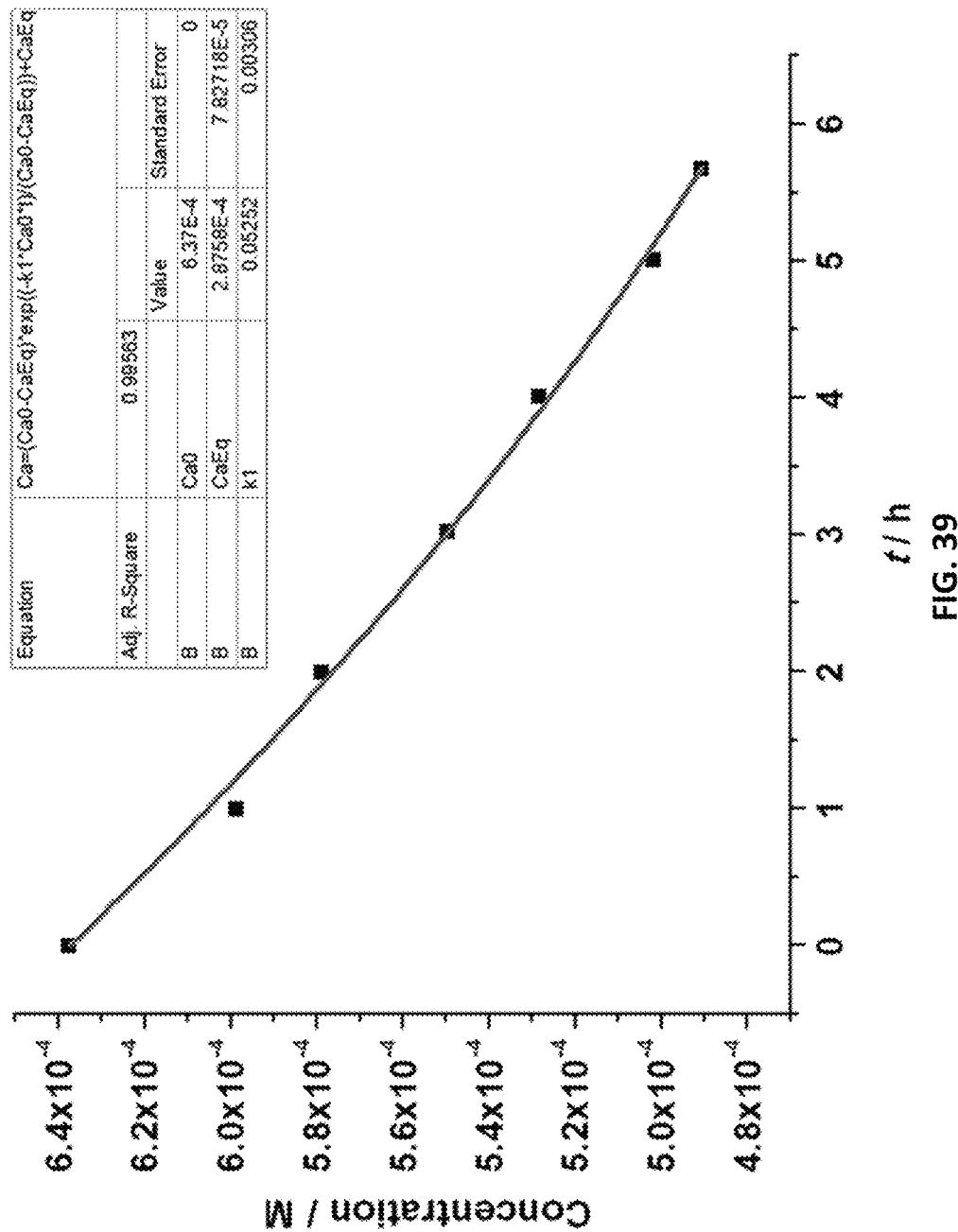
FIG. 39 illustrates thermal isomerization of 128-E→128-Z in toluene-$d_8$ at 298 K. The plot is of the concentration of 128-E as a function of time. The resulting $k_1$ value was calculated to be $(1.48\pm0.02)\times10^{-5}$ s$^{-1}$ based on three consecutive measurements at this temperature.
Figure 40:
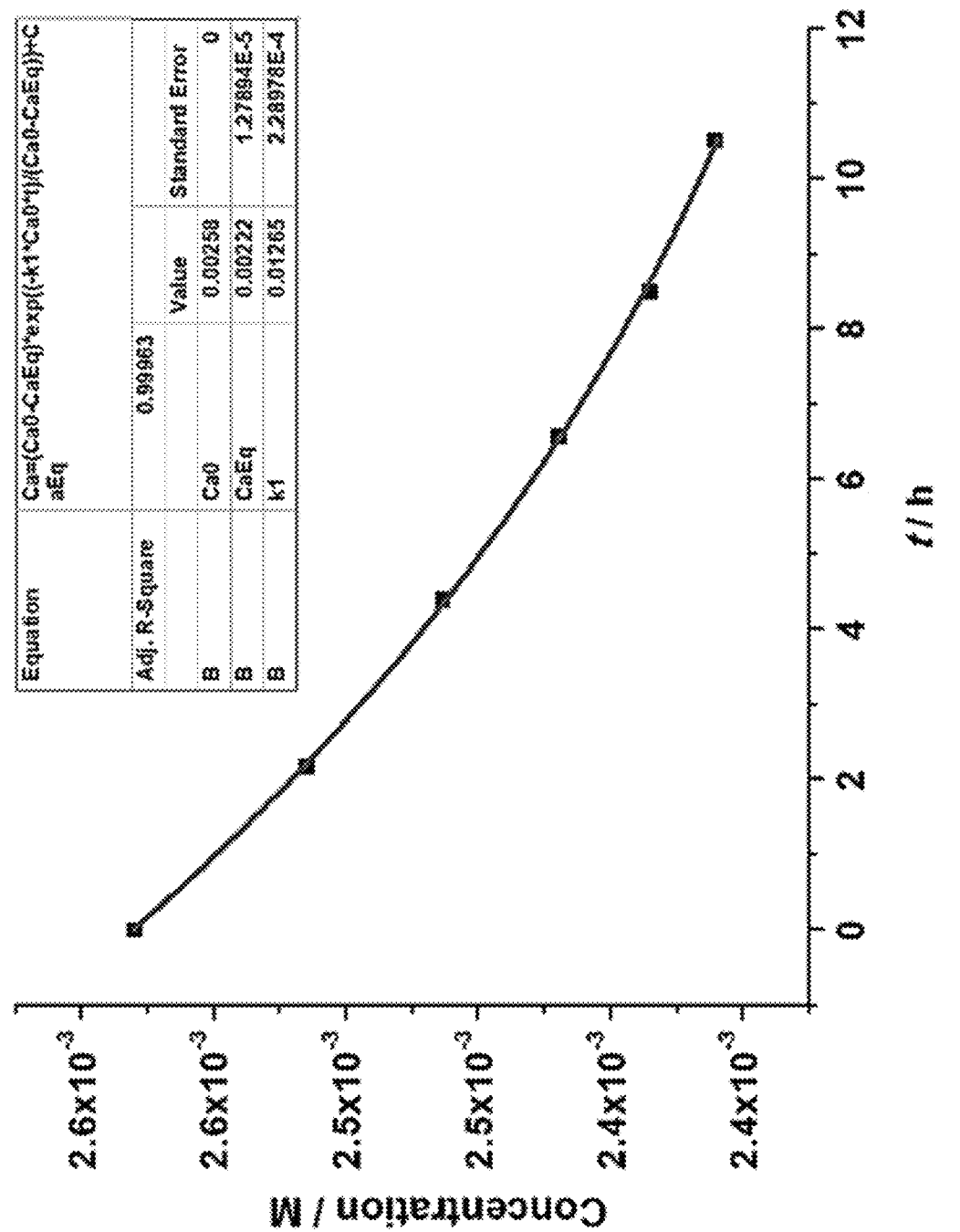
FIG. 40 illustrates thermal isomerization of 15-E→15-Z in toluene-$d_8$ at 368 K. The plot is of the concentration of 15-E as a function of time. The resulting $k_1$ value was calculated to be $(3.53\pm0.26)\times10^{-6}$ s$^{-1}$ based on three consecutive measurements at this temperature.
Figure 58:
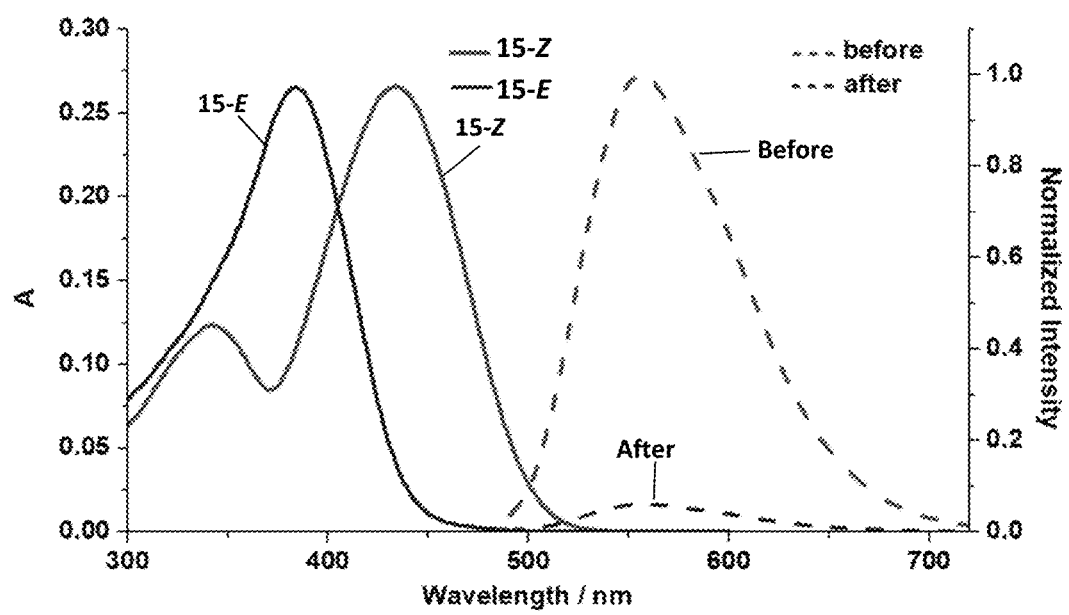
FIG. 58: Solid lines: UV-Vis absorption spectra of 15-Z and 15-E ($1\times10^{-5}$ M) in toluene; Dashed lines: fluorescence emission spectra ($5\times10^{-6}$ M) of 15 in toluene, before (red) and after (blue) switching ($\lambda_{ex}$=480 nm).

The $\lambda_{max}$ of 15-Z is red-shifted by 68 nm (to 435 nm) relative to hydrazone 10 (FIG. 58). Upon irradiation with 480 nm light, a PSS$_{480}$ of >99% E is obtained (FIG. 31b). The quantum yield of the process is significantly higher ($\Phi_{Z \to E}$=46.2±4.2%) relative to the other derivatives. The 15-E absorption band is bathochromically shifted by 50 nm ($\lambda_{max}$=384 nm) relative to 10. The back photoisomerization of 15-E is achieved using 375 nm light source to afford a PSS$_{375}$ of 96% Z (FIG. 31c) with $\Phi_{E \to Z}$=7.4±1.1%. Moreover, the E→Z isomerization process can be driven using 410 nm light (PSS$_{410}$ of 90% Z, $\Phi_{E \to Z}$=19.4±0.6%) making 15 the first member of the hydrazone photochromic family that can be solely switched with visible light (FIG. 32). These results indicate that the push-pull design strategy is a viable one for red-shifting the absorption band of the hydrazone switches.

Scheme 8. The proposed conjugation in 127, 5, and 128 that accelerates the isomerization process.

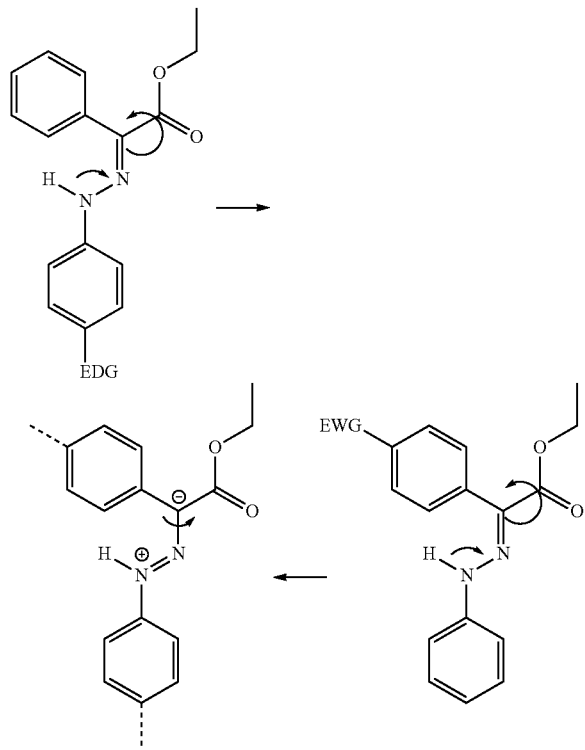

Kinetic Properties:

The thermal isomerization rates of the photochromic hydrazones were measured (in most cases) at an elevated temperature (368K) and the data were extrapolated to room temperature using the Arrhenius and Eyring equations to yield $\tau_{1/2}$ and activation barriers, respectively (FIGS. 33-40). The extremely long thermal half-lives (year scale) are retained in most of the compounds, except for the ones with EDGs at the stator phenyl group (i.e., 5 and 128), where the rate is accelerated by up to 6 orders of magnitude relative to 10. It is hypothesized that the extended conjugation in these two systems (Scheme 8) imparts a partial single bond character to the C=N double bond, which in turn facilitates the isomerization process. That is, in 5 and 128 the isomerization mechanism is no longer inversion as in the rest of the family, but rather rotation around the imine bond. Analysis of the X-ray structures of some compounds (Z-isomers because not enough crystals of the E-isomers were obtained) corroborates this hypothesis as the C=N bond is longer in 5 and 128 (1.310 and 1.317 Å, respectively) relative to 3 and 2 (1.304 and 1.299 Å), while the N—N single bond is shorter (1.323 and 1.322 Å for 5 and 128, respectively, vs. 1.334 and 1.342 Å for 3 and 2, respectively).

TABLE 6

Kinetic data for the thermal isomerization of compounds in toluene

| Hydrazone[a] | k[b]/s$^{-1}$ | $\tau_{1/2}$[c]/year | $\Delta G^{\ddagger}$[d]/ kcal · mol$^{-1}$ |
|---|---|---|---|
| 10 | (6.8 ± 0.2) × 10$^{-11}$ | 324 ± 11 | 31.5 ± 0.1 |
| 19 | (1.0 ± 0.1) × 10$^{-10}$ | 213 ± 7 | 31.2 ± 0.1 |
| 201 | (1.3 ± 0.1) × 10$^{-11}$ | 1645 ± 33 | 32.5 ± 0.1 |
| 202 | (3.3 ± 0.2) × 10$^{-11}$ | 664 ± 44 | 32.0 ± 0.2 |
| 127 | (1.1 ± 0.2) × 10$^{-9}$ | 20 ± 3 | 29.8 ± 0.1 |
| 3 | (2.1 ± 0.1) × 10$^{-11}$ | 1033 ± 52 | 32.2 ± 0.1 |
| 2 | (1.7 ± 0.1) × 10$^{-11}$ | 1286 ± 28 | 32.3 ± 0.1 |
| 5 | (5.6 ± 0.2) × 10$^{-7}$ | 0.039 ± 0.002[g] | 26.0 ± 0.1 |
| 128 | (1.5 ± 0.1) × 10$^{-5}$ | 0.0015 ± 0.0001[g] | 24.0 ± 0.1 |
| 15 | (1.8 ± 0.2) × 10$^{-10}$ | 126 ± 11 | 30.9 ± 0.1 |

[a]Thermal relaxation occurs from E→Z;
[b]The 1$^{st}$-order rate constants at 298 K were calculated using the Arrhenius equation;
[c]Half-life at 298 K;
[d]The Gibbs energy of activation was determined using the Eyring equation;
[g]The kinetic study was performed at room temperature.

Substitution at the rotor phenyl ring has a less significant effect, in general, on the thermal relaxation rates, and the half-lives are either slightly increased (201, 202) or decreased (19) relative to 10. One exception is 127 where a 2 order of magnitude acceleration in rate is measured. This observation can be explained by the conjugation between the hydrazone NH nitrogen and the nitro group, which imparts a partial single bond character to the C=N double bond (Scheme 8). The X-ray structure of 127 supports this hypothesis as the C=N double bond (1.319 Å) and N—N single bond (1.320 Å) are longer and shorter, respectively, than in 3 and 2, for example. The effect is not as drastic as in 5 or 128 because the rotor phenyl group is not co-planar with the rest of the molecule, and so the conjugation is not as effective. Finally, it is noteworthy that the half-life in 15 is 126±11 years, which is highly unusual for a push-pull system, resulting in a red shift in absorption band while maintaining bistability.

Figure 27A:
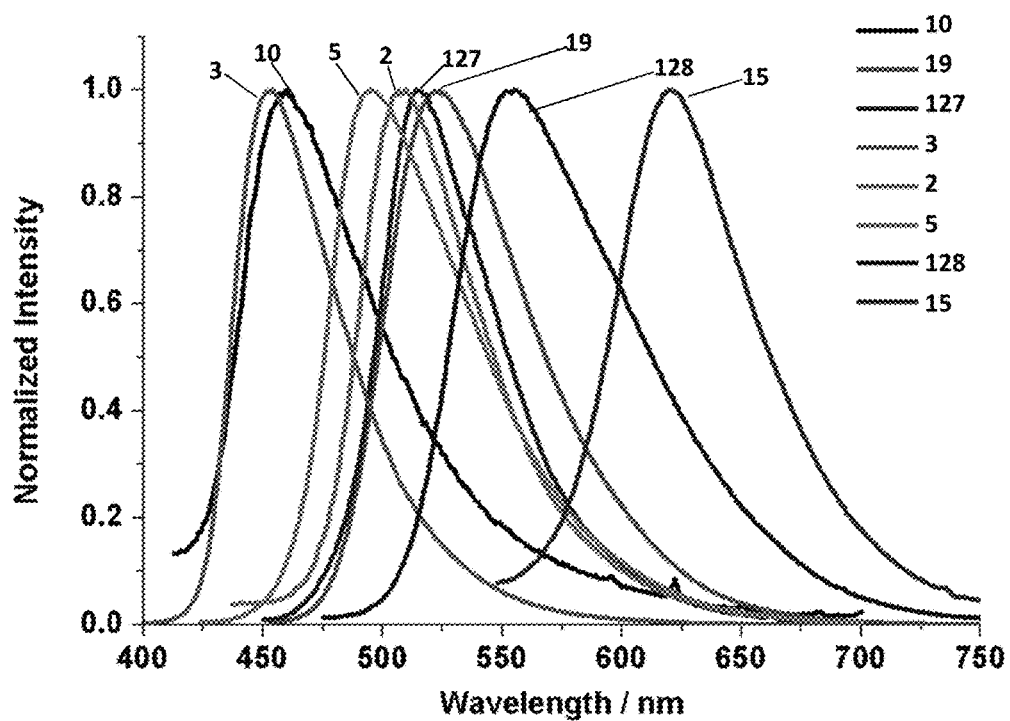
FIG. 27A illustrates the normalized solid-state fluorescence spectra of 10, 19, 127, 3, 2, 5, 128 and 15 powders (the absorption maxima in toluene were chosen as excitation wavelengths for each compound)
Figure 27B:
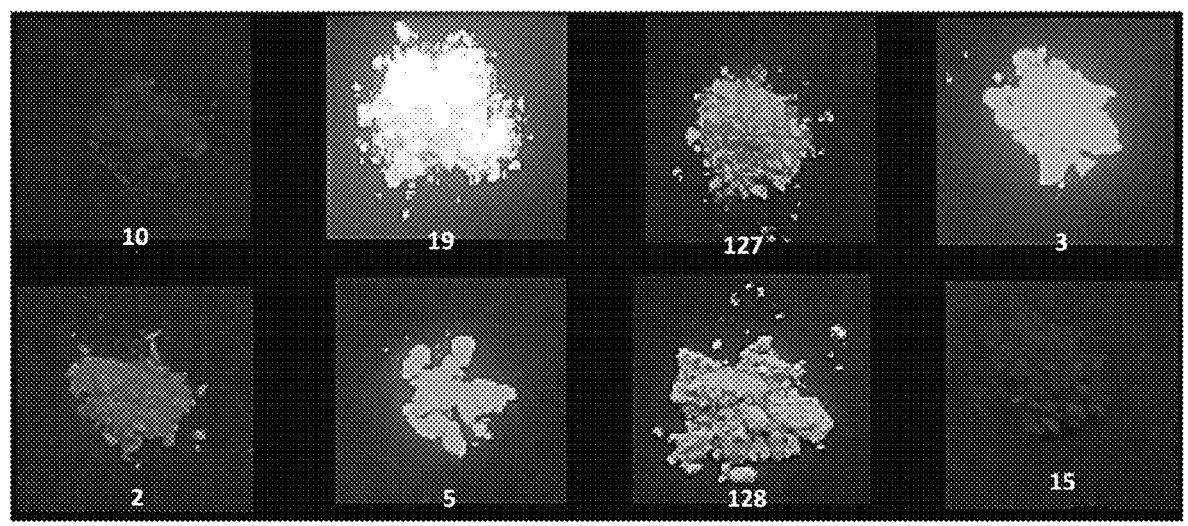
FIG. 27B illustrates fluorescence emissions from the powders of hydrazones 10, 19, 127, 3, 2, 5, 128 and 15 under 365-nm UV lamp.
Figure 28A:
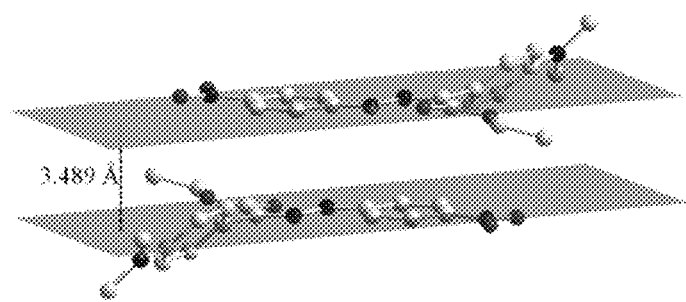
FIG. 28A illustrates the head-to-tail packing of compound 15 in the crystal structure (the distance between the planes of the hydra-zone backbones is shown)
Figure 28B:
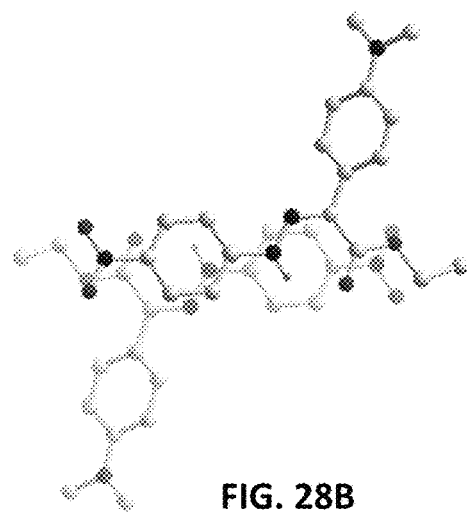
FIG. 28B illustrates the vertical view of the packing motif in 15.
Figure 28C:
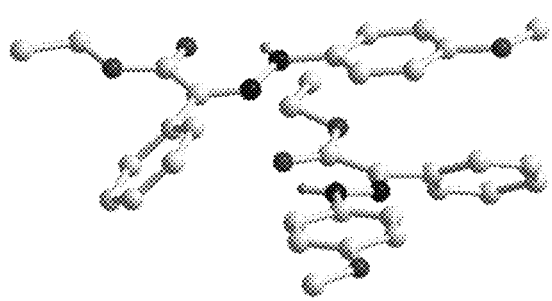
FIG. 28C illustrates the crystal packing in hydrazone 5.
Figure 28D:
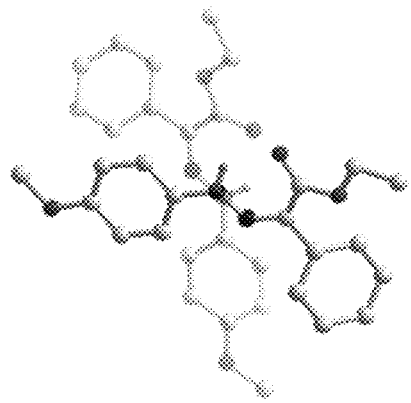
FIG. 28D illustrates the orthogonal packing in 5 viewed vertically (C—H protons are omitted for clarity).
Figure 41:
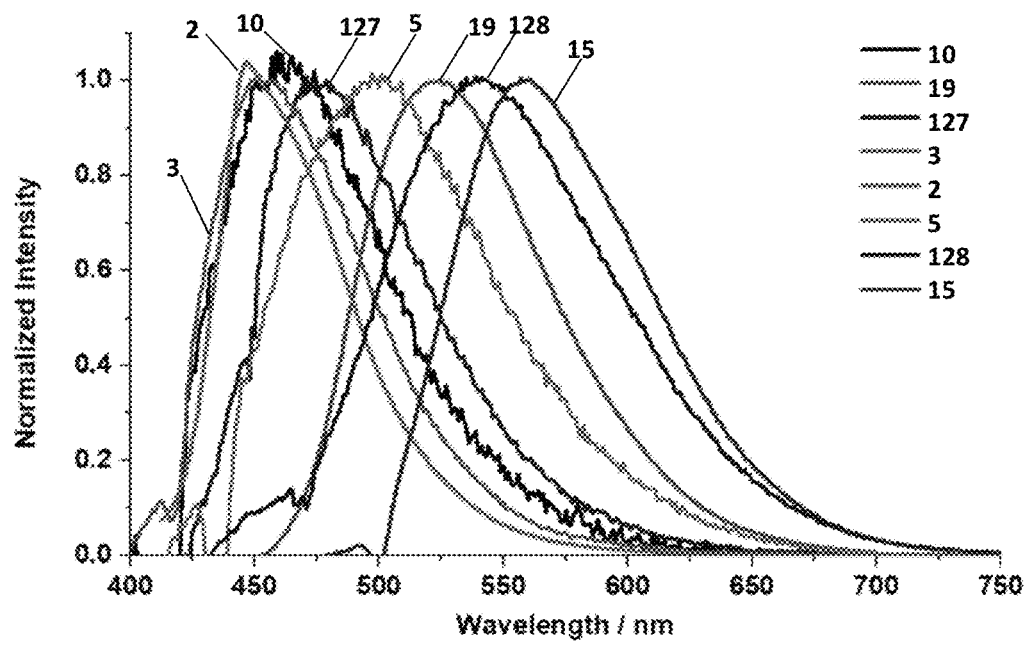
FIG. 41 illustrates the normalized solution fluorescence spectra of 10, 19, 127, 3, 2, 5, 128, and 15 ($5\times10^{-6}$ M, toluene). Absorption maxima in toluene were chosen as the excitation wavelengths for each hydrazone.
Figure 42:
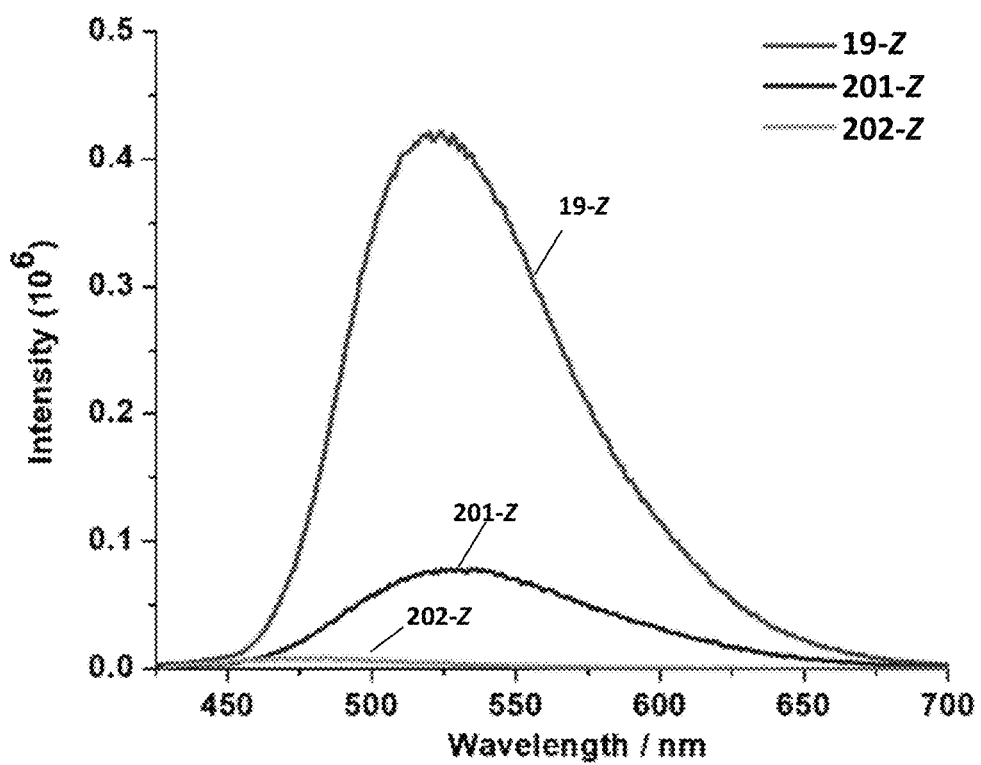
FIG. 42 illustrates fluorescence spectra of hydrazones 19-Z, 201-Z and 202-Z ($5\times10^{-6}$ M) in toluene. (Absorption maxima are used as excitation wavelengths).

Solution and Solid-State Fluorescence Properties:

The emission properties of hydrazones were first studied in solution using fluorescence spectroscopy (Table 7). The compounds show emissions with varying intensities in toluene at wavelengths ($\lambda_{em}$) ranging from 450 nm to 560 nm (FIG. 41). Hydrazones 19, 202, 5 and 128 bearing EDGs (—OMe or —NMe$_2$) exhibit emission at longer wavelengths in general, compared with those bearing electron-withdrawing groups (—CN or —NO$_2$ groups, i.e., 127, 3 and 2). It should be noted that while emission is observed for these compounds in solution its intensity is very low, and so we could not measure fluorescence quantum yields for most of them. Compound 19 is the most emissive in solution among the mono-substituted hydrazones ($\Phi_{FL}$=0.7±0.1%), and excited-state intramolecular proton transfer (ESIPT)-coupled charge transfer (CT) as the emission mechanism was previously proposed. In such a mechanism the rotor phenyl group is less twisted relative to the rest of the hydrazone core in the excited state, enhancing the conjugation between the latter and the NMe$_2$ group. To test this hypothesis compound 201 that has the NMe$_2$ group at the meta-position was synthesized and as expected a drastic quenching of emission was observed (FIG. 42). Moreover, the absorption bands of 201 are blue-shifted in both the Z (29 nm) and E (12 nm) isomers compared to 19 (Table 7) indicating that the conjugation diminishes in the ground state as well. These results validate the role of CT in enhancing hydrazone fluorescence emission and highlight the unique CT capacity of the —NMe$_2$ group in these systems. As for the "push-pull" switch 15, it shows relatively strong emission ($\Phi_{FL}$=22.6±0.5%) in solution, and has the most red-shifted emission wavelength (560 nm). It is postulated that this enhancement in emission results from the presence of the para-NO$_2$ group at the stator phenyl group, which augments the efficiency of the CT process.

cence emission bands (FIG. 27b). This may occur as a result of rigidification in the solid-state (e.g., aggregation induced emission phenomenon). In contrast with the huge red shifts observed in 2 and 15, there are no apparent changes in the emission maxima of hydrazones 19, 3 and 5, when going from solution to the solid-state. The molecular packing in these systems lends an insight into the disparity be-tween these two groups. For example, two units of 5 are loosely packed in the unit cell (FIG. 28c, 28d) with no effective interactions between them leading to the observed photophysical properties. Hydrazones 19 and 3 behave similarly in the solid-state (FIGS. 44 and 45).

Figure 46A:
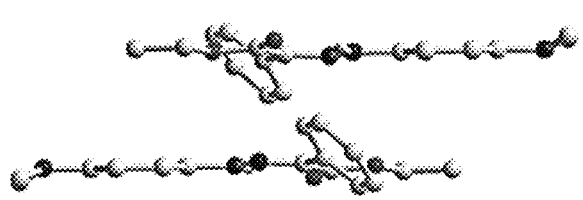
FIG. 46A illustrates the packing of 128 in the crystal structure.
Figure 46B:
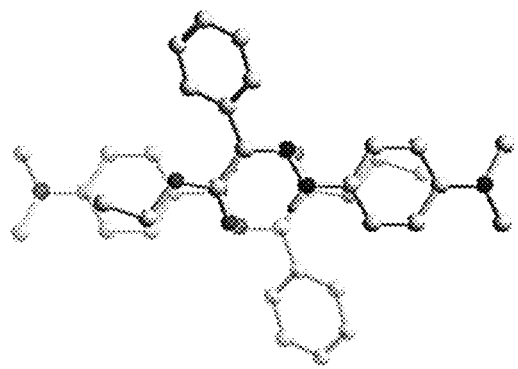
FIG. 46B illustrates the packing of 128 viewed from vertical direction (C—H protons are omitted for clarity).
Figure 59A:
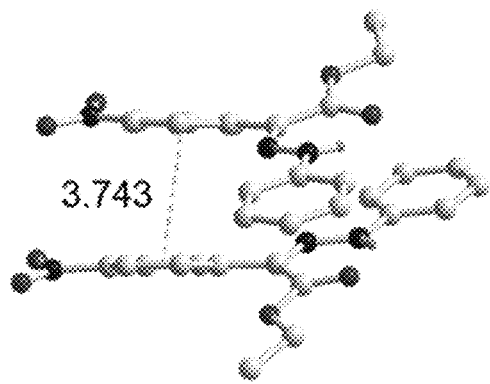
FIG. 59A illustrates the crystal packing of 127 showing a π-π interaction (3.743 Å, centroid to centroid distance between the two phenyl rings) formed between two rotary phenyl groups.
Figure 59B:
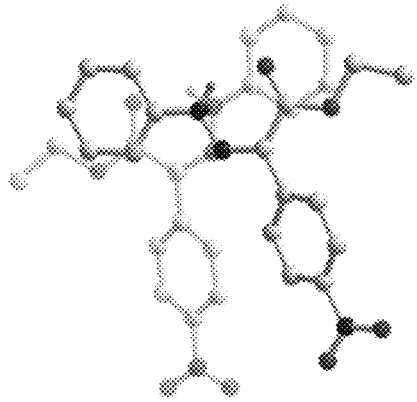
FIG. 59B illustrates the stacking of 127 from the vertical view (C—H protons are omitted for clarity).

Hydrazones 127 and 128 on the other hand show moderate shifts in emission bands and lower quantum yields than 19, 3 and 5 (Table 7). Again, the crystal structure of these systems helps in understanding this observation. Two molecules of 128 make up the unit cell and stack in a perpendicular fashion where one H-bonded six-membered ring sits on the top of another leading to a cross-shaped pattern (FIG. 46). This loose packing does not lead to complete quenching (quantum yield of ~1%) and only a small red-shift in emission (~15 nm). Hydrazone 127 exhibits a larger bathochromic shift (average of 38 nm) in emission band, and slightly higher quantum yield (~2%). In its crystal structure the rotary phenyl rings of adjacent molecules are located on the same side with a π-π distance of 3.743 Å (FIG. 59). This

TABLE 7

Summary of photophysical properties of hydrazones in solution and solid-state (powder and crystal).

| | Solution | | | | Crystal | | Powder | | |
|---|---|---|---|---|---|---|---|---|---|
| Hydrazone | $\lambda_{max}$ (nm) | $\lambda_{em}$ (nm)$^a$ | Φ (%) | τ (ns)$^b$ | $\lambda_{em}$ (nm)$^a$ | Φ (%) | $\lambda_{em}$ (nm)$^a$ | Φ (%) | τ (ps)$^b$ |
| 10 | 367 | 450 | —$^c$ | — | 464 | —$^c$ | 460 | —$^c$ | — |
| 19 | 395 | 525 | 0.7 ± 0.1 | 0.19 ± 0.01 | 520 | 23.1 ± 0.2 | 524 | 27.5 ± 1.4 | 65 ± 2 |
| 201 | 366 | 525 | —$^c$ | — | — | — | 513 | —$^c$ | — |
| 202$^e$ | 376 | 475 | —$^c$ | — | —$^e$ | —$^e$ | —$^e$ | —$^e$ | — |
| 127 | 392 | 480 | —$^c$ | — | 522 | 2.9 ± 0.2 | 514 | 1.6 ± 0.2 | 65 ± 1 |
| 3 | 368 | 456 | —$^c$ | — | 457 | 21.5 ± 0.6 | 450 | 19.7 ± 0.5 | 20 ± 2 |
| 2 | 392 | 452 | —$^c$ | — | 512 | —$^c$ | 510 | —$^c$ | — |
| 5 | 383 | 498 | —$^c$ | — | 500 | 8.6 ± 0.2 | 495 | 6.7 ± 0.1 | 57 ± 2 |
| 128 | 410 | 543 | —$^c$ | — | 560 | 0.8 ± 0.1 | 555 | 1.0 ± 0.1 | 65 ± 2 |
| 15 | 435 | 560 | 22.6 ± 0.5 | 2.7 ± 0.1 | 620 | —$^c$ | 620 | —$^c$ | — |

$^a$Absorption maxima in toluene are used as excitation wavelengths;
$^b$Fluorescence decay lifetime;
$^c$Quantum yields are too low to be measured;
$^e$Hydrazone 202 was obtained as an oil at rt.

Next, the fluorescence emission profiles of hydrazones 10, 201 and 127, 3, 2, 5, 128, and 15 in amorphous (powder) and crystalline states (compound 202 is an oil, and hence, was not including in the analysis) were tested. The quantum yield of the strongly emissive 15 decreases dramatically in the solid-state (Table 7) and a large red-shift in emission (~60 nm) is observed, indicating the formation of excimers in the solid-state. The crystal structure of 15 shows compact head-to-tail packing with an interplanar distance of 3.489 Å (FIGS. 28a and 28b), which might be responsible for the quenching effect. The nitro-substituted compound 2 arranges itself in a similar packing mode (FIG. 43) leading to a red-shifted (~60 nm) and very weak emission in the solid-state.

On the other hand, the quantum yields of hydrazones 19 (for comparison), 127, 3, 5 and 128 increase in the solid-state (Table 7), giving rise to bright blue to orange fluoresarrangement might explain the bathochromic shift observed in this system, while the loose packing prevents complete quenching.

Figure 47A:
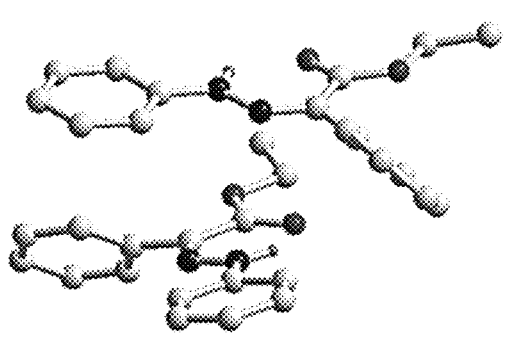
FIG. 47A illustrates the packing of 10 in the crystal structure.
Figure 47B:
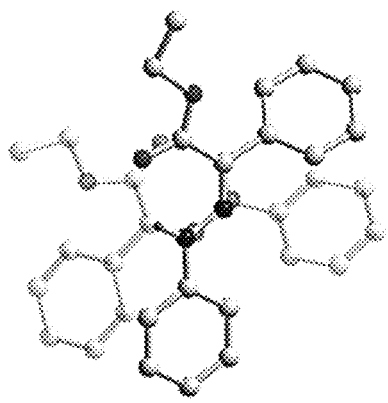
FIG. 47B illustrates the vertical view of the packing in 10 (C—H atoms are omitted for clarity).

Solid-State Photoswitching:

In addition to being emissive, some of the hydrazones can also undergo photoisomerization in the solid-state. The switching behavior of drop-casted films of the hydrazones were monitored using UV/Vis spectroscopy. It was found that the process is highly dependent on the packing mode observed in the crystal structures. That is, photoswitching is observed for hydrazones that do not have effective packing of their backbones, which matches the empirical observation that free volume is required in the solid-state for efficient isomerization to take place. For example, compounds 10 and 5 that are orthogonally stacked (i.e., minimum packing of their backbones, see FIG. 28c, 28d and FIG. 47) demonstrate highly efficient back-and-forth photoisomerization (FIGS.

Figures 49A, 49B:
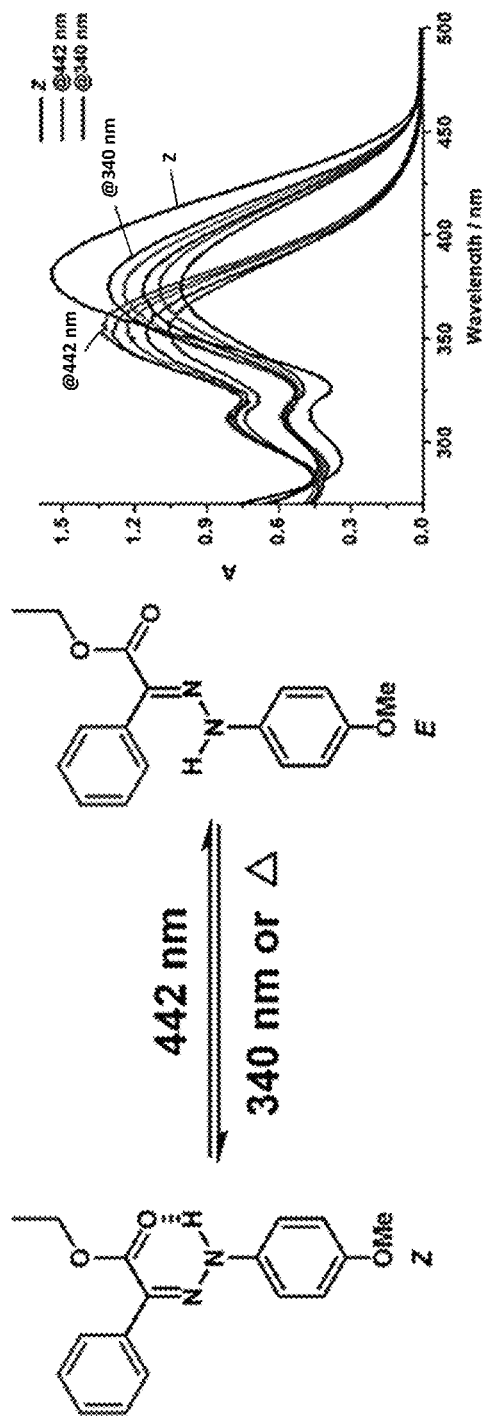
FIG. 49A illustrates the photo-induced isomerization of hydrazone 5.
FIG. 49B illustrates UV-Vis spectra of a drop-casted film of hydrazone 5, and the absorption changes upon alternating irradiation with 442 and 340 nm light.
Figure 49D:
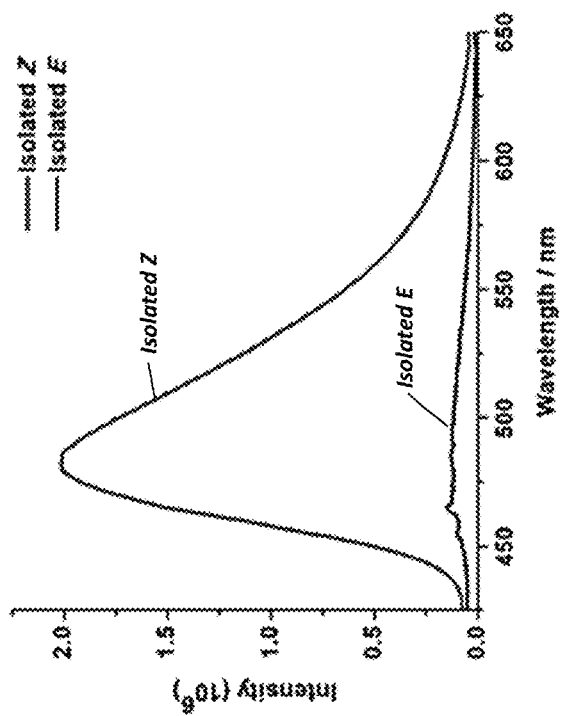
FIG. 49D illustrates the emission spectra of powders of Z and E isomers (5).
Figure 49C:
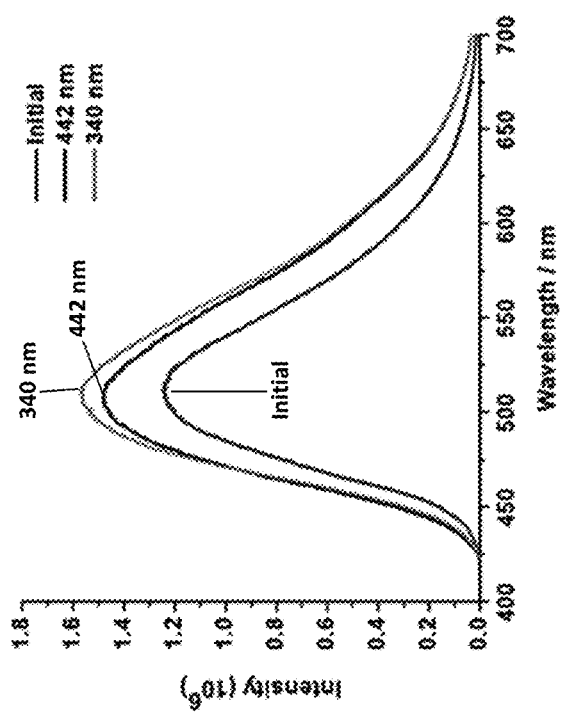
FIG. 49C illustrates changes in the emission spectra of the hydrazone 5 before and after irradiation with 442 and 340 nm light.
Figure 50A:
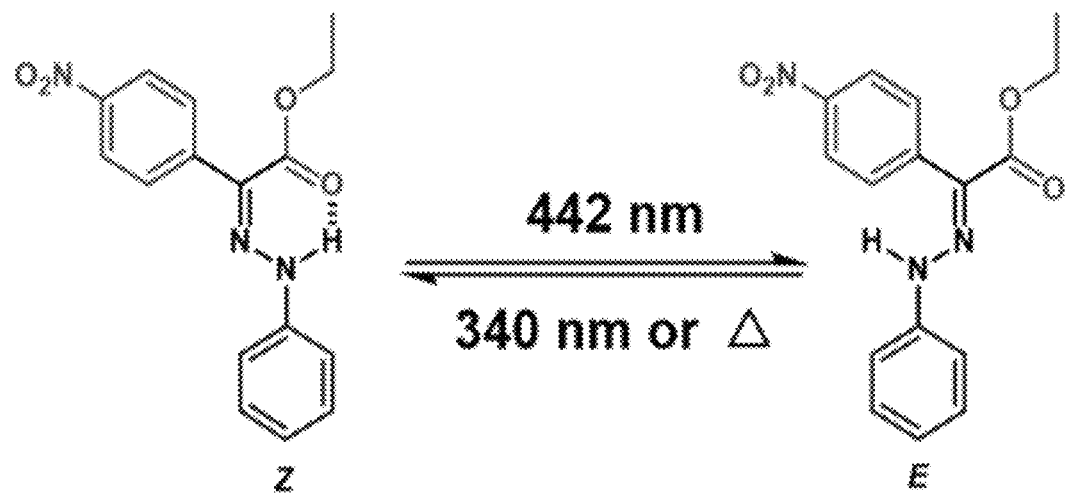
FIG. 50A illustrates the photo-induced isomerization of hydrazone 127.
Figure 50B:
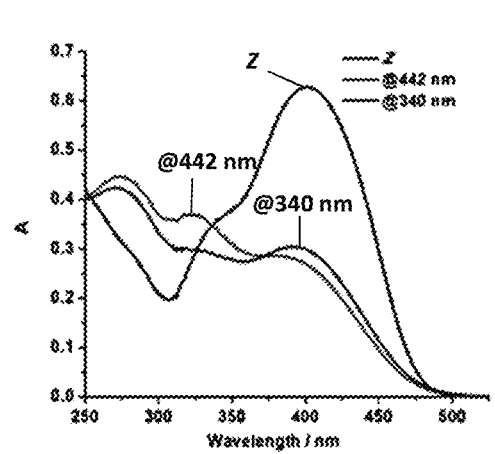
FIG. 50B illustrates UV-Vis spectra of a drop-casted film of the Z isomer, at PSS$_{442}$ (red line) and after 340 nm light irradiation.
Figure 50C:
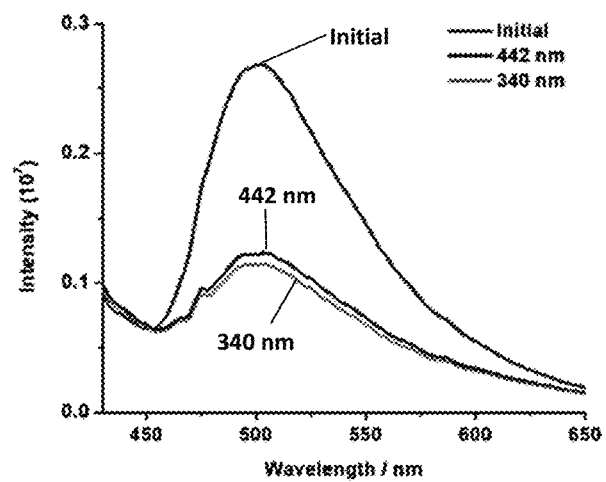
FIG. 50C illustrates changes in emission spectra of hydrazone 127 before and after irradiation with 442 and 340 nm lights.
Figure 51A:
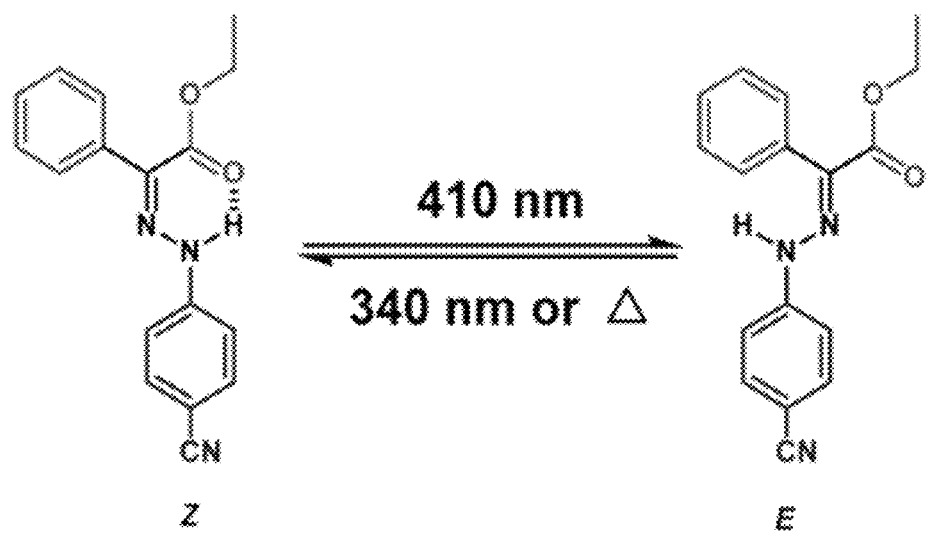
FIG. 51A illustrates the photo-induced isomerization of hydrazone 3.
Figure 51B:
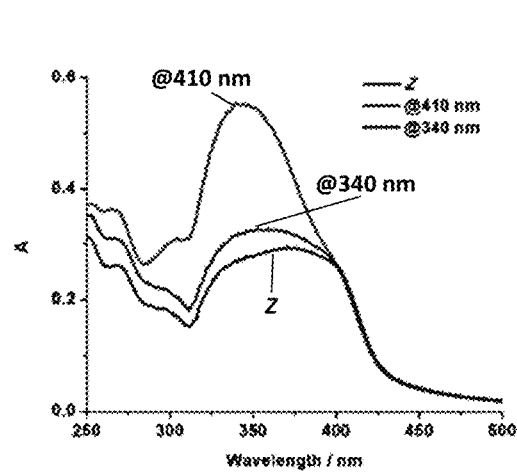
FIG. 51B illustrates UV-Vis spectra of a drop-casted film of the Z isomer, at PSS$_{410}$ (red line) and after 340 nm light irradiation.
Figure 51C:
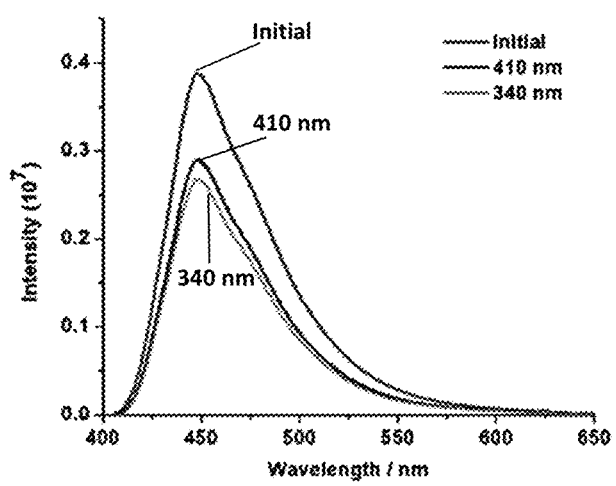
FIG. 51C illustrates changes in the emission spectra of the hydrazone 3 before and after irradiation with 410 and 340 nm lights.
Figure 52A:
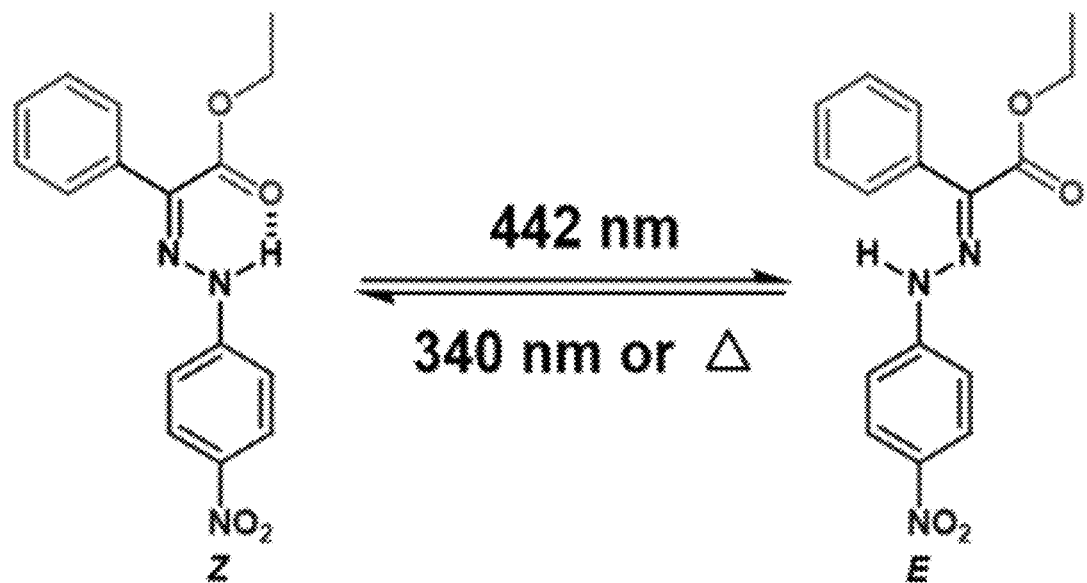
FIG. 52A illustrates the photo-induced isomerization of hydrazone 2.
Figure 52B:
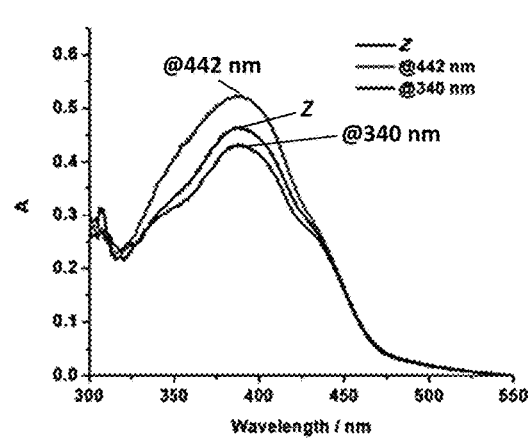
FIG. 52B UV-Vis spectra of a drop-casted film of the Z isomer, at PSS$_{442}$ (red line) and after 340 nm light irradiation.
Figure 52C:
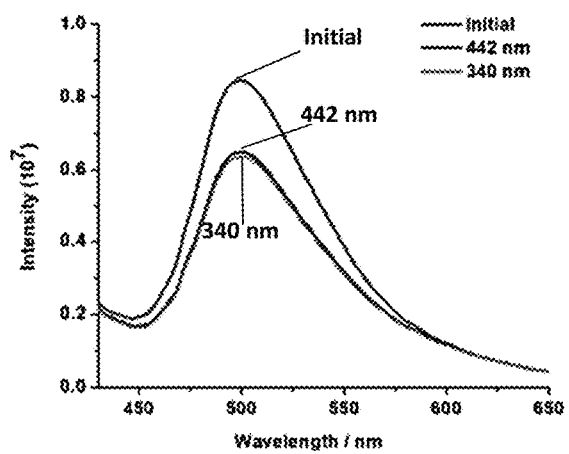
FIG. 52C illustrates changes in the emission spectra of the hydrazone 2 before and after irradiation with 442 and 340 nm lights.
Figure 53A:
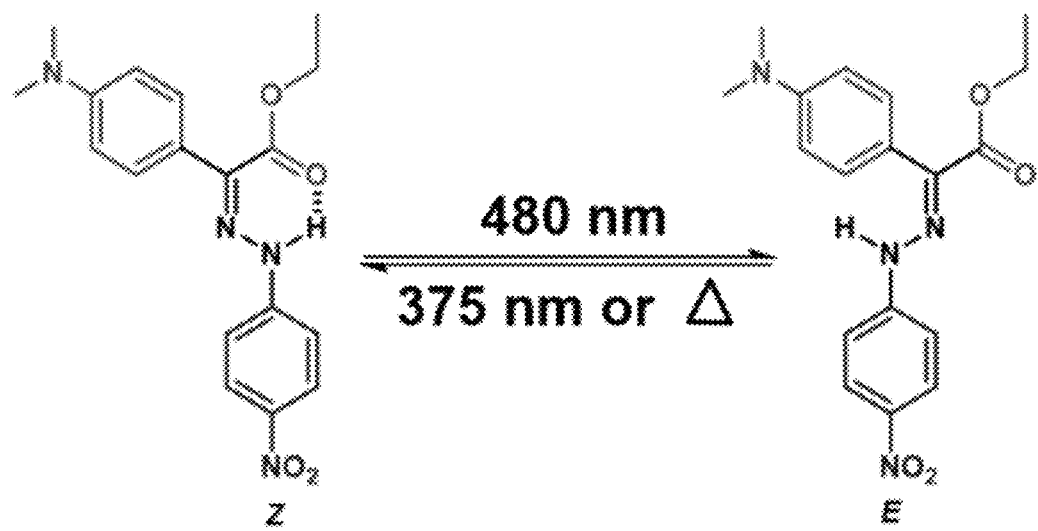
FIG. 53A illustrates the photo-induced isomerization of hydrazone 15.
Figure 53B:
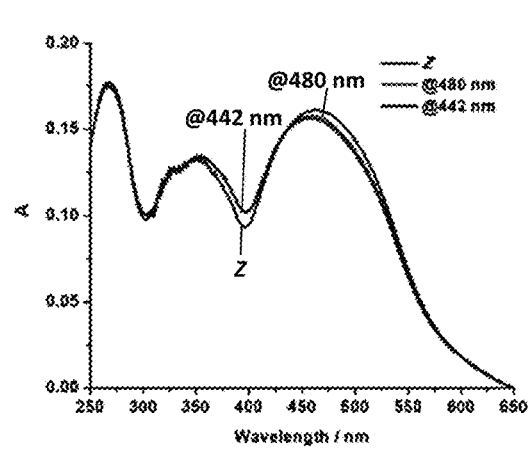
FIG. 53B illustrates UV-Vis spectra of a drop-casted film of the Z isomer and after 480 and 442 nm light irradiation.
Figure 53C:
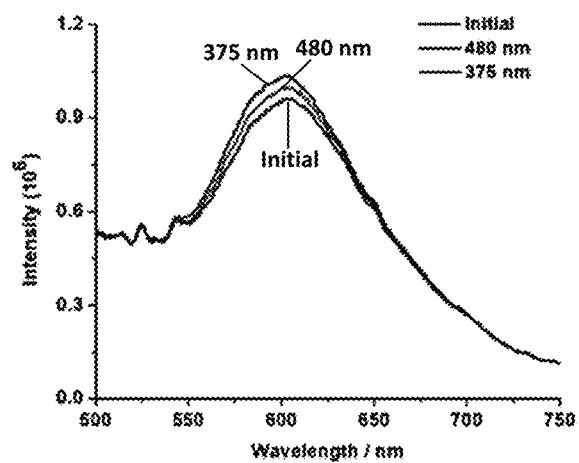
FIG. 53C illustrates changes in the emission spectra of the hydrazone 15 before and after irradiation of 480 and 375 nm lights.

48 and 49). The UV-Vis absorption bands of the Z isomers and PSSs for these compounds are similar to the ones measured in toluene, indicating that the same isomerization process is occurring in the solid-state. The absorption bands of 10 and 5 start to broaden and decrease in intensity upon switching cycles, while the peak positions remain unchanged. This phenomenon might be ascribed to changes in film morphology (i.e., thickness) upon photoisomerization rather than photodegradation or decomposition. On the other hand, the denser packed 127 and 3 show less efficient switching because of the partial overlap of the hydrazone backbone (FIGS. 50 and 51). No appreciable switching was observed in tightly packed hydrazones 2 and 15 (FIGS. 52 and 53). The solid-state emission change in these hydrazones also follows the packing mode. The emission toggling in 127, 3, 2 and 15 is not effective because of the low switching efficiency (FIGS. 50c, 51c, 52c and 53c), while in 5 the morphology change in the drop-casted film upon photoswitching diminishes the efficacy of the process (FIGS. 49c and 49d).

Most derivatives show year-scale thermal half-lives, and good absorption band separation, and hence excellent PSSs, and very good photoisomerization quantum yields. The solution phase studies resulted in the following observations: 1) substituting the hydrazone with para-EDGs and para-$NO_2$ group at either the rotor or stator phenyl rings will lead to a red-shift in the absorption profile of the Z isomer. The effect is less pronounced on the E isomer when the substitution is on the rotor phenyl group because of its twist out of the plane of the hydrazone core; 2) enhanced photoisomerization quantum yields are obtained when $NMe_2$ and $NO_2$ functional groups are introduced to the system; 3) derivatizing the rotor phenyl ring has less of an effect on thermal half-lives than substituting the stator phenyl ring; 4) EDGs at the stator phenyl group drastically accelerate the isomerization rate as a result of a hypothesized change in isomerization mechanism, whilst $NO_2$ at the non-coplanar rotor ring results in less significant acceleration; 5) push-pull systems can be used for red-shifting the absorption of both isomers while maintaining the bistability of the switch; and 6) charge transfer from para-$NMe_2$ at the rotary ring is important for efficient emission.

Figure 60:
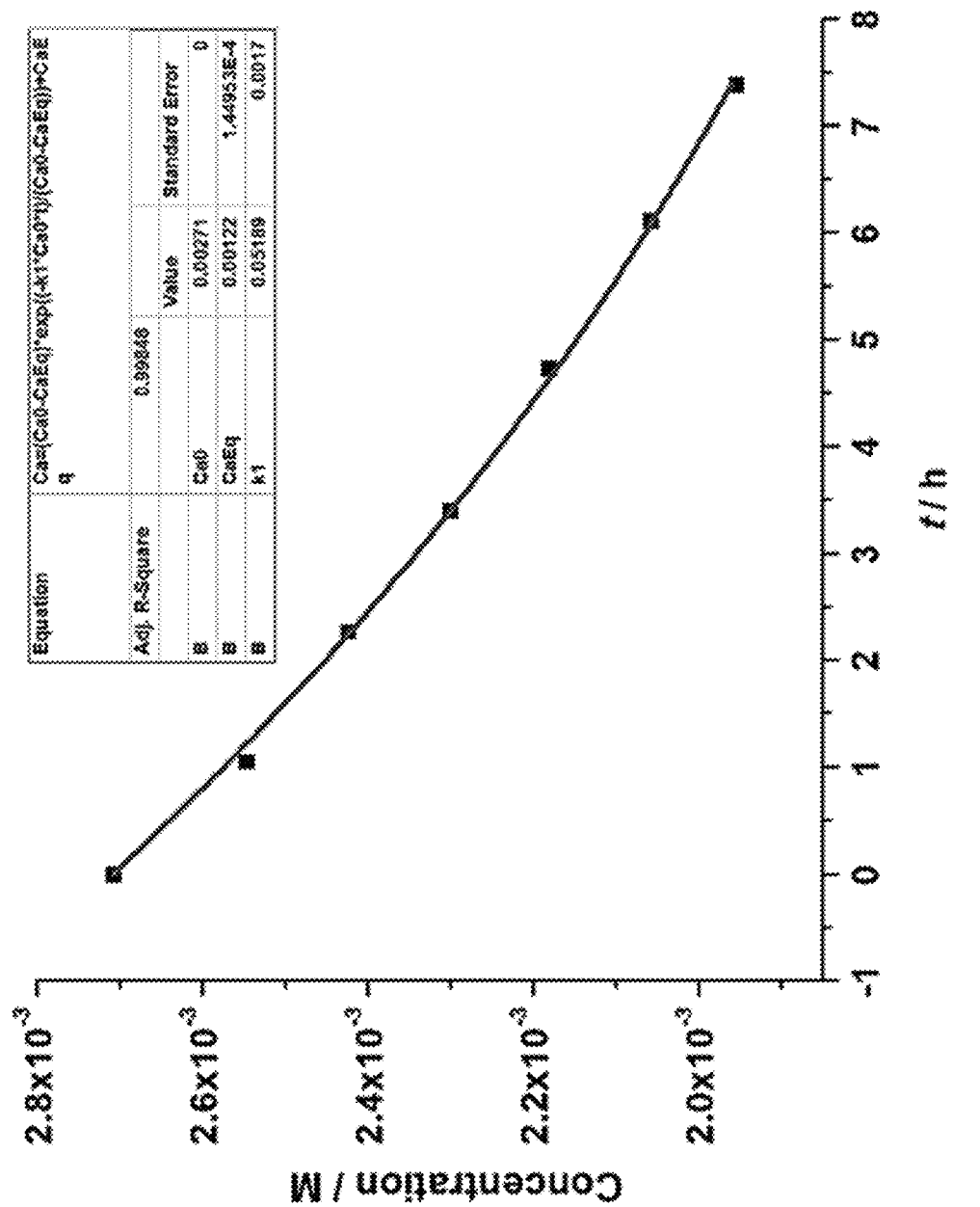
FIG. 60 illustrates thermal isomerization of 127-E→127-Z in toluene-$d_8$ at 368 K. The plot is of the concentration of 127-E as a function of time. The resulting $k_1$ value was calculated to be $(1.60\pm0.20)\times10^{-5}$ s$^{-1}$ based on three consecutive measurements at this temperature.

The analysis of the crystal structures of the Z isomers shed light on the solid-state packing-dependency of the switching performance, as well as the emission and quenching of the hydrazones in the solid-state. According to this analysis, it was found that: 1) the presence of the twisted (out of plane) rotary phenyl ring in the hydrazone (FIG. 60) is crucial as it prevents, in general, the systems from stacking effectively, which results in the emergence of solid-state emission and efficient solid-state photoswitching; 2) nitro-substitution at the stator phenyl ring is detrimental to solid-state emission as it results in head-to-tail arrangement and quenching; 3) hydrazone 10 is not emissive in the solid-state indicating that EDGs and/or EWGs are required for the hydrazones to be emissive in the solid-state; 4) the enhancement of emission in the solid-state vs solution indicates that rigidification is responsible for the observed phenomenon.

These design principles will guide practitioners in their efforts to incorporate these photochromic compounds in a myriad of applications, including but not limited to data storage, smart materials, molecular machines, photopharmacology, and super-high resolution fluorescence microscopy, among others.

What is claimed is:

1. A compound of Formula I or a salt thereof:

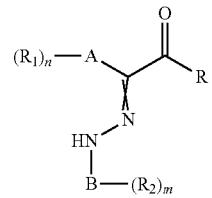

wherein represents a double bond having either E or Z stereochemistry;

A is phenyl or naphthyl;

B is phenyl or pyridine-2-yl;

R is O—R', where:

R' is azide, alkyl, alkenyl, alkynyl, cycloalkyl, heterocyclyl, alkoxyalkyl, heteroalkyl, alkoxy, aryl, or heteroaryl, where in the alkenyl and alkynyl groups for R', the double or triple bond is not at the alpha-beta position in the alkenyl or alkynyl group;

$R_1$ and $R_2$ are independently, for each occurrence, selected from the group consisting of heterocyclyl, halo, alkylamino, dialkylamino, diphenyl amino, hydroxyl, nitro, cyano, carboxyl, carboxylalkyl and carboxamido; or R and one of $R_2$ are optionally linked by a 3-8 carbon linker, which is optionally substituted;

n is 0, 1, 2, 3, 4 or 5; and m is 0, 1, 2, 3, 4, 5, 6 or 7;

provided that when n and m are both 0, at least one of A and B is not phenyl.

2. The compound of claim 1, wherein $(R_1)_n$-A- is selected from the group consisting of 4-dialkylaminophenyl, naphth-2-yl, naphth-1-yl, and 6-dialkylaminonaphth-2-yl.

3. The compound of claim 1, wherein $(R_2)_m$—B— is selected from the group consisting of 4-dialkylaminophenyl and pyridine-2-yl.

4. The compound of claim 1, wherein $(R_1)_n$-A- is selected from the group consisting of 4-dialkylaminophenyl, naphth-2-yl, naphth-1-yl, and 6-dialkylaminonaphth-2-yl, and B is selected from the group consisting of phenyl and pyridine-2-yl.

5. The compound of claim 1, wherein $(R_2)_m$—B— is selected from the group consisting of 4-dialkylaminophenyl and pyridine-2-yl, and A is selected from the group consisting of phenyl, naphth-2-yl, and naphth-1-yl.

6. The compound of claim 1, wherein R is OR' and R' is $C_{1-6}$ alkyl.

7. The compound of claim 1, wherein represents a double bond having E or Z stereochemistry.

8. The compound of claim 1 of structure:

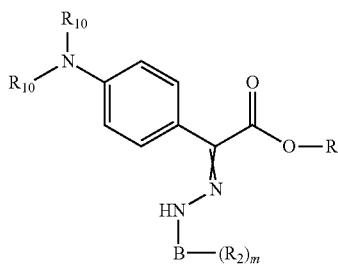

or a salt thereof,
wherein
each $R_{10}$ independently is hydrogen or alkyl;
R is OR' and R' is $C_{1-6}$ alkyl.

9. The compound of claim 8, of structure:

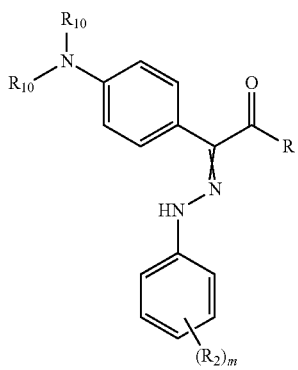

or a salt thereof.

10. The compound of claim 1 of structure:

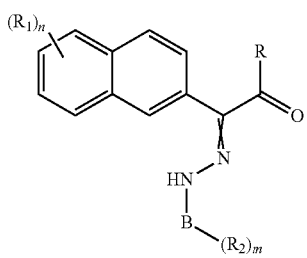

or a salt thereof, wherein R is OR' and R' is $C_{1-6}$ alkyl.

11. A molecular switch comprising a compound of claim 1.

12. A method of optically switching a compound of Formula I, or a salt thereof, or a material comprising the compound of Formula I or a salt thereof:

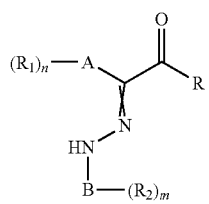

wherein

⟩ represents a double bond having either E or Z stereochemistry;

A is phenyl or naphthyl;

B is phenyl or pyridine-2-yl;

R is O—R', where:

each R' is independently azide, alkyl, alkenyl, alkynyl, cycloalkyl, heterocyclyl, alkoxyalkyl, heteroalkyl, alkoxy, aryl, or heteroaryl, where in the alkenyl and alkynyl groups for R', the double or triple bond is not at the alpha-beta position in the alkenyl or alkynyl group;

$R_1$ and $R_2$ are independently, for each occurrence, selected from the group consisting of heterocyclyl, halo, alkylamino, dialkylamino, diphenyl amino, hydroxyl, nitro, cyano, carboxyl, carboxylalkyl and carboxamido; or R and one of $R_2$ are optionally linked by a 3-8 carbon linker, which is optionally substituted;

n is 0, 1, 2, 3, 4 or 5; and m is 0, 1, 2, 3, 4, 5, 6 or 7;

provided that when n and m are both 0, at least one of A and B is not phenyl;

the method comprising irradiating said compound or material, thereby isomerizing the compound from the E stereoisomer to the Z stereoisomer, isomerizing the compound from the Z stereoisomer to the E stereoisomer.

13. The compound of claim 1 of structure selected from:

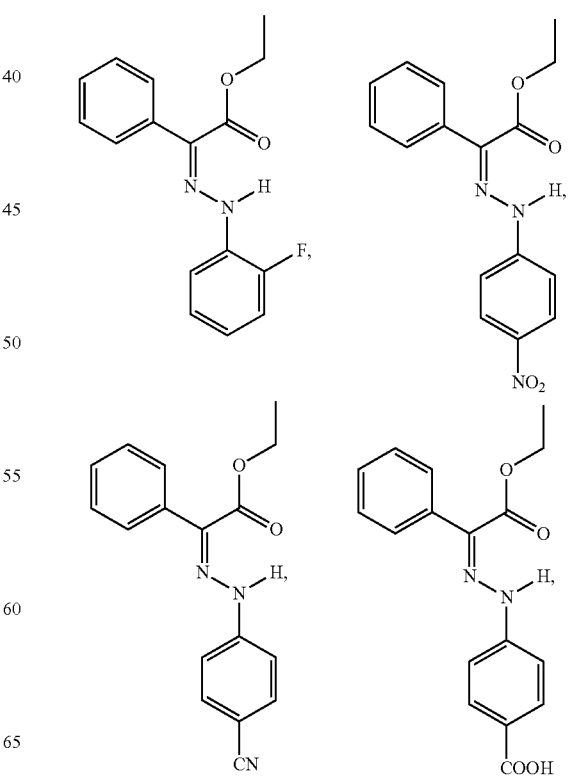

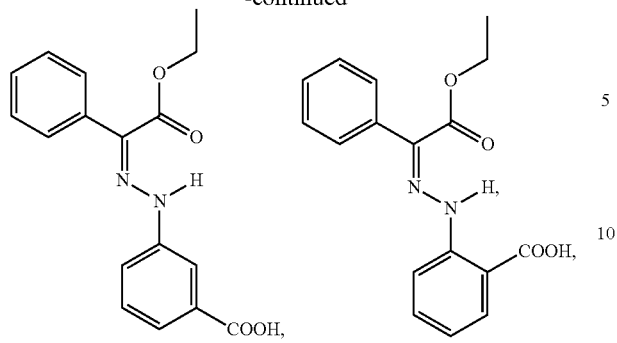
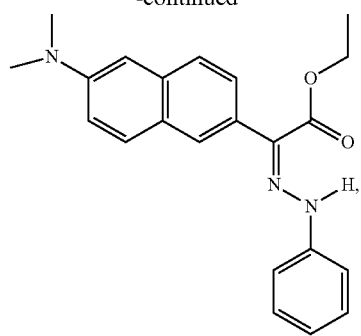
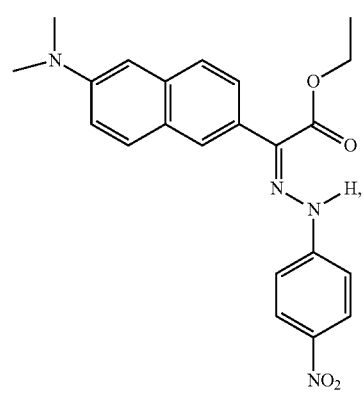
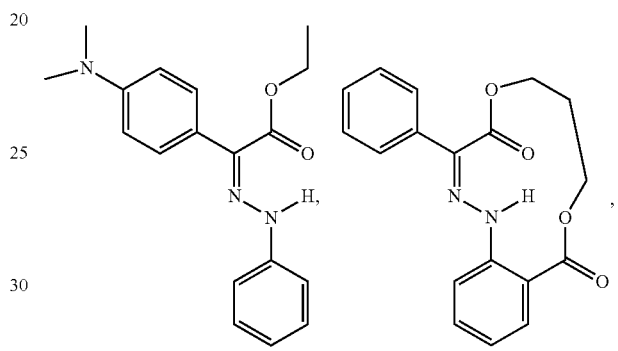
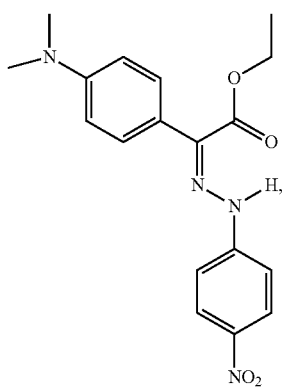
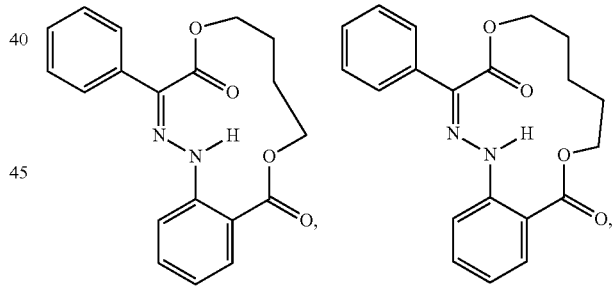
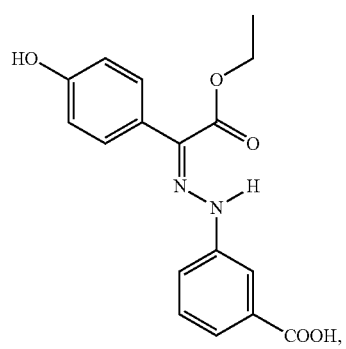
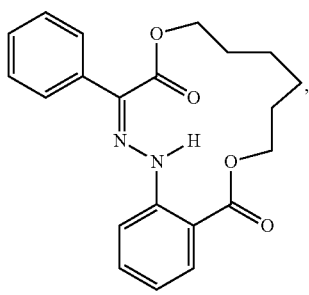

101
-continued
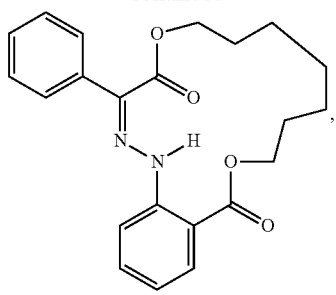
102
-continued
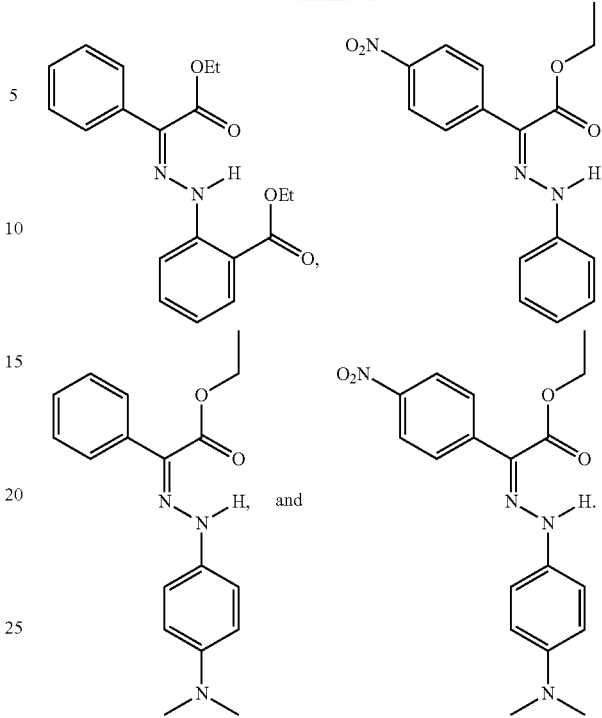
* * * * *